United States Patent
Verdine et al.

(10) Patent No.: US 10,227,390 B2
(45) Date of Patent: Mar. 12, 2019

(54) STABILIZED POLYPEPTIDE INSULIN RECEPTOR MODULATORS

(71) Applicant: President and Fellows of Harvard College, Cambridge, MA (US)

(72) Inventors: Gregory L. Verdine, Boston, MA (US); Gerard Hilinski, Somerville, MA (US); Rebecca Yue Liang, Cambridge, MA (US); Yvonne Alice Nagel, Somerville, MA (US); Minyun Zhou, Malden, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 14/898,222

(22) PCT Filed: Jun. 13, 2014

(86) PCT No.: PCT/US2014/042329
§ 371 (c)(1),
(2) Date: Dec. 14, 2015

(87) PCT Pub. No.: WO2014/201370
PCT Pub. Date: Dec. 18, 2014

(65) Prior Publication Data
US 2016/0215036 A1 Jul. 28, 2016

Related U.S. Application Data

(60) Provisional application No. 61/835,242, filed on Jun. 14, 2013.

(51) Int. Cl.
C07K 14/62 (2006.01)
C07K 14/72 (2006.01)
A61K 38/00 (2006.01)

(52) U.S. Cl.
CPC .............. *C07K 14/62* (2013.01); *C07K 14/72* (2013.01); *A61K 38/00* (2013.01)

(58) Field of Classification Search
None
See application file for complete search history.

(56) References Cited

U.S. PATENT DOCUMENTS

| | | |
|---|---|---|
| 4,270,537 A | 6/1981 | Romaine |
| 4,596,556 A | 6/1986 | Morrow et al. |
| 4,730,006 A | 3/1988 | Bohme et al. |
| 4,790,824 A | 12/1988 | Morrow et al. |
| 4,886,499 A | 12/1989 | Cirelli et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,120,859 A | 6/1992 | Webb |
| 5,141,496 A | 8/1992 | Dalto et al. |
| 5,190,521 A | 3/1993 | Hubbard et al. |
| 5,312,335 A | 5/1994 | McKinnon et al. |
| 5,328,483 A | 7/1994 | Jacoby |
| 5,334,144 A | 8/1994 | Alchas et al. |
| 5,339,163 A | 8/1994 | Homma et al. |
| 5,364,851 A | 11/1994 | Joran |
| 5,383,851 A | 1/1995 | McKinnon, Jr. et al. |
| 5,417,662 A | 5/1995 | Hjertman et al. |
| 5,446,128 A | 8/1995 | Kahn |
| 5,466,220 A | 11/1995 | Brenneman |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,599,302 A | 2/1997 | Lilley et al. |
| 5,622,852 A | 4/1997 | Korsmeyer |
| 5,649,912 A | 7/1997 | Peterson |
| 5,663,316 A | 9/1997 | Xudong |
| 5,704,911 A | 1/1998 | Parsons |
| 5,708,136 A | 1/1998 | Burrell et al. |
| 5,750,767 A | 5/1998 | Carpino et al. |
| 5,811,515 A | 9/1998 | Grubbs et al. |
| 5,824,483 A | 10/1998 | Houston, Jr. et al. |
| 5,834,209 A | 11/1998 | Korsmeyer |
| 5,856,445 A | 1/1999 | Korsmeyer |
| 5,874,529 A | 2/1999 | Gilon et al. |
| 5,893,397 A | 4/1999 | Peterson et al. |

(Continued)

FOREIGN PATENT DOCUMENTS

| | | |
|---|---|---|
| CN | 1906209 A | 1/2007 |
| CN | 101730708 A | 6/2010 |

(Continued)

OTHER PUBLICATIONS

Verdine, Gregory L. and Hilinski, Gerard J., "Stapled peptides for intracellular drug targets." Meth. Enzymol. (2012) 503 p. 3-33, available online Mar. 18, 2012.*

(Continued)

*Primary Examiner* — Fred H Reynolds
(74) *Attorney, Agent, or Firm* — McDermott Will & Emery LLP

(57) ABSTRACT

Provided herein are stabilized α-CT polypeptides comprising an alpha-helical segment, and wherein the polypeptide is of Formula (I-1) or Formula (I-2): $R^f-[X_{AA}]_s-X_{A1}-X_{A2}-X_{A3}-X_{A4}-X_{A5}-X_{A6}-X_{A7}-X_{A8}-X_{A9}-X_{A10}-X_{A11}-X_{A12}-X_{A13}-X_{A14}-[X_{AA}]_t-R^e$ (I-1) $R^f-[X_{AA}]_s-X_{C1}-X_{C2}-X_{C3}-X_{C4}-X_{C5}-X_{C6}-X_{C7}-X_{C8}-X_{C9}-X_{C10}-X_{C11}-X_{C12}-X_{C13}-X_{C14}-X_{C15}-X_{C16}-X_{C17}-X_{C18}-X_{C19}-X_{C20}-[X_{AA}]_t-R^e$ (I-2) wherein the α-CT polypeptide binds to the insulin receptor, and wherein the α-CT polypeptide includes at least one staple (i.e. two cross-linked amino acids) and/or at least one stitch (i.e. three cross-linked amino acids). Further provided are insulin analogs including the stapled or stitched α-CT polypeptides, pharmaceutical compositions thereof, methods of use, e.g., methods of treating a diabetic condition or complications thereof.

16 Claims, 41 Drawing Sheets
Specification includes a Sequence Listing.

(56) References Cited

U.S. PATENT DOCUMENTS

| | | | |
|---|---|---|---|
| 5,922,863 A | 7/1999 | Grubbs et al. | |
| 5,955,593 A | 9/1999 | Korsmeyer | |
| 5,965,703 A | 10/1999 | Horne et al. | |
| 5,993,412 A | 11/1999 | Deily et al. | |
| 5,998,583 A | 12/1999 | Korsmeyer | |
| 6,051,554 A | 4/2000 | Hornik et al. | |
| 6,153,391 A | 11/2000 | Picksley et al. | |
| 6,184,344 B1 | 2/2001 | Kent et al. | |
| 6,271,198 B1 | 8/2001 | Braisted et al. | |
| 6,326,354 B1 | 12/2001 | Gross et al. | |
| 6,348,558 B1 | 2/2002 | Harris et al. | |
| 6,444,425 B1 | 9/2002 | Reed et al. | |
| 6,610,657 B1 | 8/2003 | Goueli | |
| 6,613,874 B1 | 9/2003 | Mazur et al. | |
| 6,703,382 B2 | 3/2004 | Wang et al. | |
| 6,713,280 B1 | 3/2004 | Huang et al. | |
| 6,849,428 B1 | 2/2005 | Evans et al. | |
| 6,875,594 B2 | 4/2005 | Muir et al. | |
| 7,064,193 B1 | 6/2006 | Cory et al. | |
| 7,083,983 B2 | 8/2006 | Lane et al. | |
| 7,084,244 B2 | 8/2006 | Gilon et al. | |
| 7,183,059 B2 | 2/2007 | Verdine et al. | |
| 7,192,713 B1 | 3/2007 | Verdine et al. | |
| 7,202,332 B2 | 4/2007 | Arora et al. | |
| 7,247,700 B2 | 7/2007 | Korsmeyer et al. | |
| 7,538,190 B2 | 5/2009 | Robinson et al. | |
| 7,705,118 B2 | 4/2010 | Arora et al. | |
| 7,723,469 B2 | 5/2010 | Walensky et al. | |
| 7,745,573 B2 | 6/2010 | Robinson et al. | |
| 7,786,072 B2* | 8/2010 | Verdine | C07K 1/047 514/21.4 |
| 8,324,428 B2 | 12/2012 | Verdine et al. | |
| 8,592,377 B2* | 11/2013 | Verdine | C07K 7/06 514/21.1 |
| 8,895,699 B2* | 11/2014 | Verdine | C07K 1/047 530/345 |
| 8,957,026 B2 | 2/2015 | Verdine et al. | |
| 9,163,330 B2 | 10/2015 | Verdine et al. | |
| 9,458,189 B2* | 10/2016 | Verdine | C07K 1/107 |
| 2004/0023887 A1 | 2/2004 | Pillutla et al. | |
| 2004/0038901 A1 | 2/2004 | Basler et al. | |
| 2004/0067503 A1 | 4/2004 | Tan et al. | |
| 2005/0032800 A1 | 2/2005 | Bigot et al. | |
| 2005/0250680 A1 | 11/2005 | Walensky et al. | |
| 2006/0008848 A1 | 1/2006 | Verdine et al. | |
| 2006/0014675 A1 | 1/2006 | Arora et al. | |
| 2006/0148715 A1 | 7/2006 | Tweardy | |
| 2008/0220441 A1 | 9/2008 | Birnbaum et al. | |
| 2008/0262200 A1 | 10/2008 | Nash | |
| 2009/0047711 A1 | 2/2009 | Nash | |
| 2009/0088553 A1 | 4/2009 | Nash | |
| 2009/0149630 A1 | 6/2009 | Walensky et al. | |
| 2009/0176964 A1 | 7/2009 | Walensky et al. | |
| 2009/0326192 A1 | 12/2009 | Nash et al. | |
| 2010/0029552 A1 | 2/2010 | Watt et al. | |
| 2010/0081611 A1 | 4/2010 | Bradner et al. | |
| 2010/0152103 A1 | 6/2010 | Phadke et al. | |
| 2010/0168388 A1 | 7/2010 | Bernal et al. | |
| 2010/0184628 A1 | 7/2010 | Nash | |
| 2010/0184645 A1 | 7/2010 | Verdine et al. | |
| 2010/0216688 A1 | 8/2010 | Nash et al. | |
| 2010/0298201 A1 | 11/2010 | Nash et al. | |
| 2010/0298213 A1* | 11/2010 | Schaffer | C07K 14/72 514/6.7 |
| 2011/0028753 A1 | 2/2011 | Verdine et al. | |
| 2011/0144303 A1 | 6/2011 | Nash et al. | |
| 2011/0144306 A1 | 6/2011 | Verdine et al. | |
| 2011/0223149 A1 | 9/2011 | Nash et al. | |
| 2011/0263815 A1 | 10/2011 | Nash | |
| 2012/0082636 A1 | 4/2012 | Walensky et al. | |
| 2012/0122771 A1* | 5/2012 | Lawrence | C07K 14/72 514/4.8 |
| 2012/0172311 A1 | 7/2012 | Nash et al. | |
| 2012/0190818 A1 | 7/2012 | Nash | |
| 2012/0270800 A1 | 10/2012 | Verdine et al. | |
| 2013/0005943 A1 | 1/2013 | Arora et al. | |
| 2013/0023646 A1 | 1/2013 | Nash et al. | |
| 2013/0177979 A1 | 7/2013 | Turkson | |
| 2013/0211046 A1 | 8/2013 | Verdine et al. | |
| 2014/0005118 A1 | 1/2014 | Verdine et al. | |
| 2014/0011979 A1 | 1/2014 | Verdine et al. | |
| 2014/0162339 A1 | 6/2014 | Verdine et al. | |
| 2014/0235549 A1 | 8/2014 | Moellering et al. | |
| 2014/0256912 A1 | 9/2014 | Moellering et al. | |
| 2014/0323701 A1 | 10/2014 | Nash et al. | |
| 2015/0225471 A1 | 8/2015 | Liang et al. | |
| 2015/0239937 A1 | 8/2015 | Verdine et al. | |
| 2015/0284437 A1 | 10/2015 | Verdine et al. | |
| 2015/0376227 A1 | 12/2015 | Verdine et al. | |
| 2016/0024153 A1* | 1/2016 | Verdine | C07K 7/06 514/21.1 |
| 2018/0057565 A1* | 3/2018 | Liang | C07K 14/72 |

FOREIGN PATENT DOCUMENTS

| | | | |
|---|---|---|---|
| CN | 102510755 A | 6/2012 | |
| JP | 2008-501623 A | 1/2008 | |
| JP | 2008-510692 A | 4/2008 | |
| JP | 2010-510236 A | 4/2010 | |
| JP | 2010-522769 A | 7/2010 | |
| JP | 2012-532929 A | 12/2012 | |
| WO | WO-96/02642 A1 | 2/1996 | |
| WO | WO-96/20951 A1 | 7/1996 | |
| WO | WO-96/34878 A1 | 11/1996 | |
| WO | WO-97/13537 A1 | 4/1997 | |
| WO | WO-97/17092 A1 | 5/1997 | |
| WO | WO-97/26002 A1 | 7/1997 | |
| WO | WO-97/37705 A1 | 10/1997 | |
| WO | WO-99/14259 A1 | 3/1999 | |
| WO | WO-99/34833 A1 | 7/1999 | |
| WO | WO-99/34850 A1 | 7/1999 | |
| WO | WO-99/46367 A2 | 9/1999 | |
| WO | WO-00/06187 A2 | 2/2000 | |
| WO | WO-01/29247 A1 | 4/2001 | |
| WO | WO-02/064790 A2 | 8/2002 | |
| WO | WO-03/053996 A2 | 7/2003 | |
| WO | WO-2003/106491 A2 | 12/2003 | |
| WO | WO-2004/041275 A1 | 5/2004 | |
| WO | WO-2004/058804 A1 | 7/2004 | |
| WO | WO-2004/093798 A2 | 11/2004 | |
| WO | WO-2005/040202 A2 | 5/2005 | |
| WO | WO-2005/044839 A2 | 5/2005 | |
| WO | WO-2005/085457 A2 | 9/2005 | |
| WO | WO-2005/090388 A1 | 9/2005 | |
| WO | WO-2005/118620 A2 | 12/2005 | |
| WO | WO-2005/118634 A2 | 12/2005 | |
| WO | WO-2006018450 A2 | 2/2006 | |
| WO | WO-2006/103666 A2 | 10/2006 | |
| WO | WO-2007/013050 A1 | 2/2007 | |
| WO | WO-2007/141533 A2 | 12/2007 | |
| WO | WO-2008/061192 A2 | 5/2008 | |
| WO | WO-2008/095063 A1 | 8/2008 | |
| WO | WO-2008/121767 A2 | 10/2008 | |
| WO | WO-2009/020477 A1 | 2/2009 | |
| WO | WO-2009/042237 A2 | 4/2009 | |
| WO | WO-2009/046407 A2 | 4/2009 | |
| WO | WO-2009/126292 A2 | 10/2009 | |
| WO | WO-2010/011313 A2 | 1/2010 | |
| WO | WO-2010/034029 A1 | 3/2010 | |
| WO | WO-2010/068684 A2 | 6/2010 | |
| WO | WO 2010121288 A1 * | 10/2010 | C07K 14/72 |
| WO | WO-2011/008260 A2 | 1/2011 | |
| WO | WO-2011/146974 A1 | 12/2011 | |
| WO | WO-2012/040459 A2 | 3/2012 | |
| WO | WO-2012/065181 A2 | 5/2012 | |
| WO | WO-2012/174423 A1 | 12/2012 | |
| WO | WO-2014/047673 A1 | 4/2014 | |
| WO | WO-2014/052647 A2 | 4/2014 | |
| WO | WO-2014/055564 A1 | 4/2014 | |
| WO | WO-2014/110420 A1 | 7/2014 | |

(56) References Cited

FOREIGN PATENT DOCUMENTS

OTHER PUBLICATIONS

Hilpert, Kai et al, "Peptide arrays on cellulose support: spot synthesis, a time and cost efficientmethod for synthesis of large numbers of petpdies ina parallel and addressable fashion." Nat. Prot. (2007) 2(6) p. 1333-1349.*
The Chemguide web page on anhydrides, https://web.archive.org/web/20040325212934/https://www.chemguide.co.uk/organicprops/anhydrides/nitrogen.html, available Mar. 25, 2004.*
International Search Report for PCT/US2014/042329, dated Nov. 24, 2014.
International Preliminary Report on Patentability for PCT/US2014/042329, dated Dec. 23, 2015.
Andrews et al., "Forming Stable Helical Peptides Using Natural and Artificial Amino Acids," Tetrahedron. 55:11711-43 (1999).
Biagini et al., "Cross-metathesis of Unsaturated a-amino Acid Derivatives," J Chem Soc Perkin Trans. 1:2485-99 (1998).
Bierzynski et al., "A salt bridge stabilizes the helix formed by isolated C-peptide of Rnase A," Proc Natl Acad Sci USA. 79(8):2470-4 (1982).
Blackwell et al., "Highly Efficient Synthesis of Covalently Cross-Linked Peptide Helices by Ring-Closing Metathesis," Angew Chem Int Ed. 37(23):3281-84 (1998).
Blackwell et al., "Ring-closing metathesis of olefinic peptides: design, synthesis, and structural characterization of macrocyclic helical peptides," J Org Chem. 66(16):5291-302 (2001).
Blundell et al., "Atomic positions in rhombohedral 2-zinc insulin crystals," Nature, 231(5304):506-11 (1971).
Bode et al., "Chemoselective amide ligations by decarboxylative condensations of N-alkylhydroxylamines and alpha-ketoacid," Angew Chem Int Ed Engl., 45(8):1248-52 (2006).
Brandt et al., "Dimeric fragment of the insulin receptor alpha-subunit binds insulin with full holoreceptor affinity," J Biol Chem., 276(15): 12378-84 (2001).
Chang et al., "Insulin signaling and the regulation of glucose transport," Mol Med. 10(7-12):65-71(2004).
Chen et al., "Determination of the helix and beta form of proteins in aqueous solution by circular dichroism. Biochemistry," 13(16):3350-9 (1974).
Clark et al., "Supramolecular Design by Covalent Capture. Design of a Peptide Cylinder via Hydrogen-Bond-Promoted Intermolecular Olefin Metathesis," J Am Chem Soc. 117: 12364-65 (1995).
Cox et al., "Insulin receptor expression by human prostate cancers," Prostate. 69(1):33-40 (2009).
De Meyts et al., "Insulin interactions with its receptors: experimental evidence for negative cooperativity," Biochem Biophys Res Commun. 55(1):154-61 (1973).
De Meyts, "The structural basis of insulin and insulin-like growth factor-I receptor binding and negative co-operativity, and its relevance to mitogenic versus metabolic signalling," Diabetologia. 37 Suppl 2:S135-48 (1994).
Duronio, "Insulin receptor is phosphorylated in response to treatment of HepG2 cells with insulin-like growth factor I," Biochem J. 270(1):27-32 (1990).
Ellis et al., "Design, synthesis, and evaluation of a new generation of modular nucleophilic glycine equivalents for the efficient synthesis of sterically constrained alpha-amino acids," J Org Chem. 71(22):8572-8 (2006).
Evans et al., "The Rise of Azide-Alkyne 1,3-Dipolar 'Click' Cycloaddition and its Application to Polymer Science and Surface Modification," Australian Journal of Chemistry. 60:384-95 (2007).
Furstner et al., "Alkyne Metathesis: Development of a Novel Molybdenum-Based Catalyst System and Its Application to the Total Synthesis of Epothilone A and C," Chem Euro J. 7(24):5299-5317 (2001).
Fustero et al., "Asymmetric synthesis of new beta,beta-difluorinated cyclic quaternary alpha-amino acid derivatives," Org Lett. 8(18):4129-32 (2006).

Giannis et al., "Peptidomimetics for Receptor Ligands—Discovery, Development, and Medical Perspectives," Angew Chem Int Ed Engl. 32:1244-67 (1993).
Greenfield et al., "Computed circular dichroism spectra for the evaluation of protein conformation," Biochemistry. 8(10):4108-16 (1969).
Greenlee et al., "A General Synthesis of a-vinyl-a-amino acids," Tetrahedron Letters. 42:3999-4002 (1978).
Guo et al., "Probing the alpha-helical structural stability of stapled p53 peptides: molecular dynamics simulations and analysis," Chem Biol Drug Des. 75(4):348-59 (2010).
Huang et al., "How insulin binds: the B-chain alpha-helix contacts the L1 beta-helix of the insulin receptor," J Mol Biol. 341(2):529-50 (2004).
Jackson et al., "General Approach to the Synthesis of Short a-Helical Peptides," J Am Chem Soc. 113:9391-92 (1991).
Jensen et al., "Activation of the insulin receptor (IR) by insulin and a synthetic peptide has different effects on gene expression in IR-transfected L6 myoblasts," Biochem J. 412(3):435-45 (2008).
Karle et al., "Structural characteristics of alpha-helical peptide molecules containing Aib residues," Biochemistry. 29(29):6747-56 (1990).
Kaul et al., "Stereochemical control of peptide folding," Bioorg Med Chem. 7(1):105-17 (1999).
Kazmaier, "Sythesis of Quaternary Amino Acids Containing $\beta,\gamma$- as well as $\gamma,\delta$-Unsaturated Side Chains via Chelate-Enolate Claisen Rearrangement," Tetrahedron Letters. 37(30):5351-4 (1996).
Khalil et al., "An efficient and high yield method for the N-tert-butoxycarbonyl protection of sterically hindered amino acids," Tetrahedron Lett. 37(20):3441-44 (1996).
Kim et al., "Introduction of all-hydrocarbon i,i+3 staples into alpha-helices via ring-closing olefin metathesis," Org Lett. 12(13):3046-9 (2010).
Kim et al., "Stereochemical effects of all-hydrocarbon tethers in i,i+4 stapled peptides," Bioorg Med Chem Lett. 19(9):2533-6 (2009).
Kim et al., "Synthesis of all-hydrocarbon stapled a-helical peptides by ring-closing olefin metathesis," Nat Protoc. 6(6):761-71 (2011).
Leduc et al., "Helix-stabilized cyclic peptides as selective inhibitors of steroid receptor-coactivator interactions," Proc Natl Acad Sci USA. 100(20):11273-78 (2003).
Liskamp, "Conformationally restricted amino acids and dipeptides, (non)peptidomimetics and secondary structure mimetics," Reel Travl Chim Pays-Bas. 113:1-19 (1994).
Lou et al., "The first three domains of the insulin receptor differ structurally from the insulin-like growth factor 1 receptor in the regions governing ligand specificity," Proc Natl Acad Sci USA. 103(33):12429-34 (2006).
McKern et al., "Structure of the insulin receptor ectodomain reveals a folded-over conformation," Nature. 443(7108):218-21 (2006).
McNamara et al., "Peptides constrained by an aliphatic linkage between two C(alpha) sites: design, synthesis, and unexpected conformational properties of an i,(i+4)-linked peptide," J Org Chem. 66(13):4585-94 (2001).
Menting et al., "A thermodynamic study of ligand binding to the first three domains of the human insulin receptor: relationship between the receptor alpha-chain C-terminal peptide and the site 1 insulin mimetic peptides," Biochemistry. 48(23):5492-500 (2009).
Miller et al., "Application of Ring-Closing Metathesis to the Synthesis of Rigidified Amino Acids and Peptides," J Am Chem Soc. 118(40):9606-9614 (1996).
Miller et al., "Synthesis of Conformationally Restricted Amino Acids and Peptides Employing Olefin Metathesis," J Am Chem Soc.117(21):5855-5856 (1995).
Roos et al., "Synthesis of a-Substituted a-Amino Acids via Cationic Intermediates," J Org Chem. 58:3259-68 (1993).
Sali et al., "Stabilization of protein structure by interaction of alpha-helix dipole with a charged side chain," Nature. 335(6192):740-3 (1988).
Schaffer et al., "A novel high-affinity peptide antagonist to the insulin receptor," Biochem Biophys Res Commun. 376(2):380-3 (2008).

(56) References Cited

OTHER PUBLICATIONS

Schaffer et al., "Assembly of high-affinity insulin receptor agonists and antagonists from peptide building blocks," Proc Natl Acad Sci USA. 100(8):4435-9 (2003).
Schafmiester et al., "An All-Hydrocarbon Cross-Linking System for Enhancing the Helicity and Metabolic Stability of Peptides," J Am Chem Soc. 122:5891-92 (2000).
Schmiedeberg et al., "Reversible backbone protection enables combinatorial solid-phase ring-closing metathesis reaction (RCM) in peptides," Org Lett. 4(1):59-62 (2002).
Scholtz et al., "The mechanism of alpha-helix formation by peptides," Annu Rev Biophys Biomol Struct. 21:95-118 (1992).
Scott et al., "Evidence of insulin-stimulated phosphorylation and activation of the mammalian target of rapamycin mediated by a protein kinase B signaling pathway," Proc Natl Acad Sci USA. 95(13):7772-7 (1998).
Smith et al., "Structural resolution of a tandem hormone-binding element in the insulin receptor and its implications for design of peptide agonists," Proc Natl Acad Sci USA. 107(15):6771-6 (2010).
Surinya et al., "Role of insulin receptor dimerization domains in ligand binding, cooperativity, and modulation by anti-receptor antibodies." J Biol Chem. 277(19):16718-25 (2002).
Tanaka, "Design and synthesis of non-proteinogenic amino acids and secondary structures of their peptides," Yakugaku Zasshi. 126(10):931-44 (2006). Japanese.
Toniolo, "Conformationally restricted peptides through short-range cyclizations," Int J Pept Protein Res. 35(4):287-300 (1990).
Tsuruzoe et al., "Insulin receptor substrate 3 (IRS-3) and IRS-4 impair IRS-1- and IRS-2-mediated signaling," Mol Cell Biol. 21(1):26-38 (2001).
Ueki et al., "Increased insulin sensitivity in mice lacking p85beta subunit of phosphoinositide 3-kinase," Proc Natl Acad Sci USA. 99(1):419-24 (2002).
Williams et al., "Asymmetric Synthesis of Monosubstituted and a,a-Disubstituted a-Amino Acids via Diastereoselective Glycine Enolate Alkylations," J Am Chem Soc. 113:9276-86 (1991).
Zhang et al., "A cell-penetrating helical peptide as a potential HIV-1 inhibitor," J Mol Biol. 378(3):565-80 (2008).
Menting et al., "How insulin engages its primary binding site on the insulin receptor," Nature. 493(7431):241-5 (2013).
Supplementary Information for Menting et al., "How insulin engages its primary binding site on the insulin receptor," Nature. 493(7431):241-5 (2013).
Becker et al., "Three-dimensional structure of the Stat3beta homodimer bound to DNA," Nature 394(6689):145-51 (1998).
Zhao et al., "A cell-permeable Stat3 SH2 domain mimetic inhibits Stat3 activation and induces antitumor cell effects in vitro," J Biol Chem. 285(46):35855-65 (2010).
Robinson, "Beta-hairpin peptidomimetics: design, structures and biological activities," Acc Chem Res. 41(10):1278-88 (2008).
Oh et al., "A convergent synthesis of new beta-turn mimics by click chemistry," Chem Commun (Camb). (29):3069-71 (2006).
Holland-Nell et al., "Maintaining biological activity by using triazoles as disulfide bond mimetics," Angew Chem Int Ed Engl. 50(22):5204-6 (2011).
Isidro-Llobet et al., "Amino acid-protecting groups," Chem Rev. 109(6):2455-504 (2009).
Examination Report No. 1 for Australian Patent Application No. 2014278005, dated Nov. 10, 2017 (4 pages).
Fujimoto et al., "Development of a series of cross-linking agents that effectively stabilize alpha-helical structures in various short peptides," Chemistry. 14(3):857-63 (2008).
NCBI Blast for ID P40763. Dated Feb. 1, 1995 (17 pages).
CAS RN: 933687-70-8; STN entry date: Apr. 30, 2007; 3-(dimethylamino)-1-(2-propen-1-yl)-3-pyrrolidinecarboxylic acid (1 Page).
CAS RN: 933687-66-2; STN entry date: Apr. 30, 2007; 3-(methylamino)-1-(2-propen-1-yl)-3-pyrrolidinecarboxylic acid (1 Page).
Office Action for Chinese Application No. 201480045052.9, dated Jul. 3, 2018 (7 pages).
Office Action for Japanese Application No. 2016-519683, dated Jul. 25, 2018 (8 pages).
Menting et al., "How insulin engages its primary binding site on the insulin receptor," Available in PMC Jan. 10, 2014, published in final edited form as: Nature. 493(7431):241-5 (2013) (18 pages).
Whittaker et al., "Alpha-Helical element at the hormone-binding surface of the insulin receptor functions as a signaling element to activate its tyrosine kinase," Proc Natl Acad U S A. 109(28):11166-71 (2012).
Office Action for Israeli Application No. 243088, dated Aug. 23, 2018 (2 pages).

* cited by examiner

| αCT Residue # | 704 | 705 | 706 | 707 | 708 | 709 | 710 | 711 | 712 | 713 | 714 | 715 | | Peptide Type |
|---|---|---|---|---|---|---|---|---|---|---|---|---|---|---|
| SEQ ID NO: 1 | T | F | E | D | Y | L | H | N | V | V | F | V | | WT |
| SEQ ID NO: 87 | T | F | E | D | * | L | H | N | V | V | F | * | | i,i+7 |
| SEQ ID NO: 88 | * | F | E | D | * | L | H | N | V | V | F | V | | i,i+4 |
| SEQ ID NO: 89 | T | F | E | D | * | L | H | N | * | V | F | V | | i,i+4 |
| SEQ ID NO: 90 | * | T | F | E | * | Y | L | H | N | V | V | F | V | i,i+4 |
| SEQ ID NO: 91 | T | F | E | D | Y | L | H | N | * | V | F | V | * | i,i+4 |

Asterisks denote the position of cross-link incorporation

Polyglycine
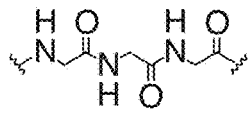 ~ 6.9 Å
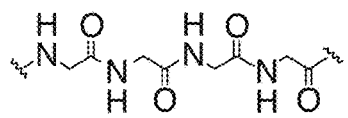 ~ 10.5 Å
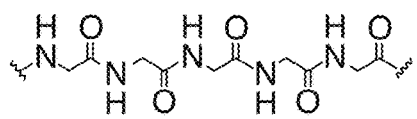 ~ 13.9 Å
G6 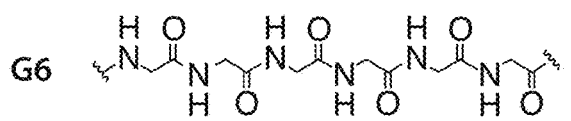 ~ 17.4 Å
Polyethylene glycol (PEG)
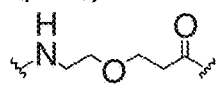 ~ 6.6 Å
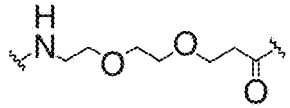 ~ 9.9 Å
(PEG)$_2$ - 13 Atoms 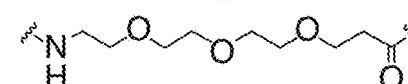 ~ 13.2 Å
(PEG)$_3$ - 16 Atoms 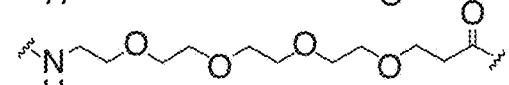 ~ 16.5 Å
(PEG)$_4$ - 19 Atoms 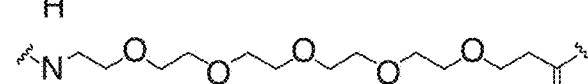 ~ 19.8 Å
(PEG)$_5$ - 22 Atoms 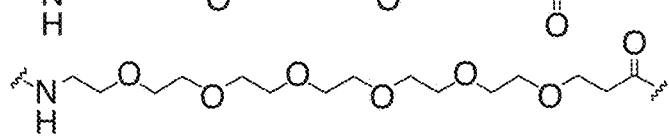 ~ 22.1 Å
Aminohexanoic acid (AHX)
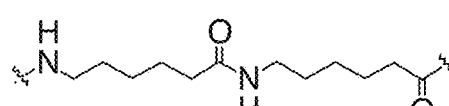 ~ 13.2 Å
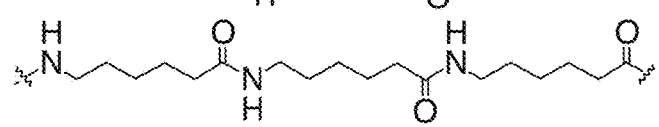 ~ 19.8 Å
Fig. 6

αCT-linker- A-chain:

SEQ ID NO:11　　　　　　　　SEQ ID NO:8
YN071-1　　NH$_2$-TFEDYLHNVVFV- PEG$_2$-GIVEQCCTSICSLYQLENYCN-CO$_2$H

YN078-1　　NH$_2$-TFEDYLHNVVFV- PEG$_5$-GIVEQCCTSICSLYQLENYCN-CO$_2$H

YN078-2　　NH$_2$-TFEDYLHNVVFV- G$_6$-GIVEQCCTSICSLYQLENYCN-CO$_2$H

SSFRKTFEDYLHNVVFV- (PEG)$_2$-GIVEQCCTSICSLYQLENYCN ⎤
SSFRKTFEDYLHNVVFV- (PEG)$_5$-GIVEQCCTSICSLYQLENYCN ⎬ with 5-residue extension to potentially improve solubility
SSFRKTFEDYLHNVVFV-G$_6$-GIVEQCCTSICSLYQLENYCN ⎦
　　SEQ ID NO:5　　　　　　　SEQ ID NO:8

B-chain:

SEQ ID NO:10
YN071-2　　NH$_2$-FVNQHLCGSHLVEALYLVCGERGFFYTKPT-CO$_2$H

Fig. 9

Insulin peptides: αCT-linker- A-chain

| | | | Synthesis | Purif. |
|---|---|---|---|---|
| YN071-1 | NH$_2$-TFEDYLHNVVFV- PEG$_2$-GIVEQCCTSICSLYQLENYCN-CO$_2$H | | √ | √ |
| | SEQ ID NO:11 | SEQ ID NO:8 | | |
| YN078-1 | NH$_2$-TFEDYLHNVVFV- PEG$_5$-GIVEQCCTSICSLYQLENYCN-CO$_2$H | | √ | not soluble |
| YN078-2 | NH$_2$-TFEDYLHNVVFV- G$_6$-GIVEQCCTSICSLYQLENYCN-CO$_2$H | | √ | (√) |

Mutated Insulin peptides: αCT-linker- A-chain

| | | | Synthesis | Purif. |
|---|---|---|---|---|
| YN094-1 | NH$_2$-TFEDYLHNAAFV- PEG$_2$-GIVEQCCTSICSLYQLENYCN-CO$_2$H | | √ | √ |
| YN094-2 | NH$_2$-TFEDYLHNAAFV- PEG$_5$-GIVEQCCTSICSLYQLENYCN-CO$_2$H | | √ | √ |
| | SEQ ID NO:2 | SEQ ID NO:8 | | |

Insulin peptides: B-chain

| | | Synthesis | Purif. |
|---|---|---|---|
| YN071-2 | FVNQHLCGSHLVEALYLVCGERGFFYTKPT | √ | √ |
| | SEQ ID NO:10 | | |

Fig. 10

Sequence 1 (Insulin lispro variant, A, B- & C-chain) (SEQ ID NO:26)
MKHHHHHHMSSGLVPRGSHMRFVNQHLCGSHLVEALYLVCGERGFFY
TKPTRREAEDLQVGQVELGGGPGAGSLQPLALEGSLQKRGIVEQCCTSI
CSLYQLENYCN → 11.8 kDa, 107 AA, estimated pI 7.11

Sequence 2 (Insulin lispro variant, αCT-linkrer-A-, B- & C-chain) (SEQ ID NO: 27)
MKHHHHHHMSSGLVPRGSHMRFVNQHLCGSHLVEALYLVCGERGFFY
TKPTRREAEDLQVGQVELGGGPGAGSLQPLALEGSLQKRTFEDYLHNVV
FVGGGSGGGSGIVEQCCTSICSLYQLENYCN → 13.9 kDa, 127 AA, estimated pI 6.53

Fig. 12

Sequence 3 (Insulin lispro variant, αCT-linkrer-A-, B- & truncated C-chain) (SEQ ID NO:28)
MKHHHHHHMSSGLVPRGSHMRFVNQHLCGSHLVEALYLVCGERGFFY
TKPTKRTFEDYLHNVVFVGGGSGGGSGIVEQCCTSICSLYQLENYCN → 10.5 kDa, 94 AA, estimated pI 7.72

Fig. 13

- Expression of Insulin in E- coli and NCL of stapled αCT:
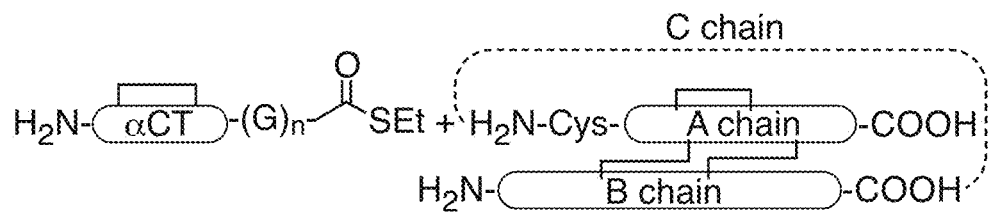
- Or expression of Insulin in E- coli and enzymatic ligation of stapled αCT:
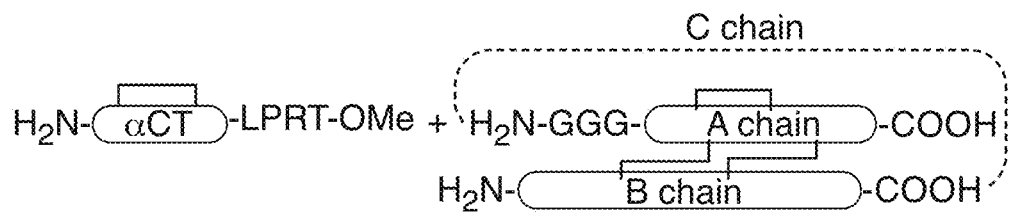
Fig. 14

SEQ ID NO: 35    s-aCT5: SSFRKTFED*LHN*VFVW
PyrR/PyrR Alloc-Stapled Peptide

SEQ ID NO: 46    s-aCT16: S*FRKTFE*YLHNVVFVW
PyrR/$S_8$ Amino-Stapled Peptide

Table 4. Exemplified αCT Sequences

| SEQ ID | Peptide | Amino Acid Sequence | Peptide Type |
|---|---|---|---|
| SEQ ID NO:80 | WT-aCT1 | Ac-TFEDYLHNVVFVW | Unmodified |
| SEQ ID NO:31 | s-aCT1 | Ac-TFED(Pyr$_R$)LHNVVF(S$_8$)W | Amino-Stapled i+7 |
| SEQ ID NO:32 | s-aCT2 | Ac-TFED(R$_G$N)LHNVVF(S$_8$)W | Amino-Stapled i+7 |
| SEQ ID NO:33 | s-aCT3 | Ac-TFED(R$_5$)LHNVVF(S$_8$)W | Hydrocarbon-Stapled i+7 |
| SEQ ID NO:34 | s-aCT4 | Ac-TFED(R$_E$N)LHNVVF(S$_8$)W | Amino-Stapled i+7 |
| SEQ ID NO:35 | s-aCT5 | SSFRKTFED(Pyr$_R$)LHN(Pyr$_R$)VFVW | Alloc-Stapled i+4 |
| SEQ ID NO:36 | s-aCT6 | TFED(Pyr$_R$)LHN(Pyr$_R$)VFVW | Alloc-Stapled i+4 |
| SEQ ID NO:37 | s-aCT7 | TFED(Az)LHN(Pyr$_S$)VFVW | Alloc-Stapled i+4 |
| SEQ ID NO:38 | s-aCT8 | TFED(Az)LHN(S$_8$)VFVW | Amino-Stapled i+4 |
| SEQ ID NO:39 | s-aCT9 | TFED(S$_E$N)LHN(S$_8$)VFVW | Amino-Stapled i+4 |
| SEQ ID NO:40 | s-aCT10 | TFED(S$_E$N)LHN(S$_{10}$)VFVW | Amino-Stapled i+4 |
| SEQ ID NO:41 | s-aCT11 | S(Pyr$_R$)FRKTFE(S$_8$)YLHNVVFVW | Alloc-Stapled i+7 |
| SEQ ID NO:42 | s-aCT12 | SS(Pyr$_R$)RKTFED(S$_8$)LHNVVFVW | Alloc-Stapled i+7 |
| SEQ ID NO:43 | s-aCT13 | TFED(S$_E$N)LHN(S$_5$)VFVW | Amino-Stapled i+4 |
| SEQ ID NO:44 | s-aCT14 | SSFRKTFED(S$_5$)LHN(S$_5$)VFVW | Hydrocarbon-Stapled i+4 |
| SEQ ID NO:2 | WT-aCT2 | TFEDYLHNAAFV | Unmodified |
| SEQ ID NO:45 | s-aCT15 | S(R$_5$)FRKTFE(S$_8$)YLHNVVFVW | Hydrocarbon-Stapled i+7 |
| SEQ ID NO:46 | s-aCT16 | S(Pyr$_R$)FRKTFE(S$_8$)YLHNVVFVW | Amino-Stapled i+7 |
| SEQ ID NO:47 | s-aCT17 | SS(R$_5$)RKTFED(S$_8$)LHNVVFVW | Hydrocarbon-Stapled i+7 |
| SEQ ID NO:48 | s-aCT18 | (S$_5$)FED(Pyr$_S$)LHNVVFVW | Amino-Stapled i+4 |
| SEQ ID NO:49 | s-aCT19 | TFED(S$_5$)LHN(Pyr$_S$)VFVW | Amino-Stapled i+4 |
| SEQ ID NO:50 | s-aCT20 | TFED(S$_5$)LHN(S$_5$)VFVW | Hydrocarbon-Stapled i+4 |
| SEQ ID NO:51 | s-aCT21 | SSFRKTFED(Az)LHN(Pyr$_S$)VFVW | Alloc-Stapled i+4 |
| SEQ ID NO:52 | s-aCT22 | (S$_5$)SFR(S$_5$)TFEDYLHNVVFV | Hydrocarbon-Stapled i+4 |
| SEQ ID NO:53 | s-aCT23 | (Pyr$_R$)SFR(PYR$_R$)TFEDYLHNVVFV | Alloc-Stapled i+4 |
| SEQ ID NO:3 | WT-aCT3 | SSFRKTFEDYLHNVVFVW | Unmodified |
| SEQ ID NO:54 | s-aCT24 | TFED(S$_E$N)LHN(S$_E$N)VFVW | Amino-Stapled i+4 |
| SEQ ID NO:55 | s-aCT25 | TFED(Pyr$_S$)LHN(S$_5$)VFVW | Amino-Stapled i+4 |
| SEQ ID NO:56 | s-aCT26 | (S$_5$)FED(S$_5$)LHNVVFVW | Hydrocarbon-Stapled i+4 |
| SEQ ID NO:57 | s-aCT27 | (Pyr$_S$)FED(S$_5$)LHNVVFVW | Amino-Stapled i+4 |
| SEQ ID NO:58 | s-aCT28 | (S$_E$N)FED(S$_E$N)LHNVVFVW | Amino-Stapled i+4 |
| SEQ ID NO:84 | WT-aCT4 | SSFRKTFEDYLHNVVFV | Unmodified |
| SEQ ID NO:85 | WT-aCT5 | SSFRKTFEDYLHNAAFV | Unmodified |
| SEQ ID NO:59 | s-aCT29 | S(R$_5$)FRKTFE(S$_8$)YLHNVVFV | Hydrocarbon-Stapled i+7 |
| SEQ ID NO:60 | s-aCT30 | S(Pyr$_R$)FRKTFE(S$_8$)YLHNVVFV | Alloc-Stapled i+7 |
| SEQ ID NO:61 | s-aCT31 | S(Pyr$_R$)FRKTFE(S$_8$)YLHNAAFV | Alloc-Stapled i+7 |
| SEQ ID NO:62 | s-aCT32 | S(R$_G$N)FRKTFE(S$_8$)YLHNVVFV | Alloc-Stapled i+7 |
| SEQ ID NO:63 | s-aCT33 | S(Pyr$_R$)FRKTFE(S$_8$)YLHNVVFV | Amino-Stapled i+7 |
| SEQ ID NO:64 | s-aCT34 | S(Pyr$_R$)FRKTFE(S$_8$)YLHNAAFV | Amino-Stapled i+7 |
| SEQ ID NO:65 | s-aCT35 | S(R$_G$N)FRKTFE(S$_8$)YLHNVVFV | Amino-Stapled i+7 |

Fig. 23

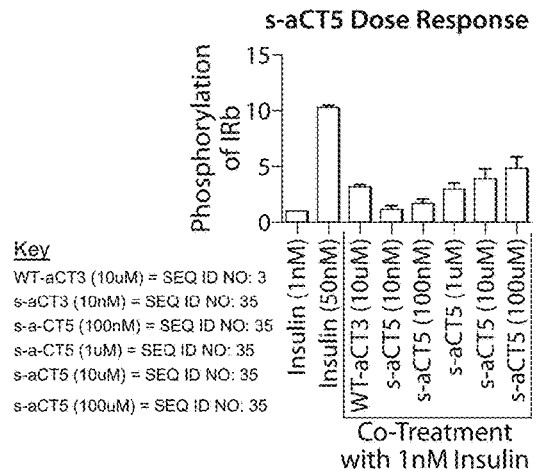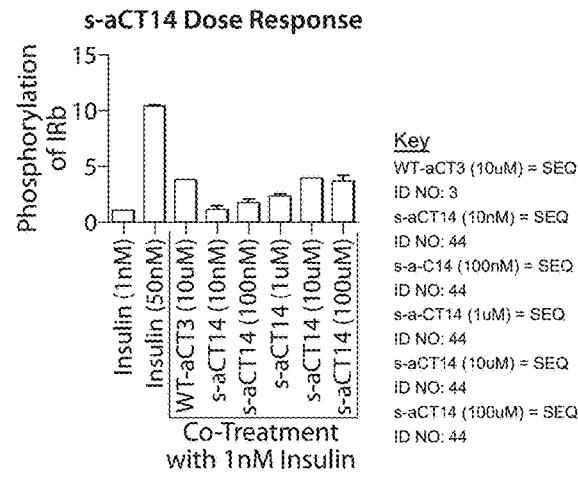
Fig. 34A    Fig. 34B
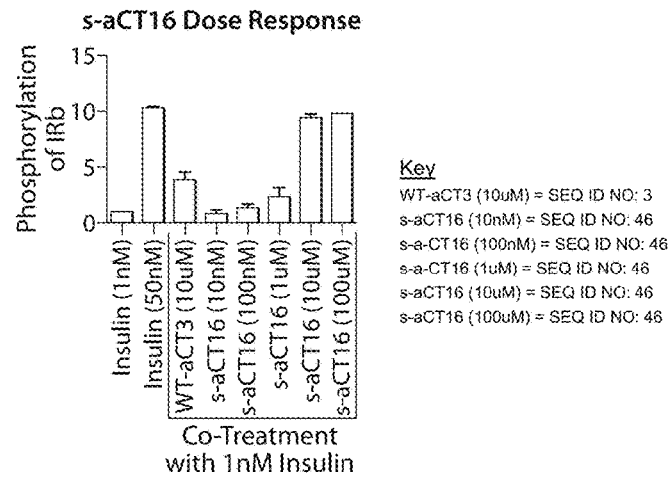
Fig. 34C

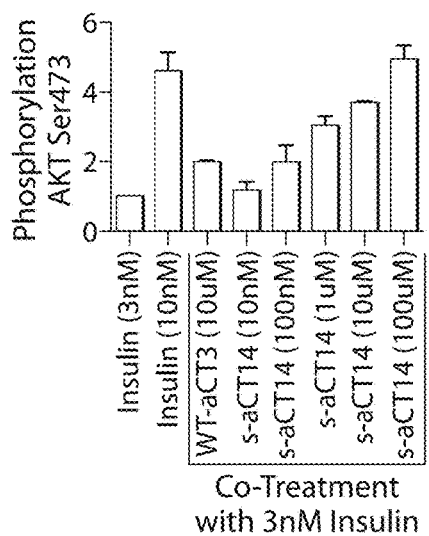
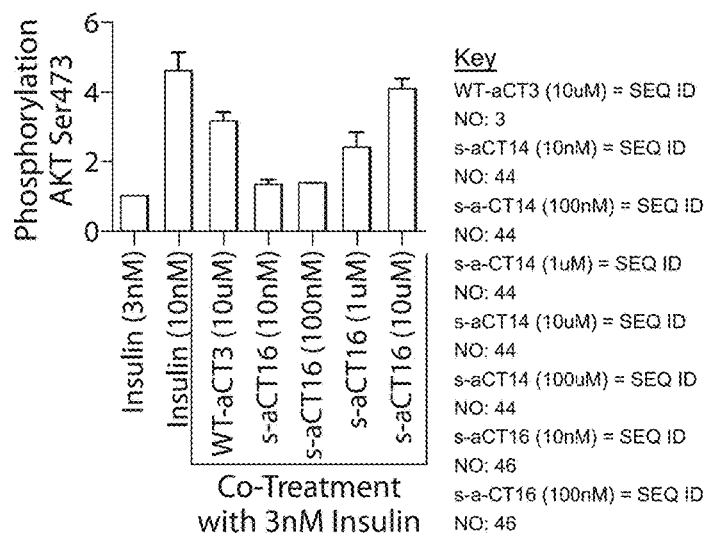
Fig. 36
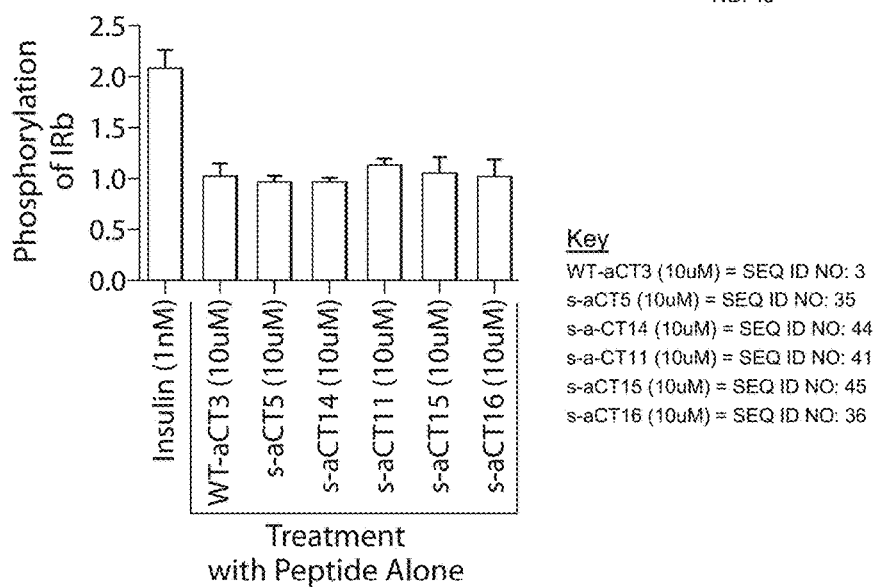
Fig. 37

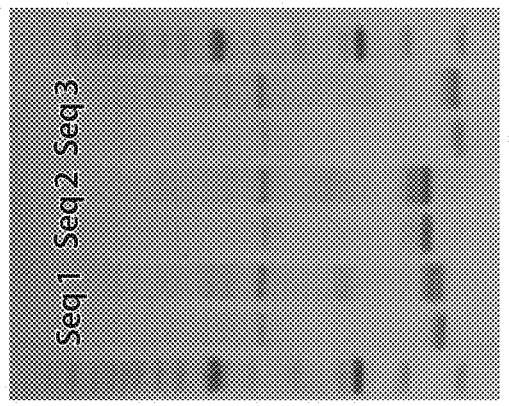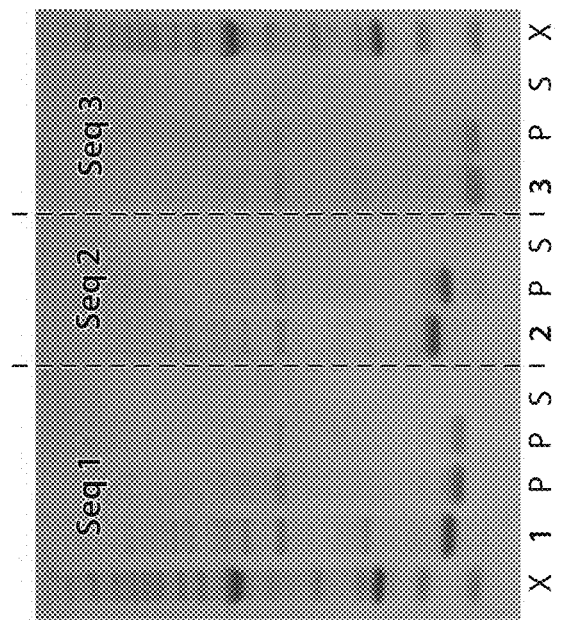
Fig. 41A
Fig. 41B

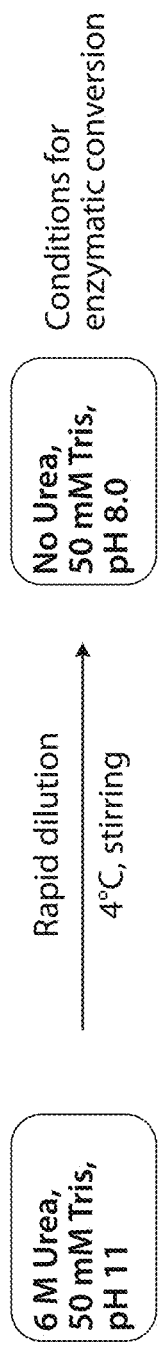
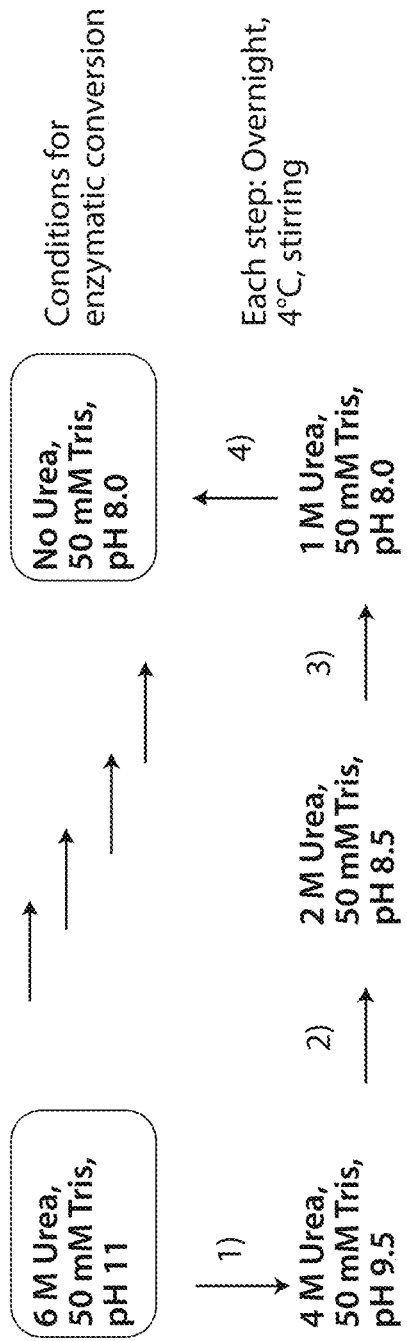
Fig. 42A
Fig. 42B

SEQUENCE LISTING

```
<160> NUMBER OF SEQ ID NOS: 95

<210> SEQ ID NO 1
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1

Thr Phe Glu Asp Tyr Leu His Asn Val Val Phe Val Trp
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 2

Thr Phe Glu Asp Tyr Leu His Asn Ala Ala Phe Val
1               5                   10

<210> SEQ ID NO 3
<211> LENGTH: 18
<212> TYPE: PRT
<213> ORGANISM: Artificial Sequence
```

```
<220> FEATURE:
<223> OTHER INFORMATION: Synthetic Polypeptide

<400> SEQUENCE: 3

Ser Ser Phe Arg Lys Thr Phe Glu Asp Tyr Leu His Asn Val Val Phe
1               5                   10                  15

Val Trp

<210> SEQ ID NO 4
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 4

Ser Ser Phe Arg Lys Thr Phe Glu Asp Tyr Leu His Asn Ala Ala Phe
1               5                   10                  15

Val Trp

<210> SEQ ID NO 5
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 5

Ser Ser Phe Arg Lys Thr Phe Glu Asp Tyr Leu His Asn Val Val Phe
1               5                   10                  15

Val

<210> SEQ ID NO 6
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 6

Ser Ser Phe Arg Lys Thr Phe Glu Asp Tyr Leu His Asn Ala Ala Phe
1               5                   10                  15

Val

<210> SEQ ID NO 7
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 7

Gly Ile Val Glu Gln Cys Cys Ala Ser Val Cys Ser Leu Tyr Gln Leu
1               5                   10                  15

Glu Asn Tyr Cys Asn
            20

<210> SEQ ID NO 8
<211> LENGTH: 21
<212> TYPE: PRT
<213> ORGANISM: Artificial Sequence
<220> FEATURE:
<223> OTHER INFORMATION: Synthetic Polypeptide
```

```
<400> SEQUENCE: 8

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 9
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 9

Phe Val Asn Gln His Leu Cys Gly Asp His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 10

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 11
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 11

Thr Phe Glu Asp Tyr Leu His Asn Val Val Phe Val
1               5                   10

<210> SEQ ID NO 12
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 12

Thr Phe Glu Asp
1

<210> SEQ ID NO 13
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 13

Leu His Asn Val Val Phe
1               5
```

```
<210> SEQ ID NO 14
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 14

Leu His Asn Val Val Phe Val
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 15

Tyr Leu His Asn Val Val Phe Val
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 16

Thr Phe Glu Asp Tyr Leu His Asn
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 17

Ser Ser Phe Arg Lys Thr Phe Glu Asp
1               5

<210> SEQ ID NO 18
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 18

Val Phe Val Trp
1

<210> SEQ ID NO 19
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 19

Phe Arg Lys Thr Phe Glu
1               5
```

-continued

<210> SEQ ID NO 20
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 20

Tyr Leu His Asn Val Val Phe Val Trp
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 21

Arg Lys Thr Phe Glu Asp
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 22

Leu His Asn Val Val Phe Val Trp
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 23

Tyr Leu His Asn Val Val Phe Val
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 24

Leu His Asn Val Val Phe Val Trp
1               5

<210> SEQ ID NO 25
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 25

Phe Val Asn Gln His Leu Cys Gly Asp His Leu Val Glu Ala Leu Tyr
1               5                   10                  15
Leu Val Cys Gly Glu Arg Gly Phe Phe Tyr Thr Lys Pro Thr
            20                  25                  30

<210> SEQ ID NO 26
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 26

```
Met Lys His His His His His Met Ser Ser Gly Leu Val Pro Arg
1               5                   10                  15

Gly Ser His Met Arg Phe Val Asn Gln His Leu Cys Gly Ser His Leu
            20                  25                  30

Val Glu Ala Leu Tyr Leu Val Cys Gly Glu Arg Gly Phe Phe Tyr Thr
        35                  40                  45

Lys Pro Thr Arg Arg Glu Ala Glu Asp Leu Gln Val Gly Gln Val Glu
    50                  55                  60

Leu Gly Gly Gly Pro Gly Ala Gly Ser Leu Gln Pro Leu Ala Leu Glu
65                  70                  75                  80

Gly Ser Leu Gln Lys Arg Gly Ile Val Glu Gln Cys Cys Thr Ser Ile
                85                  90                  95

Cys Ser Leu Tyr Gln Leu Glu Asn Tyr Cys Asn
            100                 105
```

<210> SEQ ID NO 27
<211> LENGTH: 127
<212> TYPE: PRT
<213> ORGANISM: Artificial Sequence
<220> FEATURE:
<223> OTHER INFORMATION: Synthetic Polypeptide

<400> SEQUENCE: 27

```
Met Lys His His His His His Met Ser Ser Gly Leu Val Pro Arg
1               5                   10                  15

Gly Ser His Met Arg Phe Val Asn Gln His Leu Cys Gly Ser His Leu
            20                  25                  30

Val Glu Ala Leu Tyr Leu Val Cys Gly Glu Arg Gly Phe Phe Tyr Thr
        35                  40                  45

Lys Pro Thr Arg Arg Glu Ala Glu Asp Leu Gln Val Gly Gln Val Glu
    50                  55                  60

Leu Gly Gly Gly Pro Gly Ala Gly Ser Leu Gln Pro Leu Ala Leu Glu
65                  70                  75                  80

Gly Ser Leu Gln Lys Arg Thr Phe Glu Asp Tyr Leu His Asn Val Val
                85                  90                  95

Phe Val Gly Gly Gly Ser Gly Gly Gly Ser Gly Ile Val Glu Gln Cys
            100                 105                 110

Cys Thr Ser Ile Cys Ser Leu Tyr Gln Leu Glu Asn Tyr Cys Asn
        115                 120                 125
```

<210> SEQ ID NO 28
<211> LENGTH: 94
<212> TYPE: PRT
<213> ORGANISM: Artificial Sequence
<220> FEATURE:
<223> OTHER INFORMATION: Synthetic Polypeptide

<400> SEQUENCE: 28

```
Met Lys His His His His His Met Ser Ser Gly Leu Val Pro Arg
1               5                   10                  15

Gly Ser His Met Arg Phe Val Asn Gln His Leu Cys Gly Ser His Leu
            20                  25                  30
```

```
Val Glu Ala Leu Tyr Leu Val Cys Gly Glu Arg Gly Phe Phe Tyr Thr
            35                  40                  45

Lys Pro Thr Lys Arg Thr Phe Glu Asp Tyr Leu His Asn Val Val Phe
 50                  55                  60

Val Gly Gly Gly Ser Gly Gly Ser Gly Ile Val Glu Gln Cys Cys
 65                  70                  75                  80

Thr Ser Ile Cys Ser Leu Tyr Gln Leu Glu Asn Tyr Cys Asn
                85                  90
```

<210> SEQ ID NO 29
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 29

```
Ser Ser Phe Arg Lys Thr Phe Glu Asp Leu His Asn Val Phe Val Trp
 1               5                  10                  15
```

<210> SEQ ID NO 30
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 30

```
Ser Phe Arg Lys Thr Phe Glu Tyr Leu His Asn Val Val Phe Val Trp
 1               5                  10                  15
```

<210> SEQ ID NO 31
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with Ac
<220> FEATURE:
<221> NAME/KEY: misc_feature
<222> LOCATION: (5)..(5)
<223> OTHER INFORMATION: Xaa is (R)-1-((allyloxy)carbonyl)pyrrolidine-
      3-carboxylic acid
<220> FEATURE:
<221> NAME/KEY: misc_feature
<222> LOCATION: (12)..(12)
<223> OTHER INFORMATION: Xaa is (S)-2-amino-2-methyldec-9-enoic acid

<400> SEQUENCE: 31

```
Thr Phe Glu Asp Xaa Leu His Asn Val Val Phe Xaa Trp
 1               5                  10
```

<210> SEQ ID NO 32
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with Ac

```
<220> FEATURE:
<221> NAME/KEY: misc_feature
<222> LOCATION: (5)..(5)
<223> OTHER INFORMATION: Xaa is
      (R)-3-(((allyloxy)carbonyl)(methyl)amino)-2-methylpropanoic acid
<220> FEATURE:
<221> NAME/KEY: misc_feature
<222> LOCATION: (12)..(12)
<223> OTHER INFORMATION: Xaa is (S)-2-amino-2-methyldec-9-enoic acid

<400> SEQUENCE: 32

Thr Phe Glu Asp Xaa Leu His Asn Val Val Phe Xaa Trp
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with Ac
<220> FEATURE:
<221> NAME/KEY: misc_feature
<222> LOCATION: (5)..(5)
<223> OTHER INFORMATION: Xaa is (R)-2-amino-2-methylhept-6-enoic acid
<220> FEATURE:
<221> NAME/KEY: misc_feature
<222> LOCATION: (12)..(12)
<223> OTHER INFORMATION: Xaa is (S)-2-amino-2-methyldec-9-enoic acid

<400> SEQUENCE: 33

Thr Phe Glu Asp Xaa Leu His Asn Val Val Phe Xaa Trp
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with Ac
<220> FEATURE:
<221> NAME/KEY: misc_feature
<222> LOCATION: (5)..(5)
<223> OTHER INFORMATION: Xaa is
      (R)-5-(((allyloxy)carbonyl)(methyl)amino)-2-methylpentanoic acid
<220> FEATURE:
<221> NAME/KEY: misc_feature
<222> LOCATION: (12)..(12)
<223> OTHER INFORMATION: Xaa (S)-2-amino-2-methyldec-9-enoic acid

<400> SEQUENCE: 34

Thr Phe Glu Asp Xaa Leu His Asn Val Val Phe Xaa Trp
1               5                   10

<210> SEQ ID NO 35
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (10)..(10)
<223> OTHER INFORMATION: Xaa is (R)-1-((allyloxy)carbonyl)pyrrolidine-
      3-carboxylic acid
```

```
<220> FEATURE:
<221> NAME/KEY: misc_feature
<222> LOCATION: (14)..(14)
<223> OTHER INFORMATION: Xaa is (R)-1-((allyloxy)carbonyl)pyrrolidine-
      3-carboxylic acid

<400> SEQUENCE: 35

Ser Ser Phe Arg Lys Thr Phe Glu Asp Xaa Leu His Asn Xaa Val Phe
1               5                   10                  15

Val Trp

<210> SEQ ID NO 36
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa is (R)-1-((allyloxy)carbonyl)pyrrolidine-
      3-carboxylic acid
<220> FEATURE:
<221> NAME/KEY: misc_feature
<222> LOCATION: (9)..(9)
<223> OTHER INFORMATION: Xaa is (R)-1-((allyloxy)carbonyl)pyrrolidine-
      3-carboxylic acid

<400> SEQUENCE: 36

Thr Phe Glu Asp Xaa Leu His Asn Xaa Val Phe Val Trp
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa is 1-((allyloxy)carbonyl)azetidine-3-
      carboxylic acid
<220> FEATURE:
<221> NAME/KEY: misc_feature
<222> LOCATION: (9)..(9)
<223> OTHER INFORMATION: Xaa is (S)-1-((allyloxy)carbonyl)pyrrolidine-
      3-carboxylic acid

<400> SEQUENCE: 37

Thr Phe Glu Asp Xaa Leu His Asn Xaa Val Phe Val Trp
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa is 1-((allyloxy)carbonyl)azetidine-3-
      carboxylic acid
<220> FEATURE:
<221> NAME/KEY: misc_feature
<222> LOCATION: (9)..(9)
<223> OTHER INFORMATION: Xaa is (S)-2-amino-2-methyldec-9-enoic acid
```

```
<400> SEQUENCE: 38

Thr Phe Glu Asp Xaa Leu His Asn Xaa Val Phe Val Trp
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa is
      (S)-5-(((allyloxy)carbonyl)(methyl)amino)-2-methylpentanoic acid
<220> FEATURE:
<221> NAME/KEY: misc_feature
<222> LOCATION: (9)..(9)
<223> OTHER INFORMATION: Xaa iS (S)-2-amino-2-methyldec-9-enoic acid

<400> SEQUENCE: 39

Thr Phe Glu Asp Xaa Leu His Asn Xaa Val Phe Val Trp
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa is
      (S)-5-(((allyloxy)carbonyl)(methyl)amino)-2-methylpentanoic acid
<220> FEATURE:
<221> NAME/KEY: misc_feature
<222> LOCATION: (9)..(9)
<223> OTHER INFORMATION: Xaa is (S)-2-amino-2-methyldodec-11-enoic acid

<400> SEQUENCE: 40

Thr Phe Glu Asp Xaa Leu His Asn Xaa Val Phe Val Trp
1               5                   10

<210> SEQ ID NO 41
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa is (R)-1-((allyloxy)carbonyl)pyrrolidine-
      3-carboxylic acid
<220> FEATURE:
<221> NAME/KEY: misc_feature
<222> LOCATION: (9)..(9)
<223> OTHER INFORMATION: Xaa is (S)-2-amino-2-methyldec-9-enoic acid

<400> SEQUENCE: 41

Ser Xaa Phe Arg Lys Thr Phe Glu Xaa Tyr Leu His Asn Val Val Phe
1               5                   10                  15

Val Trp

<210> SEQ ID NO 42
<211> LENGTH: 18
<212> TYPE: PRT
<213> ORGANISM: Artificial Sequence
```

-continued

```
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa is (R)-1-((allyloxy)carbonyl)pyrrolidine-
      3-carboxylic acid
<220> FEATURE:
<221> NAME/KEY: misc_feature
<222> LOCATION: (10)..(10)
<223> OTHER INFORMATION: Xaa is (S)-2-amino-2-methyldec-9-enoic acid

<400> SEQUENCE: 42

Ser Ser Xaa Arg Lys Thr Phe Glu Asp Xaa Leu His Asn Val Val Phe
1               5                   10                  15

Val Trp

<210> SEQ ID NO 43
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa is
      (S)-5-(((allyloxy)carbonyl)(methyl)amino)-2-methylpentanoic acid
<220> FEATURE:
<221> NAME/KEY: misc_feature
<222> LOCATION: (9)..(9)
<223> OTHER INFORMATION: Xaa is (S)-2-amino-2-methylhept-6-enoic acid

<400> SEQUENCE: 43

Thr Phe Glu Asp Xaa Leu His Asn Xaa Val Phe Val Trp
1               5                   10

<210> SEQ ID NO 44
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (10)..(10)
<223> OTHER INFORMATION: Xaa is (S)-2-amino-2-methylhept-6-enoic acid
<220> FEATURE:
<221> NAME/KEY: misc_feature
<222> LOCATION: (14)..(14)
<223> OTHER INFORMATION: Xaa is (S)-2-amino-2-methylhept-6-enoic acid

<400> SEQUENCE: 44

Ser Ser Phe Arg Lys Thr Phe Glu Asp Xaa Leu His Asn Xaa Val Phe
1               5                   10                  15

Val Trp

<210> SEQ ID NO 45
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa is (R)-2-amino-2-methylhept-6-enoic acid
<220> FEATURE:
<221> NAME/KEY: misc_feature
<222> LOCATION: (9)..(9)
<223> OTHER INFORMATION: Xaa is (S)-2-amino-2-methyldec-9-enoic acid
```

```
<400> SEQUENCE: 45

Ser Xaa Phe Arg Lys Thr Phe Glu Xaa Tyr Leu His Asn Val Val Phe
1               5                   10                  15

Val Trp

<210> SEQ ID NO 46
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa is (R)-1-((allyloxy)carbonyl)pyrrolidine-
      3-carboxylic acid
<220> FEATURE:
<221> NAME/KEY: misc_feature
<222> LOCATION: (9)..(9)
<223> OTHER INFORMATION: Xaa is (S)-2-amino-2-methyldec-9-enoic acid

<400> SEQUENCE: 46

Ser Xaa Phe Arg Lys Thr Phe Glu Xaa Tyr Leu His Asn Val Val Phe
1               5                   10                  15

Val Trp

<210> SEQ ID NO 47
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa is (R)-2-amino-2-methylhept-6-enoic acid
<220> FEATURE:
<221> NAME/KEY: misc_feature
<222> LOCATION: (10)..(10)
<223> OTHER INFORMATION: Xaa is (S)-2-amino-2-methyldec-9-enoic acid

<400> SEQUENCE: 47

Ser Ser Xaa Arg Lys Thr Phe Glu Asp Xaa Leu His Asn Val Val Phe
1               5                   10                  15

Val Trp

<210> SEQ ID NO 48
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is (S)-2-amino-2-methylhept-6-enoic acid
<220> FEATURE:
<221> NAME/KEY: misc_feature
<222> LOCATION: (5)..(5)
<223> OTHER INFORMATION: Xaa is (S)-1-((allyloxy)carbonyl)pyrrolidine-
      3-carboxylic acid

<400> SEQUENCE: 48

Xaa Phe Glu Asp Xaa Leu His Asn Val Val Phe Val Trp
1               5                   10
```

```
<210> SEQ ID NO 49
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa is (S)-2-amino-2-methylhept-6-enoic acid
<220> FEATURE:
<221> NAME/KEY: misc_feature
<222> LOCATION: (9)..(9)
<223> OTHER INFORMATION: Xaa is (S)-1-((allyloxy)carbonyl)pyrrolidine-
      3-carboxylic acid

<400> SEQUENCE: 49

Thr Phe Glu Asp Xaa Leu His Asn Xaa Val Phe Val Trp
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa is (S)-2-amino-2-methylhept-6-enoic acid
<220> FEATURE:
<221> NAME/KEY: misc_feature
<222> LOCATION: (9)..(9)
<223> OTHER INFORMATION: Xaa is (S)-2-amino-2-methylhept-6-enoic acid

<400> SEQUENCE: 50

Thr Phe Glu Asp Xaa Leu His Asn Xaa Val Phe Val Trp
1               5                   10

<210> SEQ ID NO 51
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (10)..(10)
<223> OTHER INFORMATION: Xaa is 1-((allyloxy)carbonyl)azetidine-3-
      carboxylic acid
<220> FEATURE:
<221> NAME/KEY: misc_feature
<222> LOCATION: (14)..(14)
<223> OTHER INFORMATION: Xaa is (S)-1-((allyloxy)carbonyl)pyrrolidine-
      3-carboxylic acid

<400> SEQUENCE: 51

Ser Ser Phe Arg Lys Thr Phe Glu Asp Xaa Leu His Asn Xaa Val Phe
1               5                   10                  15

Val Trp

<210> SEQ ID NO 52
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is (S)-2-amino-2-methylhept-6-enoic acid
```

```
<220> FEATURE:
<221> NAME/KEY: misc_feature
<222> LOCATION: (5)..(5)
<223> OTHER INFORMATION: Xaa is (S)-2-amino-2-methylhept-6-enoic acid

<400> SEQUENCE: 52

Xaa Ser Phe Arg Xaa Thr Phe Glu Asp Tyr Leu His Asn Val Val Phe
1               5                   10                  15

Val

<210> SEQ ID NO 53
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is (R)-1-((allyloxy)carbonyl)pyrrolidine-
      3-carboxylic acid
<220> FEATURE:
<221> NAME/KEY: misc_feature
<222> LOCATION: (5)..(5)
<223> OTHER INFORMATION: Xaa is (R)-1-((allyloxy)carbonyl)pyrrolidine-
      3-carboxylic acid

<400> SEQUENCE: 53

Xaa Ser Phe Arg Xaa Thr Phe Glu Asp Tyr Leu His Asn Val Val Phe
1               5                   10                  15

Val

<210> SEQ ID NO 54
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa is
      (S)-5-(((allyloxy)carbonyl)(methyl)amino)-2-methylpentanoic acid
<220> FEATURE:
<221> NAME/KEY: misc_feature
<222> LOCATION: (9)..(9)
<223> OTHER INFORMATION: Xaa is
      (S)-5-(((allyloxy)carbonyl)(methyl)amino)-2-methylpentanoic acid

<400> SEQUENCE: 54

Thr Phe Glu Asp Xaa Leu His Asn Xaa Val Phe Val Trp
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa is (S)-1-((allyloxy)carbonyl)pyrrolidine-
      3-carboxylic acid
<220> FEATURE:
<221> NAME/KEY: misc_feature
<222> LOCATION: (9)..(9)
<223> OTHER INFORMATION: Xaa is (S)-2-amino-2-methylhept-6-enoic acid
```

```
<400> SEQUENCE: 55

Thr Phe Glu Asp Xaa Leu His Asn Xaa Val Phe Val Trp
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is (S)-2-amino-2-methylhept-6-enoic acid
<220> FEATURE:
<221> NAME/KEY: misc_feature
<222> LOCATION: (5)..(5)
<223> OTHER INFORMATION: Xaa is (S)-2-amino-2-methylhept-6-enoic acid

<400> SEQUENCE: 56

Xaa Phe Glu Asp Xaa Leu His Asn Val Val Phe Val Trp
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is (S)-1-((allyloxy)carbonyl)pyrrolidine-
      3-carboxylic acid
<220> FEATURE:
<221> NAME/KEY: misc_feature
<222> LOCATION: (5)..(5)
<223> OTHER INFORMATION: Xaa is (S)-2-amino-2-methylhept-6-enoic acid

<400> SEQUENCE: 57

Xaa Phe Glu Asp Xaa Leu His Asn Val Val Phe Val Trp
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is
      (S)-5-(((allyloxy)carbonyl)(methyl)amino)-2-methylpentanoic acid
<220> FEATURE:
<221> NAME/KEY: misc_feature
<222> LOCATION: (5)..(5)
<223> OTHER INFORMATION: Xaa is
      (S)-5-(((allyloxy)carbonyl)(methyl)amino)-2-methylpentanoic acid

<400> SEQUENCE: 58

Xaa Phe Glu Asp Xaa Leu His Asn Val Val Phe Val Trp
1               5                   10

<210> SEQ ID NO 59
<211> LENGTH: 17
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: misc_feature
<222> LOCATION: (2)..(2)
<223> OTHER INFORMATION: Xaa is (R)-2-amino-2-methylhept-6-enoic acid
<220> FEATURE:
<221> NAME/KEY: misc_feature
<222> LOCATION: (9)..(9)
<223> OTHER INFORMATION: Xaa is (S)-2-amino-2-methyldec-9-enoic acid

<400> SEQUENCE: 59

Ser Xaa Phe Arg Lys Thr Phe Glu Xaa Tyr Leu His Asn Val Val Phe
1               5                   10                  15

Val

<210> SEQ ID NO 60
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa is (R)-1-((allyloxy)carbonyl)pyrrolidine-
      3-carboxylic acid
<220> FEATURE:
<221> NAME/KEY: misc_feature
<222> LOCATION: (9)..(9)
<223> OTHER INFORMATION: Xaa is (S)-2-amino-2-methyldec-9-enoic acid

<400> SEQUENCE: 60

Ser Xaa Phe Arg Lys Thr Phe Glu Xaa Tyr Leu His Asn Val Val Phe
1               5                   10                  15

Val

<210> SEQ ID NO 61
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa is (R)-1-((allyloxy)carbonyl)pyrrolidine-
      3-carboxylic acid
<220> FEATURE:
<221> NAME/KEY: misc_feature
<222> LOCATION: (9)..(9)
<223> OTHER INFORMATION: Xaa is (S)-2-amino-2-methyldec-9-enoic acid

<400> SEQUENCE: 61

Ser Xaa Phe Arg Lys Thr Phe Glu Xaa Tyr Leu His Asn Ala Ala Phe
1               5                   10                  15

Val

<210> SEQ ID NO 62
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa is
      (R)-3-(((allyloxy)carbonyl)(methyl)amino)-2-methylpropanoic acid
```

-continued

```
<220> FEATURE:
<221> NAME/KEY: misc_feature
<222> LOCATION: (9)..(9)
<223> OTHER INFORMATION: Xaa is (S)-2-amino-2-methyldec-9-enoic acid

<400> SEQUENCE: 62

Ser Xaa Phe Arg Lys Thr Phe Glu Xaa Tyr Leu His Asn Val Val Phe
1               5                   10                  15
Val

<210> SEQ ID NO 63
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa is (R)-1-((allyloxy)carbonyl)pyrrolidine-
      3-carboxylic acid
<220> FEATURE:
<221> NAME/KEY: misc_feature
<222> LOCATION: (9)..(9)
<223> OTHER INFORMATION: Xaa is (S)-2-amino-2-methyldec-9-enoic acid

<400> SEQUENCE: 63

Ser Xaa Phe Arg Lys Thr Phe Glu Xaa Tyr Leu His Asn Val Val Phe
1               5                   10                  15
Val

<210> SEQ ID NO 64
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa is (R)-1-((allyloxy)carbonyl)pyrrolidine-
      3-carboxylic acid
<220> FEATURE:
<221> NAME/KEY: misc_feature
<222> LOCATION: (9)..(9)
<223> OTHER INFORMATION: Xaa is (S)-2-amino-2-methyldec-9-enoic acid

<400> SEQUENCE: 64

Ser Xaa Phe Arg Lys Thr Phe Glu Xaa Tyr Leu His Asn Ala Ala Phe
1               5                   10                  15
Val

<210> SEQ ID NO 65
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa is
      (R)-3-(((allyloxy)carbonyl)(methyl)amino)-2-methylpropanoic acid
<220> FEATURE:
<221> NAME/KEY: misc_feature
<222> LOCATION: (9)..(9)
<223> OTHER INFORMATION: Xaa is (S)-2-amino-2-methyldec-9-enoic acid
```

```
<400> SEQUENCE: 65

Ser Xaa Phe Arg Lys Thr Phe Glu Xaa Tyr Leu His Asn Val Val Phe
1               5                   10                  15
Val

<210> SEQ ID NO 66
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 66

Thr Phe Glu Asp Leu His Asn Val Val Phe
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 67

Phe Glu Asp Leu His Asn Val Val Phe Val
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 68

Thr Phe Glu Asp Leu His Asn Val Phe Val
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 69

Thr Phe Glu Asp Leu His Asn Val Phe Val
1               5                   10

<210> SEQ ID NO 70
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 70

Ser Ser Phe Arg Lys Thr Phe Glu Asp Leu His Asn Val Phe Val
1               5                   10                  15

<210> SEQ ID NO 71
<211> LENGTH: 8
<212> TYPE: PRT
<213> ORGANISM: Artificial Sequence
<220> FEATURE:
<223> OTHER INFORMATION: Synthetic Polypeptide
```

```
<400> SEQUENCE: 71

Gly Gly Gly Ser Gly Gly Gly Ser
1               5

<210> SEQ ID NO 72
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 72

Thr Phe Glu Asp Leu His Asn Val Val Phe
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 73

Phe Glu Asp Leu His Asn Val Val Phe Val
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 74

Thr Phe Glu Asp Leu His Asn Val Phe Val
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 75

Thr Phe Glu Tyr Leu His Asn Val Val Phe Val
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 76

Thr Phe Glu Asp Tyr Leu His Asn Val Phe Val
1               5                   10

<210> SEQ ID NO 77
<211> LENGTH: 6
<212> TYPE: PRT
<213> ORGANISM: Artificial Sequence
<220> FEATURE:
<223> OTHER INFORMATION: Synthetic Polypeptide
```

```
<400> SEQUENCE: 77

Gly Gly Gly Gly Gly Gly
1               5

<210> SEQ ID NO 78
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 78

Thr Phe Glu Asp Tyr Leu His Asn Val Val Phe Val Gly Gly Gly
1               5                   10                  15

Gly Gly Gly Ile Val Glu Gln Cys Cys Thr Ser Ile Cys Ser Leu Tyr
            20                  25                  30

Gln Leu Glu Asn Tyr Cys Asn
        35

<210> SEQ ID NO 79
<211> LENGTH: 44
<212> TYPE: PRT
<213> ORGANISM: Artificial Sequence
<220> FEATURE:
<223> OTHER INFORMATION: Synthetic Polypeptide

<400> SEQUENCE: 79

Ser Ser Phe Arg Lys Thr Phe Glu Asp Tyr Leu His Asn Val Val Phe
1               5                   10                  15

Val Gly Gly Gly Gly Gly Gly Ile Val Glu Gln Cys Cys Thr Ser
            20                  25                  30

Ile Cys Ser Leu Tyr Gln Leu Glu Asn Tyr Cys Asn
        35                  40

<210> SEQ ID NO 80
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: modified with Ac

<400> SEQUENCE: 80

Thr Phe Glu Asp Tyr Leu His Asn Val Val Phe Val Trp
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: modified with Ac

<400> SEQUENCE: 81

Thr Phe Glu Asp Tyr Leu His Asn Ala Ala Phe Val
1               5                   10
```

```
<210> SEQ ID NO 82
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: modified with Ac

<400> SEQUENCE: 82

Ser Ser Phe Arg Lys Thr Phe Glu Asp Tyr Leu His Asn Val Val Phe
1               5                   10                  15

Val Trp

<210> SEQ ID NO 83
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: modified with Ac

<400> SEQUENCE: 83

Ser Ser Phe Arg Lys Thr Phe Glu Asp Tyr Leu His Asn Ala Ala Phe
1               5                   10                  15

Val Trp

<210> SEQ ID NO 84
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: modified with Ac

<400> SEQUENCE: 84

Ser Ser Phe Arg Lys Thr Phe Glu Asp Tyr Leu His Asn Val Val Phe
1               5                   10                  15

Val

<210> SEQ ID NO 85
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: modified with Ac

<400> SEQUENCE: 85

Ser Ser Phe Arg Lys Thr Phe Glu Asp Tyr Leu His Asn Ala Ala Phe
1               5                   10                  15

Val
```

```
<210> SEQ ID NO 86
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: modified with Ac

<400> SEQUENCE: 86

Thr Phe Glu Asp Tyr Leu His Asn Val Val Phe Val
1               5                   10

<210> SEQ ID NO 87
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is absent or is an amino acid which forms
      together with another amino acid a crosslink of Formula (i)
<220> FEATURE:
<221> NAME/KEY: MISC_FEATURE
<222> LOCATION: (2)..(2)
<223> OTHER INFORMATION: Xaa is Thr, Ser, any amino acid, or is an amino
      acid which forms together with another amino acid a crosslink of
      Formula (i), or is an amino acid which forms together with two
      other amino acids a crosslink of Formula (ii), or is absent
<220> FEATURE:
<221> NAME/KEY: MISC_FEATURE
<222> LOCATION: (3)..(3)
<223> OTHER INFORMATION: Xaa is Phe or absent
<220> FEATURE:
<221> NAME/KEY: MISC_FEATURE
<222> LOCATION: (4)..(4)
<223> OTHER INFORMATION: Xaa is Glu or absent
<220> FEATURE:
<221> NAME/KEY: MISC_FEATURE
<222> LOCATION: (5)..(5)
<223> OTHER INFORMATION: Xaa is Asp, Glu, any amino acid, or is an amino
      acid which forms together with another amino acid a crosslink of
      Formula (i), or is an amino acid which forms together with two
      other amino acids a crosslink of Formula (ii), or absent
<220> FEATURE:
<221> NAME/KEY: MISC_FEATURE
<222> LOCATION: (6)..(6)
<223> OTHER INFORMATION: Xaa is Tyr, Phe, Trp, or any amino acid, or is
      an amino acid which forms together with another amino acid a
      crosslink of Formula (i), or is an amino acid which forms together
      with two other amino acids a crosslink of Formula (ii)
<220> FEATURE:
<221> NAME/KEY: MISC_FEATURE
<222> LOCATION: (7)..(7)
<223> OTHER INFORMATION: Xaa is Leu
<220> FEATURE:
<221> NAME/KEY: MISC_FEATURE
<222> LOCATION: (8)..(8)
<223> OTHER INFORMATION: Xaa is His
<220> FEATURE:
<221> NAME/KEY: MISC_FEATURE
<222> LOCATION: (9)..(9)
<223> OTHER INFORMATION: Xaa is Asn
<220> FEATURE:
<221> NAME/KEY: MISC_FEATURE
<222> LOCATION: (10)..(10)
<223> OTHER INFORMATION: Xaa is Val, Ala, Ile, Leu, any amino acid, or
      is an amino acid which forms together with another amino acid a
      crosslink of Formula (i), or is an amino acid which forms together
      with two other amino acids a crosslink of Formula (ii), or absent
```

```
<220> FEATURE:
<221> NAME/KEY: MISC_FEATURE
<222> LOCATION: (11)..(11)
<223> OTHER INFORMATION: Xaa is Val, Ala, or absent
<220> FEATURE:
<221> NAME/KEY: MISC_FEATURE
<222> LOCATION: (12)..(12)
<223> OTHER INFORMATION: Xaa is Phe, Ala, or absent
<220> FEATURE:
<221> NAME/KEY: MISC_FEATURE
<222> LOCATION: (13)..(13)
<223> OTHER INFORMATION: Xaa is Val, Ala, Ile, Leu, any amino acid, or
      is an amino acid which forms together with another amino acid a
      crosslink of Formula (i), or is an amino acid which forms together
      with two other amino acids a crosslink of Formula (ii), or absent
<220> FEATURE:
<221> NAME/KEY: MISC_FEATURE
<222> LOCATION: (14)..(14)
<223> OTHER INFORMATION: Xaa is absent or is an amino acid which forms
      together with another amino acid a crosslink of Formula (i)

<400> SEQUENCE: 87

Xaa Xaa Xaa Xaa Xaa Xaa Xaa Xaa Xaa Xaa Xaa Xaa Xaa Xaa
1               5                   10

<210> SEQ ID NO 88
<211> LENGTH: 20
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is absent or is an amino acid which forms
      together with another amino acid a crosslink of Formula (i)
<220> FEATURE:
<221> NAME/KEY: MISC_FEATURE
<222> LOCATION: (2)..(2)
<223> OTHER INFORMATION: Xaa is Ser, Thr, any amino acid, or is an amino
      acid which forms together with another amino acid a crosslink of
      Formula (i), or is an amino acid which forms together with two
      other amino acids a crosslink of Formula (ii), or absent
<220> FEATURE:
<221> NAME/KEY: MISC_FEATURE
<222> LOCATION: (3)..(3)
<223> OTHER INFORMATION: Xaa is Ser, Thr, any amino acid, or is an amino
      acid which forms together with another amino acid a crosslink of
      Formula (i), or is an amino acid which forms together with two
      other amino acids a crosslink of Formula (ii), or absent
<220> FEATURE:
<221> NAME/KEY: MISC_FEATURE
<222> LOCATION: (4)..(4)
<223> OTHER INFORMATION: Xaa is Phe, Tyr, Trp, any amino acid, or is an
      amino acid which forms together with another amino acid a
      crosslink of Formula (i), or is an amino acid which forms together
      with two other amino acids a crosslink of Formula (ii), or absent
<220> FEATURE:
<221> NAME/KEY: MISC_FEATURE
<222> LOCATION: (5)..(5)
<223> OTHER INFORMATION: Xaa is Arg
<220> FEATURE:
<221> NAME/KEY: MISC_FEATURE
<222> LOCATION: (6)..(6)
<223> OTHER INFORMATION: Xaa is Lys, Arg, His, any amino acid, or is an
      amino acid which forms together with another amino acid a
      crosslink of Formula (i), or is an amino acid which forms together
      with two other amino acids a crosslink of Formula (ii), or absent
<220> FEATURE:
<221> NAME/KEY: MISC_FEATURE
<222> LOCATION: (7)..(7)
<223> OTHER INFORMATION: Xaa is Thr
<220> FEATURE:
<221> NAME/KEY: MISC_FEATURE
<222> LOCATION: (8)..(8)
<223> OTHER INFORMATION: Xaa is Phe
```

```
<220> FEATURE:
<221> NAME/KEY: MISC_FEATURE
<222> LOCATION: (9)..(9)
<223> OTHER INFORMATION: Xaa is Glu
<220> FEATURE:
<221> NAME/KEY: MISC_FEATURE
<222> LOCATION: (10)..(10)
<223> OTHER INFORMATION: Xaa is Asp, Glu, any amino acid, or is an amino
      acid which forms together with another amino acid a crosslink of
      Formula (i), or is an amino acid which forms together with two
      other amino acids a crosslink of Formula (ii), or absent
<220> FEATURE:
<221> NAME/KEY: MISC_FEATURE
<222> LOCATION: (11)..(11)
<223> OTHER INFORMATION: Xaa is Tyr, Phe, Trp, any amino acid, or is an
      amino acid which forms together with another amino acid a
      crosslink of Formula (i), or is an amino acid which forms together
      with two other amino acids a crosslink of Formula (ii), or absent
<220> FEATURE:
<221> NAME/KEY: MISC_FEATURE
<222> LOCATION: (12)..(12)
<223> OTHER INFORMATION: Xaa is Leu
<220> FEATURE:
<221> NAME/KEY: MISC_FEATURE
<222> LOCATION: (13)..(13)
<223> OTHER INFORMATION: Xaa is His
<220> FEATURE:
<221> NAME/KEY: MISC_FEATURE
<222> LOCATION: (14)..(14)
<223> OTHER INFORMATION: Xaa is Asn
<220> FEATURE:
<221> NAME/KEY: MISC_FEATURE
<222> LOCATION: (15)..(15)
<223> OTHER INFORMATION: Xaa is Val, Ala, Ile, Leu, any amino acid, or
      is an amino acid which forms together with another amino acid a
      crosslink of Formula (i), or is an amino acid which forms together
      with two other amino acids a crosslink of Formula (ii), or absent
<220> FEATURE:
<221> NAME/KEY: MISC_FEATURE
<222> LOCATION: (16)..(16)
<223> OTHER INFORMATION: Xaa is Val
<220> FEATURE:
<221> NAME/KEY: MISC_FEATURE
<222> LOCATION: (17)..(17)
<223> OTHER INFORMATION: Xaa is Phe
<220> FEATURE:
<221> NAME/KEY: MISC_FEATURE
<222> LOCATION: (18)..(18)
<223> OTHER INFORMATION: Xaa is Val
<220> FEATURE:
<221> NAME/KEY: MISC_FEATURE
<222> LOCATION: (19)..(19)
<223> OTHER INFORMATION: Xaa is Trp or absent
<220> FEATURE:
<221> NAME/KEY: MISC_FEATURE
<222> LOCATION: (20)..(20)
<223> OTHER INFORMATION: Xaa is absent or is an amino acid which forms
      together with another amino acid a crosslink of Formula (i)

<400> SEQUENCE: 88

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 89
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is absent or an amino acid of Formula (iii)
      or (iv)
```

```
<220> FEATURE:
<221> NAME/KEY: MISC_FEATURE
<222> LOCATION: (2)..(2)
<223> OTHER INFORMATION: Xaa is Thr, Ser, any amino acid, or an amino
      acid of Formula (iii), (iv), or (v), or absent
<220> FEATURE:
<221> NAME/KEY: MISC_FEATURE
<222> LOCATION: (3)..(3)
<223> OTHER INFORMATION: Xaa is Phe or absent
<220> FEATURE:
<221> NAME/KEY: MISC_FEATURE
<222> LOCATION: (4)..(4)
<223> OTHER INFORMATION: Xaa is Glu or absent
<220> FEATURE:
<221> NAME/KEY: MISC_FEATURE
<222> LOCATION: (5)..(5)
<223> OTHER INFORMATION: Xaa is Asp, Glu, any amino acid, or an amino
      acid of Formula (iii), (iv), or (v), or absent
<220> FEATURE:
<221> NAME/KEY: MISC_FEATURE
<222> LOCATION: (6)..(6)
<223> OTHER INFORMATION: Xaa is Tyr, Phe, Trp, or a natural or unnatural
      amino acid, or an amino acid of Formula (iii), (iv), or (v)
<220> FEATURE:
<221> NAME/KEY: MISC_FEATURE
<222> LOCATION: (7)..(7)
<223> OTHER INFORMATION: Xaa is Leu
<220> FEATURE:
<221> NAME/KEY: MISC_FEATURE
<222> LOCATION: (8)..(8)
<223> OTHER INFORMATION: Xaa is His
<220> FEATURE:
<221> NAME/KEY: MISC_FEATURE
<222> LOCATION: (9)..(9)
<223> OTHER INFORMATION: Xaa is Asn
<220> FEATURE:
<221> NAME/KEY: MISC_FEATURE
<222> LOCATION: (10)..(10)
<223> OTHER INFORMATION: Xaa is Val, Ala, Ile, Leu, any amino acid, or
      an amino acid of Formula (iii), (iv), or (v), or absent
<220> FEATURE:
<221> NAME/KEY: MISC_FEATURE
<222> LOCATION: (11)..(11)
<223> OTHER INFORMATION: Xaa is Val, Ala, or absent
<220> FEATURE:
<221> NAME/KEY: MISC_FEATURE
<222> LOCATION: (12)..(12)
<223> OTHER INFORMATION: Xaa is Phe, Ala, or absent
<220> FEATURE:
<221> NAME/KEY: MISC_FEATURE
<222> LOCATION: (13)..(13)
<223> OTHER INFORMATION: Xaa is Val, Ala, Ile, Leu, any amino acid, or
      an amino acid of Formula (iii), (iv), or (v), or absent
<220> FEATURE:
<221> NAME/KEY: MISC_FEATURE
<222> LOCATION: (14)..(14)
<223> OTHER INFORMATION: Xaa is absent or an amino acid of Formula (iii)
      or (iv)

<400> SEQUENCE: 89

Xaa Xaa Xaa Xaa Xaa Xaa Xaa Xaa Xaa Xaa Xaa Xaa Xaa Xaa
1               5                   10

<210> SEQ ID NO 90
<211> LENGTH: 20
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is absent or an amino acid of Formula (iii)
      or (iv)
```

```
<220> FEATURE:
<221> NAME/KEY: MISC_FEATURE
<222> LOCATION: (2)..(2)
<223> OTHER INFORMATION: Xaa is Ser, Thr, any amino acid, or is an amino
      acid of Formula (iii), (iv), or (v), or absent
<220> FEATURE:
<221> NAME/KEY: MISC_FEATURE
<222> LOCATION: (3)..(3)
<223> OTHER INFORMATION: Xaa is Ser, Thr, any amino acid, or is an amino
      acid of Formula (iii), (iv), or (v), or absent
<220> FEATURE:
<221> NAME/KEY: MISC_FEATURE
<222> LOCATION: (4)..(4)
<223> OTHER INFORMATION: Xaa is Phe, Tyr, Trp, any amino acid, or is an
      amino acid of Formula (iii), (iv), or (v), or absent
<220> FEATURE:
<221> NAME/KEY: MISC_FEATURE
<222> LOCATION: (5)..(5)
<223> OTHER INFORMATION: Xaa is Arg
<220> FEATURE:
<221> NAME/KEY: MISC_FEATURE
<222> LOCATION: (6)..(6)
<223> OTHER INFORMATION: Xaa is Lys, Arg, His, any amino acid, or is an
      amino acid of Formula (iii), (iv), or (v), or absent
<220> FEATURE:
<221> NAME/KEY: MISC_FEATURE
<222> LOCATION: (7)..(7)
<223> OTHER INFORMATION: Xaa is Thr
<220> FEATURE:
<221> NAME/KEY: MISC_FEATURE
<222> LOCATION: (8)..(8)
<223> OTHER INFORMATION: Xaa is Phe
<220> FEATURE:
<221> NAME/KEY: MISC_FEATURE
<222> LOCATION: (9)..(9)
<223> OTHER INFORMATION: Xaa is Glu
<220> FEATURE:
<221> NAME/KEY: MISC_FEATURE
<222> LOCATION: (10)..(10)
<223> OTHER INFORMATION: Xaa is Asp, Glu, any amino acid, or is an amino
      acid of Formula (iii), (iv), or (v), or absent
<220> FEATURE:
<221> NAME/KEY: MISC_FEATURE
<222> LOCATION: (11)..(11)
<223> OTHER INFORMATION: Xaa is Tyr, Phe, Trp, any amino acid, or is an
      amino acid of Formula (iii), (iv), or (v), or absent
<220> FEATURE:
<221> NAME/KEY: MISC_FEATURE
<222> LOCATION: (12)..(12)
<223> OTHER INFORMATION: Xaa is Leu
<220> FEATURE:
<221> NAME/KEY: MISC_FEATURE
<222> LOCATION: (13)..(13)
<223> OTHER INFORMATION: Xaa is His
<220> FEATURE:
<221> NAME/KEY: MISC_FEATURE
<222> LOCATION: (14)..(14)
<223> OTHER INFORMATION: Xaa is Asn
<220> FEATURE:
<221> NAME/KEY: MISC_FEATURE
<222> LOCATION: (15)..(15)
<223> OTHER INFORMATION: Xaa is Val, Ala, Ile, Leu, any amino acid, or
      an amino acid of Formula (iii), (iv), or (v), or absent
<220> FEATURE:
<221> NAME/KEY: MISC_FEATURE
<222> LOCATION: (16)..(16)
<223> OTHER INFORMATION: Xaa is Val or Ala
<220> FEATURE:
<221> NAME/KEY: MISC_FEATURE
<222> LOCATION: (17)..(17)
<223> OTHER INFORMATION: Xaa is Phe
<220> FEATURE:
<221> NAME/KEY: MISC_FEATURE
<222> LOCATION: (18)..(18)
<223> OTHER INFORMATION: Xaa is Val
<220> FEATURE:
<221> NAME/KEY: MISC_FEATURE
<222> LOCATION: (19)..(19)
<223> OTHER INFORMATION: Xaa is Trp or absent
```

```
<220> FEATURE:
<221> NAME/KEY: MISC_FEATURE
<222> LOCATION: (20)..(20)
<223> OTHER INFORMATION: Xaa is absent or an amino acid of Formula (iii)
      or (iv)

<400> SEQUENCE: 90

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 91
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(12)
<223> OTHER INFORMATION: cross-link

<400> SEQUENCE: 91

Thr Phe Glu Asp Xaa Leu His Asn Val Val Phe Xaa
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cross-link

<400> SEQUENCE: 92

Xaa Phe Glu Asp Xaa Leu His Asn Val Val Phe Val
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(9)
<223> OTHER INFORMATION: cross-link

<400> SEQUENCE: 93

Thr Phe Glu Asp Xaa Leu His Asn Xaa Val Phe Val
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cross-link
```

```
<400> SEQUENCE: 94

Xaa Thr Phe Glu Xaa Tyr Leu His Asn Val Val Phe Val
1               5                   10

<210> SEQ ID NO 95
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (9)..(13)
<223> OTHER INFORMATION: cross-link

<400> SEQUENCE: 95

Thr Phe Glu Asp Tyr Leu His Asn Xaa Val Phe Val Xaa
1               5                   10
```

STABILIZED POLYPEPTIDE INSULIN RECEPTOR MODULATORS

RELATED APPLICATIONS

The present application is a national stage filing under 35 U.S.C. § 371 of international PCT application, PCT/US2014/042329, filed Jun. 13, 2014, which claims priority under 35 U.S.C. § 119(e) to U.S. provisional patent application, U.S. Ser. No. 61/835,242 filed Jun. 14, 2013, each of which is incorporated herein by reference.

GOVERNMENT SUPPORT

This invention was made with U.S. Government support under grant number 5 R01 CA100742-10 awarded by the National Institutes of Health (NIH). The U.S. Government has certain rights in the invention.

REFERENCE TO SEQUENCE LISTING

The instant application contains a Sequence Listing which has been submitted electronically and is hereby incorporated by reference in its entirety. This contains a sequence listing text file as part of the originally filed subject matter as follows: File name: 51157-013002_Updated Sequence Listing_12.11.17_ST25; File size: 44,439 bytes; Date created: Dec. 11, 2017.

FIELD OF THE INVENTION

This invention relates to insulin receptor modulators and uses thereof.

BACKGROUND OF THE INVENTION

Insulin binding to the insulin receptor (IR) initiates a signaling cascade that plays an essential role in glucose homeostasis. Disruptions of this metabolic pathway may result in diabetes, a disease that afflicted 8.4% of the U.S. population in 2011. A key step toward combating diabetes is to understand ligand-dependent IR signaling and to develop new pharmacologic agents that modulate the IR. Remarkably, despite extensive efforts spanning several decades, the molecular mechanisms of IR activation by the binding of insulin remain unelucidated.

IR, a member of the receptor tyrosine kinase superfamily, is a glycoprotein consisting of two $\alpha$ and two $\beta$ subunits ($\alpha_2\beta_2$) covalently linked by disulfide bonds. See, e.g., Siddle et al., *Biochem Soc Trans* (2001) 29:513-525. The extracellular domain (also called the ectodomain) of the IR comprises two a subunits and the N-terminal segment of the two $\beta$ subunits, whereas the transmembrane domains and cytoplasmic tyrosine kinase (TK) domains comprise the C-terminal segments of the $\beta$ subunits. The insulin-binding determinants reside entirely within the ectodomain, which consists of leucine-rich repeat domains L1 and L2 of the $\alpha$ chain, the intervening cysteine-rich (CR) domain, and three fibronectin type III domains, namely Fn0, Fn1, and Fn2.

Although insulin itself was the first peptide hormone to be structurally elucidated by X-ray crystallography, see, e.g., Blundell et al., *Nature* (1971) 231:506-511, and has been the subject of extensive structural investigations over the past 50 years, the molecular mechanism of IR activation by insulin remains unelucidated. Menting et. al. elucidated a structure of insulin bound to the L1 domain and the aCT peptide. See Nature, 2013, 493: 241-248. Insulin binding to IR is characterized by exceptionally high-affinity binding (pM range) and negative cooperativity. See, e.g., De Meyts et al., *Biochem Biophys Res Commun* (1973) 55:154-161; De Meyts et al., *Diabetologia* (1994) 37 Suppl 2:S135-148. Evidence suggests that there are two insulin binding sites on the IR, site 1 and 2, wherein each site 1 on one monomer of IR is close to site 2' on the second monomer, and binding of insulin to site 1 induces its subsequent binding to site 2', which causes a conformational change of the IR ectodomain, leading to a reduction of the distance between the two intercellular TK domains, thereby facilitating autophosphorylation. Several lines of evidence have shown that site 1 on the IR is formed by the central $\beta$-sheet of the L1 domain and a C terminal $\alpha$-subunit peptide segment termed $\alpha$CT (aa704-aa719), while site 2 is believed to reside at the loop region between Fn0 and Fn1, since it faces site 1 of the other monomer in the dimeric structure of the IR ectodomain. See, e.g., Huang et al., *J Mol Biol* (2004) 341:529-551; Mynarcik et al., *J Biol Chem* (1997) 272:18650-18651; Kurose et al., *J Biol Chem* (1994) 269:29190-29197; Mynarcik et al., *J Biol Chem* (1996) 271:2439-2442.

Peptides that bind site 1 are either agonists or antagonists, while peptides that bind site 2 are antagonists. Further optimization of site 1 and site 2 peptides by dimerization has identified either potent agonists or antagonists (pM IR binding affinity) depending on the mode of linkage. See, e.g., Schaffer et al., *Proc Natl Acad Sci USA* (2003) 100: 4435-4439; Schaffer et al., *Biochem Biophys Res Commun* (2008) 376:380-383; Jensen et al., *Biochem J* (2008) 412: 435-445. Intriguingly, though these peptides show no sequence similarity with insulin, a close relationship was proposed between the site 1 peptide and $\alpha$-CT, indicating site 1 peptides are $\alpha$-helical. See, e.g., Smith et al., *Proc Natl Acad Sci USA* (2010) 107:6771-6776; Menting et al., *Biochemistry* (2009) 48:5492-5500. Although these peptides are attractive candidates for insulin mimetics, the potential for therapeutic use is limited due to their inherent structural instability; therefore, there remains a need for stabilized peptides that bind the IR for therapeutic as well as scientific purposes.

SUMMARY OF THE INVENTION

Peptide stapling and stitching is a synthetic strategy known to increase helix stabilization, in which adjacent or subsequent turns of an $\alpha$-helix are cross-linked by a macrocyclic bridge. See, e.g., Kim et al., *Nat. Protoc.* (2011) 6:761-771. This incorporated staple can enforce the bio active $\alpha$-helical conformation of a synthetic peptide and confer on it increased target affinity, robust cell penetration, and/or extended in vivo half-life.

The present invention seeks to build from this knowledge of stapling and stitching stabilized (stapled or stitched) $\alpha$-helical peptides that target the insulin receptor (IR), specifically the ectodomain of the IR. The invention provides stabilized peptides based on the C-terminus of the $\alpha$-chain ($\alpha$-CT), which plays an important role in insulin binding to IR. The stabilized $\alpha$-CT polypeptide can act as an insulin sensitizer, facilitating a long-postulated conformational shift in insulin into an "active" structure that is capable of having high-affinity interaction at site 1 of IR. The stabilized $\alpha$-CT polypeptide, as an insulin sensitizer, may bind to IR or insulin. The stabilized $\alpha$-CT polypeptide, as an insulin sensitizer, may bind to IR and insulin simultaneously or sequentially. Ligating the stabilized $\alpha$-CT polypeptide with insulin through a chemical linker provides a chimeric insulin analogue with IR agonist activity.

In one aspect, the present invention provides a stabilized (stapled or stitched) α-CT polypeptide comprising an alpha-helical segment, wherein the α-CT polypeptide binds to the insulin receptor. In certain embodiments, the α-CT polypeptide is of Formula (I-1) (SEQ ID NO:87):

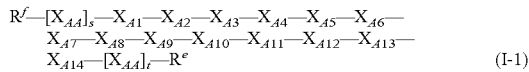
(I-1)

or a pharmaceutically acceptable salt thereof. In certain embodiments, the provided stabilized α-CT polypeptide comprises at least one instance of two cross-linked amino acids of Formula (i):

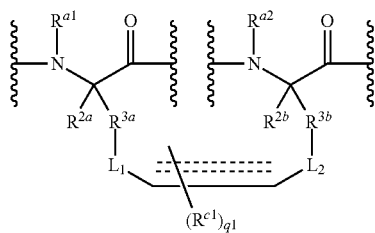
(i)

or at least one instance of three cross-linked amino acids of Formula (ii):

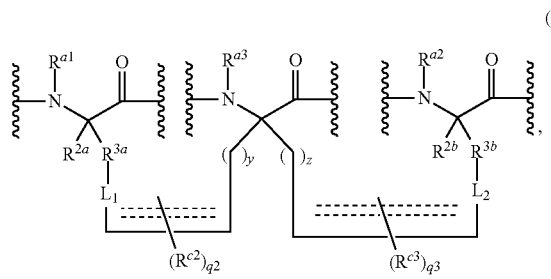
(ii)

wherein $R^f$, $X_{AA}$, s, $X_{A1}$, $X_{A2}$, $X_{A3}$, $X_{A4}$, $X_{A5}$, $X_{A6}$, $X_{A7}$, $X_{A8}$, $X_{A9}$, $X_{A10}$, $X_{A11}$, $X_{A12}$, $X_{A13}$, $X_{A14}$, t, $R^e$, $R^{a1}$, $R^{a2}$, $R^{a3}$, $R^{2a}$, $R^{3a}$, $R^{2b}$, $R^{3b}$, $R^{c1}$, $R^{c2}$, $R^{c3}$, q1, q2, q3, $L_1$, $L_2$, y, and z are as defined herein.

In other embodiments, the α-CT polypeptide is of Formula (I-2) (SEQ ID NO:88):

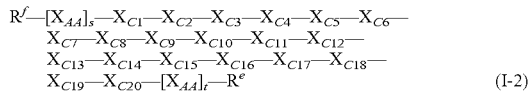
(I-2)

or a pharmaceutically acceptable salt thereof; wherein the polypeptide comprises at least one instance of two cross-linked amino acids of Formula (i):

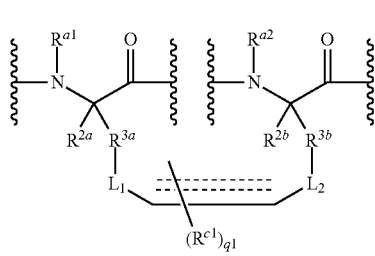
(i)

or at least one instance of three cross-linked amino acids of Formula (ii):

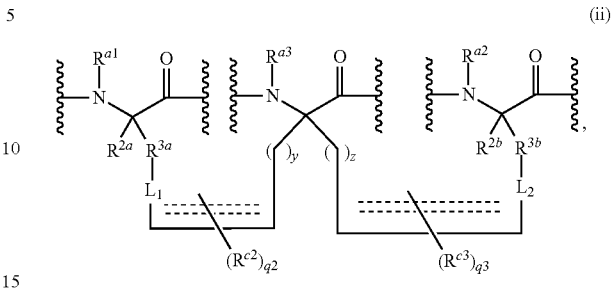
(ii)

wherein $R^f$, $X_{AA}$, s, $X_{C1}$, $X_{C2}$, $X_{C3}$, $X_{C4}$, $X_{C5}$, $X_{C6}$, $X_{C7}$, $X_{C8}$, $X_{C9}$, $X_{C10}$, $X_{C11}$, $X_{C12}$, $X_{C13}$, $X_{C14}$, $X_{C15}$, $X_{C16}$, $X_{C17}$, $X_{C18}$, $X_{C19}$, $X_{C20}$, t, $R^e$, $R^{a1}$, $R^{a2}$, $R^{a3}$, $R^{2a}$, $R^{3a}$, $R^{2b}$, $R^{3b}$, $R^{c1}$, $R^{c2}$, $R^{c3}$, q1, q2, q3, $L_1$, $L_2$, y, and z are as defined herein.

In certain embodiments, the two cross-linked amino acids of Formula (i) or the three cross-linked amino acids of Formula (ii) are amino acids of an alpha-helical segment of the α-CT polypeptide. In certain embodiments, the alpha-helical segment binds to the insulin receptor or contributes to the binding of the α-CT polypeptide to the insulin receptor.

In certain embodiments, the stabilized polypeptide of Formula (I-1) or Formula (I-2) comprises at least one instance of stapled Formula (i) at the i,i+3 position, the i,i+4 position, the i,i+6 position, or the i,i+7 position; or at least one instance of stitched Formula (ii) at the i,i+4+4 position, the i,i+3+4 position, the i,i+3+7 position, or the i,i+4+7 position.

In certain embodiments, one or more amino acids of the stabilized polypeptide of Formula (I-1) or Formula (I-2) is mutated to another natural or unnatural amino acid. In certain embodiments of Formula (I-1), one, two, three, four, five, six, or more of $X_{A1}$ through $X_{A14}$ is mutated to another natural or unnatural amino acid. In certain embodiments of Formula (I-2), one, two, three, four, five, six, seven, eight, or more of $X_{C1}$ through $X_{C20}$ is mutated to another natural or unnatural amino acid. In some embodiments, a stabilized α-CT polypeptide of Formula (I-1) or Formula (I-2) is provided comprising: (1) modifications that confer insulin sensitizer activity, including, but not limited to: (a) substitution of residues on the face of the peptide that contact IR; (b) deletion of residues at either the N- or C-terminal end; (c) insertion of residues at either the N- embodiments of Formula (I-1), the α-CT sequence has residues 704-715 from the binding pocket (FIG. 4). In certain embodiments of Formula (I-1), the α-CT sequence has modified residues 704-715 from the binding pocket.

In another aspect, provided is a precursor polypeptide comprising an alpha-helical segment, wherein the precursor polypeptide binds to the insulin receptor, and wherein the precursor polypeptide is of Formula (II-1) (SEQ ID NO:89):

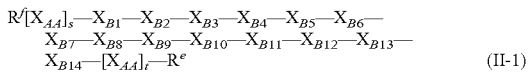

$$R^f[X_{AA}]_s—X_{B1}—X_{B2}—X_{B3}—X_{B4}—X_{B5}—X_{B6}—X_{B7}—X_{B8}—X_{B9}—X_{B10}—X_{B11}—X_{B12}—X_{B13}—X_{B14}—[X_{AA}]_t—R^e \quad \text{(II-1)}$$

or a pharmaceutically acceptable salt thereof; wherein the precursor polypeptide comprises at least one instance of two amino acids of Formula (iii), and optionally, at least one instance of amino acid of Formula (iv):

(iii)

(iv)

provided that the precursor polypeptide comprises at least two occurrences of an amino acid of Formula (iii), wherein $\equiv$, $R^f$, $X_{AA}$, s, $X_{B1}$, $X_{B2}$, $X_{B3}$, $X_{B4}$, $X_{B5}$, $X_{B6}$, $X_{B7}$, $X_{B8}$, $X_{B9}$, $X_{B10}$, $X_{B11}$, $X_{B12}$, $X_{B13}$, $X_{B14}$, t, $R^e$, $R^{a1}$, $R^{a3}$, $R^{2a}$, $R^{3a}$, $R^{c4}$, $R^{c5}$, $R^{c6}$, q4, q5, q6, $R_A$, and $R_B$ are as defined herein.

In another aspect, provided is a precursor polypeptide comprising an alpha-helical segment, wherein the precursor polypeptide binds to the insulin receptor, and wherein the precursor polypeptide is of Formula (II-2) (SEQ ID NO:90):

$$R^f—[X_{AA}]_s—X_{D1}—X_{D2}—X_{D3}—X_{D4}—X_{D5}—X_{D6}—X_{D7}—X_{D8}—X_{D9}—X_{D10}—X_{D11}—X_{D12}—X_{D13}—X_{D14}—X_{D15}—X_{D16}—X_{D17}—X_{D18}—X_{D19}—X_{D20}—[X_{AA}]_t—R^e \quad \text{(II-2)}$$

or a pharmaceutically acceptable salt thereof; wherein the precursor polypeptide comprises at least two amino acids of Formula (iii), and optionally, at least one amino acid of Formula (iv):

(iii)

-continued (iv)

provided that the precursor polypeptide comprises at least two occurrences of an amino acid of Formula (iii), $\equiv$, $R^f$, $X_{AA}$, s, $X_{D1}$, $X_{D2}$, $X_{D3}$, $X_{D4}$, $X_{D5}$, $X_{D6}$, $X_{D7}$, $X_{D8}$, $X_{D9}$, $X_{D10}$, $X_{D11}$, $X_{D12}$, $X_{D13}$, $X_{D14}$, $X_{D15}$, $X_{D16}$, $X_{D17}$, $X_{D18}$, $X_{D19}$, $X_{D20}$, t, $R^e$, $R^{a1}$, $R^{a3}$, $R^{2a}$, $R^{3a}$, $R^{c4}$, $R^{c5}$, $R^{c6}$, q4, q5, q6, $R_A$, and $R_B$ are as defined herein.

In certain embodiments, the amino acids of Formula (iii) and optionally Formula (iv) are amino acids of the alpha-helical segment of the polypeptide. In certain embodiments, the alpha-helical segment binds to or contributes to the binding of the polypeptide to the insulin receptor before stapling or stitching. In certain embodiments, the alpha-helical segment binds to or contributes to the binding of the polypeptide to the insulin receptor after stapling or stitching. In certain embodiments, the alpha-helical segment binds to or contributes to the binding of the polypeptide to the insulin receptor before and after stapling or stitching.

In certain embodiments, the precursor polypeptide of Formula (II-1) or Formula (II-2) comprises at least two independent occurrences of an amino acid of Formula (iii) separated by two (i,i+3) amino acids, three (i,i+4) amino acids, or six (i,i+7) amino acids. In certain embodiments, the polypeptide of Formula (II-1) or Formula (II-2) comprises at least one occurrence of an amino acid of Formula (iv) and at least two independent occurrences of an amino acid of Formula (iii) peripheral thereto. In certain embodiments, the polypeptide of Formula (II-1) or Formula (II-2) comprises one occurrence of an amino acid of Formula (iv), and two independent occurrences of an amino acid of Formula (iii) peripheral thereto. In certain embodiments, each occurrence of an amino acid of Formula (iv) and the two independent occurrences of an amino acid of Formula (iii) peripheral thereto are each separated by three (i,i+4+4) amino acids, separated by two and three amino acids (i,i+3+4), separated by two and six amino acids (i,i+3+7), or separated by three and six (i,i+4+7) amino acids.

In certain embodiments, one or more amino acids of the precursor polypeptides of Formula (II-1) or Formula (II-2) are mutated to another natural or unnatural amino acid. In certain embodiments of Formula (II-1), one, two, three, four, five, six, or more of $X_{B1}$ through $X_{B14}$ is mutated to another natural or unnatural amino acid. In certain embodiments of Formula (II-2), one, two, three, four, five, six, seven, eight, or more of $X_{D1}$ through $X_{D20}$ is mutated to another natural or unnatural amino acid. In some embodiments, a precursor polypeptide of Formula (II-1) or Formula (II-2) is provided comprising: (1) modifications that confer insulin sensitizer activity, including, but not limited to: (a) substitution of residues on the face of the peptide that contact IR; (b) deletion of residues at either the N- or C-terminal end; (c) insertion of residues at either the N- and/or C-terminal end; (d) retro-inverso sequence-modification, which includes peptides of reverse sequence- and chirality (Jameson et al., Nature, 368: 744-746, 1994; Brady et al., Nature, 368: 692-693, 1994) (The net result of combining D-enantiomers and reverse synthesis is that the positions of carbonyl and amino groups in each amide bond are exchanged, while the position of the side-chain groups at each alpha carbon is preserved. For example, if the peptide model is a peptide formed of L-amino acids having the sequence ABC, the retro-inverso peptide analog formed of D-amino acids would have the sequence CBA.); or (e) combinations of any one of (a)-(d). In exemplary embodiments, the α-CT related polypeptide may comprise a total of 1, up to 2, up to 3, u to 4, up to 5, up to 6, up to 7, up to 8, up to 9, or up to 10, or up to 11, or up to 12 amino acid modifications relative to the native α-CT sequence, e.g., conservative or non-conservative substitutions. In certain embodiments of Formula (II-1), the α-CT sequence has residues 704-715 from the binding pocket (FIG. 4). In certain embodiments of Formula (II-1), the α-CT sequence has modified residues 704-715 from the binding pocket.

In certain exemplary embodiments, the precursor polypeptide may comprise a total of 1, up to 2, up to 3, up to 4, up to 5, up to 6, up to 7, up to 8, up to 9, or up to 10, or up to 11, up to 12, up to 13, up to 14, up to 15, up to 16, up to 17, or up to 18 amino acid modifications relative to the native α-CT sequence, e.g., conservative or non-conservative substitutions. In certain embodiments, the α-CT sequence is TFEDYLHNVVFVW (SEQ ID NO:1) or Ac-TFEDYLHNVVFVW (SEQ ID NO:80). In certain embodiments, the α-CT sequence is TFEDYLHNAAFV (SEQ ID NO:2) or Ac-TFEDYLHNAAFV (SEQ ID NO:81) In certain embodiments, the α-CT sequence is SSFRK-TFEDYLHNVVFVW (SEQ ID NO:3) or Ac-SSFRK-TFEDYLHNVVFVW (SEQ ID NO:82). In certain embodiments, the α-CT sequence is SSFRKTFEDYLH-NAAFVW (SEQ ID NO:4) or Ac-SSFRKTFEDYLH-NAAFVW (SEQ ID NO:83). In certain embodiments, the α-CT sequence is SSFRKTFEDYLHNVVFV (SEQ ID NO:84) or Ac-SSFRKTFEDYLHNVVFV (SEQ ID NO:84). In certain embodiments, the α-CT sequence is SSFRK-TFEDYLHNAAFV (SEQ ID NO:85) or Ac-SSFRK-TFEDYLHNAAFV (SEQ ID NO:85).

In another aspect, provided are methods of preparing the precursor polypeptides of Formula (II-1) or Formula (II-2) comprising coupling at least two amino acids of Formula (iii) and at least one segment of α-CT polypeptide:

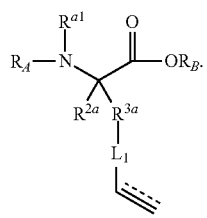

(iii)

In certain embodiments, provided are methods of preparing the precursor polypeptides of Formula (II-1) or Formula (II-2) comprising coupling at least two amino acids of Formula (iii), at least one segment of α-CT polypeptide, and at least one amino acid of Formula (v):

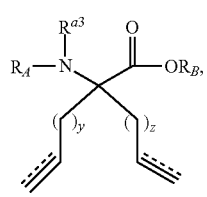

(iv-a)

with two independent occurrences of an amino acid of Formula (iii) peripheral to Formula (iv-a). In certain embodiments, provided are methods of preparing the precursor polypeptides of Formula (II-1) or Formula (II-2) comprising coupling at least one segment of α-CT polypeptide and at least one amino acid of Formula (iv-a):

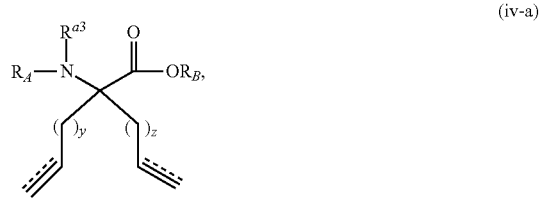

(iv-a)

with two independent occurrences of an amino acid of Formula (iii) peripheral to Formula (iv-a).

In another aspect, the present invention provides an insulin analogue comprising:
(i) a polypeptide of Formula (I-1), Formula (I-2), Formula (II-1), or Formula (II-2);
(ii) an insulin A-chain polypeptide; and
(ii) an insulin B-chain polypeptide;
wherein the polypeptide of Formula (I-1), Formula (I-2), Formula (II-1), or Formula (II-2) is linked to the insulin A chain polypeptide via a linker. In certain embodiments, the provided insulin analogue is an IR agonist.

In some embodiments, the insulin analogue having the insulin A-chain polypeptide and/or insulin B-chain polypeptide is of vertebrate origin. In some embodiments, the insulin analogue is a mammalian insulin analogue such as a human, murine, rodent, bovine, equine, or canine insulin analogue.

In certain embodiments, the linker in the insulin analogue is optionally substituted alkylene-C(=O)—, optionally substituted heteroalkylene-C(=O)—, optionally substituted alkenylene-C(=O)—, optionally substituted heteroalkenylene-C(=O)—, optionally substituted alkynylene-C(=O)—, optionally substituted heteroalkynylene-C(=O)—, optionally substituted cycloalkylene-C(=O)—, optionally substituted heterocycloalkylene-C(=O)—, optionally substituted arylene-C(=O)—, optionally substituted heteroarylene-C(=O)—, optionally substituted aralkylene-C(=O)—, or optionally substituted heteroaralkylene-C(=O)—. In certain embodiments, the linker is of Formulae (L-1), (L-2), or (L-3):

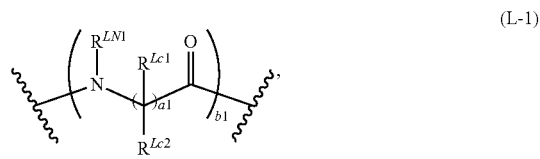

(L-1)

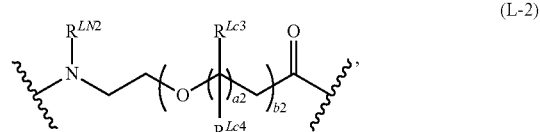

(L-2)

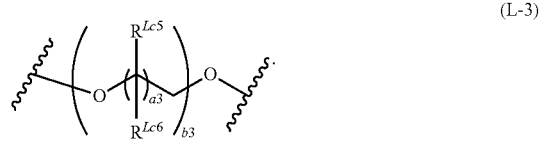

(L-3)

In certain embodiments, the linker is attached to the C-terminal amino acid of the polypeptide of Formula (I-1), Formula (I-2), Formula (II-1), or Formula (II-2) and the N-terminal amino acid of the insulin A-chain polypeptide. In certain embodiments, the insulin B-chain polypeptide is covalently associated with the insulin A-chain polypeptide via at least one disulfide bridge. In certain embodiments, the insulin B-chain polypeptide is covalently associated with the insulin A-chain polypeptide via two disulfide bridges. In certain embodiments, the insulin A-chain polypeptide and B-chain polypeptide are human insulin. In certain embodiments, the insulin A-chain polypeptide and B-chain polypeptide are native human insulin. In certain embodiments, the insulin A-chain polypeptide comprises an amino acid sequence: GIVEQCCASVCSLYQLENYCN (SEQ ID NO:7). In certain embodiments, the insulin A-chain polypeptide comprises an amino acid sequence of GIVEQCCTSICSLYQLENYCN (SEQ ID NO:8). In certain embodiments, the insulin B-chain polypeptide comprises an amino acid sequence: FVNQHLCGDHLVEALYLVCGERGFFYTPKT (SEQ ID NO:9). In certain embodiments, the insulin B-chain polypeptide comprises an amino acid sequence: FVNQHLCGSHLVEALYLVCGERGFFYTKPT (SEQ ID NO:10).

In another aspect, provided are stabilized insulin α-CT polypeptides comprising an α-CT base sequence and at least one instance of two cross-linked amino acids, wherein the two cross-linked amino acids are embedded in the α-CT base sequence and separated by at least two amino acids. In certain embodiments, the two cross-linked amino acids are of Formula (i) as described herein. In certain embodiments, the stabilized insulin α-CT polypeptide further comprises at least one instance of three cross-linked amino acids of Formula (ii) as described herein. In certain embodiments, the stabilized insulin α-CT polypeptide comprises at least one instance of two cross-linked amino acids of Formula (i) and at least one instance of three cross-linked amino acids of Formula (ii) as described herein.

In another aspect, provided are methods of preparing the insulin analogues as described herein. In some embodiments, a sequential synthetic approach comprises coupling the stabilized polypeptide of Formula (I-1), Formula (I-2), Formula (II-1), or Formula (II-2) with a chemical linker to the N-terminal of an insulin A-chain, followed by attached to an insulin B-chain. In some embodiments, a convergent synthetic approach comprises coupling the stabilized polypeptide of Formula (I-1), Formula (I-2), Formula (II-1), or Formula (II-2) with a chemical linker, followed by ligation with insulin A-chain which is already attached with insulin B-chain.

In another aspect, provided are pharmaceutical compositions comprising a stabilized (stapled or stitched) polypeptide as described herein, or a pharmaceutically acceptable salt thereof, and optionally a pharmaceutically acceptable excipient. In another aspect, provided are pharmaceutical compositions comprising an insulin analogue as described herein, or a pharmaceutically acceptable salt thereof, and optionally a pharmaceutically acceptable excipient. The pharmaceutical compositions provided herein may be useful in the treatment of diabetes or pre-diabetes.

In yet another aspect, provided are methods of treating or preventing a diabetic condition, or a complication thereof, comprising administering to a subject in need thereof an effective amount of a stabilized (stapled or stitched) polypeptide or an insulin analogue as described herein, or a pharmaceutically acceptable salt thereof. In certain embodiments, the diabetic condition is diabetes or pre-diabetes. In certain embodiments, the diabetes is Type I diabetes, Type 2 diabetes, gestational diabetes, congenital diabetes, cystic fibrosis-related diabetes, steroid diabetes, or monogenic diabetes. In certain embodiments, the complication of the diabetic condition to be treated or prevented is cardiovascular disease, ischemic heart disease, stroke, peripheral vascular disease, damage to blood vessels, diabetic retinopathy, diabetic nephropathy, chronic kidney disease, diabetic neuropathy, or diabetic foot ulcers.

In yet another aspect, provided are methods of modulating the activity of an insulin receptor in a subject comprising administering to the subject an effective amount of a stabilized (stapled or stitched) polypeptide or an insulin analogue as described herein, or a pharmaceutically acceptable salt thereof.

In yet another aspect, provided are methods of modulating the activity of an insulin receptor in a cell comprising administering to the subject an effective amount of a stabilized (stapled or stitched) polypeptide or an insulin analogue as described herein, or a pharmaceutically acceptable salt thereof.

In yet another aspect, provided are methods of lowering blood glucose levels in a subject comprising administering to the subject an effective amount of a stabilized (stapled or stitched) polypeptide or an insulin analogue as described herein, or a pharmaceutically acceptable salt thereof.

In yet another aspect, provided are methods of activating an insulin receptor comprising contacting the insulin receptor with an effective amount of a stabilized (stapled or stitched) polypeptide or an insulin analogue as described herein, or a pharmaceutically acceptable salt thereof. In certain embodiments, the insulin receptor is contacted in vivo. In certain embodiments, the insulin receptor is contacted in vitro.

In another aspect, the present invention provides kits comprising a compound of Formula (I-1) or Formula (I-2), or a pharmaceutically acceptable salt, solvate, hydrate, polymorph, co-crystal, tautomer, stereoisomer, isotopically labeled derivative, or prodrug thereof, or a pharmaceutical composition thereof. The kits of the invention may include a single dose or multiple doses of a compound of Formula (I-1) or Formula (I-2), or a pharmaceutically acceptable salt, solvate, hydrate, polymorph, co-crystal, tautomer, stereoisomer, isotopically labeled derivative, or prodrug thereof, or a pharmaceutical composition thereof. The provided kits may be useful for the treatment of metabolic diseases such as diabetes or pre-diabetes. In certain embodiments, the kits described herein further include instructions for administering the compound of Formula (I-1) or Formula (I-2), or the pharmaceutically acceptable salt, solvate, hydrate, polymorph, co-crystal, tautomer, stereoisomer, isotopically labeled derivative, or prodrug thereof, or the pharmaceutical composition thereof. The kits may also include packaging information describing the use or prescribing information for the subject or a health care professional. Such information may be required by a regulatory agency such as the U.S. Food and Drug Administration (FDA). The kit may also optionally include a device for administration of the compound or composition, for example, a syringe for parenteral administration.

BRIEF DESCRIPTION OF THE DRAWINGS

FIG. 6 depicts exemplary chemical linkers to connect the insulin A chain and α-CT to prepare the insulin analogues described herein.

FIG. 9 depicts exemplified peptides for chain combination experiments to synthesize insulin analogues as described herein.

FIG. 10 depicts exemplified synthesis of insulin analogues. Alpha-CT-linker-A-chain is soluble in pH 9 buffer, 100 mM TRIS, 8 M Urea (isoelectric point (pI): 4.0), not soluble in $H_2O$, AcCN, MeOH, DMSO, dithiothreitol (DTT), tris(2-carboxyethyl)phosphine (TCEP), or 2-mercaptoethanol (BME). Introduction of double mutations in positions of the α-CT polypeptide that are not crucial for insulin or receptor binding to improve solubility.

FIGS. 12-13 depict an exemplary biosynthesis of preproinsulin constructs. Peptides for chain combination experiments to synthesize insulin analogues are as described herein.

FIG. 14 depicts an exemplary biosynthesis of cross-linked insulin analogues.

FIG. 22 depicts does-response phosphorylation assay of exemplified insulin α-CT polypeptides in CHO-IR cells.

FIG. 23 depicts exemplified insulin α-CT polypeptides in Table 4.

FIG. 34A-34C depict the effect of exemplified insulin α-CT polypeptide s-αCT5, s-αCT14, and s-αCT16 on IRβ phosphorylation.

FIGS. 35-36 depict the effect of exemplified insulin α-CT polypeptides on Akt phosphorylation.

FIG. 37 depicts the insulin-dependence of the effect of exemplified insulin α-CT polypeptides on IRβ phosphorylation.

FIG. 41 depicts scaled up re-folding of insulin precursors. 5 mL of diluted inclusion bodies (out of 20 mL total per 1 L culture) was used. Re-folding conditions: standing at 4° C., overnight. FIG. 41A: re-folding seems to take place for Seq 1 & 2 at 4° C., standing overnight. Seq 3 does not show a shift after re-folding. However it is also the smallest of all three constructs and might not have a pronounced shift. FIG. 41B: the gel suggests that Seq 1 starts unfolding over time at pH11, whereas Seq 2 (including αCT) stays more stable. Seq 3 (truncated C-chain) might not have been successfully folded before. Sequences 1, 2, and 3: diluted inclusion bodies from FIG. 39 as reference. P: pellet; S: supernatant.

FIG. 42 depicts rapid dilution or dialysis after re-folding in the exemplified biosynthesis of insulin analogues.

DEFINITIONS

Figure 1A:
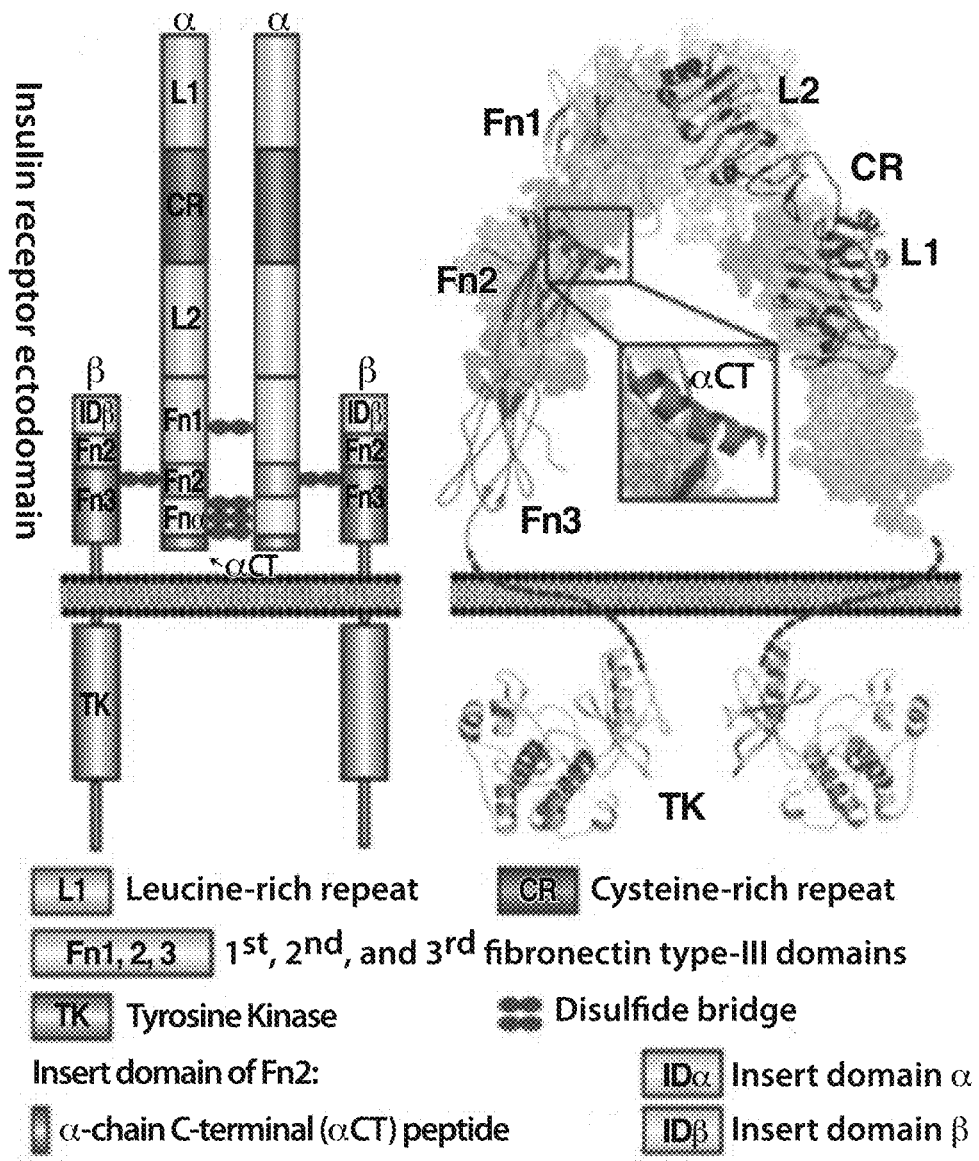
FIG. 1 depicts the insulin receptor (IR) α2β2 dimer, and the domains related to IR activation. (A) Left: Schematic of the insulin receptor (IR) $α_2β_2$ dimer. Right: Composite of high-resolution structures of both the ectodomain (PDB: 3LOH) and the tyrosine kinase domain (PDB: 1 IRK) of the IR $α_2β_2$ dimer. (B) The structure of αCT residues 693-710 bound to the unliganded IR L1 domain of the IR α-chain (PDB: 3LOH). (C) The structure of insulin in complex with the IR L1 domain and aCT residues 704-715 (purple) (PDB: 3W14).
Figure 1B:
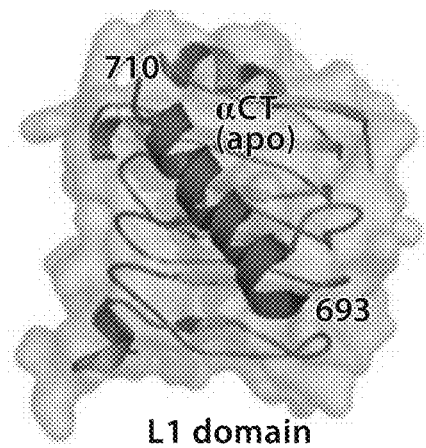
Figure 1C:
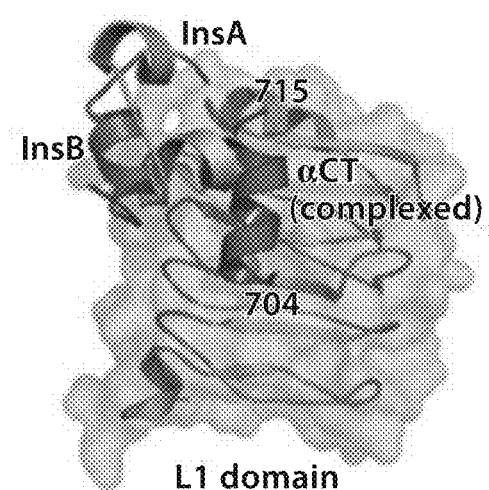

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

In a formula, - - - is absent or a single bond, and $=\!=\!=$ or $=\!\equiv\!=$ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of a carbon by a $^{13}C$- or $^{14}C$-enriched carbon are within the scope of the disclosure. Such compounds are useful, for example, as analytical tools or probes in biological assays.

When a range of values is listed, it is intended to encompass each value and sub range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

The term "haloalkyl" is a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is unspecified (e.g., —CH=CHCH$_3$ or 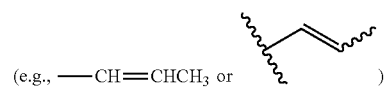 )

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-4}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4] diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b] pyranyl, 5,7-dihydro-4H-thieno[2,3-c]pyranyl, 2,3-dihydro-1H-pyrrolo[2,3-b]pyridinyl, 2,3-dihydrofuro[2,3-b] pyridinyl, 4,5,6,7-tetrahydro-1H-pyrrolo[2,3-b]pyridinyl, 4,5,6,7-tetra-hydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)

R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-5}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

The term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a mono-substituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3^+$X$^-$, wherein R$^{bb}$ and X$^-$ are as defined herein.

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

The term "sulfinyl" refers to the group —S(=O)R$^{aa}$, wherein R$^{aa}$ is as defined herein.

The term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$), —C(=NR$^{bb}$)N(R$^{bb}$)$_2$), wherein R$^{aa}$ and R$^{bb}$ are as defined herein.

As used herein, the term "acyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$), thioesters (—C(=O)SR$^{aa}$, —C(=S)SR$^{aa}$), amides (—C(=O)N(R$^{bb}$)$_2$, —C(=O)NR$^{bb}$SO$_2$R$^{aa}$), thioamides (—C(=S)N(R$^{bb}$)$_2$), and imines (—C(=NR$^{bb}$)R$^{aa}$, —C(=NR$^{bb}$)OR$^{aa}$), —C(=NR$^{bb}$)N(R$^{bb}$)$_2$), wherein R$^{aa}$ and R$^{bb}$ are as defined herein.

As used herein, the term "azido" refers to a group of the formula —N$_3$.

As used herein, the term "cyano" refers to a group of the formula —CN.

As used herein, the term "isocyano" refers to a group of the formula —NC.

As used herein, the term "nitro" refers to a group of the formula —NO$_2$.

As used herein, the term "halo" or "halogen" refers to fluorine (fluoro, —F), chlorine (chloro, —Cl), bromine (bromo, —Br), or iodine (iodo, —I).

As used herein, the term "oxo" refers to a group of the formula =O.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)R^{aa}_2$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

The term "amino acid" refers to a molecule containing both an amino group and a carboxyl group (e.g., carboxylic acid). Amino acids include alpha-amino acids and beta-amino acids, the structures of which are depicted below. In certain embodiments, the amino acid is an alpha-amino acid. In certain embodiments, the amino acid is a beta-amino acid. In certain embodiments, the amino acid is an unnatural amino acid. In certain embodiments, the amino acid is a natural amino acid. In certain embodiments, the amino acid is an unnatural amino acid. The term "unnatural amino acid" refers to amino acids that do not occur in nature but that can be incorporated into a peptide chain.

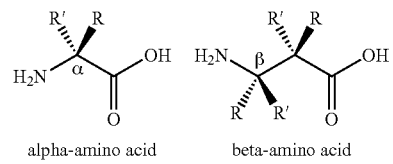

alpha-amino acid     beta-amino acid

Exemplary amino acids include, without limitation, natural alpha amino acids such as the 20 common naturally occurring alpha amino acids found in peptides (e.g., A, R, N, C, D, Q, E, G, H, I, L, K, M, F, P, S, T, W, Y, V, as provided in Table 1 depicted below), unnatural alpha-amino acids (as depicted in Tables 2 and 3 below), natural beta-amino acids (e.g., beta-alanine), and unnatural beta-amino acids.

Amino acids used in the construction of peptides of the present invention may be prepared by organic synthesis, or obtained by other routes, such as, for example, degradation of protein or peptides, or isolation from a natural source. In certain embodiments of the present invention, each instance of the formula $-[X_{AA}]-$ corresponds to an natural or unnatural amino acid of the formula:

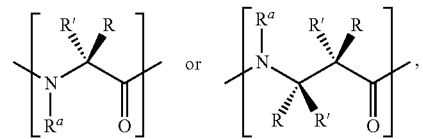

wherein R and R' correspond to an amino acid side chain, as defined below and herein, and wherein $R^a$ is hydrogen; substituted or unsubstituted aliphatic; substituted or unsubstituted heteroaliphatic; substituted or unsubstituted aryl; substituted or unsubstituted heteroaryl; acyl; or an amino protecting group.

TABLE 1

| Exemplary natural alpha-amino acids | Amino acid side chains R | R' |
|---|---|---|
| L-Alanine (A) | —$CH_3$ | —H |
| L-Arginine (R) | —$CH_2CH_2CH_2$—NHC(=NH)$NH_2$ | —H |
| L-Asparagine (N) | —$CH_2C$(=O)$NH_2$ | —H |
| L-Aspartic acid (D) | —$CH_2CO_2H$ | —H |
| L-Cysteine (C) | —$CH_2SH$ | —H |
| L-Glutamic acid (E) | —$CH_2CH_2CO_2H$ | —H |
| L-Glutamine (Q) | —$CH_2CH_2C$(=O)$NH_2$ | —H |
| Glycine (G) | —H | —H |
| L-Histidine (H) | —$CH_2$-2-(1H-imidazole) | —H |
| L-Isoleucine (I) | -sec-butyl | —H |
| L-Leucine (L) | -iso-butyl | —H |
| L-Lysine (K) | —$CH_2CH_2CH_2CH_2NH_2$ | —H |
| L-Methionine (M) | —$CH_2CH_2SCH_3$ | —H |
| L-Phenylalanine (F) | —$CH_2Ph$ | —H |
| L-Proline (P) | -2-(pyrrolidine) | —H |
| L-Serine (S) | —$CH_2OH$ | —H |
| L-Threonine (T) | —$CH_2CH(OH)(CH_3)$ | —H |
| L-Tryptophan (W) | —$CH_2$-3-(1H-indole) | —H |
| L-Tyro sine (Y) | —$CH_2$-(p-hydroxyphenyl) | —H |
| L-Valine (V) | -isopropyl | —H |

TABLE 2

| Exemplary unnatural alpha-amino acids | Amino acid side chains R | R' |
|---|---|---|
| D-Alanine | —H | —$CH_3$ |
| D-Arginine | —H | —$CH_2CH_2CH_2$—NHC(=NH)$NH_2$ |
| D-Asparagine | —H | —$CH_2C$(=O)$NH_2$ |
| D-Aspartic acid | —H | —$CH_2CO_2H$ |
| D-Cysteine | —H | —$CH_2SH$ |
| D-Glutamic acid | —H | —$CH_2CH_2CO_2H$ |
| D-Glutamine | —H | —$CH_2CH_2C$(=O)$NH_2$ |
| D-Histidine | —H | —$CH_2$-2-(1H-imidazole) |
| D-Isoleucine | —H | -sec-butyl |
| D-Leucine | —H | -iso-butyl |
| D-Lysine | —H | —$CH_2CH_2CH_2CH_2NH_2$ |
| D-Methionine | —H | —$CH_2CH_2SCH_3$ |
| D-Phenylalanine | —H | —$CH_2Ph$ |
| D-Proline | —H | -2-(pyrrolidine) |
| D-Serine | —H | —$CH_2OH$ |
| D-Threonine | —H | —$CH_2CH(OH)(CH_3)$ |
| D-Tryptophan | —H | —$CH_2$-3-(1H-indole) |
| D-Tyro sine | —H | —$CH_2$-(p-hydroxyphenyl) |
| D-Valine | —H | -isopropyl |
| Di-vinyl | —CH=$CH_2$ | —CH=$CH_2$ |

| Exemplary unnatural alpha-amino acids | R and R' are equal to: | |
|---|---|---|
| α-methyl-Alanine (Aib) | —$CH_3$ | —$CH_3$ |
| α-methyl-Arginine | —$CH_3$ | —$CH_2CH_2CH_2$—NHC(=NH)$NH_2$ |
| α-methyl-Asparagine | —$CH_3$ | —$CH_2C$(=O)$NH_2$ |
| α-methyl-Aspartic acid | —$CH_3$ | —$CH_2CO_2H$ |
| α-methyl-Cysteine | —$CH_3$ | —$CH_2SH$ |
| α-methyl-Glutamic acid | —$CH_3$ | —$CH_2CH_2CO_2H$ |
| α-methyl-Glutamine | —$CH_3$ | —$CH_2CH_2C$(=O)$NH_2$ |
| α-methyl-Histidine | —$CH_3$ | —$CH_2$-2-(1H-imidazole) |
| α-methyl-Isoleucine | —$CH_3$ | -sec-butyl |
| α-methyl-Leucine | —$CH_3$ | -iso-butyl |
| α-methyl-Lysine | —$CH_3$ | —$CH_2CH_2CH_2CH_2NH_2$ |
| α-methyl-Methionine | —$CH_3$ | —$CH_2CH_2SCH_3$ |
| α-methyl-Phenylalanine | —$CH_3$ | —$CH_2Ph$ |
| α-methyl-Proline | —$CH_3$ | -2-(pyrrolidine) |
| α-methyl-Serine | —$CH_3$ | —$CH_2OH$ |
| α-methyl-Threonine | —$CH_3$ | —$CH_2CH(OH)(CH_3)$ |
| α-methyl-Tryptophan | —$CH_3$ | —$CH_2$-3-(1H-indole) |
| α-methyl-Tyrosine | —$CH_3$ | —$CH_2$-(p-hydroxyphenyl) |
| α-methyl-Valine | —$CH_3$ | -isopropyl |
| Di-vinyl | —CH=$CH_2$ | —CH=$CH_2$ |
| Norleucine | —H | —$CH_2CH_2CH_2CH_3$ |

TABLE 3

| Exemplary unnatural alpha-amino acids | Amino acid side chains R and R' is equal to hydrogen or —$CH_3$, and: |
|---|---|
| Terminally unsaturated alpha-amino acids and bis(alpha-amino acids) (e.g., modified cysteine, modified lysine, modified tryptophan, modified serine, modified threonine, modified proline, modified histidine, or modified alanine). | —$(CH_2)_g$—S—$(CH_2)_g$CH=$CH_2$, <br> —$(CH_2)_g$—O—$(CH_2)_g$CH=$CH_2$, <br> —$(CH_2)_g$—NH—$(CH_2)_g$CH=$CH_2$, <br> —$(CH_2)_g$—(C=O)—S—$(CH_2)_g$CH=$CH_2$, <br> —$(CH_2)_g$—(C=O)—O—$(CH_2)_g$CH=$CH_2$, <br> —$(CH_2)_g$—(C=O)—NH—$(CH_2)_g$CH=$CH_2$, <br> —$CH_2CH_2CH_2$—NH—$(CH_2)_g$CH=$CH_2$, <br> —$(C_6H_5)$—p-O—$(CH_2)_g$CH=$CH_2$, <br> —$CH(CH_3)$—O—$(CH_2)_g$CH=$CH_2$, <br> —$CH_2CH$(—O—CH=$CH_2$)($CH_3$), <br> -histidine-N(($CH_2)_g$CH=$CH_2$), <br> -tryptophan-N(($CH_2)_g$CH=$CH_2$), and <br> —$(CH_2)_{g+1}$(CH=$CH_2$), <br> wherein each instance of g is, independently, 0 to 10. |

There are many known unnatural amino acids any of which may be included in the peptides of the present invention. See for example, S. Hunt, *The Non-Protein Amino Acids: In Chemistry and Biochemistry of the Amino Acids*, edited by G. C. Barrett, Chapman and Hall, 1985. Some non-limiting examples of unnatural amino acids include, but are not limited to, 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with —C(=O)C$_6$H$_5$; —CF$_3$; —CN; -halo; —NO$_2$; CH$_3$), disubstituted phenylalanines, substituted tyrosines (e.g., further substituted with —C(=O)C$_6$H$_5$; —CF$_3$; —CN; -halo; —NO$_2$; CH$_3$), and statine. Additionally, the amino acids suitable for use in the present invention may be derivatized to include amino acid residues that are hydroxylated, phosphorylated, sulfonated, acylated, lipidated, farnesylated, and glycosylated, to name a few.

The term "amino acid side chain" refers to a group attached to the alpha- or beta-carbon of an amino acid, and includes, but is not limited to, any of the amino acid side chains as defined herein, and as provided in Tables 1 to 3. Exemplary amino acid side chains include, but are not limited to, methyl (as the alpha-amino acid side chain for alanine is methyl), 4-hydroxyphenylmethyl (as the alpha-amino acid side chain for tyrosine is 4-hydroxyphenylmethyl), and thiomethyl (as the alpha-amino acid side chain for cysteine is thiomethyl), etc.

A "terminally unsaturated amino acid side chain" refers to an amino acid side chain bearing a terminally unsaturated moiety, such as a substituted or unsubstituted, double bond (e.g., olefinic or alkenyl) or a triple bond (e.g., acetylenic or alkynyl), that can participate in a cross-linking reaction with another terminally unsaturated moiety in the polypeptide chain. In certain embodiments, a "terminally unsaturated amino acid side chain" is a terminal olefinic amino acid side chain. In certain embodiments, a "terminally unsaturated amino acid side chain" is a terminal acetylenic amino acid side chain. In certain embodiments, the terminal moiety of a "terminally unsaturated amino acid side chain" is not further substituted. Terminally unsaturated amino acid side chains include, but are not limited to, side chains as depicted in Table 3.

A "peptide" or "polypeptide" comprises a polymer of amino acid residues linked together by peptide (amide) bonds. The term(s), as used herein, refers to proteins, polypeptides, and peptide of any size, structure, or function. Typically, a peptide or polypeptide will be at least three amino acids long, e.g., at least 3 to 100 or more amino acids in length. A peptide or polypeptide may refer to an individual protein or a collection of proteins. Proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a polypeptide or protein may be modified, for example, by the addition of a chemical entity such as a carbohydrate group, a hydroxyl group, a lipid group, a phosphate group, a farnesyl group, an isofarnesyl group, a fatty acid group, a linker for conjugation, functionalization, or other modification. A polypeptide may also be a single molecule or may be a multi-molecular complex, such as a protein. A polypeptide or protein may be just a fragment of a naturally occurring protein or peptide. A polypeptide or protein may be naturally occurring, recombinant, or synthetic, or any combination thereof. As used herein "dipeptide" refers to two covalently linked amino acids.

The term "homologous" is a term that refers to polypeptides and proteins that are highly related at the level of the amino acid sequence. Polypeptides and proteins that are homologous to each other are termed homologues. Homologous may refer to the degree of sequence similarity between two sequences. Two polypeptide or protein sequences are considered to be homologous if least one stretch of at least 20 amino acids of the polypeptide or protein are at least about 50-60% identical, preferably about 70% identical. The homology percentage reflects the maximal homology possible between two sequences, i.e. the percent homology when the two sequences are so aligned as to have the greatest number of matched (homologous) positions. Homology can be readily calculated by known methods such as those described in: *Computational Molecular Biology*, Lesk, A. M., ed., Oxford University Press, New York, 1988; *Biocomputing: Informatics and Genome Projects*, Smith, D. W., ed., Academic Press, New York, 1993; *Sequence Analysis in Molecular Biology*, von Heinje, G., Academic Press, 1987; *Computer Analysis of Sequence Data*, Part I, Griffin, A. M., and Griffin, H. G., eds., Humana Press, New Jersey, 1994; and *Sequence Analysis Primer*, Gribskov, M. and Devereux, J., eds., M Stockton Press, New York, 1991. Methods commonly employed to determinehomology between sequences include, but are not limited to, those disclosed in Carillo, H., and Lipman, D., *SIAM J Applied Math.*, 48:1073 (1988). Techniques for determining homology are codified in publicly available computer programs. Exemplary computer software to determine homology between two sequences include, but are not limited to, the GCG program package, Devereux, J., et al., *Nucleic Acids Research*, 12(1), 387 (1984)), BLASTP, BLASTN, and FASTA Atschul, S. F. et al., *J Molec. Biol.*, 215, 403 (1990)).

As used herein, the term "salt" or "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, quaternary salts, e.g., cationic trisubstituted amino groups, e.g., as defined herein.

As used herein, when two entities are "conjugated" to one another they are linked by a direct or indirect covalent or non-covalent interaction. In certain embodiments, the association is covalent. In other embodiments, the association is non-covalent. Non-covalent interactions include, but are not limited to, hydrogen bonding, van der Waals interactions, hydrophobic interactions, magnetic interactions, and electrostatic interactions. An indirect covalent interaction is when two entities are covalently connected, optionally through a linker.

As used herein, a "label" refers to a moiety that has at least one element, isotope, or functional group incorporated into the moiety which enables detection of the inventive polypeptide to which the label is attached. Labels can be directly attached (i.e., via a bond) or can be attached by a linker (e.g., such as, for example, a substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted arylene; substituted or unsubstituted heteroarylene; acylene, or any combination thereof, which can make up a linker). It will be appreciated that the label may be attached to the inventive polypeptide at any position that does not interfere with the biological activity or characteristic of the inventive polypeptide that is being detected.

In general, a label can fall into any one (or more) of five classes: a) a label which contains isotopic moieties, which may be radioactive or heavy isotopes, including, but not limited to, $^2H$, $^3H$, $^{13}C$, $^{14}C$, $^{15}N$, $^{18}F$, $^{31}P$, $^{32}P$, $^{35}S$, $^{67}Ga$, $^{99m}Tc$ (Tc-99m), $^{111}In$, $^{123}I$, $^{125}I$, $^{169}Yb$, and $^{186}Re$; b) a label which contains an immune moiety, which may be antibodies or antigens, which may be bound to enzymes (e.g., such as horseradish peroxidase); c) a label which is a colored, luminescent, phosphorescent, or fluorescent moieties (e.g., such as the fluorescent label FITC); d) a label which has one or more photoaffinity moieties; and e) a label which has a ligand moiety with one or more known binding partners (such as biotin-streptavidin, FK506-FKBP, etc.). Any of these type of labels as described above may also be referred to as "diagnostic agents" as defined herein.

In certain embodiments, such as in the identification of a biological target, label comprises a radioactive isotope, preferably an isotope which emits detectable particles, such as β particles. In certain embodiments, the label comprises one or more photoaffinity moieties for the direct elucidation of intermolecular interactions in biological systems. A variety of known photophores can be employed, most relying on photoconversion of diazo compounds, azides, or diazirines to nitrenes or carbenes (see, Bayley, H., *Photogenerated Reagents in Biochemistry and Molecular Biology* (1983), Elsevier, Amsterdam, the entire contents of which are incorporated herein by reference). In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

In certain embodiments, the label comprises one or more fluorescent moieties. In certain embodiments, the label is the fluorescent label FITC. In certain embodiments, the label comprises a ligand moiety with one or more known binding partners. In certain embodiments, the label comprises the ligand moiety biotin.

As used herein, a "diagnostic agent" refers to an imaging agent. Exemplary imaging agents include, but are not limited to, those used in positron emissions tomography (PET), computer assisted tomography (CAT), single photon emission computerized tomography, x-ray, fluoroscopy, and magnetic resonance imaging (MRI); anti-emetics; and contrast agents. Exemplary diagnostic agents include but are not limited to, fluorescent moieties, luminescent moieties, magnetic moieties; gadolinium chelates (e.g., gadolinium chelates with DTPA, DTPA-BMA, DOTA and HP-DO3A), iron chelates, magnesium chelates, manganese chelates, copper chelates, chromium chelates, iodine-based materials useful for CAT and x-ray imaging, and radionuclides. Suitable radionuclides include, but are not limited to, $^{123}I$, $^{125}I$, $^{130}I$, $^{131}I$, $^{133}I$, $^{135}I$, $^{47}Sc$, $^{72}As$, $^{72}Se$, $^{90}Y$, $^{88}Y$, $^{97}Ru$, $^{100}Pd$, $^{101}mRh$, $^{119}Sb$, $^{128}Ba$, $^{197}Hg$, $^{211}At$, $^{212}Bi$, $^{212}Pb$, $^{109}Pd$, $^{11}In$, $^{67}Ga$, $^{68}Ga$, $^{67}Cu$, $^{75}Br$, $^{77}Br$, $^{99m}Tc$, $^{14}C$, $^{13}N$, $^{15}O$, $^{32}P$, $^{33}P$, and $^{18}F$. Fluorescent and luminescent moieties include, but are not limited to, a variety of different organic or inorganic small molecules commonly referred to as "dyes," "labels," or "indicators." Examples include, but are not limited to, fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g., U.S. Patent Publication 2004/0067503; Valeur, B., "Molecular Fluorescence: Principles and Applications," John Wiley and Sons, 2002; and *Handbook of Fluorescent Probes and Research Products*, Molecular Probes, 9$^{th}$ edition, 2002).

As used herein "at least one instance" refers to at least 1, 2, 3, 4, or more instances.

The terms "composition" and "formulation" are used interchangeably.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is a non-human animal. In certain embodiments, the animal is a fish or reptile. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

An "agent" refers to any therapeutic agent, and includes a stapled or stitched polypeptide as described herein.

The terminology "conservative amino acid substitutions" is well known in the art, which relates to substitution of a particular amino acid by one having a similar characteristic (e.g., similar charge or hydrophobicity, similar bulkiness). Examples include aspartic acid for glutamic acid, or isoleucine for leucine. A list of exemplary conservative amino acid substitutions is given in the table below. A conservative substitution mutant or variant will 1) have only conservative amino acid substitutions relative to the parent sequence, 2) will have at least 90% sequence identity with respect to the parent sequence, preferably at least 95% identity, 96% identity, 97% identity, 98% identity or 99%.

TABLE AA

Conservative Amino Acid Substitutions

| For Amino Acid | Code | Replace With |
| --- | --- | --- |
| Alanine | A | D-ala, Gly, Aib, β-Ala, Acp, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Aib, β-Ala, Acp |
| Isoleucine | I | D-Ile, Val, D-Val, AdaA, AdaG, Leu, D-Leu, Met, D-Met |
| Leucine | L | D-Leu, Val, D-Val, AdaA, AdaG, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4 or 5-phenylproline, AdaA, AdaG, cis-3,4 or 5-phenylproline, Bpa, D-Bpa |
| Proline | P | D-Pro, L-I-thioazolidine-4-carboxylic acid, D-or-L-1-oxazolidine-4-carboxylic acid (Kauer, U.S. Pat. No. (4,511,390) |
| Serine | S | D-Ser, Thr, D-Thr, allo-Thr, Met, D-Met, Met (O), D-Met (O), L-Cys, D-Cys |
| Threonine | T | D-Thr, Ser, D-Ser, allo-Thr, Met, D-Met, Met (O), D-Met (O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met, AdaA, AdaG |

A non-conservative mutation is any other amino acid substitution other than the conservative substitutions noted in the above table.

As used herein, "cross-linking" peptides refers to either covalently cross-linking peptides or non-covalently cross-linking peptides. In certain embodiments, the peptides are covalently associated. Covalent interaction is when two peptides are covalently connected through a linker group such as a natural or non-natural amino acid side chain. In other embodiments, the peptides are non-covalently associated. Non-covalent interactions include hydrogen bonding, van der Waals interactions, hydrophobic interactions, magnetic interactions, and electrostatic interactions. The peptides may also comprise natural or non-natural amino acids capable of cross-linking the peptide with another peptide.

A "stapled" or "stitched" protein means that the protein underwent peptide stapling or stitching. "Peptide stapling" is one method for crosslinking within a peptide (intrapeptide) or between different peptides (interpeptide). Peptide stapling describes a synthetic methodology wherein two olefin-containing sidechains present in a peptide or different peptides are covalently joined ("stapled") using a ring-closing metathesis (RCM) reaction to form a crosslink (see, the cover art for *J. Org. Chem.* (2001) vol. 66, issue 16 describing metathesis-based crosslinking of alpha-helical peptides; Blackwell et al.; *Angew Chem. Int. Ed*. (1994) 37:3281; and U.S. Pat. No. 7,192,713). "Peptide stitching" involves multiple "stapling" events in a single polypeptide chain to provide a multiply stapled (also known as "stitched") polypeptide (see, for example, Walensky et al., *Science* (2004) 305:1466-1470; U.S. Pat. Nos. 8,592,377; 7,192,713; U.S. Patent Application Publication No. 2006/0008848; U.S. Patent Application Publication No. 2012/0270800; International Publication No. WO 2008/121767, and International Publication No. WO 2011/008260). Stapling of a peptide using all-hydrocarbon crosslinks has been shown to help maintain its native conformation and/or secondary structure, particularly under physiologically relevant disorders (see Schafmiester et al., *J. Am. Chem. Soc.* (2000) 122:5891-5892; Walensky et al., *Science* (2004) 305:1466-1470). In certain embodiments, the non-natural amino acids found in the fusion proteins described herein comprise a side chain capable of being covalently joined using olefin moieties (i.e., "stapled together") using a cross-linking reaction such as a ring-closing metathesis (RCM) reaction.

As used herein, "at least one segment" refers to any portion of the peptide sequence having at least two amino acids.

DETAILED DESCRIPTION OF CERTAIN
EMBODIMENTS OF THE INVENTION

Insulin elicits a biological response by binding to the ectodomain of the insulin receptor (IR) and inducing conformational changes that lead to autophosphorylation of the intracellular tyrosine kinase (TK) domain and subsequent phosphorylation of insulin receptor substrate (IRS) proteins (Taguchi, A. & White, M. F. Insulin-like signaling, nutrient homeostasis, and life span. Annual review of physiology 70, 191-212 (2008); Taniguchi, C. M., Emanuelli, B. & Kahn, C. R. Critical nodes in signalling pathways: insights into insulin action. Nature reviews. Molecular cell biology 7, 85-96 (2006)). Upon activation of the insulin signaling pathway, a cascade of protein-protein interactions and phosphorylation events results in glucose uptake and glycogen synthesis. Type 1 and type 2 diabetes, the two major chronic forms of diabetes mellitus, are each characterized by deficiencies in the insulin signaling pathway.

The C-terminus of the IR α-chain (α-CT) segment plays an important role in mediating insulin binding to IR. The crystal structure of the insulin-bound IR shows that twelve αCT residues (704-715) form an α-helix that mediates the interaction between insulin and the L1 domain of the insulin receptor (Menting, J. G. et al. How insulin engages its primary binding site on the insulin receptor. *Nature* 493, 241-245 (2013); McKern, N. M. et al. Structure of the insulin receptor ectodomain reveals a folded-over conformation. *Nature* 443, 218-221 (2006)). The present invention provides structurally-stabilized αCT polypeptide as insulin sensitizers, enhancing the potency of insulin by cooperatively binding both IR and insulin with higher affinity than the native αCT segment. Further, the invention provides insulin analogues having the stabilized αCT polypeptide fused to insulin through a chemical linker. The provided insulin analogues induce insulin to adopt the active conformation observed upon binding to IR, exhibiting IR agonist activity As generally described above, the present invention provides polypeptides comprising a stapled or stitched alpha-helical insulin receptor (IR) binding segment, and "unstapled" or "unstitched" precursor polypeptides thereof. Further provided are insulin analogues comprising a stapled or stitched polypeptide of Formula (I-1) or Formula (I-2) as described herein; an insulin A-chain polypeptide; and an insulin B-chain polypeptide. Further provided are methods of making the stapled or stitched polypeptides, methods of making the insulin analogues, pharmaceutical compositions thereof, uses thereof, methods of using the stapled or stitched peptides and insulin analogues, and methods of treating and/or preventing diabetes or pre-diabetes. In certain embodiments, the stabilized polypeptide of Formula (I-1) or Formula (I-2) binds to the ectodomain of the insulin receptor (IR). In certain embodiments, the stabilized polypeptide of Formula (I-1) or Formula (I-2) binds to site 1 of the IR. In certain embodiments, the stabilized polypeptide of Formula (I-1) or Formula (I-2) binds to the L1 domain of site 1 of the IR. In some embodiments, the stabilized polypeptide of Formula (I-1) or Formula (I-2) acts as an insulin sensitizer and binds to IR. In some embodiments, the stabilized polypeptide of Formula (I-1) or Formula (I-2) acts as an insulin sensitizer and bind to IR and insulin. In some embodiments, the stabilized polypeptide of Formula (I-1) or Formula (I-2) acts as an insulin sensitizer and binds to IR and insulin simultaneously. In some embodiments, the stabilized polypeptide of Formula (I-1) or Formula (I-2) acts as an insulin sensitizer and binds to IR and insulin sequentially.

The staples and/or stitches of the stabilized polypeptide are ideally situated in order to not interfere with binding of the polypeptide to the IR. In certain embodiments, the staples and/or stitches increase helicity of the stabilized polypeptide and enhance binding.

"Stapling" as used herein, is a process by which two terminally unsaturated amino acid side chains in a polypeptide chain react with each other in the presence of a ring closing metathesis (RCM) catalyst to generate a C—C double bonded cross-link between the two amino acids (a "staple"). See, e.g., Bernal et al., *J. Am. Chem. Soc.* (2007) 129: 2456-2457. In certain embodiments, the RCM catalyst is a ruthenuim catalyst. Suitable RCM catalysts are described in, for example, Grubbs et al., *Acc. Chem. Res.* 1995, 28, 446-452; U.S. Pat. No. 5,811,515; Schrock et al., *Organometallics* (1982) 1 1645; Gallivan et al., *Tetrahedron Letters* (2005) 46:2577-2580; Furstner et al., *J. Am. Chem. Soc.* (1999) 121:9453; and *Chem. Eur. J.* (2001) 7:5299. Stapling engenders constraint on a secondary structure, such as an alpha-helical structure. The length and geometry of the cross-link can be optimized to improve the yield of the desired secondary structure content. The constraint provided can, for example, prevent the secondary structure to unfold and/or can reinforce the shape of the secondary structure, and thus makes the secondary structure more stable. Stapled peptides may have increased half-lives in vivo and may have oral bioavailability.

A stapled polypeptide may contain more than one staple, i.e., two, three, four, five, six, seven, eight, nine, ten, or more staples. In certain embodiments, wherein the stapled polypeptide comprises more than one staple, the polypeptide may also be referred to as a "stitched" polypeptide. A stitched polypeptide is generated from a polypeptide comprising at least one central amino acid which comprises two terminally unsaturated amino acid side chains and at least two amino acids peripheral to (located on either side of) the central amino acid, each of which comprises at least one terminally unsaturated amino acid side chain. The "stitching" occurs when the central and peripheral amino acids react with each other in the presence of a ring closing metathesis catalyst to generate two C—C double bonded cross-links, i.e., one staple linking one peripheral amino acid to the central amino acid, and the other staple linking the other peripheral amino acid to the central amino acid, i.e., to provide a "stitch". The concept of stapling and stitching is generally known in the art. See, e.g., U.S. Pat. Nos. 8,592,377; 8,324,428; 7,192,713; 7,723,469; 7,786,072; U.S. Patent Application Publication Nos: 2014-0011979; 2014-0005118; 2012-0270800; 2011-0257251; 2011-0144306; 2010-0184645; 2010-0168388; 2010-0081611; 2009-0176964; 2009-0149630; and 2006-0008848; PCT Application Publication Nos: WO 2014/052647; WO 2014/055564; WO 2012/174423; WO 2012/040459; WO 2012/174409; WO 2011/008260; WO 2010/011313; WO 2008/121767; WO 2008/095063; WO 2008/061192; and WO 2005/044839; which depict stapling and stitching of polypeptides, and which are incorporated herein by reference.

In general, the stabilized polypeptides contemplated herein comprise an alpha-helical segment, wherein the polypeptide binds to the insulin receptor, and wherein the polypeptide is of Formula (I-1):

$$R^f—[X_{AA}]_s—X_{A1}—X_{A2}—X_{A3}—X_{A4}—X_{A5}—X_{A6}—X_{A7}—X_{A8}—X_{A9}—X_{A10}—X_{A11}—X_{A12}—X_{A13}—X_{A14}—[X_{AA}]_t—R^e \quad (I\text{-}1)$$

or a pharmaceutically acceptable salt thereof;
and wherein the polypeptide comprises at least one instance of two cross-linked amino acids of Formula (i):

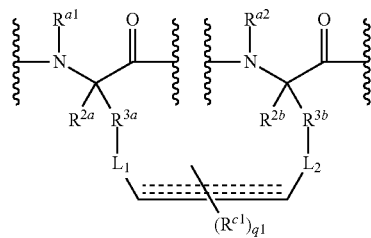

(i)

or at least one instance of three cross-linked amino acids of Formula (ii):

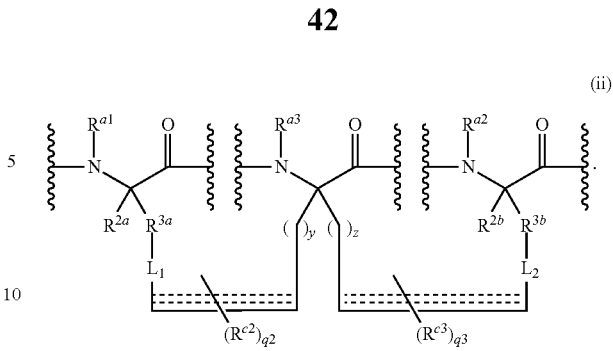

(ii)

The stabilized (stapled or stitched) polypeptides as described herein can be prepared from a precursor polypeptide described herein with a ring closing metathesis (RCM) catalyst. In certain embodiments, the stabilized (stapled or stitched) polypeptides as described herein can be prepared from a precursor polypeptide described herein with a ring closing metathesis (RCM) catalyst, followed by additional synthetic modification(s) of the staples such as —C(═O)O— extrusion, reduction of the resulting olefin, or addition of a targeting moiety.

In general, the precursor polypeptide to prepare the stabilized polypeptides contemplated herein comprises an alpha-helical segment, wherein the precursor polypeptide binds to the insulin receptor, and wherein the precursor polypeptide is of Formula (II-1):

$$R^f—[X_{AA}]_s—X_{B1}—X_{B2}—X_{B3}—X_{B4}—X_{B5}—X_{B6}—X_{B7}—X_{B8}—X_{B9}—X_{B10}—X_{B11}—X_{B12}—X_{B13}—X_{B14}—[X_{AA}]_t—R^e \quad (II\text{-}1)$$

or a pharmaceutically acceptable salt thereof;
and wherein the precursor polypeptide comprises at least two amino acids of Formula (iii),
and optionally, at least one amino acid of Formula (iv):

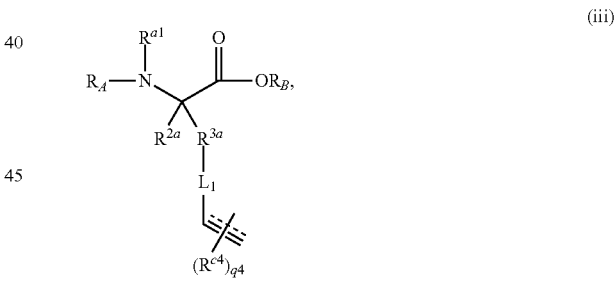

(iii)

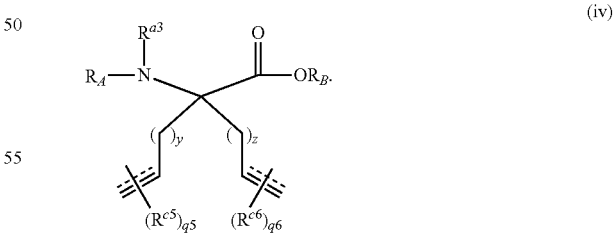

(iv)

In certain embodiments, the amino acids of Formula (iii) and optionally Formula (iv) are amino acids of an alpha-helical segment.

In certain embodiments, the two cross-linked amino acids of Formula (i) or the three cross-linked amino acids of Formula (ii) are amino acids of the alpha-helical segment. Stabilization of the alpha-helical secondary structure by stapling or stitching results in, for example, increased alpha helicity, decreased susceptibility to enzymatic degradation, and/or increased thermal stability, as compared to the precursor polypeptide or the polypeptide without amino acids suitable for stapling or stitching.

In certain embodiments, the polypeptide of Formula (I-1), Formula (II-1), Formula (I-2), or Formula (II-2) is derived from a wild insulin α-CT sequence. In certain embodiments, the polypeptide of Formula (I-1), Formula (II-1), Formula (I-2), or Formula (II-2) is derived from a wild insulin α-CT sequence comprising a total of 1, up to 2, up to 3, up to 4, up to 5, up to 6, up to 7, up to 8, up to 9, or up to 10, or up to 11, up to 12, up to 13, or up to 14 amino acid modifications relative to the native α-CT sequence, e.g., conservative or non-conservative substitutions. In certain embodiments, the α-CT sequence is SSFRKTFEDYLHNVVFVW (SEQ ID NO:31 or Ac-SSFRKTFEDYLHNVVFVW (SEQ ID NO:82). In certain embodiments, the α-CT sequence is SSFRKTFEDYLHNVVFV (SEQ ID NO:5) or Ac-SSFRKTFEDYLHNVVFV (SEQ ID NO:84). In certain embodiments, the α-CT sequence is SSFRKTFEDYLHNAAFVW (SEQ ID NO:4) or Ac-SSFRKTFEDYLHNAAFVW (SEQ ID NO:83). In certain embodiments, the α-CT sequence is SSFRKTFEDYLHNAAFV (SEQ ID NO:6) or Ac-SSFRKTFEDYLHNAAFV (SEQ ID NO:85). In certain embodiments, the α-CT sequence is TFEDYLHNVVFV (SEQ ID NO:1) or Ac-TFEDYLHNVVFV (SEQ ID NO:80). In certain embodiments, the α-CT sequence is TFEDYLHNAAFV (SEQ ID NO:2) or Ac-TFEDYLHNAAFV (SEQ ID NO:81).

In general, the polypeptide region targeting the IR is alpha-helical or substantially alpha-helical, and the staples or stitches stabilize this alpha-helical region. In certain embodiments, the polypeptides that target the IR comprise sequences that are approximately 5, 6, 7, 8, 9, 10, 11, 12, 13, 14, 15, 16, 17, 18, 19, 20, 21, 22, 23, 24, 25, 26, 27, 28, 29, or 30 amino acids long. In other embodiments, the polypeptides are approximately 5-10, 5-20, 5-30, 5-40, 5-50, 10-20, 10-16, 10-18, 12-18, 114-18, 15-17, 15-20, or 16-20 amino acids long. In certain embodiments, the polypeptides provided herein that target the IR comprise sequences that are derived from an alpha-helical segment of insulin. In certain embodiments, the polypeptides provided herein that target the IR comprise sequences that are derived from an alpha-helical segment of C-terminus of the α-chain (αCT) segment. In certain embodiments, the polypeptides provided herein bind both IR and insulin. The invention is based, in part, on the discovery that stapled versions of the αCT segment have the ability to mediate insulin binding to IR. In certain embodiments, the mediation is related to insulin binding to the site 1 of IR. In certain embodiments, the provided polypeptides function as insulin sensitizers, enhancing the potency of insulin by cooperatively binding both IR and insulin with higher affinity than the native αCT segment. In certain embodiments, the provided polypeptides function as agents to agonize IR activity.

As used herein, the phrase "substantially alpha-helical" refers to a polypeptide adopting, on average, backbone (φ, ψ) dihedral angles in a range from about (−90°, −15°) to about (−35°, −70°). Alternatively, the phrase "substantially alpha-helical" refers to a polypeptide adopting dihedral angles such that the ψ dihedral angle of one residue and the φ dihedral angle of the next residue sums, on average, to about −80° to about −125°. In certain embodiments, the polypeptide adopts dihedral angles such that the ψ dihedral angle of one residue and the φ dihedral angle of the next residue sums, on average, to about −100° to about −110°. In certain embodiments, the polypeptide adopts dihedral angles such that the ψ dihedral angle of one residue and the φ dihedral angle of the next residue sums, on average, to about −105°. Furthermore, the phrase "substantially alpha-helical" may also refer to a polypeptide having at least 50%, at least 60%, at least 70%, at least 80%, at least 90%, or at least 95% of the amino acids provided in the polypeptide chain in an alpha-helical conformation, or with dihedral angles as specified herein. Confirmation of a polypeptide's alpha-helical secondary structure may be ascertained by known analytical techniques, such as x-ray crystallography, electron crystallography, fiber diffraction, fluorescence anisotropy, circular dichroism (CD), and nuclear magnetic resonance (NMR) spectroscopy.

Figure 2:
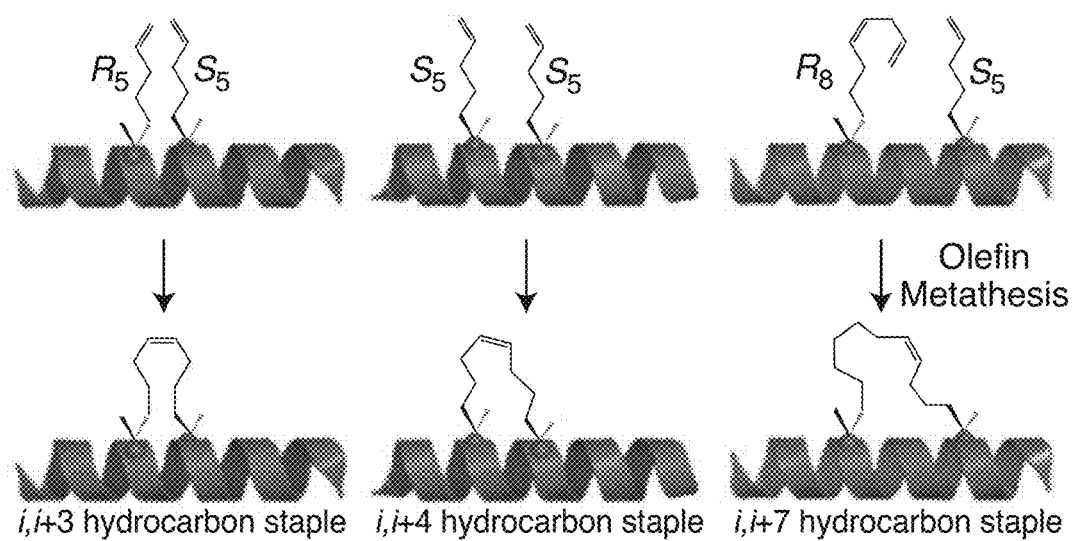
FIG. 2 depicts a representation of the first generation of stapled polypeptides: three exemplified hydrocarbon stapled polypeptides. Olefin metathesis creates an all-hydrocarbon cross-link, termed a "staple," which templates α-helical character throughout the peptide. The α-methyl,α-alkenyl-glycine amino acids utilized for production of each staple type are indicated using the naming convention $X_Y$, where X is the stereochemistry at the α carbon (Cahn-Ingold-Prelog designations), and Y is the length, in carbons, of the alkenyl side chain.
Figure 3A:
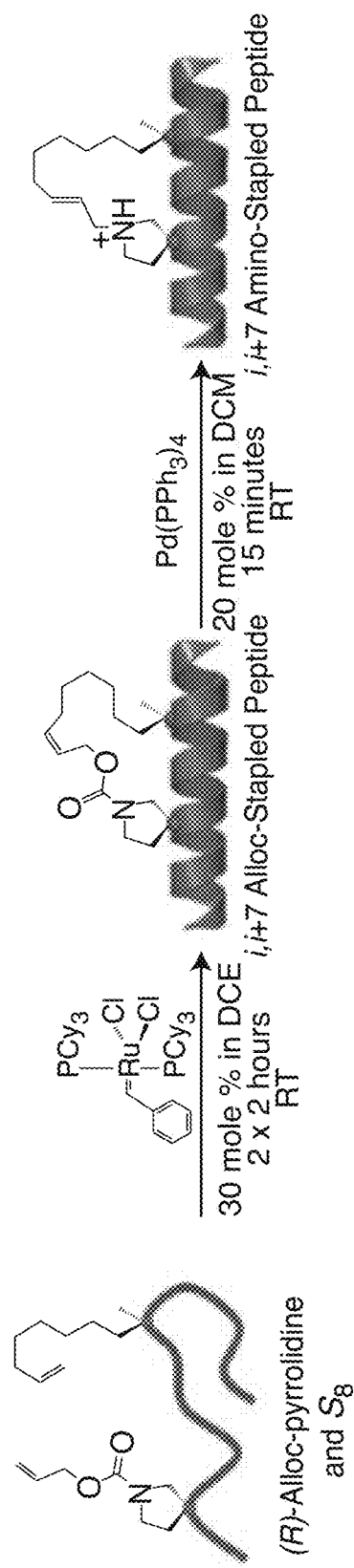
FIG. 3 depicts a representation of the second generation of stapled polypeptides: an exemplified amino-stapled polypeptide. (A) (R)-Alloc-pyrrolidine was incorporated at the i position and S8 at the i+7 position in an exemplified polypeptide sequence. After ring closing metathesis (RCM), an Alloc-stapled intermediate was obtained. This intermediate was subjected to Pd-mediated $CO_2$ extrusion, which gave an i,i+7 amino-stapled peptide. (B) Circular dichroism (CD) spectroscopy showed comparable levels of helix induction by the first-generation all-hydrocarbon staple in the exemplified peptide and second generation amino-stapled version. α-Helical peptides display a CD spectrum with dual minima at 208 nm and 222 nm.
Figure 3B:
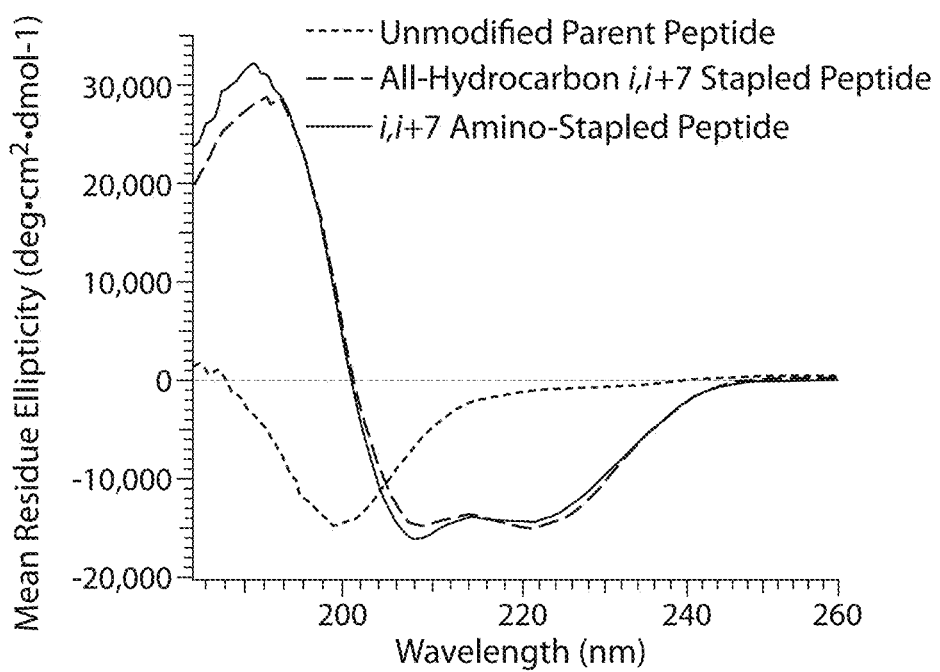

In general, the staple extends across the length of one or two helical turns (i.e., about 3, about 4, or about 7 amino acids), and amino acids positioned at i and i+3; i and i+4; or i and i+7 may be used for crosslinking. In certain embodiments, stapling may occur at the i,i+3 positions, i,i+4 positions, and/or i,i+7 positions. In certain embodiments, stitching may occur at the i,i+4+4 positions, the i,i+3+4 positions, the i,i+3+7 positions, or the i,i+4+7 positions. Examples of these stapling and stitching motifs are depicted in FIG. 2. In certain embodiments, the length of each staple (i.e., of a single staple or part of a stitch) is independently 6 to 20 atoms in length, i.e., 6, 7, 8, 9, 10, 11, 12, 13, 14, 15, 16, 17, 18, 19, or 20 atoms in length, measured from alpha carbon to alpha carbon and including each alpha carbon of each unnatural amino acid. In certain embodiments, the length of each staple (i.e., of a single staple or part of a stitch) is independently 6 to 14 atoms in length, i.e., 6, 7, 8, 9, 10, 11, 12, 13, or 14 in length, measured from alpha carbon to alpha carbon and including each alpha carbon of each unnatural amino acid.

Polypeptides and Precursors

Figures 4A, 4B:
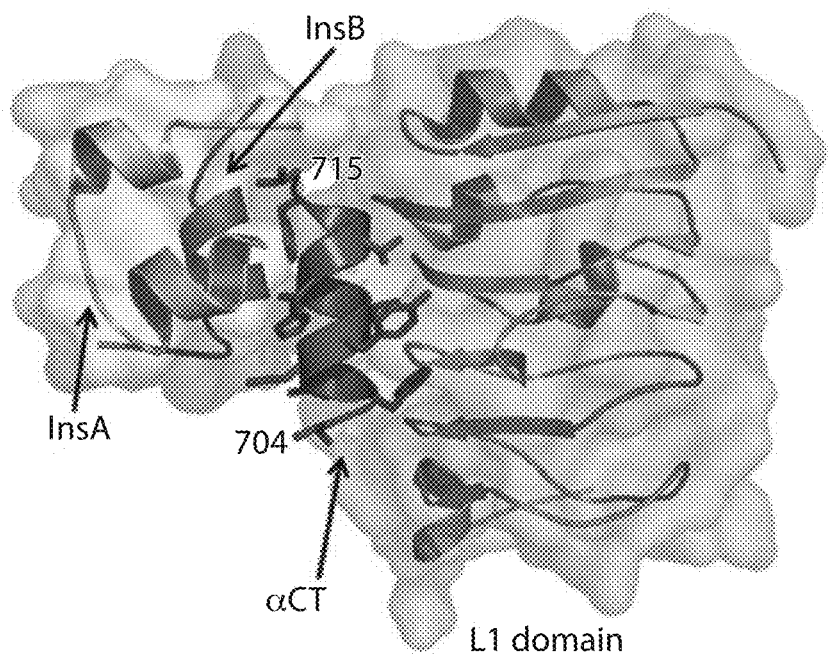
FIG. 4 depicts the structure of insulin and the aCT segment. (A) The structure of insulin (A chain and B chain) in complex with the IR L1 domain and aCT residues 704-715. (B) Top: The sequence of residues 704-715 of the αCT peptide is shown. Bottom: A panel of exemplified amino-stapled aCT peptides. Residues having little interaction with L1 or insulin are candidates for replacement with non-natural cross-linking amino acids. These non-natural cross-linking amino acids are designated with asterisks. In two cases, the αCT segment were extended by one amino acid on either terminus to create an additional position for the incorporation of an amino-stapling residue.

The invention specifically contemplates stabilized forms of the IR αCT segment, and unstitched and unstapled precursor polypeptides thereof. The amino acid sequence of an exemplary αCT segment is provided in FIG. 4.

As generally described herein, provided is a precursor "unstapled" and "unstitched" polypeptide comprising an alpha-helical segment, wherein the polypeptide binds to the insulin receptor. In certain embodiments, the precursor polypeptide is of Formula (II-1):

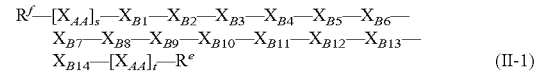

or a pharmaceutically acceptable salt thereof;
and wherein the polypeptide comprises at least two amino acids of Formula (iii), and optionally, at least one amino acid of Formula (iv):

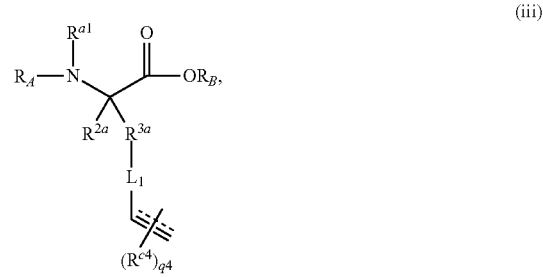

-continued

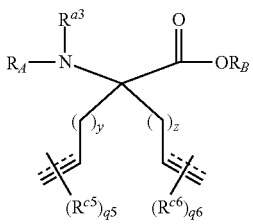

(iv)

wherein:

each instance of ========== independently represents a single bond, a double bond, or a triple bond;

each instance of $R^{a1}$ and $R^{a3}$ is, independently, hydrogen; acyl; optionally substituted $C_{1-6}$ alkyl; or an amino protecting group;

$R^{2a}$ is independently, optionally substituted alkyl; optionally substituted alkenyl; optionally substituted alkynyl; optionally substituted heteroalkyl; optionally substituted carbocyclyl; or optionally substituted heterocyclyl;

$R^{3a}$ is independently, optionally substituted alkylene; unsubstituted heteroalkylene; optionally substituted carbocyclylene; or optionally substituted heterocyclylene; or optionally $R^{2a}$ and $R^{3a}$ are joined to form a ring;

$L_1$ is independently, a bond, optionally substituted $C_{1-10}$ alkylene, or —C(=O)$OR^{L1}$—;

$R^{L1}$ is independently optionally substituted $C_{1-10}$ alkylene;

each instance of $R^{c4}$, $R^{c5}$, $R^{c6}$, and $R^{c7}$ is independently hydrogen; optionally substituted aliphatic; optionally substituted heteroaliphatic; optionally substituted aryl; optionally substituted heteroaryl; acyl; optionally substituted hydroxyl; optionally substituted thiol; optionally substituted amino; azido; cyano; isocyano; halogen; or nitro;

each instance of q4, q5, and q6 is independently 0, 1, or 2;

$R_A$ is, independently; —$R_C$; —$OR_C$; —N($R_C$)$_2$; or —$SR_C$; wherein each instance of $R_C$ is, independently, hydrogen; cyclic or acyclic, branched or unbranched aliphatic; cyclic or acyclic, branched or unbranched heteroaliphatic; aryl; heteroaryl; acyl; a resin; a hydroxyl, amino, or thiol protecting group; or two $R_C$ groups together form a 5- to 6-membered heterocyclic or heteroaromatic ring;

$R_B$ is, independently, hydrogen; cyclic or acyclic, branched or unbranched aliphatic; cyclic or acyclic, branched or unbranched heteroaliphatic; aryl; heteroaryl; acyl; a resin; an amino protecting group; a label optionally joined by a linker, wherein the linker is selected from cyclic or acyclic, branched or unbranched alkylene; cyclic or acyclic, branched or unbranched alkenylene; cyclic or acyclic, branched or unbranched, alkynylene; cyclic or acyclic, branched or unbranched heteroalkylene; cyclic or acyclic, branched or unbranched heteroalkenylene; cyclic or acyclic, branched or unbranched heteroalkynylene; arylene; heteroarylene; or acylene; or $R_A$ and $R_B$ together form a 5- to 6-membered heterocyclic or heteroaromatic ring;

each of y and z is independently an integer between 1 and 10, inclusive;

$X_{B1}$ is absent or an amino acid of Formula (iii) or (iv);

$X_{B2}$ is a natural or unnatural amino acid; or an amino acid of Formula (iii), (iv), or (v);

$X_{B3}$ is amino acid F;

$X_{B4}$ is amino acid E;

$X_{B5}$ is a natural or unnatural amino acid; or an amino acid of Formula (iii), (iv), or (v);

$X_{B6}$ is a natural or unnatural amino acid; or an amino acid of Formula (iii), (iv), or (v);

$X_{B7}$ is amino acid L;

$X_{B8}$ is amino acid H;

$X_{B9}$ is amino acid N;

$X_{B10}$ is a natural or unnatural amino acid; or an amino acid of Formula (iii), (iv), or (v);

$X_{B11}$ is amino acid V or A;

$X_{B12}$ is amino acid F or A; and $X_{B13}$ is a natural or unnatural amino acid; or an amino acid of Formula (iii), (iv), or (v); and $X_{B14}$ is absent or an amino acid of Formula (iii) or (iv);

provided that the polypeptide comprises at least two occurrences of an amino acid of Formula (iii).

In certain embodiments, the precursor polypeptide comprising an alpha-helical segment, wherein the precursor polypeptide binds to the insulin receptor, and wherein the precursor polypeptide is of Formula (II-2):

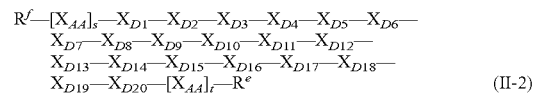

(II-2)

or a pharmaceutically acceptable salt thereof; wherein the polypeptide comprises at least two amino acids of Formula (iii), and optionally, at least one amino acid of Formula (iv):

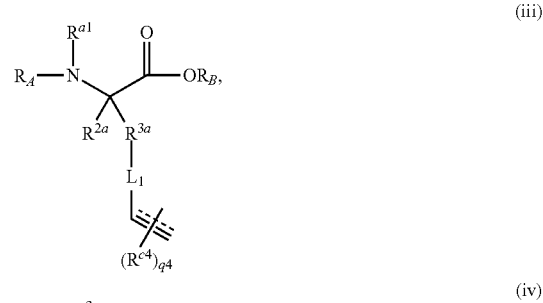

(iii)

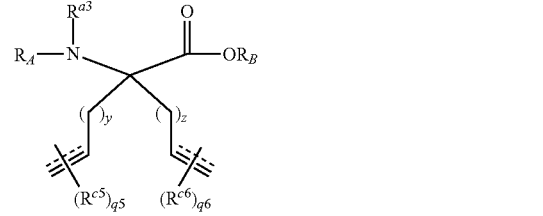

(iv)

wherein:

each instance of ========== independently represents a single bond, a double bond, or a triple bond;

each instance of $R^{a1}$ and $R^{a3}$ is, independently, hydrogen; acyl; optionally substituted $C_{1-6}$ alkyl; or an amino protecting group;

$R^{2a}$ is independently, optionally substituted alkyl; optionally substituted alkenyl; optionally substituted alkynyl; optionally substituted heteroalkyl; optionally substituted carbocyclyl; or optionally substituted heterocyclyl;

$R^{3a}$ is independently, optionally substituted alkylene; unsubstituted heteroalkylene; optionally substituted carbocyclylene; or optionally substituted heterocyclylene; or optionally $R^{2a}$ and $R^{3a}$ are joined to form a ring;

$L_1$ is independently, a bond, optionally substituted $C_{1-10}$ alkylene, or —C(=O)$OR^{L1}$—;

$R^{L1}$ is independently optionally substituted $C_{1-10}$ alkylene;

each instance of $R^{c4}$, $R^{c5}$, and $R^{c6}$ is independently hydrogen; optionally substituted aliphatic; optionally substituted heteroaliphatic; optionally substituted aryl; optionally substituted heteroaryl; acyl; optionally substituted hydroxyl; optionally substituted thiol; optionally substituted amino; azido; cyano; isocyano; halogen; or nitro;

each instance of q4, q5, and q6 is independently 0, 1, or 2;

$R_A$ is, independently; —$R_C$; —$OR_C$; —$N(R_C)_2$; or —$SR_C$; wherein each instance of $R_C$ is, independently, hydrogen; cyclic or acyclic, branched or unbranched aliphatic; cyclic or acyclic, branched or unbranched heteroaliphatic; aryl; heteroaryl; acyl; a resin; a hydroxyl, amino, or thiol protecting group; or two $R_C$ groups together form a 5- to 6-membered heterocyclic or heteroaromatic ring;

$R_B$ is, independently, hydrogen; cyclic or acyclic, branched or unbranched aliphatic; cyclic or acyclic, branched or unbranched heteroaliphatic; aryl; heteroaryl; acyl; a resin; an amino protecting group; a label optionally joined by a linker, wherein the linker is selected from cyclic or acyclic, branched or unbranched alkylene; cyclic or acyclic, branched or unbranched alkenylene; cyclic or acyclic, branched or unbranched, alkynylene; cyclic or acyclic, branched or unbranched heteroalkylene; cyclic or acyclic, branched or unbranched heteroalkenylene; cyclic or acyclic, branched or unbranched heteroalkynylene; arylene; heteroarylene; or acylene; or $R_A$ and $R_B$ together form a 5- to 6-membered heterocyclic or heteroaromatic ring;

each of y and z is independently an integer between 1 and 10, inclusive;

$X_{D1}$ is absent or an amino acid of Formula (iii) or (iv);

$X_{D2}$ is a natural or unnatural amino acid; or is an amino acid of Formula (iii), (iv), or (v);

$X_{D3}$ is a natural or unnatural amino acid; or is an amino acid of Formula (iii), (iv), or (v);

$X_{D4}$ is a natural or unnatural amino acid; or is an amino acid of Formula (iii), (iv), or (v);

$X_{D5}$ is amino acid R;

$X_{D6}$ is a natural or unnatural amino acid; or is an amino acid of Formula (iii), (iv), or (v);

$X_{D7}$ is amino acid T;

$X_{D8}$ is amino acid F;

$X_{D9}$ is amino acid E;

$X_{D10}$ is a natural or unnatural amino acid; or is an amino acid of Formula (iii), (iv), or (v);

$X_{D11}$ is a natural or unnatural amino acid; or is an amino acid of Formula (iii), (iv), or (v);

$X_{D12}$ is amino acid L;

$X_{D13}$ is amino acid H;

$X_{D14}$ is amino acid N;

$X_{D15}$ is a natural or unnatural amino acid; or an amino acid of Formula (iii), (iv), or (v);

$X_{D16}$ is amino acid V or A;

$X_{D17}$ is amino acid F;

$X_{D18}$ is amino acid V;

$X_{D19}$ is absent or amino acid W;

$X_{D20}$ is absent or an amino acid of Formula (iii) or (iv);

provided that the polypeptide comprises at least two occurrences of an amino acid of Formula (iii).

In certain embodiments, the precursor polypeptide of Formula (II-1) or Formula (II-2) comprises two independent occurrences of an amino acid of Formula (iii) separated by two (i,i+3) amino acids, three (i,i+4) amino acids, or six (i,i+7) amino acids, and/or one occurrence of Formula (iv) and two amino acids of Formula (iii) peripheral thereto each separated by three (i,i+4+4) amino acids, separated by two and three amino acids (i,i+3+4), separated by two and six amino acids (i,i+3+7), or separated by three and six (i,i+4+7) amino acids.

As used in Formula (II-1), $X_{B2}$ is a natural or unnatural amino acid; or an amino acid of Formula (iii), (iv), or (v). In certain embodiments, $X_{B2}$ is a natural or unnatural amino acid. In certain embodiments, $X_{B2}$ is an amino acid T. In certain embodiments, $X_{B2}$ is an amino acid S. In certain embodiments, $X_{B2}$ is an amino acid of Formula (iii), (iv), or (v).

As used in Formula (II-1), $X_{B5}$ is a natural or unnatural amino acid; or an amino acid of Formula (iii), (iv), or (v). In certain embodiments, $X_{B5}$ is a natural or unnatural amino acid. In certain embodiments, $X_{B5}$ is an amino acid D. In certain embodiments, $X_{B5}$ is an amino acid E. In certain embodiments, $X_{B5}$ is an amino acid of Formula (iii), (iv), or (v).

As used in Formula (II-1), $X_{B6}$ is a natural or unnatural amino acid; or an amino acid of Formula (iii), (iv), or (v). In certain embodiments, $X_{B6}$ is a natural or unnatural amino acid. In certain embodiments, $X_{B6}$ is an amino acid Y. In certain embodiments, $X_{B6}$ is an amino acid F. In certain embodiments, $X_{B6}$ is an amino acid W. In certain embodiments, $X_{B6}$ is an amino acid of Formula (iii), (iv), or (v).

As used in Formula (II-1), $X_{B10}$ is a natural or unnatural amino acid; or an amino acid of Formula (iii), (iv), or (v). In certain embodiments, $X_{B10}$ is a natural or unnatural amino acid. In certain embodiments, $X_{B10}$ is an amino acid V. In certain embodiments, $X_{B10}$ is an amino acid A. In certain embodiments, $X_{B10}$ is an amino acid I. In certain embodiments, $X_{B10}$ is an amino acid L. In certain embodiments, $X_{B10}$ is an amino acid of Formula (iii), (iv), or (v).

As used in Formula (II-1), $X_{B13}$ is a natural or unnatural amino acid; or an amino acid of Formula (iii), (iv), or (v). In certain embodiments, $X_{B13}$ is a natural or unnatural amino acid. In certain embodiments, $X_{B13}$ is an amino acid V. In certain embodiments, $X_{B13}$ is an amino acid A. In certain embodiments, $X_{B13}$ is an amino acid I. In certain embodiments, $X_{B13}$ is an amino acid L. In certain embodiments, $X_{B13}$ is an amino acid of Formula (iii), (iv), or (v).

In certain embodiments, the precursor polypeptide of Formula (II-1) has $X_{B2}$ as T, and/or $X_{B5}$ as D, and/or $X_{B6}$ as Y, and/or $X_{B10}$ as V or A; and/or $X_{B13}$ as V; provided that the polypeptide comprises at least two occurrences of an amino acid of Formula (iii).

Stapling of the precursor polypeptide of Formula (II-1) by ring closing metathesis, and optionally synthetically modifying the resulting double bond of the staple, provides a stapled or stitched polypeptide of Formula (I-1):

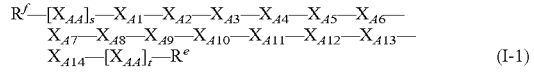

or a pharmaceutically acceptable salt thereof; wherein the polypeptide comprises at least one instance of two cross-linked amino acids of Formula (i):

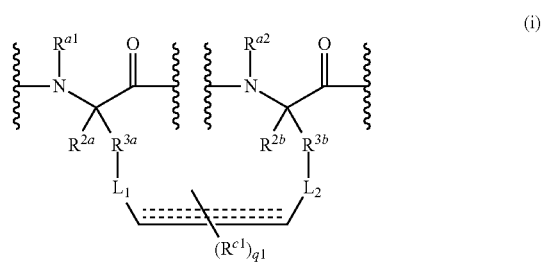

or at least one instance of three cross-linked amino acids of Formula (ii):

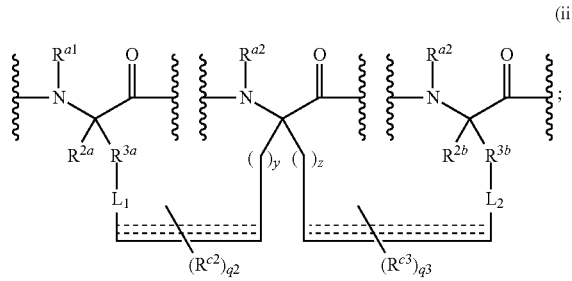

wherein:
each instance of ========== independently represents a single bond, a double bond, or a triple bond;
each instance of $R^{a1}$, $R^{a2}$, and $R^{a3}$ is, independently, hydrogen; acyl; optionally substituted $C_{1-6}$ alkyl; or an amino protecting group;
each of $R^{2a}$ and $R^{2b}$ is, independently, optionally substituted alkyl; optionally substituted alkenyl; optionally substituted alkynyl; optionally substituted heteroalkyl; optionally substituted carbocyclyl; optionally substituted heterocyclyl;
each of $R^{3a}$ and $R^{3b}$ is, independently, optionally substituted alkylene; unsubstituted heteroalkylene; optionally substituted carbocyclylene; or optionally substituted heterocyclylene; or optionally $R^{2a}$ and $R^{3a}$ are joined to form a ring; or optionally $R^{2b}$ and $R^{3b}$ are joined to form a ring;
$L_1$ is independently, a bond; optionally substituted $C_{1-10}$ alkylene; or —C(=O)O$R^{L1}$—;
$L_2$ is independently, a bond; optionally substituted $C_{1-10}$ alkylene; or —C(=O)O$R^{L2}$—;
each of $R^{L1}$ and $R^{L2}$ is independently optionally substituted $C_{1-10}$ alkylene;
each instance of $R^{c1}$, $R^{c2}$, and $R^{c3}$ is independently hydrogen; optionally substituted aliphatic; optionally substituted heteroaliphatic; optionally substituted aryl; optionally substituted heteroaryl; acyl; optionally substituted hydroxyl; optionally substituted thiol; optionally substituted amino; azido; cyano; isocyano; halogen; or nitro;
each instance of q1, q2, and q3 is independently 0, 1, or 2;
each of y and z is independently an integer between 1 and 10, inclusive;
each [$X_{AA}$] is independently a natural or unnatural amino acid;
s is 0 or an integer of between 1 to 50, inclusive;
t is 0 or an integer of between 1 to 50, inclusive;
$R^f$ is an N-terminal group selected from the group consisting of hydrogen; substituted and unsubstituted aliphatic; substituted and unsubstituted heteroaliphatic; substituted and unsubstituted aryl; substituted and unsubstituted heteroaryl; acyl; a resin; an amino protecting group; and a label optionally joined by a linker, wherein the linker is a group consisting of one or more combinations of substituted and unsubstituted alkylene; substituted and unsubstituted alkenylene; substituted and unsubstituted alkynylene; substituted and unsubstituted heteroalkylene; substituted and unsubstituted heteroalkenylene; substituted and unsubstituted heteroalkynylene; substituted and unsubstituted arylene; substituted and unsubstituted heteroarylene; and acylene;

$R^e$ is a C-terminal group selected from the group consisting of hydrogen; substituted and unsubstituted aliphatic; substituted and unsubstituted heteroaliphatic; substituted and unsubstituted aryl; substituted and unsubstituted heteroaryl; —OR$^E$; —N(R$^E$)$_2$; and —SR$^E$, wherein each instance of R$^E$ is, independently, hydrogen; optionally substituted aliphatic; optionally substituted heteroaliphatic; optionally substituted aryl; optionally substituted heteroaryl; acyl; a resin; a protecting group; or two R$^E$ groups taken together form an optionally substituted heterocyclic or optionally substituted heteroaryl ring;
$X_{A1}$ is absent or is an amino acid which forms together with another amino acid a crosslink of Formula (i);
$X_{A2}$ is a natural or unnatural amino acid; or is an amino acid which forms together with another amino acid a crosslink of Formula (i); or is an amino acid which forms together with two other amino acids a crosslink of Formula (ii);
$X_{A3}$ is amino acid F;
$X_{A4}$ is amino acid E;
$X_{A5}$ is a natural or unnatural amino acid; or is an amino acid which forms together with another amino acid a crosslink of Formula (i), or is an amino acid which forms together with two other amino acids a crosslink of Formula (ii);
$X_{A6}$ is a natural or unnatural amino acid; or is an amino acid which forms together with another amino acid a crosslink of Formula (i), or is an amino acid which forms together with two other amino acids a crosslink of Formula (ii);
$X_{A7}$ is amino acid L;
$X_{A8}$ is amino acid H;
$X_{A9}$ is amino acid N;
$X_{A10}$ is a natural or unnatural amino acid; or is an amino acid which forms together with another amino acid a crosslink of Formula (i), or is an amino acid which forms together with two other amino acids a crosslink of Formula (ii);
$X_{A11}$ is amino acid V or A;
$X_{A12}$ is amino acid F or A; and
$X_{A13}$ is a natural or unnatural amino acid; or is an amino acid which forms together with another amino acid a crosslink of Formula (i), or is an amino acid which forms together with two other amino acids a crosslink of Formula (ii); and
$X_{A14}$ is absent or is an amino acid which forms together with another amino acid a crosslink of Formula (i).
Stapling of the precursor polypeptide of Formula (II-2) by ring closing metathesis, and optionally synthetically modifying the resulting double bond of the staple, provides a stapled or stitched polypeptide of Formula (I-2):

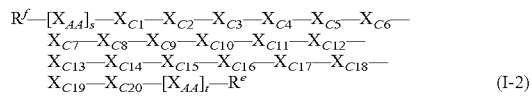

or a pharmaceutically acceptable salt thereof;
and wherein the polypeptide comprises at least one instance of two cross-linked amino acids of Formula (i):

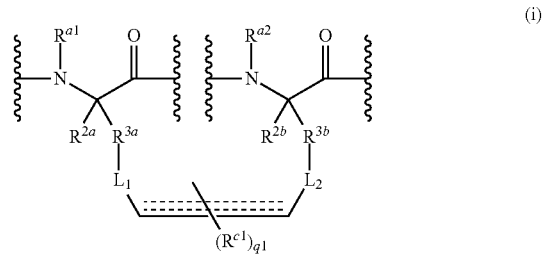

or at least one instance of three cross-linked amino acids of Formula (ii):

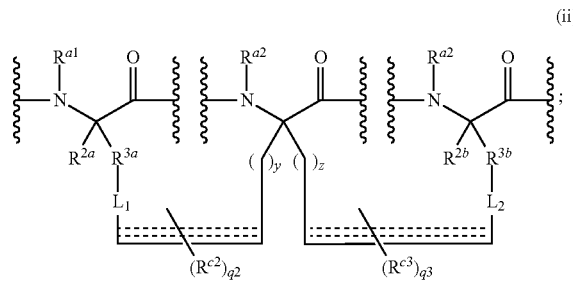

wherein:

each instance of ========== independently represents a single bond, a double bond, or a triple bond;

each instance of $R^{a1}$, $R^{a2}$, and $R^{a3}$, is, independently, hydrogen; acyl; optionally substituted $C_{1-6}$ alkyl; or an amino protecting group;

each of $R^{2a}$ and $R^{2b}$ is, independently, optionally substituted alkyl; optionally substituted alkenyl; optionally substituted alkynyl; optionally substituted heteroalkyl; optionally substituted carbocyclyl; optionally substituted heterocyclyl;

each of $R^{3a}$ and $R^{3b}$ is, independently, optionally substituted alkylene; unsubstituted heteroalkylene; optionally substituted carbocyclylene; or optionally substituted heterocyclylene; or optionally $R^{2a}$ and $R^{3a}$ are joined to form a ring; or optionally $R^{2b}$ and $R^{3b}$ are joined to form a ring;

$L_1$ is independently, a bond; optionally substituted $C_{1-10}$ alkylene; or —C(=O)OR$^{L1}$—;

$L_2$ is independently, a bond; optionally substituted $C_{1-10}$ alkylene; or —C(=O)OR$^{L2}$—;

each of $R^{L1}$ and $R^{L2}$ is independently optionally substituted $C_{1-10}$ alkylene;

each instance of $R^{c1}$, $R^{c2}$, and $R^{c3}$ is independently hydrogen; optionally substituted aliphatic; optionally substituted heteroaliphatic; optionally substituted aryl; optionally substituted heteroaryl; acyl; optionally substituted hydroxyl; optionally substituted thiol; optionally substituted amino; azido; cyano; isocyano; halogen; or nitro;

each instance of q1, q2, and q3 is independently 0, 1, or 2;

each of y and z is independently an integer between 1 and 10, inclusive;

each [$X_{AA}$] is independently a natural or unnatural amino acid;

s is 0 or an integer of between 1 to 50, inclusive;

t is 0 or an integer of between 1 to 50, inclusive;

$R^f$ is an N-terminal group selected from the group consisting of hydrogen; substituted and unsubstituted aliphatic; substituted and unsubstituted heteroaliphatic; substituted and unsubstituted aryl; substituted and unsubstituted heteroaryl; acyl; a resin; an amino protecting group; and a label optionally joined by a linker, wherein the linker is a group consisting of one or more combinations of substituted and unsubstituted alkylene; substituted and unsubstituted alkenylene; substituted and unsubstituted alkynylene; substituted and unsubstituted heteroalkylene; substituted and unsubstituted heteroalkenylene; substituted and unsubstituted heteroalkynylene; substituted and unsubstituted arylene; substituted and unsubstituted heteroarylene; and acylene;

$R^e$ is a C-terminal group selected from the group consisting of hydrogen; substituted and unsubstituted aliphatic; substituted and unsubstituted heteroaliphatic; substituted and unsubstituted aryl; substituted and unsubstituted heteroaryl; —OR$^E$; —N(R$^E$)$_2$; and —SR$^E$, wherein each instance of R$^E$ is, independently, hydrogen; optionally substituted aliphatic; optionally substituted heteroaliphatic; optionally substituted aryl; optionally substituted heteroaryl; acyl; a resin; a protecting group; or two R$^E$ groups taken together form an optionally substituted heterocyclic or optionally substituted heteroaryl ring;

$X_{C1}$ is absent or is an amino acid which forms together with another amino acid a crosslink of Formula (i);

$X_{C2}$ is a natural or unnatural amino acid; or is an amino acid which forms together with another amino acid a crosslink of Formula (i); or is an amino acid which forms together with two other amino acids a crosslink of Formula (ii);

$X_{C3}$ is a natural or unnatural amino acid; or is an amino acid which forms together with another amino acid a crosslink of Formula (i); or is an amino acid which forms together with two other amino acids a crosslink of Formula (ii);

$X_{C4}$ is a natural or unnatural amino acid; or is an amino acid which forms together with another amino acid a crosslink of Formula (i); or is an amino acid which forms together with two other amino acids a crosslink of Formula (ii);

$X_{C5}$ is amino acid R;

$X_{C6}$ is a natural or unnatural amino acid; or is an amino acid which forms together with another amino acid a crosslink of Formula (i), or is an amino acid which forms together with two other amino acids a crosslink of Formula (ii);

$X_{C7}$ is amino acid T;

$X_{C8}$ is amino acid F;

$X_{C9}$ is amino acid E;

$X_{C10}$ is a natural or unnatural amino acid; or is an amino acid which forms together with another amino acid a crosslink of Formula (i), or is an amino acid which forms together with two other amino acids a crosslink of Formula (ii);

$X_{C11}$ is a natural or unnatural amino acid; or is an amino acid which forms together with another amino acid a crosslink of Formula (i), or is an amino acid which forms together with two other amino acids a crosslink of Formula (ii);

$X_{C12}$ is amino acid L;

$X_{C13}$ is amino acid H;

$X_{C14}$ is amino acid N;

$X_{C15}$ is a natural or unnatural amino acid; or is an amino acid which forms together with another amino acid a crosslink of Formula (i), or is an amino acid which forms together with two other amino acids a crosslink of Formula (ii);

$X_{C16}$ is amino acid V;

$X_{C17}$ is amino acid F;

$X_{C18}$ is amino acid V;

$X_{C19}$ is absent or amino acid W;

$X_{C20}$ is absent or is an amino acid which forms together with another amino acid a crosslink of Formula (i).

In certain embodiments of Formula (I-1) or Formula (I-2), the polypeptide comprises at least one staple of Formula (i) at the i,i+3 position, the i,i+4 position, or the i,i+7 position; and/or at least one stitch of Formula (ii) at the i,i+4+4 position, the i,i+3+4 position, the i,i+3+7 position, or the i,i+4+7 position.

As generally understood herein, the amino acid regions of Formula (I-1) [$X_{A1}$—$X_{A2}$—$X_{A3}$—$X_{A4}$—$X_{A5}$—$X_{A6}$—$X_{A7}$—$X_{A8}$—$X_{A9}$—$X_{A10}$—$X_{A11}$—$X_{A12}$—$X_{A13}$—$X_{A14}$] and Formula (II-1) [$X_{B1}$—$X_{B2}$—$X_{B3}$—$X_{B4}$—$X_{B5}$—$X_{B6}$—$X_{B7}$—$X_{B8}$—$X_{B9}$—$X_{B10}$—$X_{B11}$—$X_{B12}$—$X_{B13}$—$X_{B14}$] adopt an alpha-helical secondary structure, and stapling or stitching further stabilizes this structure.

As used in Formula (I-1), $X_{A2}$ is a natural or unnatural amino acid; or is an amino acid which forms together with another amino acid a crosslink of Formula (i); or is an amino acid which forms together with two other amino acids a crosslink of Formula (ii). In certain embodiments, $X_{A2}$ is a natural or unnatural amino acid. In certain embodiments, $X_{A2}$ is an amino acid T. In certain embodiments, $X_{A2}$ is an amino acid S. In certain embodiments, $X_{A2}$ is an amino acid which forms together with another amino acid a crosslink of Formula (i); or is an amino acid which forms together with two other amino acids a crosslink of Formula (ii).

As used in Formula (I-1), $X_{A5}$ is a natural or unnatural amino acid; or is an amino acid which forms together with another amino acid a crosslink of Formula (i); or is an amino acid which forms together with two other amino acids a crosslink of Formula (ii). In certain embodiments, $X_{A5}$ is a natural or unnatural amino acid. In certain embodiments, $X_{A5}$ is an amino acid D. In certain embodiments, $X_{A5}$ is an amino acid E. In certain embodiments, $X_{A5}$ is an amino acid which forms together with another amino acid a crosslink of Formula (i); or is an amino acid which forms together with two other amino acids a crosslink of Formula (ii).

As used in Formula (I-1), $X_{A6}$ is a natural or unnatural amino acid; or is an amino acid which forms together with another amino acid a crosslink of Formula (i); or is an amino acid which forms together with two other amino acids a crosslink of Formula (ii). In certain embodiments, $X_{A6}$ is a natural or unnatural amino acid. In certain embodiments, $X_{A6}$ is an amino acid Y. In certain embodiments, $X_{A6}$ is an amino acid F. In certain embodiments, $X_{A6}$ is an amino acid W. In certain embodiments, $X_{A6}$ is an amino acid which forms together with another amino acid a crosslink of Formula (i); or is an amino acid which forms together with two other amino acids a crosslink of Formula (ii).

As used in Formula (I-1), $X_{A10}$ is a natural or unnatural amino acid; or is an amino acid which forms together with another amino acid a crosslink of Formula (i); or is an amino acid which forms together with two other amino acids a crosslink of Formula (ii). In certain embodiments, $X_{A10}$ is a natural or unnatural amino acid. In certain embodiments, $X_{A10}$ is an amino acid V. In certain embodiments, $X_{A10}$ is an amino acid A. In certain embodiments, $X_{A10}$ is an amino acid I. In certain embodiments, $X_{A10}$ is an amino acid L. In certain embodiments, $X_{A10}$ is an amino acid which forms together with another amino acid a crosslink of Formula (i); or is an amino acid which forms together with two other amino acids a crosslink of Formula (ii).

As used in Formula (I-1), $X_{A13}$ is a natural or unnatural amino acid; or is an amino acid which forms together with another amino acid a crosslink of Formula (i); or is an amino acid which forms together with two other amino acids a crosslink of Formula (ii). In certain embodiments, $X_{A13}$ is a natural or unnatural amino acid. In certain embodiments, $X_{A13}$ is an amino acid V. In certain embodiments, $X_{A13}$ is an amino acid A. In certain embodiments, $X_{A13}$ is an amino acid I. In certain embodiments, $X_{A13}$ is an amino acid L. In certain embodiments, $X_{A13}$ is an amino acid which forms together with another amino acid a crosslink of Formula (i); or is an amino acid which forms together with two other amino acids a crosslink of Formula (ii).

As generally understood herein, the amino acid regions of Formula (I-2) $[X_{C1}-X_{C2}-X_{C3}-X_{C4}-X_{C5}-X_{C6}-X_{C7}-X_{C8}-X_{C9}-X_{C10}-X_{C11}-X_{C12}-X_{C13}-X_{C14}-X_{C15}-X_{C16}-X_{C17}-X_{C18}-X_{C19}-X_{C20}]$ and Formula (II-2) $[X_{D1}-X_{D2}-X_{D3}-X_{D4}-X_{D5}-X_{D6}-X_{D7}-X_{D8}-X_{D9}-X_{D10}-X_{D11}-X_{D12}-X_{D13}-X_{D14}-X_{D15}-X_{D16}-X_{D17}-X_{D18}-X_{D19}-X_{D20}]$ adopt an alpha-helical secondary structure, and stapling or stitching further stabilizes this structure.

As used in Formula (I-2), $X_{C2}$ is a natural or unnatural amino acid; or is an amino acid which forms together with another amino acid a crosslink of Formula (i); or is an amino acid which forms together with two other amino acids a crosslink of Formula (ii). In certain embodiments, $X_{C2}$ is a natural or unnatural amino acid. In certain embodiments, $X_{C2}$ is an amino acid S. In certain embodiments, $X_{C2}$ is an amino acid T. In certain embodiments, $X_{C2}$ is an amino acid which forms together with another amino acid a crosslink of Formula (i); or is an amino acid which forms together with two other amino acids a crosslink of Formula (ii).

As used in Formula (I-2), $X_{C3}$ is a natural or unnatural amino acid; or is an amino acid which forms together with another amino acid a crosslink of Formula (i); or is an amino acid which forms together with two other amino acids a crosslink of Formula (ii). In certain embodiments, $X_{C3}$ is a natural or unnatural amino acid. In certain embodiments, $X_{C3}$ is an amino acid S. In certain embodiments, $X_{C3}$ is an amino acid T. In certain embodiments, $X_{C3}$ is an amino acid which forms together with another amino acid a crosslink of Formula (i); or is an amino acid which forms together with two other amino acids a crosslink of Formula (ii).

As used in Formula (I-2), $X_{C4}$ is a natural or unnatural amino acid; or is an amino acid which forms together with another amino acid a crosslink of Formula (i); or is an amino acid which forms together with two other amino acids a crosslink of Formula (ii). In certain embodiments, $X_{C4}$ is a natural or unnatural amino acid. In certain embodiments, $X_{C4}$ is an amino acid F. In certain embodiments, $X_{C4}$ is an amino acid Y. In certain embodiments, $X_{C4}$ is an amino acid W. In certain embodiments, $X_{C4}$ is an amino acid which forms together with another amino acid a crosslink of Formula (i); or is an amino acid which forms together with two other amino acids a crosslink of Formula (ii).

As used in Formula (I-2), $X_{C6}$ is a natural or unnatural amino acid; or is an amino acid which forms together with another amino acid a crosslink of Formula (i); or is an amino acid which forms together with two other amino acids a crosslink of Formula (ii). In certain embodiments, $X_{C6}$ is a natural or unnatural amino acid. In certain embodiments, $X_{C6}$ is an amino acid K. In certain embodiments, $X_{C6}$ is an amino acid R. In certain embodiments, $X_{C6}$ is an amino acid H. In certain embodiments, $X_{C6}$ is an amino acid which forms together with another amino acid a crosslink of Formula (i); or is an amino acid which forms together with two other amino acids a crosslink of Formula (ii).

As used in Formula (I-2), $X_{C10}$ is a natural or unnatural amino acid; or is an amino acid which forms together with another amino acid a crosslink of Formula (i); or is an amino acid which forms together with two other amino acids a crosslink of Formula (ii). In certain embodiments, $X_{C10}$ is a natural or unnatural amino acid. In certain embodiments, $X_{C10}$ is an amino acid D. In certain embodiments, $X_{C10}$ is an amino acid E. In certain embodiments, $X_{C10}$ is an amino acid which forms together with another amino acid a crosslink of Formula (i); or is an amino acid which forms together with two other amino acids a crosslink of Formula (ii).

As used in Formula (I-2), $X_{C11}$ is a natural or unnatural amino acid; or is an amino acid which forms together with another amino acid a crosslink of Formula (i); or is an amino acid which forms together with two other amino acids a crosslink of Formula (ii). In certain embodiments, $X_{C11}$ is a natural or unnatural amino acid. In certain embodiments, $X_{C11}$ is an amino acid Y. In certain embodiments, $X_{C11}$ is an amino acid F. In certain embodiments, $X_{C11}$ is an amino acid W. In certain embodiments, $X_{C11}$ is an amino acid which forms together with another amino acid a crosslink of Formula (i); or is an amino acid which forms together with two other amino acids a crosslink of Formula (ii).

As used in Formula (I-2), $X_{C15}$ is a natural or unnatural amino acid; or is an amino acid which forms together with another amino acid a crosslink of Formula (i); or is an amino acid which forms together with two other amino acids a crosslink of Formula (ii). In certain embodiments, $X_{C15}$ is a natural or unnatural amino acid. In certain embodiments, $X_{C15}$ is an amino acid V. In certain embodiments, $X_{C15}$ is an amino acid A. In certain embodiments, $X_{C15}$ is an amino acid I. In certain embodiments, $X_{C15}$ is an amino acid L. In certain embodiments, $X_{C15}$ is an amino acid which forms together with another amino acid a crosslink of Formula (i); or is an amino acid which forms together with two other amino acids a crosslink of Formula (ii).

In another aspect, provided herein are stabilized insulin α-CT polypeptides comprising an α-CT base sequence and at least one instance of two cross-linked amino acids, wherein the two cross-linked amino acids are embedded in the α-CT base sequence and separated by at least two amino acids.

In certain embodiments, the α-CT base sequence is a wild α-CT sequence. In certain embodiments, the α-CT base sequence is derived from a wild α-CT sequence. In certain embodiments, the α-CT base sequence is a segment of a wild α-CT sequence. In certain embodiments, the α-CT base sequence is TFEDYLHNVVFV (SEQ ID NO:1). In certain embodiments, the α-CT base sequence is a mutant α-CT sequence. In certain embodiments, the α-CT base sequence is TFEDYLHNAAFV (SEQ ID NO:2). In certain embodiments, the α-CT base sequence is a synthetic α-CT sequence. In certain embodiments, the α-CT base sequence is SSFRKTFEDYLHNVVFVW (SEQ ID NO:3) or Ac-SSFRKTFEDYLHNVVFVW (SEQ ID NO:82). In certain embodiments, the α-CT base sequence is SSFRK-TFEDYLHNVVFV SEQ ID NO:5) or Ac-SSFRK-TFEDYLHNVVFV (SEQ ID NO:84). In certain embodiments, the α-CT base sequence is SSFRKTFEDYLHNAAFVW (SEQ ID NO:4) or Ac-SS-FRKTFEDYLHNAAFVW (SEQ ID NO:83). In certain embodiments, the α-CT base sequence is SSFRK-TFEDYLHNAAFV (SEQ ID NO:6) or Ac-SSFRK-TFEDYLHNAAFV (SEQ ID NO:85). In certain embodiments, the α-CT base sequence is Ac-TFEDYLHNVVFV (SEQ ID NO:81). In certain embodiments, the α-CT base sequence is Ac-TFEDYLHNVVFVW (SEQ ID NO:80).

In certain embodiments of the stabilized insulin α-CT polypeptides, each instance of the two cross-linked amino acids is independently of Formula (i), wherein Formula (i) is as defined herein. In certain embodiments, the stabilized insulin α-CT polypeptides further comprise at least one instance of three cross-linked amino acids of Formula (ii), wherein Formula (ii) is as defined herein. In certain embodiments, the stabilized insulin α-CT polypeptides comprise at least one instance of two cross-linked amino acids are of Formula (i) and at least one instance of three cross-linked amino acids of Formula (ii), wherein Formula (i) and Formula (ii) are as defined herein. In certain embodiments, the stabilized insulin α-CT polypeptides comprise one instance of two cross-linked amino acids are of Formula (i) and one instance of three cross-linked amino acids of Formula (ii), wherein Formula (i) and Formula (ii) are as defined herein.

In certain embodiments, the two cross-linked amino acids of each instance are independently separated by two, three, or six amino acids. In certain embodiments, the two cross-linked amino acids of each instance are independently separated by two, three, or six amino acids of the α-CT base sequence. In certain embodiments, the two cross-linked amino acids of each instance are independently separated by two amino acids (i,i+3) of the α-CT base sequence. In certain embodiments, the two cross-linked amino acids of each instance are independently separated by three amino acids (i,i+4) of the α-CT base sequence. In certain embodiments, the two cross-linked amino acids of each instance are independently separated by six amino acids (i,i+7) of the α-CT base sequence.

In certain embodiments, the three cross-linked amino acids in each instance are independently separated by two and three, two and six, three and three, three and six, or six and six amino acids. In certain embodiments, the three cross-linked amino acids in each instance are independently separated by two and three, two and six, three and three, three and six, or six and six amino acids of the α-CT base sequence. In certain embodiments, the three cross-linked amino acids in each instance are independently separated by two and three (i,i+3,i+7) amino acids. In certain embodiments, the three cross-linked amino acids in each instance are independently separated by two and six (i,i+3,i+10) amino acids of the α-CT base sequence. In certain embodiments, the three cross-linked amino acids in each instance are independently separated by three and three (i,i+4,i+8) amino acids of the α-CT base sequence. In certain embodiments, the three cross-linked amino acids in each instance are independently separated by six and six (i,i+7,i+14) amino acids of the α-CT base sequence. In certain embodiments, the three cross-linked amino acids in each instance are independently separated by six and six (i,i+4,i+11) amino acids of the α-CT base sequence. In certain embodiments, the three cross-linked amino acids in each instance are independently separated by six and six (i,i+7,i+11) amino acids of the α-CT base sequence.

In certain embodiments, the two cross-linked amino acids in each instance are independently separated by two, three, or six amino acids, and the three cross-linked amino acids in each instance are independently separated by two and three, two and six, three and three, three and six, or six and six amino acids.

Substitution of an amino acid for another amino acid with similar chemical properties is contemplated by the present invention. For example, methionine (M), alanine (A), leucine (L), glutamate (E), and lysine (K) have especially high alpha-helix forming propensities. In contrast, proline (P) and glycine (G) are alpha-helix disrupters, but proline (P) has also been found to be an initiator of alpha-helix formation. Arginine (R), histidine (H), and lysine (L) contain amino functionalized side chains, which are basic and may be positively charged. Aspartic acid (D) and glutamic acid (E) contain carboxylic acid ($-CO_2H$) functionalized side chains, which are acidic and may be negatively charged at physiological pH. Serine (S) and threonine (T) each contain hydroxyl ($-OH$) functionalized side chains. Asaparagine (N) and glutamine (G) each contain amide ($-CONH_2$) functionalized side chains. Alanine (A), valine (V), isoleucine (I), leucine (L), methionine (M), phenylalanine (F), and tryptophan (W) are classified as hydrophobic. Phenylalanine (F), tyrosine (Y), tryptophan (W), and histidine (H) include aromatic side chains.

Figure 5A:
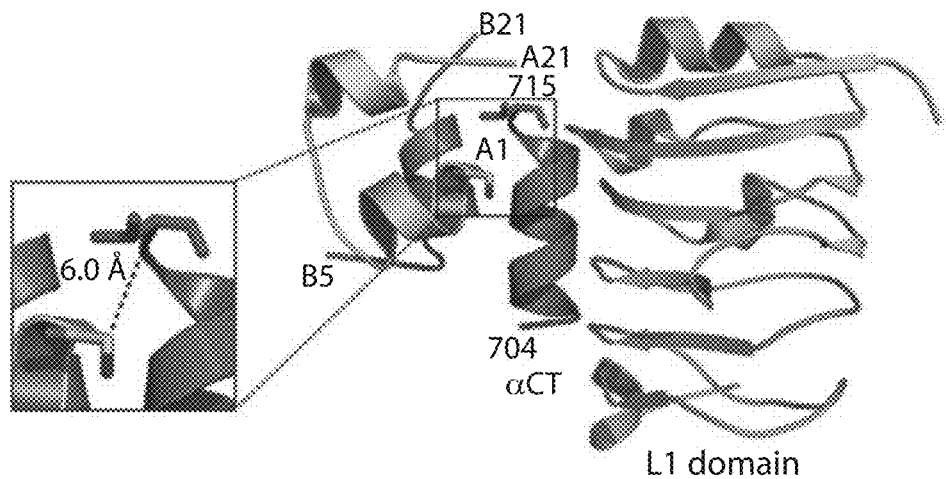
FIG. 5A depicts the structure of the complex formed between insulin, αCT, and the L1 domain of the insulin receptor. Inset: The distance between the N-terminus of the insulin A chain and the C-terminus of αCT is approximately 6 Å (PDB: 3W14).
Figure 5B:
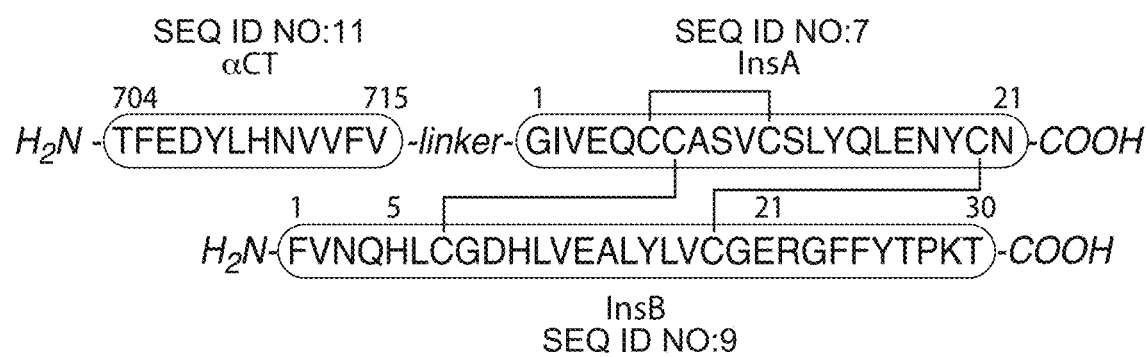
FIG. 5B is a schematic representation of an insulin analogue as an insulin/αCT chimera. The insulin A chain and αCT are fused via a chemical linker.

The present invention contemplates one or more point mutations to the amino acid sequences, as recited above and herein, by substitution of one or more amino acids for one or more different amino acids. In certain embodiments, the polypeptide includes one, two, three, four, or five point mutations. In certain embodiments, these point mutations may be conservative changes as described in the preceding paragraph (e.g., mutation of a serine to a threonine). In certain embodiments, the polypeptide includes one, two, three, four, five, or more additional amino acids. In certain embodiments, the polypeptide has one, two, three, four, or five amino acids removed from the sequence. In certain embodiments, the resulting amino acid sequence is at least 90%, at least 95%, at least 97%, at least 98%, or at least 99% homologous or identical to the amino acid sequence described herein; see, for example, the amino acids sequences depicted in FIG. 5. In certain embodiments, the polypeptides may be further modified to increase cell permeability, for example, by a) introducing an additional R, Q, or W residue, and/or b) adding one or more additional R, Q, or W residues at the N- and/or C-terminus of the polypeptide.

Method of synthesizing the cross-linked amino acids of Formula (i) or (ii) and the precursor polypeptide of Formula (iii) or (iv) are as described in U.S. Provisional Application Nos. 61/708,371, filed on Oct. 1, 2012, 61/779,917 filed on Mar. 13, 2013, 61/705,950, filed on Sep. 26, 2012, 61/789,157, filed Mar. 15, 2013, and International Application No. PCT/US2008/058575, filed on Mar. 28, 2008, all of which are incorporated by references herein. Additional description of the stapling and/or stitching technology can be found in U.S. Pat. Nos. 7,192,713; 7,723,469; 7,786,072; U.S. Patent Application Publication Nos: 2010-0184645; 2010-0168388; 2010-0081611; 2009-0176964; 2009-0149630; and 2006-0008848; PCT Application Publication Nos: WO 2010/011313; WO 2008/121767; WO 2008/095063; WO 2008/061192; and WO 2005/044839, as well as PCT Application No. PCT/US2014/025544; all of which are incorporated by reference herein.

Groups $R^f$ and $R^e$

As generally defined above for Formula (I-1), (I-2), (II-1), and (II-2), $R^f$ is an N-terminal group selected from the group consisting of hydrogen; substituted and unsubstituted aliphatic; substituted and unsubstituted heteroaliphatic; substituted and unsubstituted aryl; substituted and unsubstituted heteroaryl; acyl; a resin; an amino protecting group; and a label optionally joined to the polypeptide by a linker, wherein the linker is a group consisting of a combination of one or more of substituted and unsubstituted alkylene; substituted and unsubstituted alkenylene; substituted and unsubstituted alkynylene; substituted and unsubstituted heteroalkylene; substituted and unsubstituted heteroalkenylene; substituted and unsubstituted heteroalkynylene; substituted and unsubstituted arylene; substituted and unsubstituted heteroarylene; and acylene.

In certain embodiments, $R^f$ is hydrogen to provide a —$NH_2$ end group. In certain embodiments, $R^f$ is substituted or unsubstituted aliphatic (e.g., —$CH_3$, —$CH_2CH_3$). In certain embodiments, $R^f$ is substituted or unsubstituted heteroaliphatic. In certain embodiments, $R^f$ is substituted or unsubstituted aryl. In certain embodiments, $R^f$ is substituted or unsubstituted heteroaryl. In certain embodiments, $R^f$ is acyl (e.g., acetyl (—$COCH_3$)). In certain embodiments, $R^f$ is a resin. In certain embodiments, $R^f$ is an amino protecting group (e.g., -Boc, -Fmoc).

In certain embodiments, $R^f$ comprises a label optionally joined by a linker to the polypeptide, wherein the linker is a group consisting of a combination of one or more of substituted and unsubstituted alkylene; substituted and unsubstituted alkenylene; substituted and unsubstituted alkynylene; substituted and unsubstituted heteroalkylene; substituted and unsubstituted heteroalkenylene; substituted and unsubstituted heteroalkynylene; substituted and unsubstituted arylene; substituted and unsubstituted heteroarylene; and acylene. Exemplary labels include, but are not limited to, FITC and biotin.

In certain embodiments, $R^f$ is a label directly joined to the polypeptide (i.e., through a bond). In certain embodiments, $R^f$ is a label indirectly joined to the polypeptide through a linker, wherein the linker is selected from the group consisting of substituted and unsubstituted alkylene; substituted and unsubstituted alkenylene; substituted and unsubstituted alkynylene; substituted and unsubstituted heteroalkylene; substituted and unsubstituted heteroalkenylene; substituted and unsubstituted heteroalkynylene; substituted and unsubstituted arylene; substituted and unsubstituted heteroarylene; acylene; and combinations thereof.

In some embodiments, the linker joining the label to the polypeptide is substituted or unsubstituted alkylene. In some embodiments, the linker is substituted or unsubstituted alkenylene. In some embodiments, the linker is substituted or unsubstituted alkynylene. In some embodiments, the linker is substituted or unsubstituted heteroalkylene. In some embodiments, the linker is substituted or unsubstituted heteroalkenylene. In some embodiments, the linker is substituted or unsubstituted heteroalkynylene. In some embodiments, the linker is substituted or unsubstituted arylene. In some embodiments, the linker is substituted or unsubstituted heteroarylene. In certain embodiments, the linker is acylene.

As generally defined above for Formula (I-1), (I-2), (II), or (II-2), $R^e$ is a C-terminal group selected from the group consisting of hydrogen; substituted and unsubstituted aliphatic; substituted and unsubstituted heteroaliphatic; substituted and unsubstituted aryl; substituted and unsubstituted heteroaryl; —$OR^E$, —$N(R^E)_2$, and —$SR^E$, wherein each instance of $R^E$ is, independently, hydrogen; substituted or unsubstituted aliphatic; substituted or unsubstituted heteroaliphatic; substituted or unsubstituted aryl; substituted or unsubstituted heteroaryl; acyl; a resin; a protecting group; or two $R^E$ groups taken together form a substituted or unsubstituted heterocyclic or substituted or unsubstituted heteroaryl ring.

In certain embodiments, $R^e$ is hydrogen, e.g., to provide an aldehyde (—CHO) as the C-terminal group. In certain embodiments, $R^e$ is substituted or unsubstituted aliphatic; substituted or unsubstituted heteroaliphatic; substituted or unsubstituted aryl; or substituted or unsubstituted heteroaryl in order to provide a ketone as the C-terminal group.

In certain embodiments, $R^e$ is —$OR^E$, and $R^E$ is hydrogen; substituted or unsubstituted aliphatic; substituted or unsubstituted heteroaliphatic; substituted or unsubstituted aryl; substituted or unsubstituted heteroaryl; acyl; a resin; or a hydroxyl protecting group, e.g., to provide a carboxylic acid or ester C-terminal group. In certain embodiments, $R^e$ is —OH, e.g., to provide a carboxylic acid (—$CO_2H$) as the C-terminal group. In some embodiments, $R^e$ is —$OCH_3$.

In certain embodiments, $R^e$ is —$SR^E$, and $R^E$ is hydrogen; substituted or unsubstituted aliphatic; substituted or unsubstituted heteroaliphatic; substituted or unsubstituted aryl; substituted or unsubstituted heteroaryl; acyl; a resin; or a suitable thiol protecting group, e.g., to provide a thioacid or thioester C-terminal group.

In certain embodiments, $R^e$ is —$N(R^E)_2$, and each instance of $R^E$ is, independently, hydrogen; substituted or unsubstituted aliphatic; substituted or unsubstituted heteroaliphatic; substituted or unsubstituted aryl; substituted or unsubstituted heteroaryl; acyl; a resin; an amino protecting group; or two $R^E$ groups together form a substituted or unsubstituted 5- to 6-membered heterocyclic or heteroaromatic ring, e.g., to provide an amide as the C-terminal group. In certain embodiments, $R^e$ is —NH$_2$.

In certain embodiments, $R^f$ is acyl and $R^e$ is hydrogen.

Groups $R^{2a}$, $R^{2b}$, $R^{3a}$, $R^{3b}$, $L_1$, and $L_2$

As generally defined above, $R^{2a}$ is, independently, substituted or unsubstituted alkyl; substituted or unsubstituted alkenyl; substituted or unsubstituted alkynyl; substituted or unsubstituted heteroalkyl; substituted or unsubstituted carbocyclyl; substituted or unsubstituted heterocyclyl. In certain embodiments, $R^{2a}$ is substituted or unsubstituted $C_{1-10}$alkyl. In certain embodiments, $R^{2a}$ is substituted methyl. In certain embodiments, $R^{2a}$ is unsubstituted methyl. In certain embodiments, $R^{2a}$ is substituted ethyl. In certain embodiments, $R^{2a}$ is unsubstituted ethyl. In certain embodiments, $R^{2a}$ is substituted n-propyl. In certain embodiments, $R^{2a}$ is unsubstituted n-propyl. In certain embodiments, $R^{2a}$ is substituted iso-propyl. In certain embodiments, $R^{2a}$ is unsubstituted iso-propyl. In certain embodiments, $R^{2a}$ is substituted or unsubstituted heteroalkyl. In certain embodiments, $R^{2a}$ is substituted or unsubstituted heteroalkyl with at least one nitrogen. In certain embodiments, $R^{2a}$ is unsubstituted heteroalkyl containing at least one nitrogen. In certain embodiments, $R^{2a}$ is substituted heteroalkyl containing at least one nitrogen.

As generally defined above, $R^{3a}$ is independently substituted or unsubstituted alkylene; substituted or unsubstituted heteroalkylene; substituted or unsubstituted carbocyclylene; or substituted or unsubstituted heterocyclylene; or optionally $R^{2a}$, $R^{3a}$ and the carbon to which $R^{2a}$ and $R^{3a}$ are attached are joined to form a ring. In certain embodiments, $R^{3a}$ is substituted or unsubstituted alkylene. In certain embodiments, $R^{3a}$ is substituted or unsubstituted $C_{1-10}$ alkylene. In certain embodiments, $R^{3a}$ is substituted $C_{1-10}$ alkylene. In certain embodiments, $R^{3a}$ is unsubstituted $C_{1-10}$ alkylene. In certain embodiments, $R^{3a}$ is substituted or unsubstituted heteroalkylene. In certain embodiments, $R^{3a}$ is substituted heteroalkylene. In certain embodiments, $R^{3a}$ is unsubstituted heteroalkylene. In certain embodiments, $R^{3a}$ is substituted or unsubstituted heteroalkylene containing at least one nitrogen. In certain embodiments, $R^{3a}$ is —(CH$_2$)$_j$—Y$_1$—, wherein j is independently an integer between 0 and 10, inclusive; and Y$_1$ is independently a bond, —CR$^5$R$^6$— or —NR$^1$—, wherein each of R$^5$ and R$^6$ is independently hydrogen, halogen, or $C_{1-6}$ alkyl; and R$^1$ is hydrogen; acyl; optionally substituted $C_{1-6}$ alkyl; or an amino protecting group. In certain embodiments, $R^{3a}$ is —(CH$_2$)$_j$—. In certain embodiments, $R^{3a}$ is —(CH$_2$)$_j$—NR$^1$—. In certain embodiments, $R^{3a}$ is —(CH$_2$)$_j$—NH—. In certain embodiments, $R^{3a}$ is —(CH$_2$)$_{j+1}$—. In certain embodiments, j is 0. In certain embodiments, j is 1. In certain embodiments, j is 2. In certain embodiments, j is 3. In certain embodiments, j is 4. In certain embodiments, j is 5. In certain embodiments, j is 6. In certain embodiments, j is 7. In certain embodiments, j is 8. In certain embodiments, j is 9. In certain embodiments, j is 10.

As generally defined above, each instance of $R^1$ is, independently, hydrogen; acyl; optionally substituted $C_{1-6}$ alkyl; or an amino protecting group. In certain embodiments, $R^1$ is hydrogen. In certain embodiments, $R^1$ is acyl; optionally substituted $C_{1-6}$ alkyl; or an amino protecting group. In certain embodiments, $R^1$ is acyl or optionally substituted $C_{1-6}$ alkyl. In certain embodiments, $R^1$ is substituted or unsubstituted alkyl. In certain embodiments, $R^1$ is substituted or unsubstituted $C_{1-6}$ alkyl. In certain embodiments, $R^1$ is unsubstituted $C_{1-6}$ alkyl. In certain embodiments, $R^1$ is methyl, ethyl, or propyl. In certain embodiments, $R^1$ is acyl. In certain embodiments, $R^1$ is acetyl (—C(=O)CH$_3$). In certain embodiments, $R^1$ is an amino protecting group. In certain embodiments, $R^1$ is TBS, TBPS, Bn, BOC, Cbz, Fmoc, trifluoroacetyl, triphenylmethyl, or Ts.

In certain embodiments, at least one instance of $R^{2a}$ and $R^{3a}$ together with the carbon atom to which they are attached, are joined to form a ring. In this instance, in certain embodiments, the ring formed by $R^{2a}$ and $R^{3a}$ together with the carbon atom to which they are attached is substituted or unsubstituted $C_{3-6}$ carbocyclyl or heterocyclyl. In certain embodiments, the ring formed by $R^{2a}$ and $R^{3a}$ together with the carbon atom to which they are attached is substituted or unsubstituted $C_{3-6}$ carbocyclyl. In certain embodiments, the ring formed by $R^{2a}$ and $R^{3a}$ together with the carbon atom to which they are attached is substituted or unsubstituted $C_{3-6}$ heterocyclyl. In certain embodiments, the ring formed by $R^{2a}$ and $R^{3a}$ together with the carbon atom to which they are attached is substituted or unsubstituted $C_{3-6}$ heterocyclyl containing at least one O, N, or S atom. In certain embodiments, the ring formed by $R^{2a}$ and $R^{3a}$ together with the carbon atom to which they are attached is substituted or unsubstituted $C_{3-6}$ heterocyclyl containing at least one nitrogen atom. In certain embodiments, the ring formed by $R^{2a}$ and $R^{3a}$ together with the carbon atom to which they are attached is substituted or unsubstituted $C_{3-6}$ heterocyclyl containing one nitrogen atom. In certain embodiments, the ring formed by $R^{2a}$ and $R^{3a}$ together with the carbon atom to which they are attached is unsubstituted $C_{3-6}$ heterocyclyl containing one nitrogen atom.

In certain embodiments, $R^{2a}$, $R^{3a}$, and the carbon to which $R^{2a}$ and $R^{3a}$ are attached are joined to form a ring. In certain embodiments, the ring formed by $R^{2a}$, $R^{3a}$, and the carbon to which $R^{2a}$ and $R^{3a}$ are attached is of the formula:

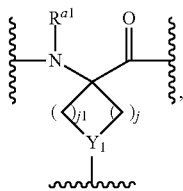

wherein Y$_1$ is independently —CR$^5$— or —N—, each of j and j1 is independently 0, 1, 2, 3, 4, 5, or 6. In certain embodiments, j1 is zero, and the ring formed by $R^{2a}$, $R^{3a}$ and the carbon to which $R^{2a}$ and $R^{3a}$ are attached is of the formula:

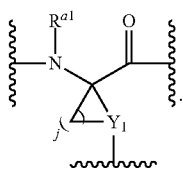

In certain embodiments, j is 0 and Y$_1$ is directly linked to the alpha-carbon of the amino acid. In certain embodiments, the ring formed by $R^{2a}$, $R^{3a}$ and the carbon to which $R^{2a}$ and $R^{3a}$ are attached is of the formula:

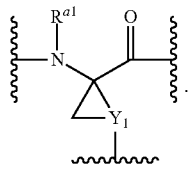

In certain embodiments, the ring formed by $R^{2a}$, $R^{3a}$ and the carbon to which $R^{2a}$ and $R^{3a}$ are attached is of the formula:

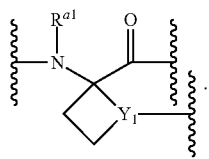

In certain embodiments, the ring formed by $R^{2a}$, $R^{3a}$ and the carbon to which $R^{2a}$ and $R^{3a}$ are attached is of the formula:

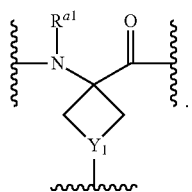

In certain embodiments, the ring formed by $R^{2a}$, $R^{3a}$ and the carbon to which $R^{2a}$ and $R^{3a}$ are attached is of the formula:

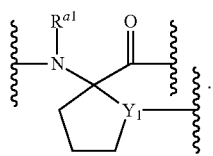

In certain embodiments, the ring formed by $R^{2a}$, $R^{3a}$ and the carbon to which $R^{2a}$ and $R^{3a}$ are attached is of the formula:

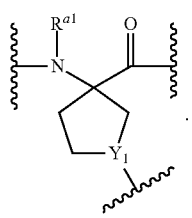

In certain embodiments, the ring formed by $R^{2a}$, $R^{3a}$ and the carbon to which $R^{2a}$ and $R^{3a}$ are attached is of the formula:

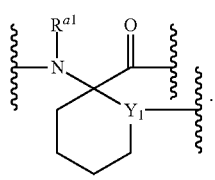

In certain embodiments, the ring formed by $R^{2a}$, $R^{3a}$ and the carbon to which $R^{2a}$ and $R^{3a}$ are attached is of the formula:

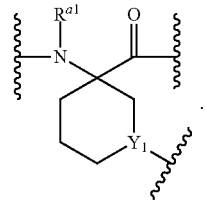

In certain embodiments, the ring formed by $R^{2a}$, $R^{3a}$ and the carbon to which $R^{2a}$ and $R^{3a}$ are attached is of the formula:

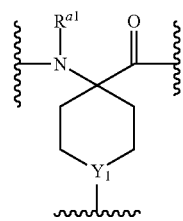

In certain embodiments, the ring formed by $R^{2a}$, $R^{3a}$ and the carbon to which $R^{2a}$ and $R^{3a}$ are attached is of the formula:

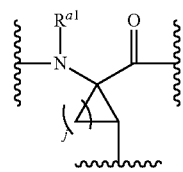

In certain embodiments, the ring formed by $R^{2a}$, $R^{3a}$ and the carbon to which $R^{2a}$ and $R^{3a}$ are attached is of the formula:

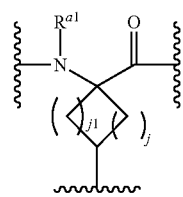

In certain embodiments, the ring formed by $R^{2a}$, $R^{3a}$ and the carbon to which $R^{2a}$ and $R^{3a}$ are attached is of the formula:

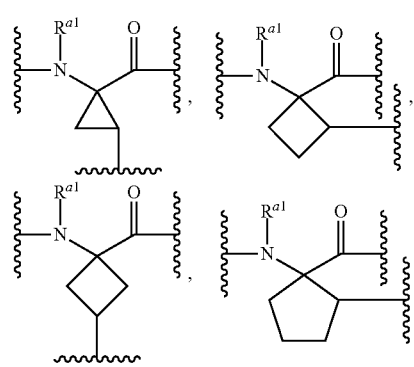

-continued

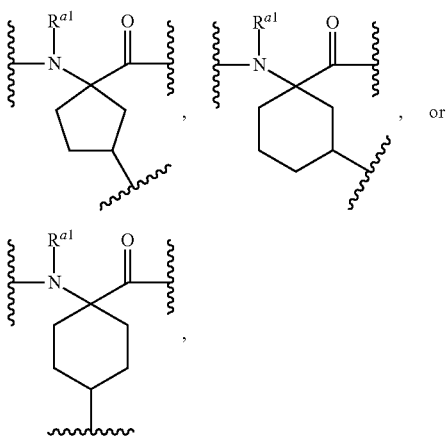

or stereoisomers thereof.

In certain embodiments, the ring formed by $R^{2a}$, $R^{3a}$ and the carbon to which $R^{2a}$ and $R^{3a}$ are attached is of the formula:

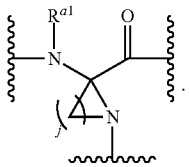

In certain embodiments, the ring formed by $R^{2a}$, $R^{3a}$ and the carbon to which $R^{2a}$ and $R^{3a}$ are attached is of the formula:

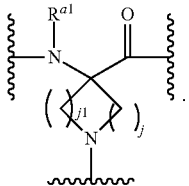

In certain embodiments, the ring formed by $R^{2a}$, $R^{3a}$ and the carbon to which $R^{2a}$ and $R^{3a}$ are attached is of the formula:

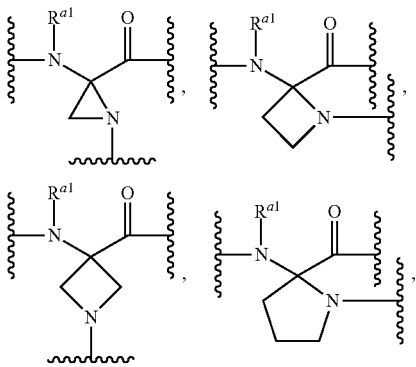

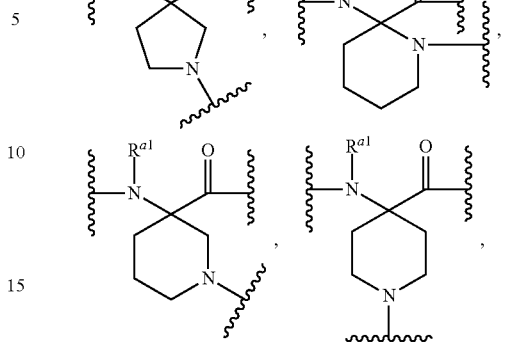

or stereoisomers thereof.

As used herein, each of j and j1 is independently an integer between 1 and 10, inclusive. In some embodiments, j is 1. In some embodiments, j is 2. In some embodiments, j is 3. In some embodiments, j is 4. In some embodiments, j is 5. In some embodiments, j is 6. In some embodiments, j is 7. In some embodiments, j is 8. In some embodiments, j is 9. In some embodiments, j is 10. In some embodiments, j1 is 1. In some embodiments, j1 is 2. In some embodiments, j1 is 3. In some embodiments, j1 is 4. In some embodiments, j1 is 5. In some embodiments, j1 is 6. In some embodiments, j1 is 7. In some embodiments, j1 is 8. In some embodiments, j1 is 9. In some embodiments, j1 is 10.

In some embodiments, $R^{2a}$, $R^{3a}$ and the carbon to which $R^{2a}$ and $R^{3a}$ are attached are not joined to form a ring. In this instance, $R^{3a}$ is independently substituted or unsubstituted alkylene, substituted or unsubstituted alkenylene, substituted or unsubstituted alkynylene, substituted or unsubstituted heteroalkylene, or substituted or unsubstituted heterocyclylene. In some embodiments, $R^{3a}$ is independently substituted or unsubstituted $C_{1-10}$ alkylene. In some embodiments, $R^{3a}$ is substituted $C_{1-10}$ alkylene. In some embodiments, $R^{3a}$ is independently —$(CH_2)_j$—, wherein j is an integer between 0 and 10, inclusive.

In some embodiments, $R^{2a}$, $R^{3a}$ and the carbon to which $R^{2a}$ and $R^{3a}$ are attached are not joined to form a ring. In this instance, $R^{2a}$ is independently substituted or unsubstituted alkyl, substituted or unsubstituted alkenyl, substituted or unsubstituted alkynyl, substituted or unsubstituted heteroalkyl, or substituted or unsubstituted heterocyclyl. In some embodiments, $R^{2a}$ is independently substituted or unsubstituted $C_{1-10}$ alkyl. In some embodiments, $R^{2a}$ is independently substituted methyl. In some embodiments, $R^{2a}$ is independently unsubstituted methyl. In some embodiments, $R^{2a}$ is independently substituted ethyl. In some embodiments, $R^{2a}$ is independently unsubstituted ethyl. In some embodiments, $R^{2a}$ is independently substituted or unsubstituted $C_{2-6}$ alkyl.

As generally described above, $R^{3b}$ is independently substituted or unsubstituted alkylene; substituted or unsubstituted heteroalkylene; substituted or unsubstituted carbocyclylene; or substituted or unsubstituted heterocyclylene; or optionally $R^{2b}$, $R^{3b}$ and the carbon to which $R^{2b}$ and $R^{3b}$ are attached are joined to form a ring. In some embodiments, $R^{3b}$ is substituted or unsubstituted $C_{1-10}$ alkylene. In some embodiments, $R^{3b}$ is substituted $C_{1-10}$ alkylene. In some embodiments, $R^{3b}$ is unsubstituted $C_{1-10}$ alkylene. In some embodiments, $R^{3b}$ is substituted or unsubstituted heteroalkylene. In some embodiments, $R^{3b}$ is substituted heteroalkylene. In some embodiments, $R^{3b}$ is unsubstituted heteroalkylene. In some embodiments, $R^{3b}$ is substituted or unsubstituted heteroalkylene with at least one nitrogen. In some embodiments, $R^{3b}$ is —$(CH_2)_k$—$Y_2$—, wherein k is independently an integer between 0 and 10, inclusive, and $Y_2$ is independently a bond, —$CR^5R^6$—, or —$NR^1$—, wherein $R^1$, $R^5$ and $R^6$ are as defined herein. In some embodiments, $R^{3b}$ is —$(CH_2)_k$—. In some embodiments, $R^{3b}$ is —$(CH_2)_k$—$NR^1$. In some embodiments, $R^{3b}$ is —$(CH_2)_k$—NH—. In some embodiments, $R^{3b}$ is —$(CH_2)_{k+1}$—. In some embodiments, k is 0. In some embodiments, k is 1. In some embodiments, k is 2. In some embodiments, k is 3. In some embodiments, k is 4. In some embodiments, k is 5. In some embodiments, k is 6. In some embodiments, k is 7. In some embodiments, k is 8. In some embodiments, k is 9. In some embodiments, k is 10.

As generally described above, $R^{2b}$ is, independently, substituted or unsubstituted alkyl; substituted or unsubstituted alkenyl; substituted or unsubstituted alkynyl; substituted or unsubstituted heteroalkyl; substituted or unsubstituted carbocyclyl; or substituted or unsubstituted heterocyclyl. In some embodiments, $R^{2b}$ is substituted or unsubstituted $C_{1-10}$ alkyl. In some embodiments, $R^{2b}$ is substituted or unsubstituted heteroalkyl. In some embodiments, $R^{2b}$ is substituted or unsubstituted heteroalkyl with at least one nitrogen atom. In some embodiments, $R^{2b}$ is unsubstituted heteroalkyl with at least one nitrogen atom. In some embodiments, $R^{2b}$ is substituted heteroalkyl with at least one nitrogen atom.

In some embodiments, for at least one instance, $R^{2b}$, $R^{3b}$ and the carbon to which $R^{2b}$ and $R^{3b}$ are attached are joined to form a ring. In this instance, in some embodiments, the ring formed by $R^{2b}$ and $R^{3b}$ together with the carbon atom to which they are attached is substituted or unsubstituted $C_{3-6}$ carbocyclyl or heterocyclyl. In some embodiments, the ring formed by $R^{2b}$ and $R^{3b}$ together with the carbon atom to which they are attached is substituted or unsubstituted $C_{3-6}$ carbocyclyl. In some embodiments, the ring formed by $R^{2b}$ and $R^{3b}$ together with the carbon atom to which they are attached is substituted or unsubstituted $C_{3-6}$ heterocyclyl. In some embodiments, the ring formed by $R^{2b}$ and $R^{3b}$ together with the carbon atom to which they are attached is substituted or unsubstituted $C_{3-6}$ heterocyclyl with at least one O, N, or S atom. In some embodiments, the ring formed by $R^{2b}$ and $R^{3b}$ together with the carbon atom to which they are attached is substituted or unsubstituted $C_{3-6}$ heterocyclyl with at least one N. In some embodiments, the ring formed by $R^{2b}$ and $R^{3b}$ together with the carbon atom to which they are attached is substituted or unsubstituted $C_{3-6}$ heterocyclyl with one N. In some embodiments, the ring formed by $R^{2b}$ and $R^{3b}$ together with the carbon atom to which they are attached is unsubstituted $C_{3-6}$ heterocyclyl with one N.

In some embodiments, the ring formed by $R^{2b}$, $R^{3b}$ and the carbon to which $R^{2b}$ and $R^{3b}$ are attached is of the formula:

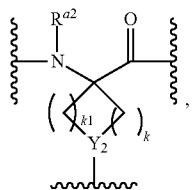

wherein $Y_2$ is independently —$CR^5$— or —N—; k is independently 0, or an integer from 1 to 10, inclusive; and k1 is independently an integer from 1 to 10, inclusive. In some embodiments, k1 is zero, and the ring formed by $R^{2b}$, $R^{3b}$ and the carbon to which $R^{2b}$ and $R^{3b}$ are attached is of the formula:

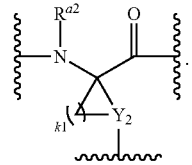

In some embodiments, the ring formed by $R^{2b}$, $R^{3b}$ and the carbon to which $R^{2b}$ and $R^{3b}$ are attached is of the formula:

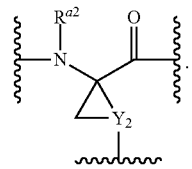

In some embodiments, the ring formed by $R^{2b}$, $R^{3b}$ and the carbon to which $R^{2b}$ and $R^{3b}$ are attached is of the formula:

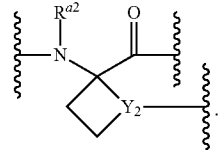

In some embodiments, the ring formed by $R^{2b}$, $R^{3b}$ and the carbon to which $R^{2b}$ and $R^{3b}$ are attached is of the formula:

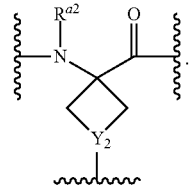

In some embodiments, the ring formed by $R^{2b}$, $R^{3b}$ and the carbon to which $R^{2b}$ and $R^{3b}$ are attached is of the formula:

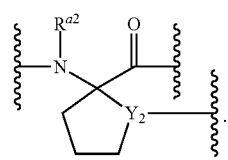

In some embodiments, the ring formed by $R^{2b}$, $R^{3b}$ and the carbon to which $R^{2b}$ and $R^{3b}$ are attached is of the formula:

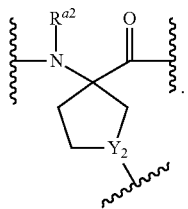

In some embodiments, the ring formed by $R^{2b}$, $R^{3b}$ and the carbon to which $R^{2b}$ and $R^{3b}$ are attached is of the formula:

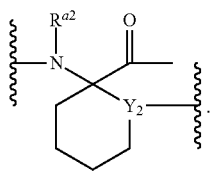

In some embodiments, the ring formed by $R^{2b}$, $R^{3b}$ and the carbon to which $R^{2b}$ and $R^{3b}$ are attached is of the formula:

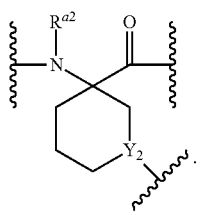

In some embodiments, the ring formed by $R^{2b}$, $R^{3b}$ and the carbon to which $R^{2b}$ and $R^{3b}$ are attached is of the formula:

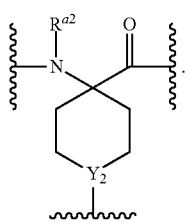

In some embodiments, the ring formed by $R^{2b}$, $R^{3b}$ and the carbon to which $R^{2b}$ and $R^{3b}$ are attached is of the formula:

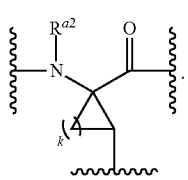

In some embodiments, the ring formed by $R^{2b}$, $R^{3b}$ and the carbon to which $R^{2b}$ and $R^{3b}$ are attached is of the formula:

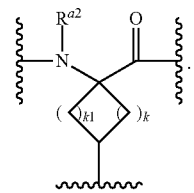

In some embodiments, the ring formed by $R^{2b}$, $R^{3b}$ and the carbon to which $R^{2b}$ and $R^{3b}$ are attached is of the formula:

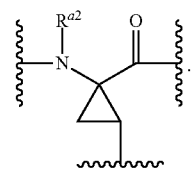

In some embodiments, the ring formed by $R^{2b}$, $R^{3b}$ and the carbon to which $R^{2b}$ and $R^{3b}$ are attached is of the formula:

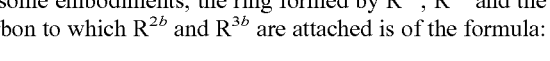
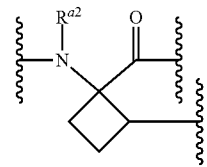
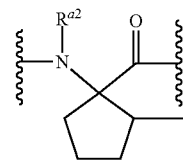
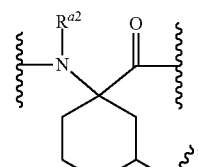
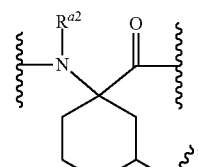
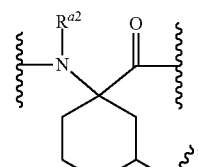

or stereoisomers thereof. In some embodiments, the ring formed by $R^{2b}$, $R^{3b}$ and the carbon to which $R^{2b}$ and $R^{3b}$ are attached is of the formula:

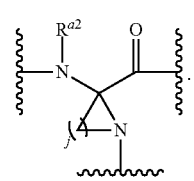

In some embodiments, the ring formed by $R^{2b}$, $R^{3b}$ and the carbon to which $R^{2b}$ and $R^{3b}$ are attached is of the formula:

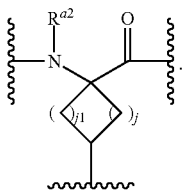

In some embodiments, the ring formed by $R^{2b}$, $R^{3b}$ and the carbon to which $R^{2b}$ and $R^{3b}$ are attached is of the formula:

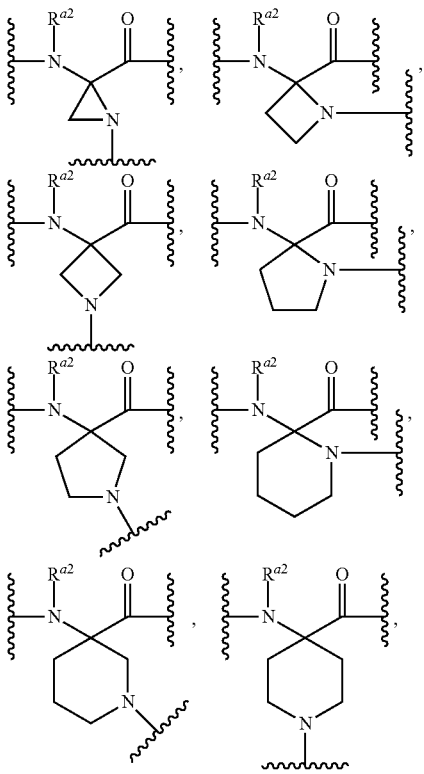

or stereoisomers thereof.

As used herein, k is an integer between 0 and 10, inclusive; and k1 is independently an integer between 1 and 10, inclusive. In some embodiments, k is 0. In some embodiments, k is 1. In some embodiments, k is 2. In some embodiments, k is 3. In some embodiments, k is 4. In some embodiments, k is 5. In some embodiments, k is 6. In some embodiments, k is 7. In some embodiments, k is 8. In some embodiments, k is 9. In some embodiments, k is 10. In some embodiments, k1 is 1. In some embodiments, k1 is 2. In some embodiments, k1 is 3. In some embodiments, k1 is 4. In some embodiments, k1 is 5. In some embodiments, k1 is 6. In some embodiments, k1 is 7. In some embodiments, k1 is 8. In some embodiments, k1 is 9. In some embodiments, k1 is 10.

In some embodiments, $R^{2b}$, $R^{3b}$ and the carbon to which $R^{2b}$ and $R^{3b}$ are attached are not joined to form a ring. In this instance, $R^{3b}$ is independently substituted or unsubstituted alkylene, substituted or unsubstituted alkenylene, substituted or unsubstituted alkynylene, substituted or unsubstituted heteroalkylene, or substituted or unsubstituted heterocyclylene. In some embodiments, $R^{3b}$ is independently substituted or unsubstituted $C_{1-10}$ alkylene. In some embodiments, $R^{3b}$ is substituted $C_{1-10}$ alkylene. In some embodiments, $R^{3b}$ is independently $-(CH_2)_k-$, wherein k is as defined above.

In some embodiments, $R^{2b}$, $R^{3b}$ and the carbon to which $R^{2b}$ and $R^{3b}$ are attached are not joined to form a ring. In this instance, in some embodiments, $R^{2b}$ is independently substituted or unsubstituted $C_{1-10}$ alkyl, substituted or unsubstituted alkenyl, substituted or unsubstituted alkynyl, substituted or unsubstituted heteroalkyl, or substituted or unsubstituted heterocyclyl. In some embodiments, $R^{2b}$ is independently substituted or unsubstituted $C_{1-10}$ alkyl. In some embodiments, $R^{2b}$ is independently substituted methyl. In some embodiments, $R^{2b}$ is independently unsubstituted methyl. In some embodiments, $R^{2b}$ is independently substituted ethyl. In some embodiments, $R^{2b}$ is independently unsubstituted ethyl. In some embodiments, $R^{2b}$ is independently substituted or unsubstituted $C_{2-6}$ alkyl.

In some embodiments, for at least one instance, $R^{2a}$, $R^{3a}$, and the carbon to which $R^{2a}$ and $R^{3a}$ are attached are not joined to form a ring, and $R^{2b}$, $R^{3b}$, and the carbon to which $R^{2b}$ and $R^{3b}$ are attached are not joined form a ring. In some embodiments, $R^{2a}$, $R^{3a}$ and the carbon to which $R^{2a}$ and $R^{3a}$ are attached are not joined to form a ring, and $R^{2b}$, $R^{3b}$ and the carbon to which $R^{2b}$ and $R^{3b}$ are attached are joined form a ring. In some embodiments, $R^{2a}$, $R^{3a}$ and the carbon to which $R^{2a}$ and $R^{3a}$ are attached are joined to form a ring, and $R^{2b}$, $R^{3b}$ and the carbon to which $R^{2b}$ and $R^{3b}$ are attached are not joined form a ring. In some embodiments, for at least one instance, $R^{2a}$, $R^{3a}$ and the carbon to which $R^{2a}$ and $R^{3a}$ are attached are joined to form a ring, and $R^{2b}$, $R^{3b}$ and the carbon to which $R^{2b}$ and $R^{3b}$ are attached are joined form a ring.

In some embodiments, each instance of $R^{3a}$ and $R^{3b}$ are the same. In some embodiments, each instance of $R^{3a}$ and $R^{3b}$ are different.

As generally described above, $L_1$ is independently, a bond, substituted or unsubstituted $C_{1-10}$ alkylene, or $-C(=O)OR^{L1}-$, wherein $R^{L1}$ is optionally substituted $C_{1-10}$ alkylene. In some embodiments, $L_1$ is substituted or unsubstituted $C_{1-10}$ alkylene. In some embodiments, $L_1$ is substituted $C_{1-10}$ alkylene. In some embodiments, $L_1$ is $-(CH_2)_g-$, wherein g is 0 or an integer between 1 and 10. In some embodiments, g is 0, and $L_1$ is a bond. In some embodiments, g is 1. In some embodiments, g is 2. In some embodiments, g is 3. In some embodiments, g is 4. In some embodiments, g is 5. In some embodiments, g is 6. In some embodiments, g is 7. In some embodiments, g is 8. In some embodiments, g is 9. In some embodiments, g is 10. In some embodiments, $R^{L1}$ is substituted $C_{1-10}$ alkylene. In some embodiments, $R^{L1}$ is $-C(=O)O(CH_2)_{g1}-$, wherein g1 is an integer between 1 and 10 inclusive. In some embodiments, g1 is 1. In some embodiments, g1 is 2. In some embodiments, g1 is 3. In some embodiments, g1 is 4. In some embodiments, g1 is 5. In some embodiments, g1 is 6. In some embodiments, g1 is 7. In some embodiments, g1 is 8. In some embodiments, g1 is 9. In some embodiments, g1 is 10.

As generally described above, $L_2$ is independently, a bond, substituted or unsubstituted $C_{1-10}$ alkylene, or $-C(=O)OR^{L2}-$, wherein $R^{L2}$ is optionally substituted $C_{1-10}$ alkylene. In some embodiments, $L_2$ is substituted or unsubstituted $C_{1-10}$ alkylene. In some embodiments, $L_2$ is substituted $C_{1-10}$ alkylene. In some embodiments, $L_2$ is $-(CH_2)_h-$, wherein h is 0 or an integer between 1 and 10 inclusive. In some embodiments, h is 0, and $L_2$ is a bond. In some embodiments, h is 1. In some embodiments, h is 2. In some embodiments, h is 3. In some embodiments, h is 4. In some embodiments, h is 5. In some embodiments, h is 6. In some embodiments, h is 7. In some embodiments, h is 8. In some embodiments, h is 9. In some embodiments, h is 10. In some embodiments, $R^{L2}$ is substituted $C_{1-10}$ alkylene. In some embodiments, $R^{L2}$ is —C(=O)O(CH$_2$)$_{h1}$—, wherein h1 is an integer between 1 and 10 inclusive. In some embodiments, h1 is 1. In some embodiments, h1 is 2. In some embodiments, h1 is 3. In some embodiments, h1 is 4. In some embodiments, h1 is 5. In some embodiments, h1 is 6. In some embodiments, h1 is 7. In some embodiments, h1 is 8. In some embodiments, h1 is 9. In some embodiments, h1 is 10.

In some embodiments, each instance of $L_1$ and $L_2$ is the same. In some embodiments, each instance of $L_1$ and $L_2$ is different.

Group $R^a$

As generally defined above, each instance of $R^{a1}$, $R^{a2}$, and $R^{a3}$ is, independently, hydrogen; acyl; optionally substituted $C_{1-6}$ alkyl; or an amino protecting group.

In some embodiments, $R^{a1}$ is hydrogen. In some embodiments, $R^{a1}$ is acyl; optionally substituted $C_{1-6}$ alkyl; or an amino protecting group. In some embodiments, $R^{a1}$ is acyl or optionally substituted $C_{1-6}$ alkyl.

In some embodiments, $R^{a1}$ is substituted or unsubstituted alkyl. In some embodiments, $R^{a1}$ is substituted or unsubstituted $C_{1-6}$ alkyl. In some embodiments, $R^{a1}$ is unsubstituted $C_{1-6}$ alkyl. In some embodiments, $R^{a1}$ is methyl, ethyl, or propyl.

In some embodiments, $R^{a1}$ is acyl. In some embodiments, $R^{a1}$ is acetyl (—C(=O)CH$_3$).

In some embodiments, $R^{a1}$ is an amino protecting group. In some embodiments, $R^{a1}$ is TBS, TBPS, Bn, BOC, Cbz, Fmoc, trifluoroacetyl, triphenylmethyl, or Ts.

In some embodiments, $R^{a2}$ is hydrogen. In some embodiments, $R^{a2}$ is acyl; optionally substituted $C_{1-6}$ alkyl; or an amino protecting group. In some embodiments, $R^{a2}$ is acyl or optionally substituted $C_{1-6}$alkyl.

In some embodiments, $R^{a2}$ is substituted or unsubstituted alkyl. In some embodiments, $R^{a2}$ is substituted or unsubstituted $C_{1-6}$ alkyl. In some embodiments, $R^{a2}$ is unsubstituted $C_{1-6}$ alkyl. In some embodiments, $R^{a2}$ is methyl, ethyl, or propyl.

In some embodiments, $R^{a2}$ is acyl. In some embodiments, $R^{a2}$ is acetyl (—C(=O)CH$_3$).

In some embodiments, $R^{a2}$ is an amino protecting group. In some embodiments, $R^{a2}$ is TBS, TBPS, Bn, BOC, Cbz, Fmoc, trifluoroacetyl, triphenylmethyl, or Ts.

In some embodiments, $R^{a3}$ is hydrogen. In some embodiments, $R^a$ is acyl; optionally substituted $C_{1-6}$alkyl; or an amino protecting group. In some embodiments, $R^{a3}$ is acyl or optionally substituted $C_{1-6}$alkyl.

In some embodiments, $R^{a3}$ is substituted or unsubstituted alkyl. In some embodiments, $R^{a3}$ is substituted or unsubstituted $C_{1-6}$ alkyl. In some embodiments, $R^{a3}$ is unsubstituted $C_{1-6}$ alkyl. In some embodiments, $R^{a3}$ is methyl, ethyl, or propyl.

In some embodiments, $R^{a3}$ is acyl. In some embodiments, $R^{a3}$ is acetyl (—C(=O)CH$_3$).

In some embodiments, $R^{a3}$ is an amino protecting group. In some embodiments, $R^{a3}$ is TBS, TBPS, Bn, BOC, Cbz, Fmoc, trifluoroacetyl, triphenylmethyl, or Ts.

In some embodiments, each instance of $R^{a1}$ and $R^{a2}$ is, independently, hydrogen, $C_{1-6}$ alkyl (e.g., methyl), or acyl. In some embodiments, each instance of $R^{a1}$ and $R^{a2}$ is hydrogen.

In some embodiments, each instance of $R^{a1}$, $R^{a2}$, and $R^{a3}$ is, independently, hydrogen, optionally substituted $C_{1-6}$ alkyl (e.g., methyl), or acyl. In some embodiments, each instance of $R^{a1}$, $R^{a2}$, and $R^{a3}$ is, independently, hydrogen, methyl, or acetyl. In some embodiments, each instance of $R^{a1}$, $R^{a2}$, and $R^{a3}$ is, independently, hydrogen or methyl. In some embodiments, each instance of $R^{a1}$, $R^{a2}$, and $R^{a3}$ is hydrogen. In some embodiments, each instance of $R^{a1}$, $R^{a2}$, and $R^{a3}$ is methyl.

Groups ======, $R^c$ and q

As generally defined above, each instance of ======== independently represents a single bond, a double bond, or a triple bond. In some embodiments, at least one instance of ====== is a single bond. In some embodiments, each instance of ====== represents a single bond. In some embodiments, at least one instance of ====== is a double bond. In some embodiments, each instance of ====== represents a double bond.

As generally defined above, each instance of $R^{c1}$, $R^{c2}$, $R^{c3}$, $R^{c4}$, $R^{c5}$, and $R^{c6}$ is independently hydrogen; optionally substituted aliphatic; optionally substituted heteroaliphatic; substituted or unsubstituted aryl; optionally substituted heteroaryl; acyl; optionally substituted hydroxyl; optionally substituted thiol; optionally substituted amino; azido; cyano; isocyano; halo; or nitro.

As generally defined above, and each instance of $q^1$, $q^2$, $q^3$, $q^4$, $q^5$, and $q^6$ is independently 0, 1, or 2.

In some embodiments, each instance of $q^1$, $q^2$, and $q^3$ is 0, and thus each instance of $R^{c1}$, $R^{c2}$, and $R^{c3}$ is absent to provide an unsubstituted crosslink. In some embodiments at least one instance of $q^1$, $q^2$, and $q^3$ is 1, and thus at least one instance of $R^{c1}$, $R^{c2}$, and $R^{c3}$ is a non-hydrogen substituent.

In some embodiments, and each instance of $q^4$, $q^5$, and $q^6$ is 0, and thus each instance of $R^{c4}$, $R^{c5}$, and $R^{c6}$ is absent to provide an unsubstituted terminally unsaturated moiety. In some embodiments at least one instance of $q^4$, $q^5$, and $q^6$ is 1, and thus at least one instance of $R^{c4}$, $R^{c5}$, and $R^{c6}$ is a non-hydrogen substituent.

[$X_{AA}$], s, and t

As generally defined above for Formula (I-1), (I-2), (II-1), and (II-2), each instance of $X_{AA}$ is independently a natural amino acid or an unnatural amino acid, i.e., of the formula:

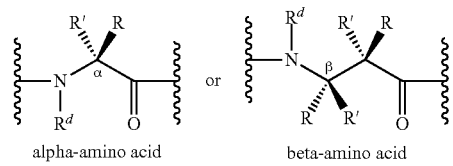

alpha-amino acid        beta-amino acid wherein each instance of R and R' independently are selected from the group consisting of hydrogen; substituted and unsubstituted aliphatic, substituted and unsubstituted heteroaliphatic, substituted and unsubstituted aryl, substituted and unsubstituted heteroaryl; and $R^a$ is hydrogen; substituted or unsubstituted aliphatic; substituted or unsubstituted heteroaliphatic; substituted or unsubstituted aryl; substituted or unsubstituted heteroaryl; acyl; or an amino protecting group. In some embodiments, each instance of $X_{AA}$ is an alpha-amino acid of the formula

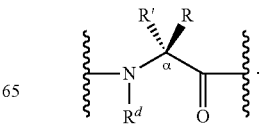

In some embodiments, $R^a$ is an amino protecting group. In some embodiments, $R^a$ is hydrogen. In some embodiments, $R^a$ is $-CH_3$. In some embodiments, $R^a$ is acetyl.

In some embodiments, R and R' are groups as listed in Tables 1 or 2. For example, in some embodiments, each instance of $X_{AA}$ is independently a natural amino acid (e.g., selected from a natural alpha-amino acid as listed in Table 1 or a natural beta-amino acid, e.g., beta-alanine) or an unnatural amino acid (e.g., selected from an unnatural alpha-amino acid as listed in Table 2). In some embodiments, each instance of $X_{AA}$ is independently a natural alpha-amino acid or natural beta-amino acid. In some embodiments, each instance of $X_{AA}$ is independently a natural alpha amino acid as listed in Table 1. In some embodiments, each instance of $X_{AA}$ is a natural alpha amino acid independently selected from the group consisting of S, W, L, N, V, K, E, F, R, D, T, P, A, Y, H, and Q. In some embodiments, at least one instance of $X_{AA}$ is W. In some embodiments, at least one instance of $X_{AA}$ is an unnatural amino acid, e.g., an unnatural alpha-amino acid as listed in Table 2.

As generally defined above for Formulae (I-1), (I-2), (II-1), and (II-2), s and t define the number of amino acids $X_{AA}$ at the N-terminus and C-terminus, respectively. In some embodiments, s is 0 or an integer between 1 and 50, inclusive; between 1 and 40, inclusive; between 1 and 30, inclusive; between 1 and 20, inclusive; between 1 and 10, inclusive; or between 1 and 5 (e.g., 1, 2, 3, 4, or 5), inclusive. In some embodiments, s is 0, 1, 2, 3, or 4. In some embodiments, t is 0 or an integer between 1 and 50, inclusive; between 1 and 40, inclusive; between 1 and 30, inclusive; between 1 and 20, inclusive; between 1 and 10, inclusive; or between 1 and 5 (e.g., 1, 2, 3, 4, or 5), inclusive. In some embodiments, t is 0, 1, 2, 3, or 4.

In some embodiments, s is 0 or an integer between 1 and 40, inclusive; and t is 0 or an integer between 1 and 40, inclusive. In some embodiments, s is 0 or an integer between 1 and 30, inclusive; and t is 0 or an integer between 1 and 30, inclusive. In some embodiments, s is 0 or an integer between 1 and 20, inclusive; and t is 0 or an integer between 1 and 20, inclusive. In some embodiments, s is 0 or an integer between 1 and 10, inclusive; and t is 0 or an integer between 1 and 10, inclusive. In some embodiments, s and t are both 0.

Formulae (i), (ii), (iii), and (iv)

As generally defined above, the precursor polypeptides of Formula (II-1) or (II-2) comprise at least two amino acid moieties of Formula (iii), and optionally, one amino acid of Formula (iv), as part of the polypeptide sequence:

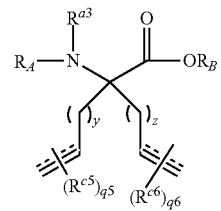

(iii)

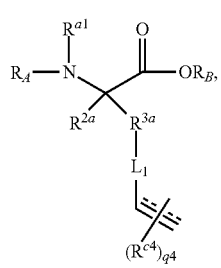

(iv)

which upon treatment of the precursor polypeptide with a RCM catalyst, provides polypeptides of Formula (I-1) or (II-2) comprising a staple of Formula (i):

(i)

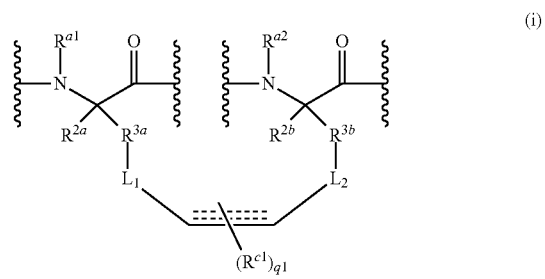

and/or polypeptides comprising multiple staples (a "stitch") of Formula (ii):

(ii)

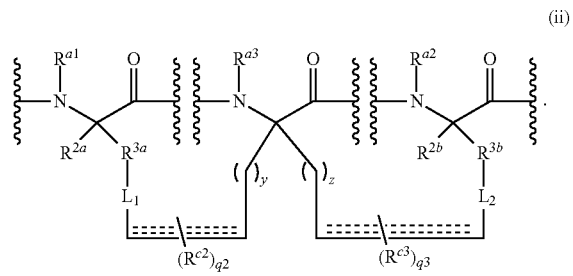

In some embodiments of Formula (iii) and (iv), wherein q4, q5, and q6 are 0, provided are amino acids of Formula (iii-a) and (iv-a):

(iii-a)

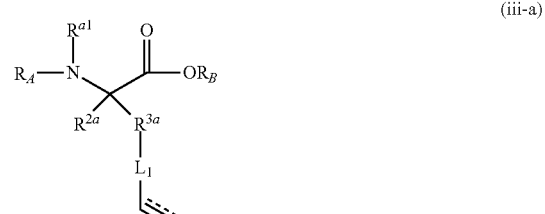

(iv-a)

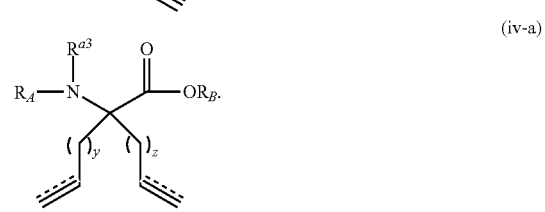

In some embodiments of Formula (iii-a), wherein $R^{2a}$ is methyl, provided is an amino acid of Formula (iii-b):

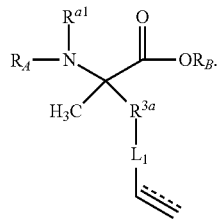
(iii-b)

In some embodiments of Formula (iii-b), wherein $R^{3a}$ is of Formula (G-1):

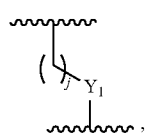
(G-1)

provided is an amino acid of Formula (iii-c):

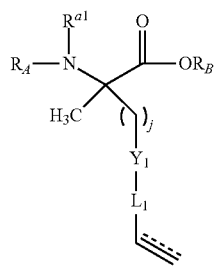
(iii-c)

wherein j, $Y_1$, $L_1$, $R_A$, $R_B$, and $R^{a1}$ are as defined herein. In some embodiments, both $Y_1$ and $L_1$ are bond. In some embodiments, $Y_1$ is —$CR^5R^6$—, and $L_1$ is a bond. In some embodiments, $Y_1$ is —$NR^1$—, and $L_1$ is a bond. In some embodiments, $Y_1$ is —$CR^5R^6$—, and $L_1$ is an optionally substituted $C_{1-10}$ alkylene. In some embodiments, $Y_1$ is —$NR^1$—, and $L_1$ is an optionally substituted $C_{1-10}$ alkylene. In some embodiments, $Y_1$ is —$CR^5R^6$—, and $L_1$ is —$(CH_2)_g$—, wherein g is 0 or an integer of 1 to 10, inclusive. In some embodiments, $Y_1$ is —$NR^1$—, and $L_1$ is —$(CH_2)_g$—, wherein g is 0 or an integer of 1 to 10, inclusive. In some embodiments, $Y_1$ is —$CR^5R^6$—, and $L_1$ is —$C(=O)O(CH_2)_{g1}$—, wherein g is 0 or an integer of 1 to 10, inclusive. In some embodiments, $Y_1$ is —$NR^1$—, and $L_1$ is —$C(=O)O(CH_2)_{g1}$—, wherein g1 is 0 or an integer of 1 to 10, inclusive.

In some embodiments of formula (iv-a), each instance of y and z is 1. In some embodiments, each instance of y and z is 2. In some embodiments, each instance of y and z is 3. In some embodiments, each instance of y and z is 4. In some embodiments, each instance of y and z is 5. In some embodiments, each instance of y and z is 6. In some embodiments, each instance of y and z is 7. In some embodiments, each instance of y and z is 8. In some embodiments, each instance of y and z is 9. In some embodiments, each instance of y and z is 10.

In some embodiments, the amino acid of Formula (iii) is selected from the group consisting of:

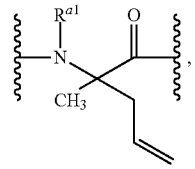
$A_3$
,

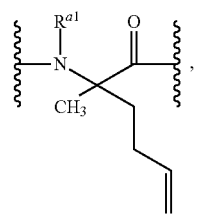
$A_4$
,

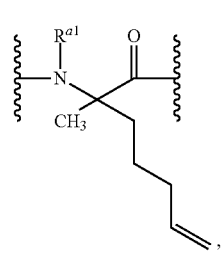
$A_5$
,

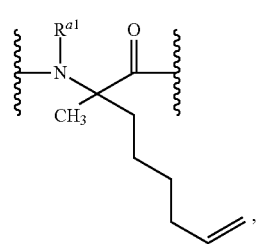
$A_6$
,

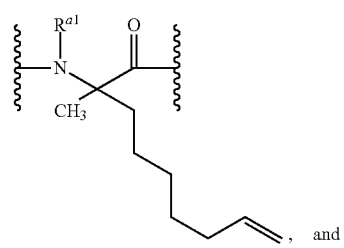
$A_7$
, and

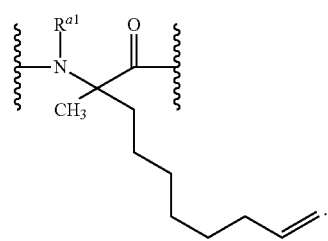
$A_8$
.

In some embodiments, at least one instance of the amino acid of Formula (iii) is $A_5$. In some embodiments, at least one of the amino acid of Formula (iii) is $A_8$.

In some embodiments, the alpha carbon of the amino acid of Formula (iii) is in the (S) configuration. In some embodiments, the alpha carbon of the amino acid of Formula (iii) is in the (R) configuration.

In some embodiments, the amino acid of Formula (iii) is one of the following formulae:

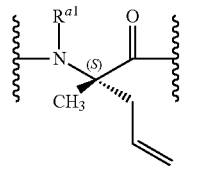
S-A$_3$

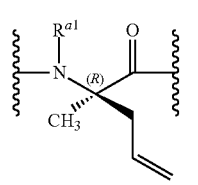
R-A$_3$

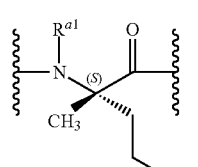
S-A$_4$

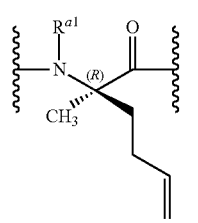
R-A$_4$

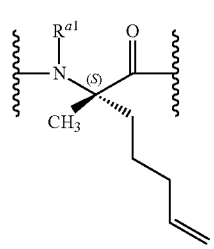
S-A$_5$

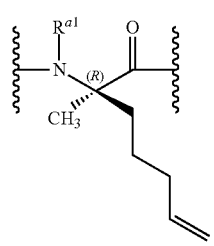
R-A$_5$

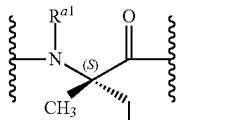
S-A$_6$

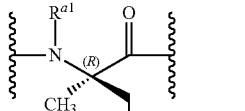
R-A$_6$

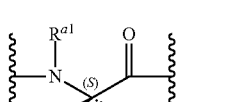
S-A$_7$

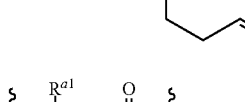
R-A$_7$

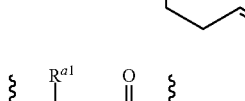
S-A$_8$

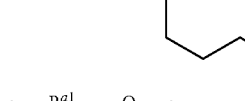
R-A$_8$

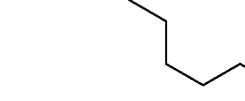

In some embodiments, at least one of the amino acid of Formula (iii) is S-A$_5$ (also referred to herein as S$_5$). In some embodiments, at least one instance of the amino acid of Formula (iii) is S-A$_8$ (also referred to herein as S$_8$). In some embodiments, at least one of the amino acid of Formula (iii) is R-A$_5$ (also referred to herein as R$_5$). In some embodiments, at least one instance of the amino acid of Formula (iii) is R-A$_8$ (also referred to herein as R$_8$).

Exemplary amino acids of Formula (iv) include, but are not limited to,

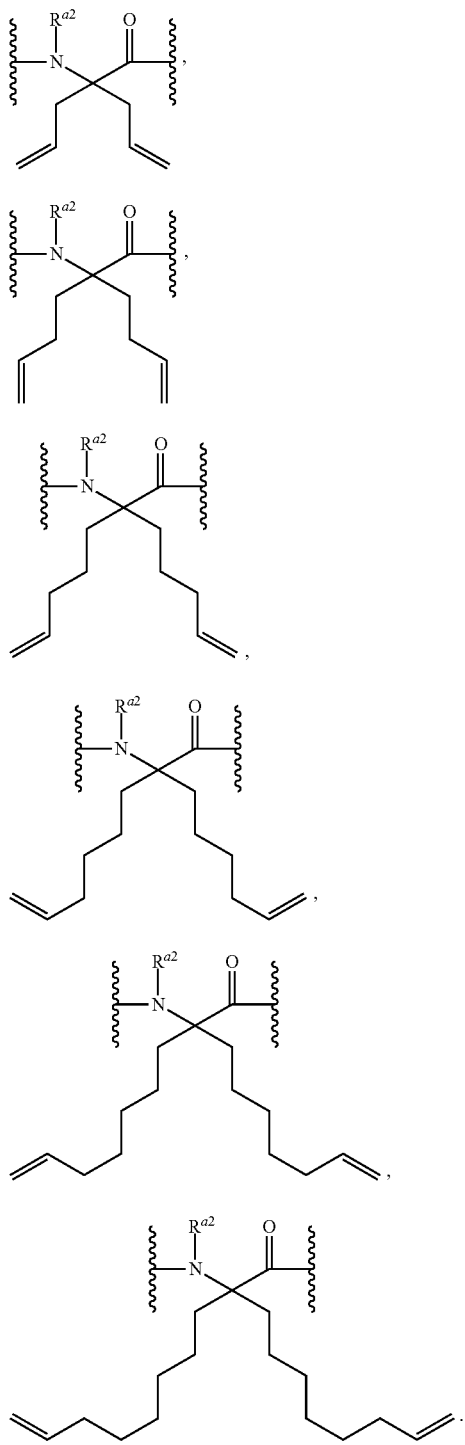

In some embodiments, each instance of the amino acid of Formula (iv) is B$_5$.

In some embodiments, at least one instance of the amino acid of Formula (iii) is A$_5$ and each instance of the amino acid of Formula (iv) is B$_5$. In some embodiments, at least one instance of the amino acid of Formula (iii) is S$_5$ and each instance of the amino acid of Formula (iv) is B$_5$. In some embodiments, at least one instance of the amino acid of Formula (iii) is R$_5$ and each instance of the amino acid of Formula (iv) is B$_5$.

In some embodiments, at least one instance of the amino acid of Formula (iii) is A$_8$ and each instance of the amino acid of Formula (iv) is B$_5$. In some embodiments, at least one instance of the amino acid of Formula (iii) is S$_8$ and each instance of the amino acid of Formula (iv) is B$_5$. In some embodiments, at least one instance of the amino acid of Formula (iii) is R$_8$ and each instance of the amino acid of Formula (iv) is B$_5$.

The stapled or stitched polypeptide can be prepared from the polypeptide of Formula (iii) or (iv), comprising the steps of:

(a) providing an amino acid of Formula (iii):

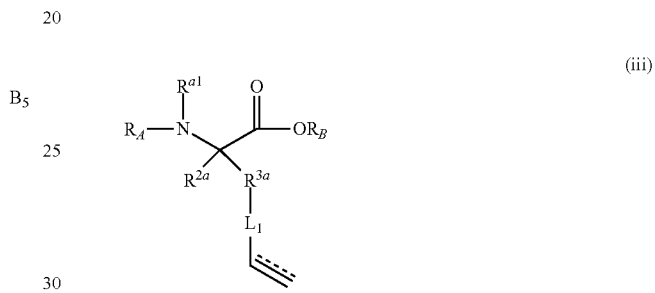

or a salt thereof;

(b) providing an amino acid of Formula (v):

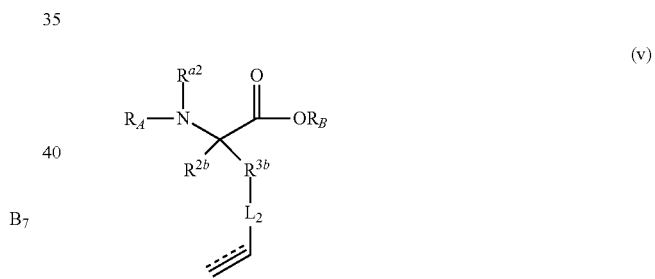

or a salt thereof; and (c) coupling the amino acids of Formulae (iii) and (v) and at least one segment of α-CT polypeptide.

In some embodiments, the method further comprises the steps of:

(d) providing a bis-amino acid of Formula (iv-a):

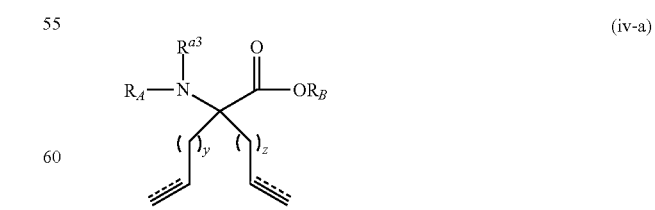

(e) coupling the amino acids of Formulae (iii), (v), and (iv-a), and at least one segment of α-CT polypeptide.

In some embodiments, the coupling step of (c) or (e) is a ring closing metathesis. In some embodiments, the ROM is carried out in the presence of a catalyst. In some embodiments, the ROM catalyst is a ruthenium catalyst.

As used herein, the segment of α-CT polypeptide can be a single amino acid or an amino acid sequence comprising at least one amino acid. In some embodiments, the segment of α-CT polypeptide is selected from the group consisting of TFED (SEQ ID NO:12), LHNVVF (SEQ ID NO:13), FED, LHNVVFV (SEQ ID NO:14), TFED (SEQ ID NO:12), LHN, VFV, TFE, YLHNVVFV (SEQ ID NO:15), TFEDYLHN (SEQ ID NO:16), VFV, TFEDYLHNAAFV (SEQ ID NO:2), SSFRKTFED (SEQ ID NO:17), VFVW (SEQ ID NO:18), S, FRKTFE (SEQ ID NO:19), YLHNVVFVW (SEQ ID NO:20), SS, RKTFED (SEQ ID NO:21), LHNVVFVW (SEQ ID NO:22), SFR, TFEDYLHNVVFV (SEQ ID NO:1), W, SSFRKTFED (SEQ ID NO:17), FRKTFE (SEQ ID NO:19), YLHNVVFV (SEQ ID NO:23), and LHNVVFVW (SEQ ID NO:24). In some embodiments, one, two, three, four, five, six, or more of the segments of α-CT polypeptide is mutated to another natural or unnatural amino acid. In some embodiments, modifications of the segment of α-CT polypeptide include, but are not limited to: (a) substitution of residues on the face of the peptide that contact IR; (b) deletion of residues at either the N- or C-terminal end; (c) insertion of residues at either the N- and or C-terminal end; (d) retro-inverso sequence-modification, which includes peptides of reverse sequence- and chirality (Jameson et al., Nature, 368: 744-746, 1994; Brady et al., Nature, 368: 692-693, 1994) (The net result of combining D-enantiomers and reverse synthesis is that the positions of carbonyl and amino groups in each amide bond are exchanged, while the position of the side-chain groups at each alpha carbon is preserved. For example, if the peptide model is a peptide formed of L-amino acids having the sequence ABC, the retro-inverso peptide analog formed of D-amino acids would have the sequence CBA.); or (e) combinations of any one of (a)-(d). In exemplary embodiments, the α-CT related polypeptide may comprise a total of 1, up to 2, up to 3, u to 4, up to 5, up to 6, up to 7, up to 8, up to 9, or up to 10, or up to 11, or up to 12 amino acid modifications relative to the native α-CT sequence, e.g. conservative or non-conservative substitutions. In exemplary embodiments, the α-CT related polypeptide may comprise a total of 1, up to 2, up to 3, up to 4, up to 5, up to 6, up to 7, up to 8, up to 9, or up to 10, or up to 11, up to 12, up to 13, up to 14, up to 15, up to 16, up to 17, up to 18, up to 19, or up to 20 amino acid modifications relative to the native α-CT sequence, e.g. conservative and/or non-conservative substitutions. In some embodiments, the α-CT segment is from residues 704 to 715 of the α-CT sequence in the binding pocket. In some embodiments, α-CT segment is modified residues 704 to 715 of the α-CT sequence in the binding pocket.

As used herein, conservative substitutions include, but are not limited to, substituting hydrophobic amino acids with hydrophobic amino acids, bulky amino acids for bulky amino acids, hydrophilic amino acids for hydrophilic amino acids. Non-conservative substitutions include inserting the non-naturally-occurring amino acid in a location that is not required for activity.

A variety of biochemical and structural approaches can be employed to select the desired sites for substitution with a non-natural amino acids having the olefin moieties within the inventive polypeptide. It is readily apparent to those of ordinary skill in the art that any position of the polypeptide chain is suitable for selection to incorporate a non-naturally amino acid, and selection may be based on rational design or by random selection for any or no particular desired purpose. Selection of desired sites may be for producing an α-CT analog having any desired property or activity, including but not limited to, agonists, super-agonists, inverse agonists, antagonists, receptor binding modulators, receptor activity modulators, dimer or multimer formation, no change to activity or property compared to the native molecule, or manipulating any physical or chemical property of the polypeptide such as solubility, aggregation, or stability. For example, locations in the polypeptide required for biological activity of the inventive polypeptides can be identified using point mutation analysis, alanine scanning, saturation mutagenesis and screening for biological activity, or homolog scanning methods known in the art. Residues that are critical for the bioactivity, residues that are involved with pharmaceutical stability, antibody epitopes, or receptor or heparin binding residues may be mutated. U.S. Pat. Nos. 5,580,723; 5,834,250; 6,013,478; 6,428,954; and 6,451,561, which are incorporated by reference herein, describe methods for the systematic analysis of the structure and function of polypeptides by identifying active domains which influence the activity of the polypeptide with a target substance. Residues other than those identified as critical to biological activity by alanine or homolog scanning mutagenesis may be good candidates for substitution with a non-naturally encoded amino acid depending on the desired activity sought for the polypeptide. Alternatively, the sites identified as critical to biological activity may also be good candidates for substitution with a non-natural amino acid, again depending on the desired activity sought for the polypeptide.

Another alternative would be to simply make serial substitutions in each position on the polypeptide chain with a non-natural amino acid and observe the effect on the activities of the polypeptide. It is readily apparent to those of ordinary skill in the art that any means, technique, or method for selecting a position for substitution with a non-natural amino acid into any polypeptide is suitable for use in the present invention.

The polypeptides of Formula (I-1), (I-2), (II-1), or (II-2) can be prepared by combinatorial synthetic methods and screening for a desired activity (e.g., insulin receptor binding) For example, beads having a target protein (e.g. insulin or insulin receptor) and a fluorescent dye are mixed with the inventive polypeptides. The beads that interact with this polypeptide are then isolated and identified for structure/sequence determination.

The polypeptides of Formula (I-1), (I-2), (II-1), or (II-2) may be screened (e.g. using phage display) for binding to the target protein (e.g. insulin receptor). Phage display is well known to one skilled in the art to rapidly identify drug candidates that bind with high specificity and affinity to targets of therapeutic interest (Bratkovic et al., *Appl. Biochem. Biotechnol.,* 2005, 127(2): 125-131; Bratkovic T et al., *Biochem. Biophys. Res. Commun.,* 2005, 332(3): 897-903; Bratkovic T et al., *J. Lipid Res.,* 2005, 46(7): 1512-1516)

In some embodiments, $X_{A1}$ and $X_{A14}$ are absent from the polypeptide of Formula (I-1). In some embodiments, $X_{A1}$, $X_{A2}$, $X_{A13}$, and $X_{A14}$ are absent from the polypeptide of Formula (I-1). In some embodiments, $X_{A1}$, $X_{A2}$, $X_{A3}$, $X_{A4}$, $X_{A5}$, $X_{A10}$, $X_{A11}$, $X_{A12}$, $X_{A13}$, and $X_{A14}$ are absent from the polypeptide of Formula (I-1).

In some embodiments, $X_{B1}$ and $X_{B14}$ are absent from the polypeptide of Formula (II). In some embodiments, $X_{B1}$, $X_{B2}$, $X_{B13}$, and $X_{B14}$ are absent from the polypeptide of Formula (II). In some embodiments, $X_{B1}$, $X_{B2}$, $X_{B3}$, $X_{B4}$, $X_{B5}$, $X_{B10}$, $X_{B11}$, $X_{B12}$, $X_{B13}$, and $X_{B14}$ are absent from the polypeptide of Formula (II-1).

In some embodiments of Formula (I-1), $X_{A2}$, $X_{A5}$, $X_{A6}$, $X_{A10}$, or $X_{A13}$ is any natural or unnatural amino acid. In some embodiments of Formula (I-1), $X_{A2}$, $X_{A5}$, $X_{A6}$, $X_{A10}$, or $X_{A13}$ is any naturally-occurring amino acid. In some embodiments of Formula (I-1), $X_{A2}$ is any naturally-occurring amino acid. In some embodiments of Formula (I-1), $X_{A2}$ is T. In some embodiments of Formula (I-1), $X_{A5}$ is any naturally-occurring amino acid. In some embodiments of Formula (I-1), $X_{A5}$ is D. In some embodiments of Formula (I-1), $X_{A6}$ is any naturally-occurring amino acid. In some embodiments of Formula (I-1), $X_{A6}$ is Y. In some embodiments of Formula (I-1), $X_{A10}$ is any naturally-occurring amino acid. In some embodiments of Formula (I-1), $X_{A10}$ is V. In some embodiments of Formula (I-1), $X_{A13}$ is any naturally-occurring amino acid. In some embodiments, $X_{A13}$ is V.

In some embodiments of Formula (II-1), $X_{B2}$, $X_{B5}$, $X_{B6}$, $X_{B10}$, or $X_{B13}$ is any natural or unnatural amino acid. In some embodiments of Formula (II-1), $X_{B2}$, $X_{B5}$, $X_{B6}$, $X_{B10}$, or $X_{B13}$ is any naturally-occurring amino acid. In some embodiments of Formula (II-1), $X_{B2}$ is any naturally-occurring amino acid. In some embodiments of Formula (II-1), $X_{B2}$ is T. In some embodiments of Formula (II-1), $X_{B5}$ is any naturally-occurring amino acid. In some embodiments of Formula (II-1), $X_{B5}$ is D. In some embodiments of Formula (II-1), $X_{B6}$ is any naturally-occurring amino acid. In some embodiments of Formula (II-1), $X_{B6}$ is Y. In some embodiments of Formula (II-1), $X_{B10}$ is any naturally-occurring amino acid. In some embodiments of Formula (II-1), $X_{B10}$ is V. In some embodiments of Formula (II-1), $X_{B13}$ is any naturally-occurring amino acid. In some embodiments, $X_{B13}$ is V.

In some embodiments, $X_{C1}$ and $X_{C20}$ are absent from the polypeptide of Formula (I-2). In some embodiments, $X_{C1}$, $X_{C19}$, and $X_{C20}$ are absent from the polypeptide of Formula (I-2). In some embodiments, $X_{C1}$, $X_{C2}$, $X_{C19}$, and $X_{C20}$ are absent from the polypeptide of Formula (I-2). In some embodiments, $X_{C1}$, $X_{C11}$, $X_{C15}$, and $X_{C20}$ are absent from the polypeptide of Formula (I-2). In some embodiments, $X_{C1}$, $X_{C3}$, $X_{C10}$, and $X_{C20}$ are absent from the polypeptide of Formula (I-2). In some embodiments, $X_{C1}$, $X_{C4}$, $X_{C11}$, and $X_{C20}$ are absent from the polypeptide of Formula (I-2). In some embodiments, $X_{C1}$, $X_{C2}$, $X_{C6}$, and $X_{C20}$ are absent from the polypeptide of Formula (I-2).

In some embodiments, $X_{D1}$ and $X_{D20}$ are absent from the polypeptide of Formula (II-2). In some embodiments, $X_{D1}$, $X_{D19}$, and $X_{D20}$ are absent from the polypeptide of Formula (II-2). In some embodiments, $X_{D1}$, $X_{D2}$, $X_{D19}$, and $X_{D20}$ are absent from the polypeptide of Formula (II-2). In some embodiments, $X_{D1}$, $X_{D11}$, $X_{D15}$, and $X_{D20}$ are absent from the polypeptide of Formula (II-2). In some embodiments, $X_{D1}$, $X_{D3}$, $X_{D10}$, and $X_{D20}$ are absent from the polypeptide of Formula (II-2). In some embodiments, $X_{D1}$, $X_{D4}$, $X_{D11}$, and $X_{D20}$ are absent from the polypeptide of Formula (II-2). In some embodiments, $X_{D1}$, $X_{D2}$, $X_{D6}$, and $X_{D20}$ are absent from the polypeptide of Formula (II-2).

In some embodiments of Formula (I-2), $X_{C2}$, $X_{C3}$, $X_{C4}$, $X_{C6}$, $X_{C10}$, $X_{C11}$, or $X_{C15}$ is any natural or unnatural amino acid. In some embodiments of Formula (I-2), $X_{C2}$, $X_{C3}$, $X_{C4}$, $X_{C6}$, $X_{C10}$, $X_{C11}$, or $X_{C15}$ is any naturally-occurring amino acid. In some embodiments of Formula (I-2), $X_{C2}$ is any naturally-occurring amino acid. In some embodiments of Formula (I-2), $X_{C2}$ is S. In some embodiments of Formula (I-2), $X_{C3}$ is any naturally-occurring amino acid. In some embodiments of Formula (I-2), $X_{C3}$ is S. In some embodiments of Formula (I-2), $X_{C4}$ is any naturally-occurring amino acid. In some embodiments of Formula (I-2), $X_{C4}$ is F. In some embodiments of Formula (I-2), $X_{C6}$ is any naturally-occurring amino acid. In some embodiments of Formula (I-2), $X_{C6}$ is K. In some embodiments of Formula (I-2), $X_{C10}$ is any naturally-occurring amino acid. In some embodiments of Formula (I-2), $X_{C10}$ is D. In some embodiments of Formula (I-2), $X_{C11}$ is any naturally-occurring amino acid. In some embodiments of Formula (I-2), $X_{C11}$ is Y. In some embodiments of Formula (I-2), $X_{C15}$ is any naturally-occurring amino acid. In some embodiments of Formula (I-2), $X_{C15}$ is V or A.

In some embodiments of Formula (II-2), $X_{D2}$, $X_{D3}$, $X_{D4}$, $X_{D6}$, $X_{D10}$, $X_{D11}$, or $X_{D15}$ is any natural or unnatural amino acid. In some embodiments of Formula (II-2), $X_{D2}$, $X_{D3}$, $X_{D4}$, $X_{D6}$, $X_{D10}$, $X_{D11}$, or $X_{D15}$ is any naturally-occurring amino acid. In some embodiments of Formula (II-2), $X_{D2}$ is any naturally-occurring amino acid. In some embodiments of Formula (II-2), $X_{D2}$ is S. In some embodiments of Formula (II-2), $X_{D2}$ is T. In some embodiments of Formula (II-2), $X_{D3}$ is any naturally-occurring amino acid. In some embodiments of Formula (II-2), $X_{D3}$ is S. In some embodiments of Formula (II-2), $X_{D3}$ is T. In some embodiments of Formula (II-2), $X_{D4}$ is any naturally-occurring amino acid. In some embodiments of Formula (II-2), $X_{D4}$ is F. In some embodiments of Formula (II-2), $X_{D4}$ is Y. In some embodiments of Formula (II-2), $X_{D4}$ is W. In some embodiments of Formula (II-2), $X_{D6}$ is any naturally-occurring amino acid. In some embodiments of Formula (II-2), $X_{D6}$ is K. In some embodiments of Formula (II-2), $X_{D6}$ is R. In some embodiments of Formula (II-2), $X_{D6}$ is H. In some embodiments of Formula (II-2), $X_{D10}$ is any naturally-occurring amino acid. In some embodiments of Formula (II-2), $X_{D10}$ is D. In some embodiments of Formula (II-2), $X_{D10}$ is E. In some embodiments of Formula (II-2), $X_{D11}$ is any naturally-occurring amino acid. In some embodiments of Formula (II-2), $X_{D11}$ is Y. In some embodiments of Formula (II-2), $X_{D11}$ is F. In some embodiments of Formula (II-2), $X_{D11}$ is W. In some embodiments of Formula (II-2), $X_{D15}$ is any naturally-occurring amino acid. In some embodiments of Formula (II-2), $X_{D15}$ is V. In some embodiments of Formula (II-2), $X_{D15}$ is A. In some embodiments of Formula (II-2), $X_{D15}$ is I. In some embodiments of Formula (II-2), $X_{D15}$ is L.

In some embodiments, after stapling of an inventive polypeptide, the method further comprises additional synthetic modification of the unsaturated staple or stitch of the cross-linked peptides. Any chemical or biological modification to the stapled or stitched polypeptide may be made. In some embodiments, the modifications are carried out on the Alloc moiety of a polypeptide. In some embodiments, the modifications extrude $CO_2$ from the Alloc moiety from the stapled peptides. In some embodiments, the $CO_2$ extrusion is carried out in the presence of a palladium catalyst. In some embodiments, the $CO_2$ extrusion is carried out in the presence of $Pd(PPh_3)_4$. In some embodiments, the modification comprises alkyation on the amide group of the staple or stitch.

In some embodiments, additional modifications of the stapled or stitched peptides include reduction, oxidation, and nucleophilic or electrophilic additions to the double bond provided from a metathesis reaction to provide a synthetically modified polypeptide. Other modifications may include conjugation of a stapled polypeptide, or a synthetically modifying the stapled polypeptide with a therapeutically active agent, label, or diagnostic agent anywhere on the stapled polypeptide scaffold, e.g., such as at the N-terminus of the stapled polypeptide, the C-terminus of the stapled polypeptide, on an amino acid side chain of the stapled polypeptide, or at one or more modified or unmodified stapled sites (i.e., to a staple). Such modification may be useful in delivery of the peptide or therapeutically active agent to a cell, tissue, or organ. Such modifications may, in some embodiments, allow for targeting to a particular type of cell or tissue.

The staples or stitches of the polypeptide may further comprise additional synthetic modification(s). Any chemical or biological modification may be made. In some embodiments, the staple or stitch has an Alloc group. In some embodiments, the modifications are carried out on the Alloc moiety of a polypeptide. In some embodiments, the modifications extrude $CO_2$ from the Alloc moiety from the stapled peptides. In some embodiments, the $CO_2$ extrusion is carried out in the presence of a palladium catalyst. In some embodiments, the $CO_2$ extrusion is carried out in the presence of $Pd(PPh_3)_4$. In some embodiments, such modifications include reduction, oxidation, and nucleophilic or electrophilic additions to the double bond provided from a metathesis reaction of the cross-link to provide a synthetically modified stapled or stitched polypeptide. One of ordinary skill in the art will appreciate that a wide variety of conditions may be employed to promote such transformations, therefore, a wide variety of conditions are envisioned; see generally, *March's Advanced Organic Chemistry: Reactions, Mechanisms, and Structure*, M. B. Smith and J. March, 5$^{th}$ Edition, John Wiley & Sons, 2001; *Advanced Organic Chemistry, Part B: Reactions and Synthesis*, Carey and Sundberg, 3$^{rd}$ Edition, Plenum Press, New York, 1993; and *Comprehensive Organic Transformations*, R. C. Larock, 2$^{nd}$ Edition, John Wiley & Sons, 1999, the entirety of each of which is hereby incorporated herein by reference. In other embodiments, the staple(s) of the polypeptide are not further modified.

In some embodiments, the staple or stitch has a double bond. In some embodiments, the modifications are carried out on the double bond of the stapled or stitched polypeptide. Exemplary conditions may be any reagent reactive with a double bond. In some embodiments, the reagent is able to react with a double bond, for example, via a hydrogenation, osmylation, hydroxylation (mono- or di-), amination, halogenation, cycloaddition (e.g., cyclopropanation, aziridination, epoxidation), oxy-mercuration, and/or a hydroboronation reaction, to provide a functionalized single bond. As one of ordinary skill in the art will clearly recognize, these above-described transformations will introduce functionalities compatible with the particular stabilized structures and the desired biological interactions; such functionalities include, but are not limited to, hydrogen; substituted or unsubstituted aliphatic; substituted or unsubstituted heteroaliphatic; substituted or unsubstituted aryl; substituted or unsubstituted heteroaryl; acyl; substituted or unsubstituted hydroxyl; substituted or unsubstituted amino; substituted or unsubstituted thiol, halo; cyano; nitro; azido; imino; oxo; and thiooxo.

Other modifications may further include conjugation of the stapled or stitched polypeptide, or a synthetically modified stapled or stitched polypeptide, with a biologically active agent, label, targeting moiety, diagnostic agent, anywhere on the polypeptide scaffold, e.g., such as at the N-terminus of the polypeptide, the C-terminus of the polypeptide, on an amino acid side chain of the polypeptide, or at one or more modified or unmodified stapled sites. Such modification may be useful in delivery of the peptide or biologically active agent to a cell, tissue, or organ. Such modifications may allow for targeting of the stabilized polypeptide to a particular type of cell or tissue. Conjugation of an agent (e.g., a label, a diagnostic agent, a biologically active agent, a targeting moiety) to the stapled polypeptide may be achieved in a variety of different ways. The agent may be covalently conjugated, directly or indirectly, to the polypeptide at the site of stapling, or to the N-terminus or the C-terminus of the polypeptide. Alternatively, the agent may be noncovalently conjugated, directly or indirectly, to the polypeptide at the site of stapling, or to the N-terminus or the C-terminus of the polypeptide, or any other site on the polypeptide. Indirect covalent conjugation is by means of one or more covalent bonds. Indirect non-covalent conjugation is by means of one or more non-covalent interactions. Conjugation may also be via a combination of non-covalent and covalent interactions. The agent may also be conjugated to the polypeptide through a linker. Any number of covalent bonds may be used in the conjugation of a biologically active agent and/or diagnostic agent to the inventive polypeptide of the present invention. Such bonds include amide linkages, ester linkages, disulfide linkages, carbon-carbon bonds, carbamate linkages, carbonate linkages, urea linkages, hydrazide linkages, and the like. In some embodiments, the bond is cleavable under physiological conditions (e.g., enzymatically cleavable, cleavable at a high or low pH, with heat, light, ultrasound, x-ray, etc.). However, in some embodiments, the bond is not cleavable.

Furthermore, the stapled or stitched polypeptide may be ligated, e.g., covalently conjugated, either directly or indirectly, to a protein, e.g., a recombinant protein, to provide a bifunctional polypeptide. See, e.g., PCT/US2009/004260. For example, one domain of the polypeptide, such as the alpha-helix, acts as a targeting moiety that binds to the IR; the targeting domain is conjugated to a peptide or protein which is brought in close proximity to the IR or recruits another biomolecule into close proximity to the IR.

In some embodiments, the additional modification is PEGylation. The PEGylation of the stapled or stitched polypeptide can be carried out using any of the PEGylation reactions known in the art. Such reactions are described, for example, in the following references: Francis et al., (1992), Focus on Growth Factors 3: 4-10; European Patent Nos. 0 154 316 and 0 401 384; and U.S. Pat. No. 4,179,337. For example, PEGylation can be carried out via an acylation reaction or an alkylation reaction with a reactive polyethylene glycol molecule (or an analogous reactive water-soluble polymer) as described herein. For the acylation reactions, a selected polymer should have a single reactive ester group. For reductive alkylation, a selected polymer should have a single reactive aldehyde group. A reactive aldehyde is, for example, polyethylene glycol propionaldehyde, which is water stable, or mono $C_{1-10}$ alkoxy or aryloxy derivatives thereof (see, e.g., U.S. Pat. No. 5,252,714).

In some embodiments, the alpha-amino acid used in step (c) or (e) is a natural or unnatural amino acid. In some embodiments, the alpha-amino acid used in step (c) or (e) is independently selected from the group consisting of G, A, V, L, I, M, F, W, P, S, T, C, Y, N, Q, D, E, K, R, and H. In some embodiments, the alpha-amino acid used in step (c) or (e) is independently selected from T, F, E, D, Y, L, H, N, V, V, F, and V.

General methods of preparing the stapled or stitched peptides and addition modifications are described in U.S. Pat. Nos. 7,192,713; 7,723,469; 7,786,072; U.S. Patent Application Publication Nos: 2010-0184645; 2010-0168388; 2010-0081611; 2009-0176964; 2009-0149630; and 2006-0008848; PCT Application Publication Nos: WO 2010/011313; WO 2008/121767; WO 2008/095063; WO 2008/061192; and WO 2005/044839, as well as PCT Application No. PCT/US2014/025544; all of which are incorporated by references herein.

In some embodiments of Formula (i) and (ii), wherein q1, q2, and q3 are 0, provided are amino acids of Formula (i-a) and (ii-a):

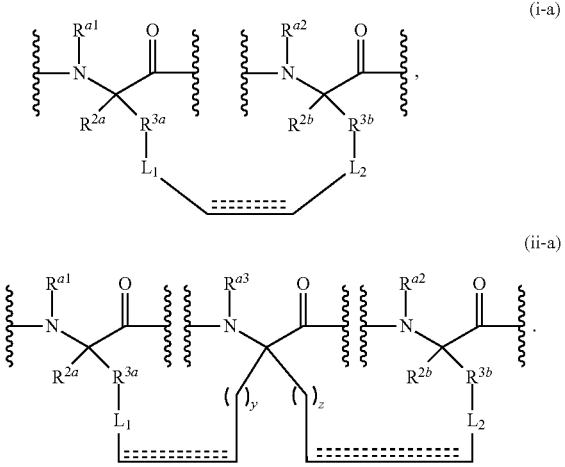

(i-a)

(ii-a)

In some embodiments of Formula (i-a) or (ii-a), wherein $R^{2a}$ and $R^{2b}$ are methyl, provided is an amino acids of Formula (i-b) or (ii-b):

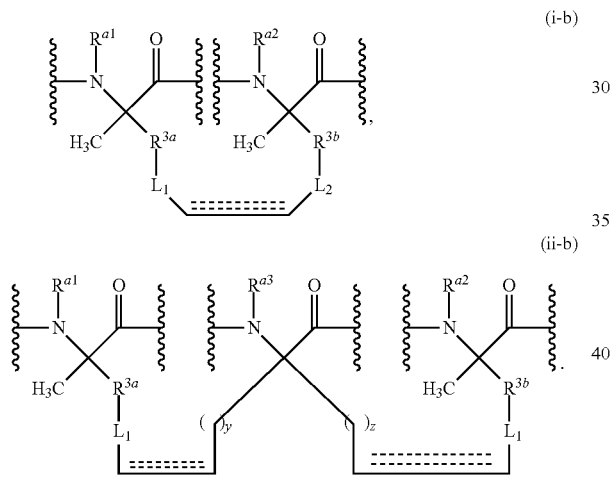

(i-b)

(ii-b)

In some embodiments of formula (i-b), wherein $R^{3a}$ is of Formula (G-1)

(G-1)

and $R^{3b}$ is of Formula (G-6)

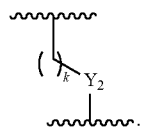

(G-6)

In some embodiments of formula (i-b), $R^{3a}$ is of Formula (G-1), $R^{3b}$ is of Formula (G-6), $Y_1$, $L_1$, $Y_2$, and $L_2$ are bond, and ≡≡≡≡≡ corresponds to a double bond, provided is a staple of Formula (i-c):

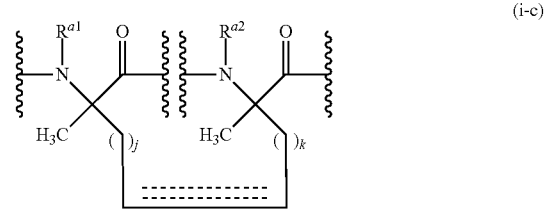

(i-c)

wherein j and k are as defined herein. In some embodiments, both j and k are 1. In some embodiments, both j and k are 2. In some embodiments, both j and k are 3. In some embodiments, both j and k are 4. In some embodiments, both j and k are 5. In some embodiments, both j and k are 6. In some embodiments, both j and k are 7. In some embodiments, both j and k are 8. In some embodiments, both j and k are 9. In some embodiments, both j and k are 10. When both j and k are 3, the amino acids are referred to as stapled $A_5$-$A_5$. When both j and k are 6, the amino acids are referred to as stapled $A_8$-$A_8$. When j is 3 and k is 6, the amino acids are referred to as stapled $A_5$-$A_8$. When j is 6 and k is 3, the amino acids are referred to as stapled $A_8$-$A_5$.

In some embodiments of Formula (ii-b), wherein $R^{3a}$ is of Formula (G-1)

(G-1)

and $R^{3b}$ is of Formula (G-6)

(G-6)

In some embodiments of formula (ii-b), $R^{3a}$ is of Formula (G-1), $R^{3b}$ is of Formula (G-6), $Y_1$, $L_1$, $Y_2$, and $L_2$ are bond, and ≡≡≡≡≡ corresponds to a single or a double bond, provided is a stitch of Formula (iv-c):

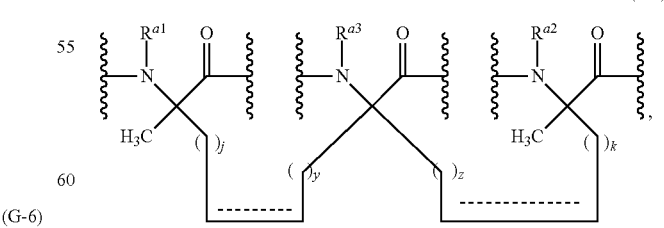

(ii-c)

wherein each instance of j, k, y, and z is independently an integer between 1 and 10 inclusive. In some embodiments, each instance of j, k, y, and z are 1. In some embodiments, each instance of j, k, y, and z are 2. In some embodiments, each instance of j, k, y, and z are 3. In some embodiments, each instance of j, k, y, and z are 4. In some embodiments, each instance of j, k, y, and z are 5. In some embodiments, each instance of j, k, y, and z are 6. When each instance of j, k, y, and z is 3, the amino acids are referred to as stapled $A_5$-$B_5$-$A_5$. When each instance of j, k, y, and z is 6, the amino acids are referred to as stapled $A_8$-$B_8$-$A_8$. When each instance of j, y, and z are 3 and k is 6, the amino acids are referred to as stapled $A_5$-$B_5$-$A_8$. When each instance of j, y, and z are 6 and k is 3, the amino acids are referred to as stapled $A_8$-$B_8$-$A_5$.

In some embodiments, the cross-linked amino acids of Formula (i) or (ii) are of Formula (i-d), (ii-d), (i-e), or (ii-e):

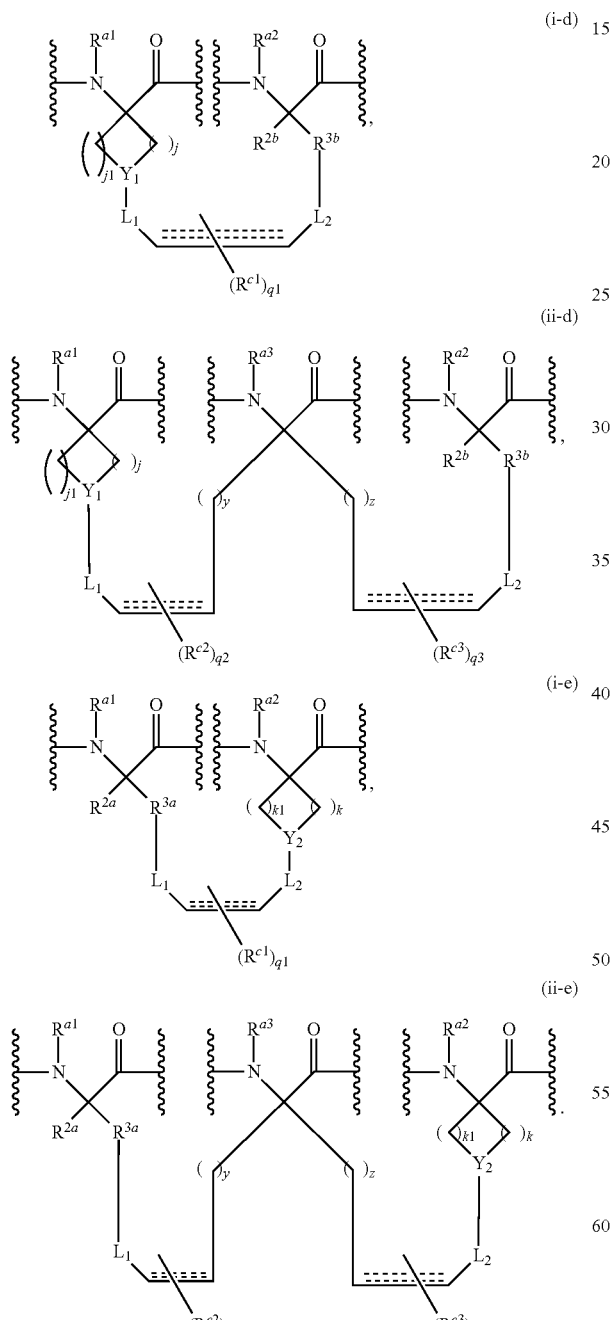

In some embodiments, the amino acid of Formula (iii) is one of the following formulae:

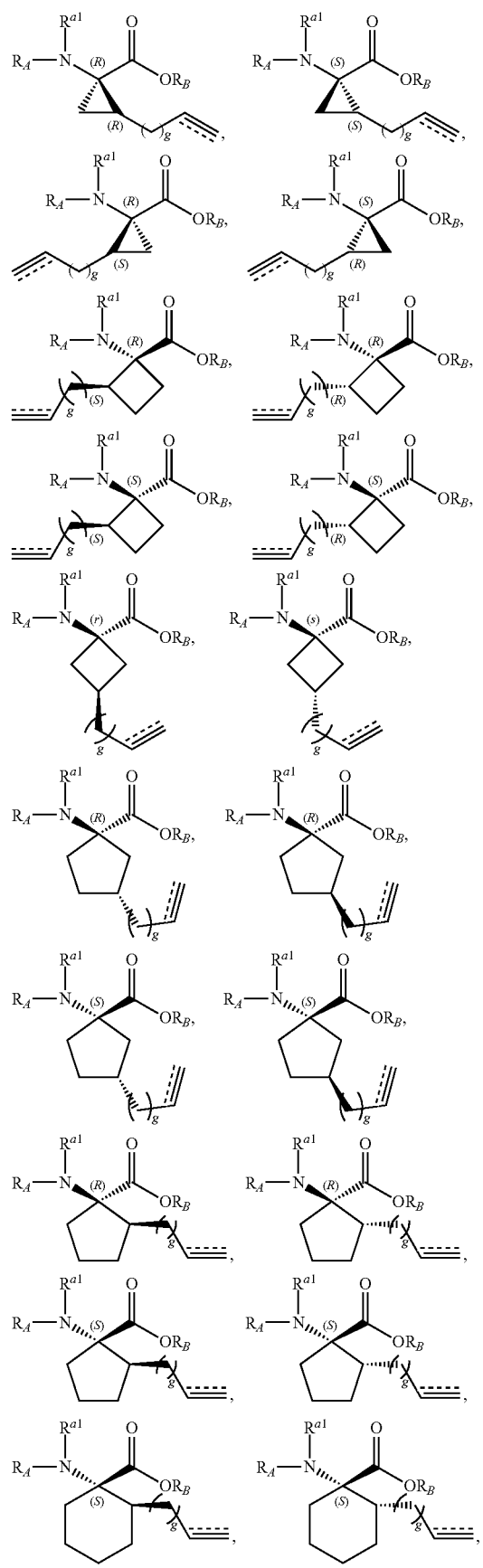

91
-continued
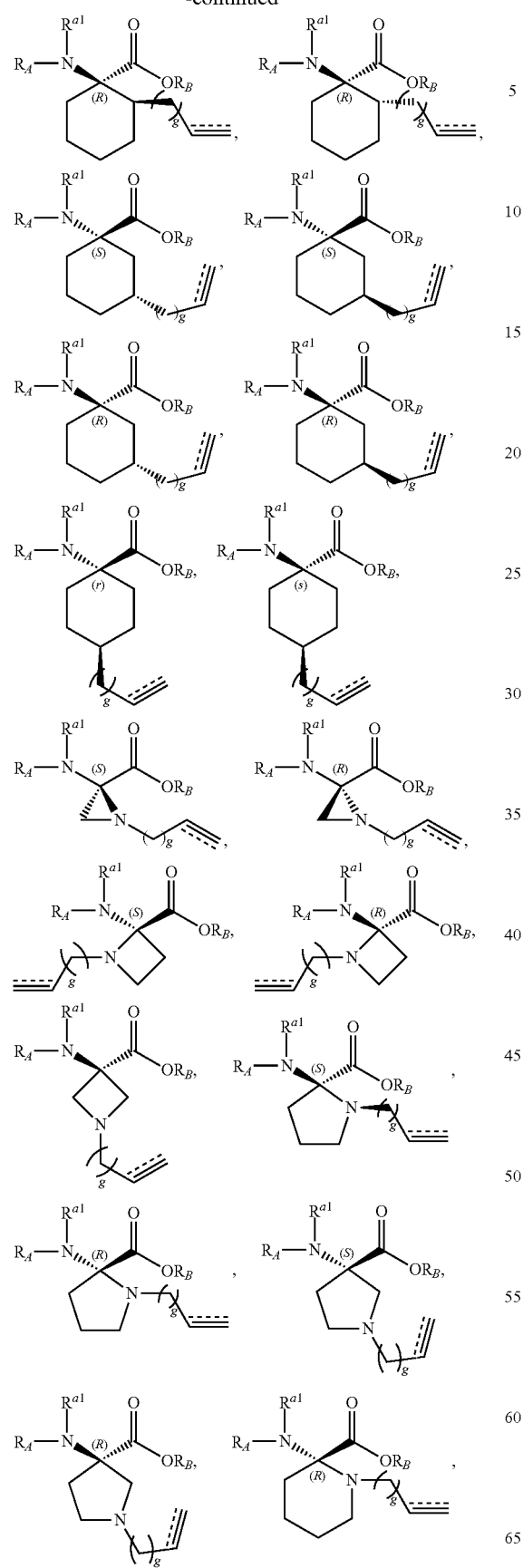
92
-continued
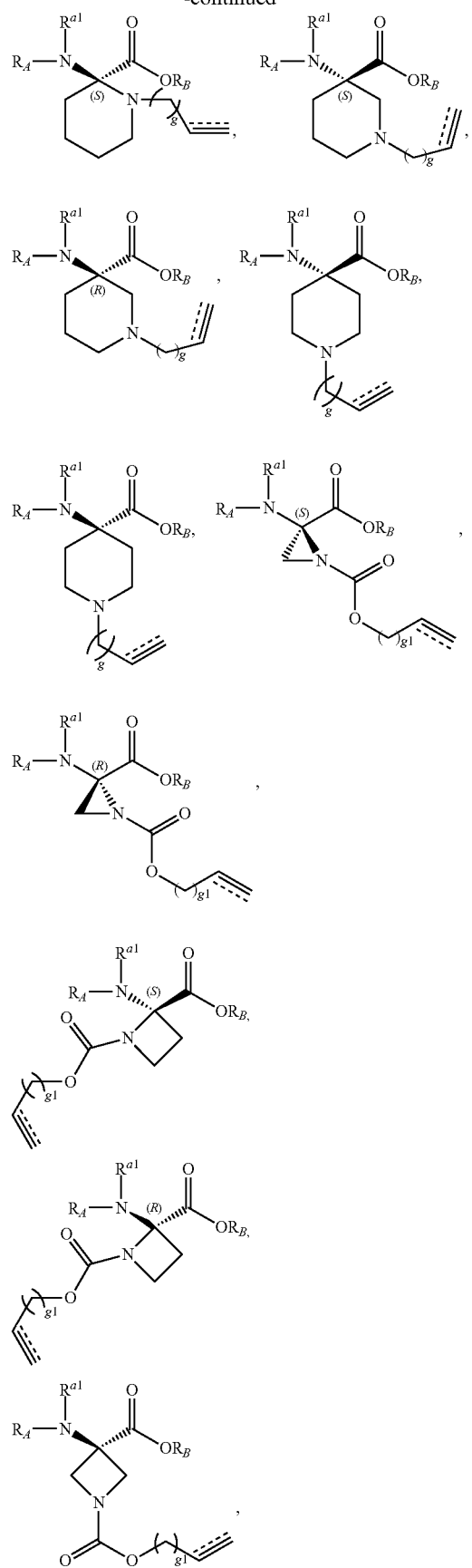

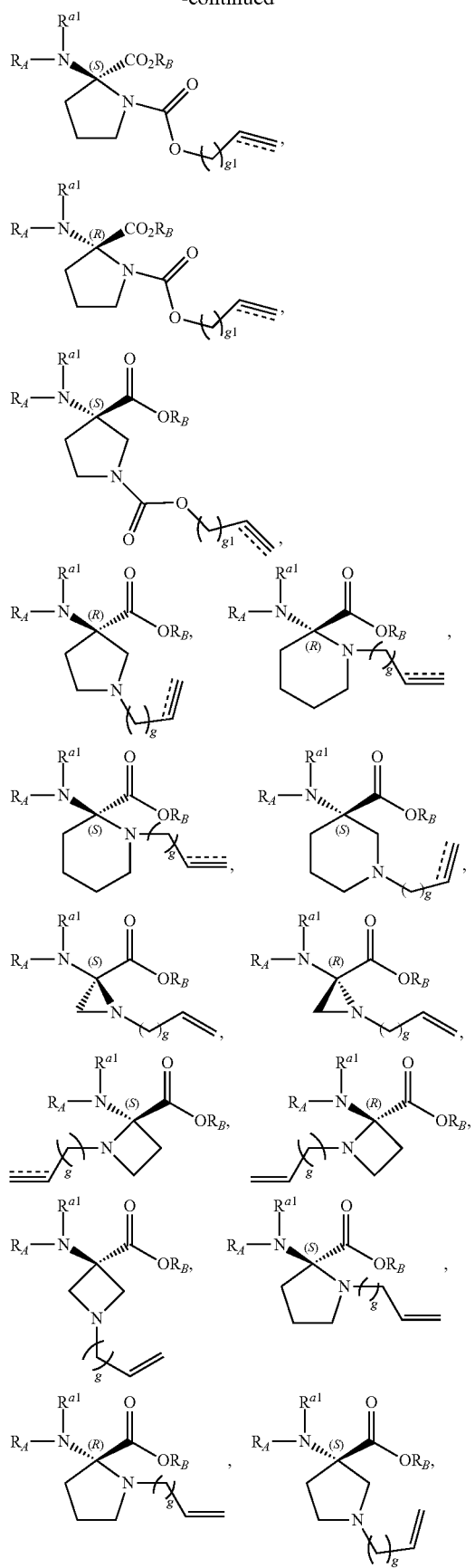
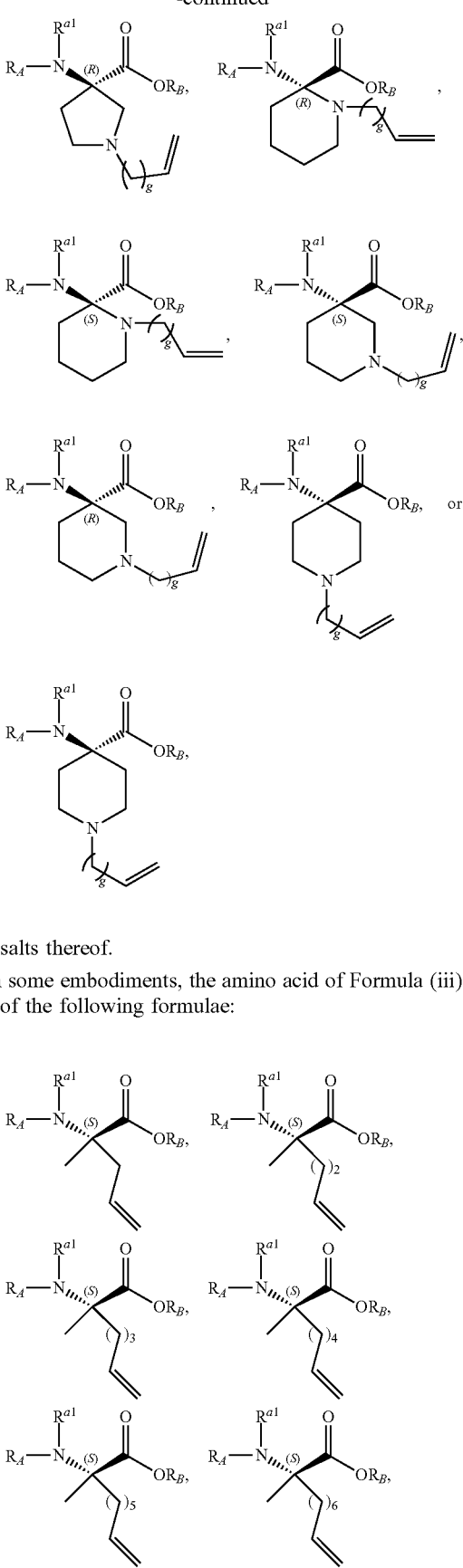
and salts thereof.
In some embodiments, the amino acid of Formula (iii) is one of the following formulae:

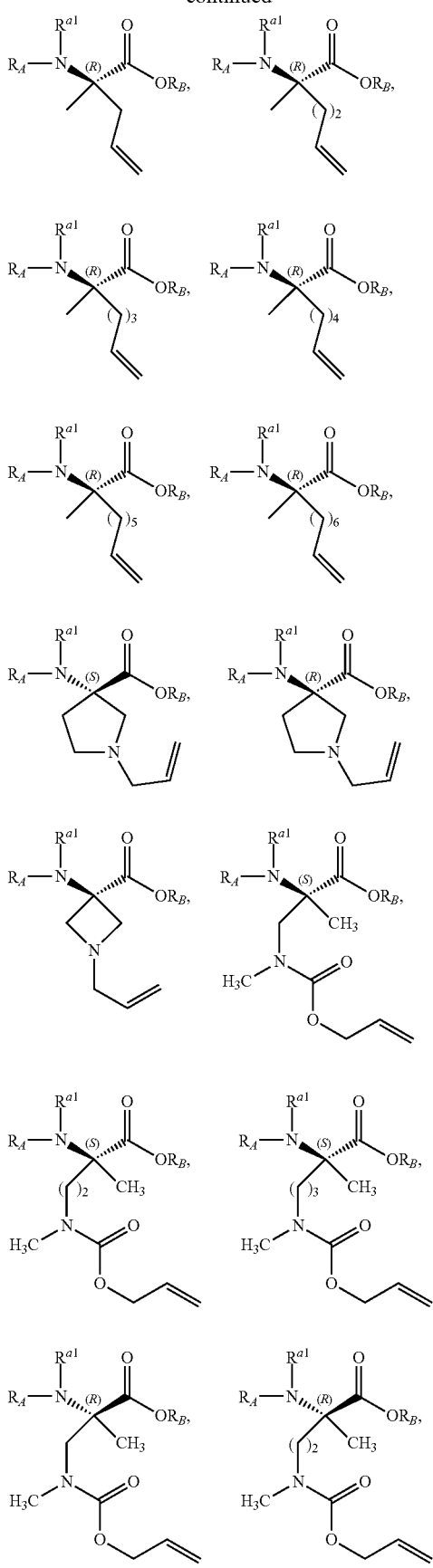
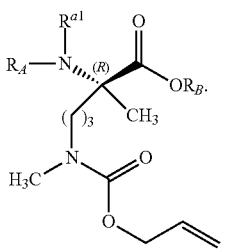
In some embodiments, the amino acid of Formula (iv) is one of the following formulae:
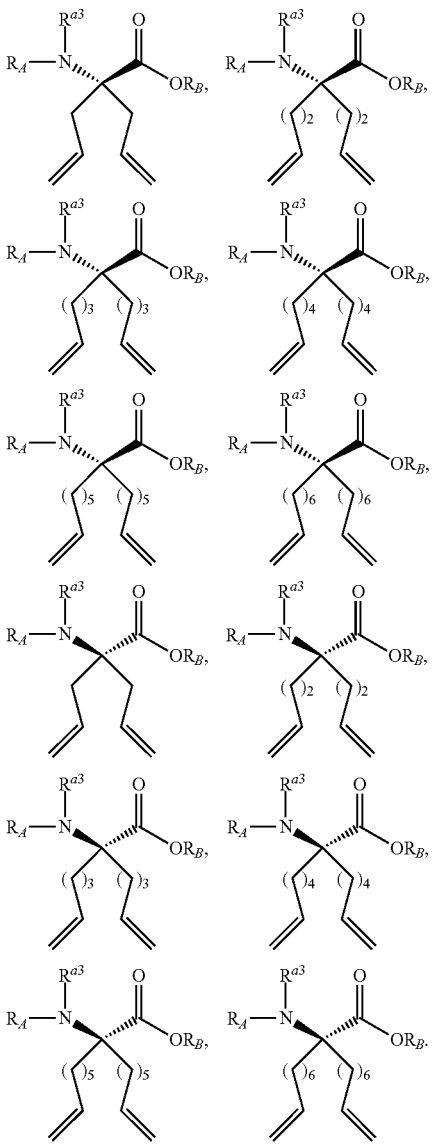
Pro-Lock
In some embodiments, the precursor polypeptides described herein comprise an amino acid of Formula (vi) as a replacement of or in addition to an amino acid of Formula (iii):

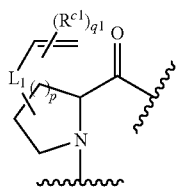

(vi)

wherein p is 1 or 2, and $L_1$, $R^{c1}$, and q1 are as defined herein.

In certain further embodiments, an amino acid of Formula (vi) is of the Formula (vi-a) or (vi-b):

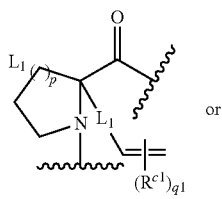

(vi-a)

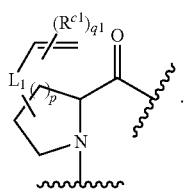

(vi-b)

In some embodiments, the precursor polypeptide comprising an amino acid of Formula (vi) and (iii), upon contact with a ring closing metathesis catalyst, generates a stapled polypeptide of Formula (vi):

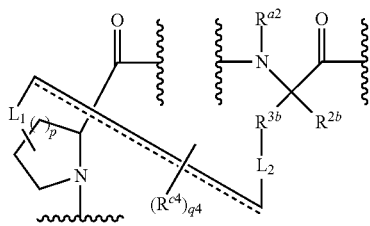

(vii)

wherein p is 1 or 2, and $L_1$, $L_2$, $R^{3b}$, $R^{2b}$, $R^{a2}$, $R^{c4}$, p, and q4 are as defined herein.

In some embodiments, the precursor polypeptide comprising an amino acid of Formula (vi), (iii), and (iv), upon contact with a ring closing metathesis catalyst, generates a stitched polypeptide of Formula (viii):

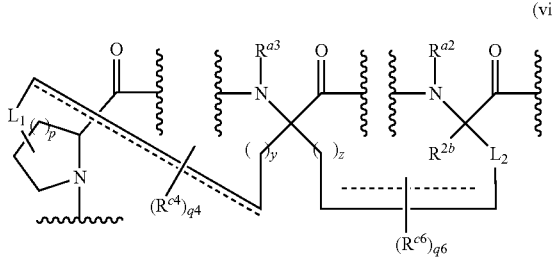

(vii)

wherein p is 1 or 2, and $L_1$, $L_2$, $R^{2b}$, $R^{a2}$, $R^{a3}$, $R^{c5}$, $R^{c6}$, q5, q6, $R^{c5}$, and $R^{c6}$ are as defined herein.

In some embodiments, the "pro-lock" motif is located at the N-terminus of the polypeptide.

Insulin Analogues

The present disclosure also provides insulin analogues combining the motifs of insulin and insulin sensitizer αCT polypeptide. The insulin analogues provided herein show high binding affinity toward IR, thereby extending the active conformation of IR. The provided insulin analogues comprises:

(i) a polypeptide as described herein;
(ii) an insulin A-chain polypeptide; and
(ii) an insulin B-chain polypeptide;

wherein the polypeptide is linked to the insulin A chain polypeptide via a linker; and the linker is optionally substituted alkylene-C(=O)—, optionally substituted heteroalkylene-C(=O)—, optionally substituted alkenylene-C(=O)—, optionally substituted heteroalkenylene-C(=O)—, optionally substituted alkynylene-C(=O)—, optionally substituted heteroalkynylene-C(=O)—, optionally substituted cycloalkylene-C(=O)—, optionally substituted heterocycloalkylene-C(=O)—, optionally substituted arylene-C(=O)—, optionally substituted heteroarylene-C(=O)—, optionally substituted aralkylene-C(=O)—, or optionally substituted heteroaralkylene-C(=O)—.

The provided insulin analogue may be an analogue of any vertebrate insulin or insulin analogue containing a fused A-chain and B-chain known in the art. In some embodiments, the insulin analogue is a mammalian insulin analogue such as human, murine, rodent, bovine, equine, or canine insulin analogues. In other embodiments, the insulin analogue is an analogue of sheep, whale, rat, elephant, guinea pig or chinchilla insulin.

In some embodiments, the provided insulin analogue has the isoelectric point similar to or less than that of wild-type human insulin, thereby preserving the solubility of the protein at neutral pH conditions.

It is further envisioned that the provided insulin analogues may also utilize any of a number of changes present in existing insulin analogues, modified insulins, or within various pharmaceutical formulations, such as regular insulin, NPH insulin, lente insulin or ultralente insulin, in addition to human insulin. The provided insulin analogues may also contain substitutions present in analogues of human insulin that, while not clinically used, are still useful experimentally, such as DKP-insulin, which contains the substitutions AspB10, LysB28 and ProB29 or the AspB9 substitution. The present invention is not, however, limited to human insulin and its analogues. It is also envisioned that these substitutions may also be made in animal insulins such as porcine, bovine, equine, and canine insulins, by way of non-limiting examples. Furthermore, in view of the similarity between human and animal insulins, and use in the past of animal insulins in human diabetic patients, it is also envisioned that other minor modifications in the sequence of insulin may be introduced, especially those substitutions considered "conservative" substitutions. In some embodiments, the insulin A-chain polypeptide and B-chain polypeptide are human insulin. In some embodiments, the insulin A-chain polypeptide and B-chain polypeptide are native human insulin. In some embodiments, the insulin A-chain polypeptide comprises an amino acid sequence of GIVEQC-CASVCSLYQLENYCN (SEQ ID NO:7). In some embodiments, the insulin A-chain polypeptide comprises an amino acid sequence: GIVEQCCTSICSLYQLENYCN (SEQ ID NO:8). In some embodiments, the insulin B-chain polypeptide comprises an amino acid sequence: FVNQHLCGD-HLVEALYLVCGERGFFYTPKT (SEQ ID NO:9). In some embodiments, the insulin B-chain polypeptide comprises an amino acid sequence: FVNQHLCGDHLVEALYL-VCGERGFFYTKPT (SEQ ID NO:10).

In some embodiments, the provided insulin analogue has the insulin B-chain polypeptide covalently connected to the insulin A-chain polypeptide via at least one disulfide bridges. In some embodiments, the provided insulin analogue has the insulin B-chain polypeptide covalently connected to the insulin A-chain polypeptide via two disulfide bridges.

The linker is a linear hydrophilic polymer chain containing a linkage functional group at each end of the chain for attaching the stapled or stitched peptide and the insulin A-chain. In some embodiments, the linker is attached to the C-terminal amino acid of the polypeptide and the N-terminal amino acid of the insulin A-chain polypeptide. In some embodiments, the linker in the insulin analogue is optionally substituted alkylene-C(=O)—, optionally substituted heteroalkylene-C(=O)—, optionally substituted alkenylene-C(=O)—, optionally substituted heteroalkenylene-C(=O)—, optionally substituted alkynylene-C(=O)—, optionally substituted heteroalkynylene-C(=O)—, optionally substituted cycloalkylene-C(=O)—, optionally substituted heterocycloalkylene-C(=O)—, optionally substituted arylene-C(=O)—, optionally substituted heteroarylene-C(=O)—, optionally substituted aralkylene-C(=O)—, or optionally substituted heteroaralkylene-C(=O)—. In some embodiments, the linker is polyglycine, polyethylene glycol, polypropylene glycol, polymethacrylamide, polyhydroxyethylacrylate, polyhydroxypropylmethacrylate, 8-amino-3,6-dioxaoctanoic acid, or polyoxyalkene. In some embodiments, the linker is polyglcycine or polyethylene glycol. In some embodiments, the linker is one of Formula (L-1) to Formula (L-3):

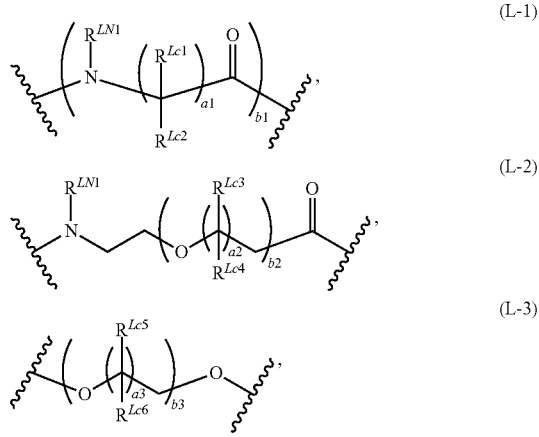

wherein
each of $R^{LN1}$ or $R^{LN2}$ is independently hydrogen; optionally substituted $C_{1-6}$ alkyl; or a nitrogen protecting group;
each of $R^{Lc1}$, $R^{Lc2}$, $R^{Lc3}$, $R^{Lc4}$, $R^{Lc5}$, and $R^{Lc6}$ is independently hydrogen; optionally substituted aliphatic; optionally substituted heteroaliphatic; optionally substituted aryl; optionally substituted heteroaryl; acyl; optionally substituted hydroxyl; optionally substituted thiol; optionally substituted amino; azido; cyano; isocyano; halogen; or nitro;
each of a1, a2, a3, b1, b2, and b3 is independently an integer of 1 to 10, inclusive.

In some embodiments, the linker is of the formula

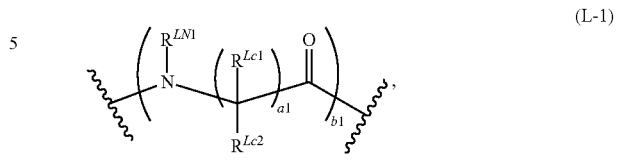

wherein $R^{LN1}$ is hydrogen; optionally substituted $C_{1-6}$ alkyl; or a nitrogen protecting group; each of $R^{Lc1}$ and $R^{Lc2}$ is independently hydrogen; optionally substituted aliphatic; optionally substituted heteroaliphatic; optionally substituted aryl; optionally substituted heteroaryl; acyl; optionally substituted hydroxyl; optionally substituted thiol; optionally substituted amino; azido; cyano; isocyano; halogen; or nitro; and each of a1 and b1 is independently an integer of 1 to 10, inclusive.

In some embodiments, $R^{LN1}$ is hydrogen. In some embodiments, $R^{LN1}$ is optionally substituted $C_{1-6}$ alkyl or a nitrogen protecting group. In some embodiments, $R^{LN1}$ is methyl, ethyl, or propyl. In some embodiments, $R^{LN1}$ is a nitrogen protecting group. a nitrogen protecting group is TBS, TBPS, Bn, BOC, Cbz, Fmoc, trifluoroacetyl, triphenylmethyl, or Ts.

In some embodiments, $R^{Lc1}$ is independently hydrogen; optionally substituted aliphatic; optionally substituted heteroaliphatic; optionally substituted aryl; optionally substituted heteroaryl; acyl; optionally substituted hydroxyl; optionally substituted thiol; optionally substituted amino; azido; cyano; isocyano; halogen; or nitro. In some embodiments, $R^{Lc1}$ is hydrogen. In some embodiments, $R^{Lc1}$ is optionally substituted aliphatic; optionally substituted heteroaliphatic; optionally substituted aryl; optionally substituted heteroaryl; acyl; optionally substituted hydroxyl; optionally substituted thiol; optionally substituted amino; azido; cyano; isocyano; halogen; or nitro. In some embodiments, $R^{Lc1}$ is optionally substituted $C_{1-6}$ alkyl. In some embodiments, $R^{Lc1}$ is methyl, ethyl, or propyl.

In some embodiments, $R^{Lc2}$ is independently hydrogen; optionally substituted aliphatic; optionally substituted heteroaliphatic; optionally substituted aryl; optionally substituted heteroaryl; acyl; optionally substituted hydroxyl; optionally substituted thiol; optionally substituted amino; azido; cyano; isocyano; halogen; or nitro. In some embodiments, $R^{Lc2}$ is hydrogen. In some embodiments, $R^{Lc2}$ is optionally substituted aliphatic; optionally substituted heteroaliphatic; optionally substituted aryl; optionally substituted heteroaryl; acyl; optionally substituted hydroxyl; optionally substituted thiol; optionally substituted amino; azido; cyano; isocyano; halogen; or nitro. In some embodiments, $R^{L2}$ is optionally substituted $C_{1-6}$ alkyl. In some embodiments, $R^{Lc2}$ is methyl, ethyl, or propyl.

In some embodiments, a1 is 1. In some embodiments, a1 is 2. In some embodiments, a1 is 3. In some embodiments, a1 is 4. In some embodiments, a1 is 5. In some embodiments, a1 is 6. In some embodiments, a1 is 7. In some embodiments, a1 is 8. In some embodiments, a1 is 9. In some embodiments, a1 is 10. In some embodiments, b1 is 1. In some embodiments, b1 is 2. In some embodiments, b1 is 3. In some embodiments, b1 is 4. In some embodiments, b1 is 5. In some embodiments, b1 is 6. In some embodiments, b1 is 7. In some embodiments, b1 is 8. In some embodiments, b1 is 9. In some embodiments, b1 is 10.

In some embodiments, the linker is of the formula

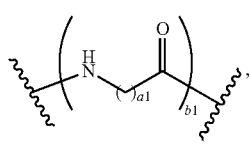

(L-1-a)

wherein each of a1 and b1 is independently an integer of 1 to 10, inclusive. In some embodiments, a1 is 1, and b1 is 1. In some embodiments, a1 is 1, and b1 is 2. In some embodiments, a1 is 1, and b1 is 3. In some embodiments, a1 is 1, and b1 is 4. In some embodiments, a1 is 1, and b1 is 5. In some embodiments, a1 is 1, and b1 is 6. In some embodiments, a1 is 1, and b1 is 7. In some embodiments, a1 is 1, and b1 is 8. In some embodiments, a1 is 2, and b1 is 1. In some embodiments, a1 is 2, and b1 is 2. In some embodiments, a1 is 2, and b1 is 3. In some embodiments, a1 is 2, and b1 is 4. In some embodiments, a1 is 2, and b1 is 5. In some embodiments, a1 is 2, and b1 is 6. In some embodiments, a1 is 2, and b1 is 7. In some embodiments, a1 is 2, and b1 is 8. In some embodiments, a1 is 3, and b1 is 1. In some embodiments, a1 is 3, and b1 is 2. In some embodiments, a1 is 3, and b1 is 3. In some embodiments, a1 is 3, and b1 is 4. In some embodiments, a1 is 3, and b1 is 5. In some embodiments, a1 is 3, and b1 is 6. In some embodiments, a1 is 3, and b1 is 7. In some embodiments, a1 is 3, and b1 is 8. In some embodiments, a1 is 4, and b1 is 1. In some embodiments, a1 is 4, and b1 is 2. In some embodiments, a1 is 4, and b1 is 3. In some embodiments, a1 is 4, and b1 is 4. In some embodiments, a1 is 4, and b1 is 5. In some embodiments, a1 is 4, and b1 is 6. In some embodiments, a1 is 4, and b1 is 7. In some embodiments, a1 is 4, and b1 is 8. In some embodiments, a1 is 5, and b1 is 1. In some embodiments, a1 is 5, and b1 is 2. In some embodiments, a1 is 5, and b1 is 3. In some embodiments, a1 is 5, and b1 is 4. In some embodiments, a1 is 5, and b1 is 5. In some embodiments, a1 is 5, and b1 is 6. In some embodiments, a1 is 5, and b1 is 7. In some embodiments, a1 is 5, and b1 is 8. In some embodiments, a1 is 1, and b1 is 1, 2, 3, 4, or 5.

In some embodiments, the linker is of the formula

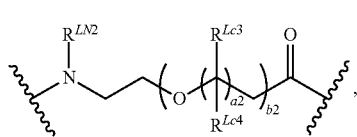

(L-2)

wherein $R^{LN2}$ is hydrogen; optionally substituted $C_{1-6}$ alkyl; or a nitrogen protecting group; each of $R^{Lc3}$ and $R^{Lc4}$ is independently hydrogen; optionally substituted aliphatic; optionally substituted heteroaliphatic; optionally substituted aryl; optionally substituted heteroaryl; acyl; optionally substituted hydroxyl; optionally substituted thiol; optionally substituted amino; azido; cyano; isocyano; halogen; or nitro; and each of a2 and b2 is independently an integer of 1 to 10, inclusive.

In some embodiments, $R^{LN2}$ is hydrogen. In some embodiments, $R^{LN2}$ is optionally substituted $C_{1-6}$ alkyl or a nitrogen protecting group. In some embodiments, $R^{LN2}$ is methyl, ethyl, or propyl. In some embodiments, $R^{LN2}$ is a nitrogen protecting group. a nitrogen protecting group is TBS, TBPS, Bn, BOC, Cbz, Fmoc, trifluoroacetyl, triphenylmethyl, or Ts.

In some embodiments, $R^{Lc3}$ is independently hydrogen; optionally substituted aliphatic; optionally substituted heteroaliphatic; optionally substituted aryl; optionally substituted heteroaryl; acyl; optionally substituted hydroxyl; optionally substituted thiol; optionally substituted amino; azido; cyano; isocyano; halogen; or nitro. In some embodiments, $R^{Lc3}$ is hydrogen. In some embodiments, $R^{Lc3}$ is optionally substituted aliphatic; optionally substituted heteroaliphatic; optionally substituted aryl; optionally substituted heteroaryl; acyl; optionally substituted hydroxyl; optionally substituted thiol; optionally substituted amino; azido; cyano; isocyano; halogen; or nitro. In some embodiments, $R^{Lc3}$ is optionally substituted $C_{1-6}$ alkyl. In some embodiments, $R^{Lc3}$ is methyl, ethyl, or propyl.

In some embodiments, $R^{L4}$ is independently hydrogen; optionally substituted aliphatic; optionally substituted heteroaliphatic; optionally substituted aryl; optionally substituted heteroaryl; acyl; optionally substituted hydroxyl; optionally substituted thiol; optionally substituted amino; azido; cyano; isocyano; halogen; or nitro. In some embodiments, $R^{Lc4}$ is hydrogen. In some embodiments, $R^{Lc4}$ is optionally substituted aliphatic; optionally substituted heteroaliphatic; optionally substituted aryl; optionally substituted heteroaryl; acyl; optionally substituted hydroxyl; optionally substituted thiol; optionally substituted amino; azido; cyano; isocyano; halogen; or nitro. In some embodiments, $R^{L4}$ is optionally substituted $C_{1-6}$ alkyl. In some embodiments, $R^{Lc4}$ is methyl, ethyl, or propyl.

In some embodiments, a2 is 1. In some embodiments, a2 is 2. In some embodiments, a2 is 3. In some embodiments, a2 is 4. In some embodiments, a2 is 5. In some embodiments, a2 is 6. In some embodiments, a2 is 7. In some embodiments, a2 is 8. In some embodiments, a2 is 9. In some embodiments, a2 is 10. In some embodiments, b2 is 1. In some embodiments, b2 is 2. In some embodiments, b2 is 3. In some embodiments, b2 is 4. In some embodiments, b2 is 5. In some embodiments, b2 is 6. In some embodiments, b2 is 7. In some embodiments, b2 is 8. In some embodiments, b2 is 9. In some embodiments, b2 is 10.

In some embodiments, the linker is

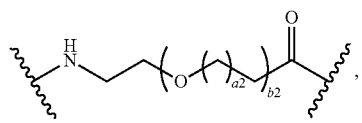

(L-a-a)

wherein each of a2 and b2 is independently an integer of 1 to 10, inclusive. In some embodiments, a2 is 1, and b2 is 1. In some embodiments, a2 is 1, and b2 is 2. In some embodiments, a2 is 1, and b2 is 3. In some embodiments, a2 is 1, and b2 is 4. In some embodiments, a2 is 1, and b2 is 5. In some embodiments, a2 is 1, and b2 is 6. In some embodiments, a2 is 1, and b2 is 7. In some embodiments, a2 is 1, and b2 is 8. In some embodiments, a2 is 2, and b2 is 1. In some embodiments, a2 is 2, and b2 is 2. In some embodiments, a2 is 2, and b2 is 3. In some embodiments, a2 is 2, and b2 is 4. In some embodiments, a2 is 2, and b2 is 5. In some embodiments, a2 is 2, and b2 is 6. In some embodiments, a2 is 2, and b2 is 7. In some embodiments, a2 is 2, and b2 is 8. In some embodiments, a2 is 3, and b2 is 1. In some embodiments, a2 is 3, and b2 is 2. In some embodiments, a2 is 3, and b2 is 3. In some embodiments, a2 is 3, and b2 is 4. In some embodiments, a2 is 3, and b2 is 5. In some embodiments, a2 is 3, and b2 is 6. In some embodiments, a2 is 3, and b2 is 7. In some embodiments, a2 is 3, and b2 is 8. In some embodiments, a2 is 4, and b2 is 1. In some embodiments, a2 is 4, and b2 is 2. In some embodiments, a2 is 4, and b2 is 3. In some embodiments, a2 is 4, and b2 is 4. In some embodiments, a2 is 4, and b2 is 5. In some embodiments, a2 is 4, and b2 is 6. In some embodiments, a2 is 4, and b2 is 7. In some embodiments, a2 is 4, and b2 is 8. In some embodiments, a2 is 5, and b2 is 1. In some embodiments, a2 is 5, and b2 is 2. In some embodiments, a2 is 5, and b2 is 3. In some embodiments, a2 is 5, and b2 is 4. In some embodiments, a2 is 5, and b2 is 5. In some embodiments, a2 is 5, and b2 is 6. In some embodiments, a2 is 5, and b2 is 7. In some embodiments, a2 is 5, and b2 is 8. In some embodiments, a2 is 1, and b2 is 1, 2, or 3.

In some embodiments, the linker is

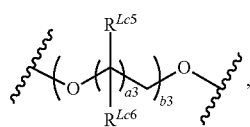

(L-3)

wherein each of $R^{Lc5}$ and $R^{Lc6}$ is independently hydrogen; optionally substituted aliphatic; optionally substituted heteroaliphatic; optionally substituted aryl; optionally substituted heteroaryl; acyl; optionally substituted hydroxyl; optionally substituted thiol; optionally substituted amino; azido; cyano; isocyano; halogen; or nitro; and each of a3 and b3 is independently an integer of 1 to 10, inclusive.

In some embodiments, $R^{Lc5}$ is independently hydrogen; optionally substituted aliphatic; optionally substituted heteroaliphatic; optionally substituted aryl; optionally substituted heteroaryl; acyl; optionally substituted hydroxyl; optionally substituted thiol; optionally substituted amino; azido; cyano; isocyano; halogen; or nitro. In some embodiments, $R^{Lc5}$ is hydrogen. In some embodiments, $R^{Lc5}$ is optionally substituted aliphatic; optionally substituted heteroaliphatic; optionally substituted aryl; optionally substituted heteroaryl; acyl; optionally substituted hydroxyl; optionally substituted thiol; optionally substituted amino; azido; cyano; isocyano; halogen; or nitro. In some embodiments, $R^{Lc5}$ is optionally substituted $C_{1-6}$ alkyl. In some embodiments, $R^{Lc5}$ is methyl, ethyl, or propyl.

In some embodiments, $R^{Lc6}$ is independently hydrogen; optionally substituted aliphatic; optionally substituted heteroaliphatic; optionally substituted aryl; optionally substituted heteroaryl; acyl; optionally substituted hydroxyl; optionally substituted thiol; optionally substituted amino; azido; cyano; isocyano; halogen; or nitro. In some embodiments, $R^{Lc6}$ is hydrogen. In some embodiments, $R^{Lc6}$ is optionally substituted aliphatic; optionally substituted heteroaliphatic; optionally substituted aryl; optionally substituted heteroaryl; acyl; optionally substituted hydroxyl; optionally substituted thiol; optionally substituted amino; azido; cyano; isocyano; halogen; or nitro. In some embodiments, $R^{Lc6}$ is optionally substituted $C_{1-6}$ alkyl. In some embodiments, $R^{Lc6}$ is methyl, ethyl, or propyl.

In some embodiments, a3 is 1. In some embodiments, a3 is 2. In some embodiments, a3 is 3. In some embodiments, a3 is 4. In some embodiments, a3 is 5. In some embodiments, a3 is 6. In some embodiments, a3 is 7. In some embodiments, a3 is 8. In some embodiments, a3 is 9. In some embodiments, a3 is 10. In some embodiments, b3 is 1. In some embodiments, b3 is 2. In some embodiments, b3 is 3. In some embodiments, b3 is 4. In some embodiments, b3 is 5. In some embodiments, b3 is 6. In some embodiments, b3 is 7. In some embodiments, b3 is 8. In some embodiments, b3 is 9. In some embodiments, b3 is 10.

In some embodiments, the linker is

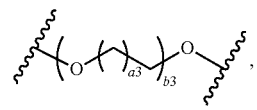

(L-3-a)

wherein each of a3 and b3 is independently an integer of 1 to 10, inclusive. In some embodiments, a3 is 1, and b3 is 1. In some embodiments, a3 is 1, and b3 is 2. In some embodiments, a3 is 1, and b3 is 3. In some embodiments, a3 is 1, and b3 is 4. In some embodiments, a3 is 1, and b3 is 5. In some embodiments, a3 is 1, and b3 is 6. In some embodiments, a3 is 1, and b3 is 7. In some embodiments, a3 is 1, and b3 is 8. In some embodiments, a3 is 2, and b3 is 1. In some embodiments, a3 is 2, and b3 is 2. In some embodiments, a3 is 2, and b3 is 3. In some embodiments, a3 is 2, and b3 is 4. In some embodiments, a3 is 2, and b3 is 5. In some embodiments, a3 is 2, and b3 is 6. In some embodiments, a3 is 2, and b3 is 7. In some embodiments, a3 is 2, and b3 is 8. In some embodiments, a3 is 3, and b3 is 1. In some embodiments, a3 is 3, and b3 is 2. In some embodiments, a3 is 3, and b3 is 3. In some embodiments, a3 is 3, and b3 is 4. In some embodiments, a3 is 3, and b3 is 5. In some embodiments, a3 is 3, and b3 is 6. In some embodiments, a3 is 3, and b3 is 7. In some embodiments, a3 is 3, and b3 is 8. In some embodiments, a3 is 4, and b3 is 1. In some embodiments, a3 is 4, and b3 is 2. In some embodiments, a3 is 4, and b3 is 3. In some embodiments, a3 is 4, and b3 is 4. In some embodiments, a3 is 4, and b3 is 5. In some embodiments, a3 is 4, and b3 is 6. In some embodiments, a3 is 4, and b3 is 7. In some embodiments, a3 is 4, and b3 is 8. In some embodiments, a3 is 5, and b3 is 1. In some embodiments, a3 is 5, and b3 is 2. In some embodiments, a3 is 5, and b3 is 3. In some embodiments, a3 is 5, and b3 is 4. In some embodiments, a3 is 5, and b3 is 5. In some embodiments, a3 is 5, and b3 is 6. In some embodiments, a3 is 5, and b3 is 7. In some embodiments, a3 is 5, and b3 is 8. In some embodiments, a3 is 1, and b3 is 1, 2, or 3.

The provided insulin analogues can be made by chemical synthesis either by a sequential approach or a convergent approach. As a general sequential synthetic approach, a method of preparing an insulin analogue as described herein comprising the steps of:

(a) coupling the C-terminal amino acid of the polypeptide as described herein with a linker to give a polypeptide-linker adduct;

(b) coupling the polypeptide-linker adduct from step (a) with the N-terminal amino acid of an insulin A-chain polypeptide to give a polypeptide-linker-A-chain adduct; and (c) coupling the polypeptide-linker-A-chain adduct with the N-terminal amino acid of an insulin B-chain polypeptide.

Figure 7:
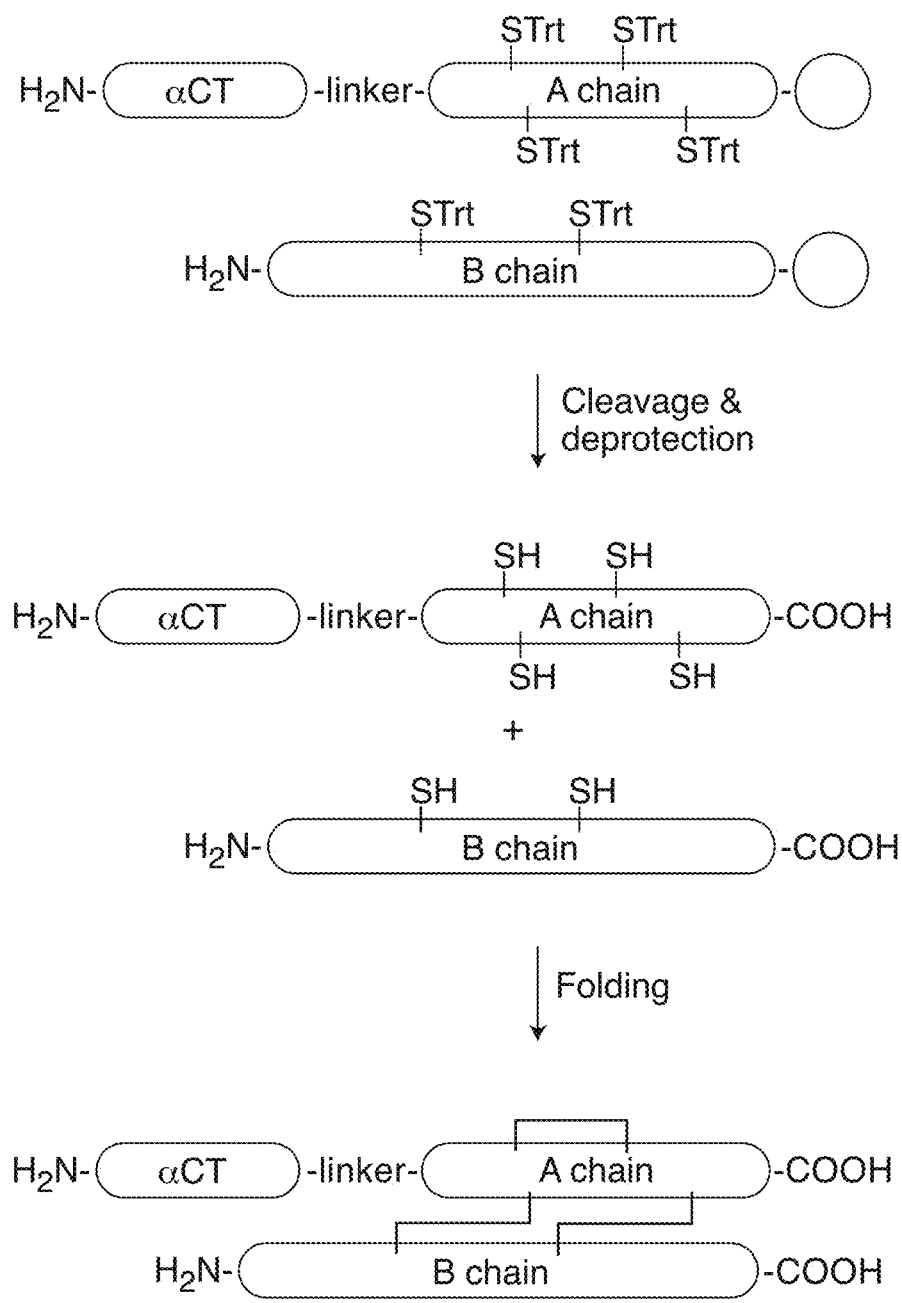
FIG. 7 depicts an exemplary sequential approach to preparing the insulin analogues described herein. The insulin A chain and the stabilized αCT polypeptide connected by a chemical linker is synthesized by solid phase polypeptide synthesis (SPPS) with trityl protecting groups on the insulin A chain cysteines. Preparation of the insulin B chain follows a similar approach. After cleavage from the resin and deprotection, the two fragments are combined in an appropriate folding buffer to obtain a construct with the three native disulfide bonds found in insulin.

An exemplified sequential synthetic approach is shown in FIG. 7: the C-terminal amino acid of the stapled or stitched polypeptide (i.e. stabilized αCT polypeptide) of Formula (I) is coupled with a linker to give a polypeptide-linker adduct using SPPS techniques; the insulin A-chain is then fused to the polypeptide-linker adduct using standard SPPS techniques. After cleaving the polypeptide-linker-A-chain adduct from the solid support, polypeptide-linker-A-chain adduct is incubated with insulin B-chain under folding conditions to attain a chimeric insulin/αCT construct bearing the three disulfide bridges found in native insulin. This sequential approach provides a straightforward route toward the panel of insulin analogues bearing a variety of chemical linkers.

Another exemplary sequential approach is silyl chloride-sulfoxide method (Akaji, K., Fujino, K., Tatsumi, T. & Kiso, Y. Total synthesis of human insulin by regioselective disulfide formation using the silyl chloride-sulfoxide method. J Am Chem Soc 115, 11384-11392 (1993)). In this strategy, pairs of cysteines with three different orthogonal thiol-protecting groups (trityl, acetamidomethyl, and tert-butyl) are introduced into the insulin A and B chain via SPPS. After cleavage of the peptides from the resin, the protecting groups are removed successively to release one pair of thiol groups at a time for directed disulfide bond formation Alternatively, the provided insulin analogues can be synthesized by a convergent approach. As a general convergent synthetic approach, a method of preparing an insulin analogue as described herein comprising the steps of:

(a) coupling the C-terminal amino acid of the polypeptide of claim 1 with a linker to give a polypeptide-linker adduct;

(b) coupling the insulin A-chain with the insulin B-chain via at least one disulfide bridge to give a A-chain-B-chain adduct;

(c) coupling the polypeptide-linker adduct from step (a) with the N-terminal amino acid of the A-chain-B-chain adduct of step (b).

Figure 8:
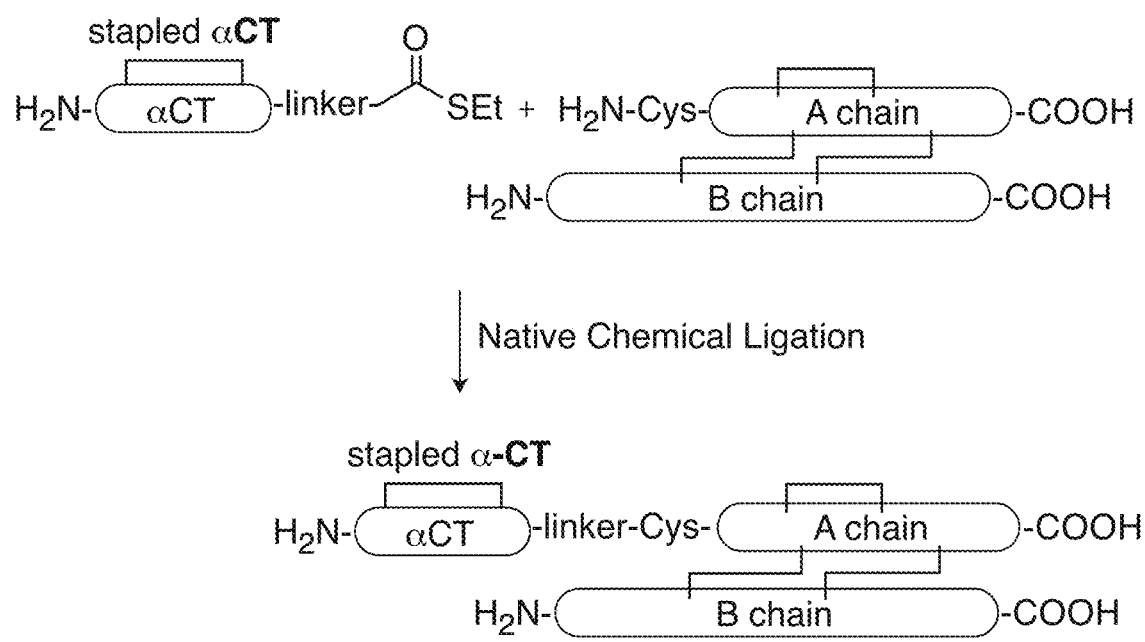
FIG. 8 depicts an exemplary convergent approach to preparing the insulin analogues described herein. The stabilized αCT polypeptide bearing a chemical linker and C-terminal thioester are synthesized by SPPS. Insulin, having both an A-chain and B-chain, is synthesized and folded. The resulting insulin bears an additional cysteine on the N-terminus of the A chain. Native chemical ligation (NCL) is then used to produce the inventive insulin analogues as stapled or stitched insulin/αCT chimera.
Figure 11:
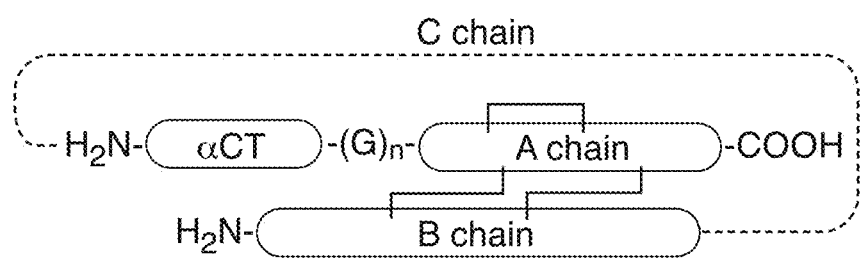
FIG. 11 depicts an example of the biosynthesis of insulin analogues by expressing αCT-linker-preproinsulin in *E. coli* (BL21) using vector pD444-NH. Three vector constructs are employed: original vector for insulin (Lispro variant, with C-chain), vector for insulin analogue (including $(GGGS)_2$-linker and αCT, with C-chain), vector for insulin analogue (including $(GGGS)_2$-linker and αCT, truncated C-chain). Constructs of different total lengths (with original or truncated C-chain) are expressed in *E. coli*. The resulting inclusion bodies are purified, and the preproinsulin constructs subsequently re-folded. Enzymatic cleavage of the His-tag and C-chain provides the insulin analogues. This process is adjusted from the methods provided in US Patent Application Publication, US 2012/0058513, which avoids the sulfitolysis step, therefore directing refolding of the reduced polypeptide to increase folding yields.
Figure 15:
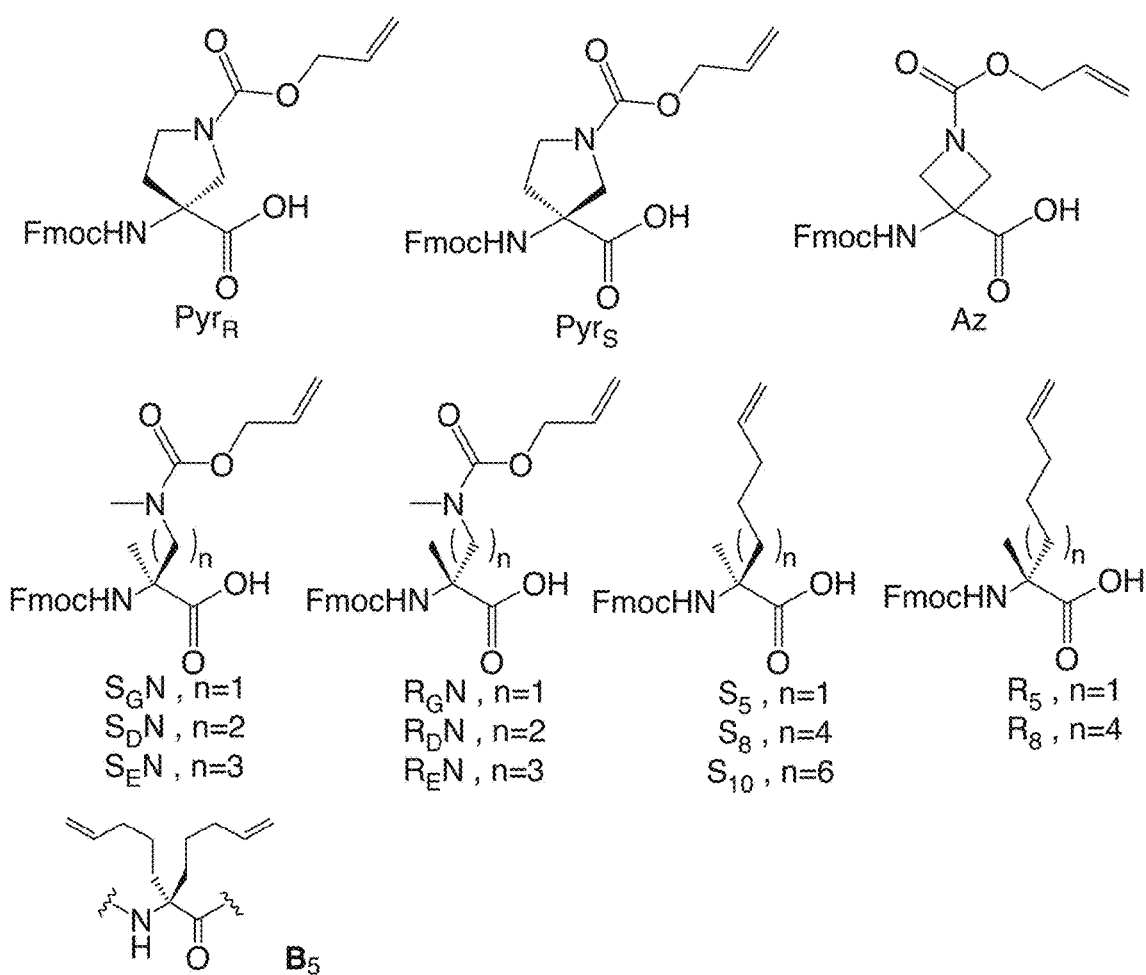
FIG. 15 depicts exemplary non-natural amino acids used in the synthesis of insulin analogues.
Figure 16:
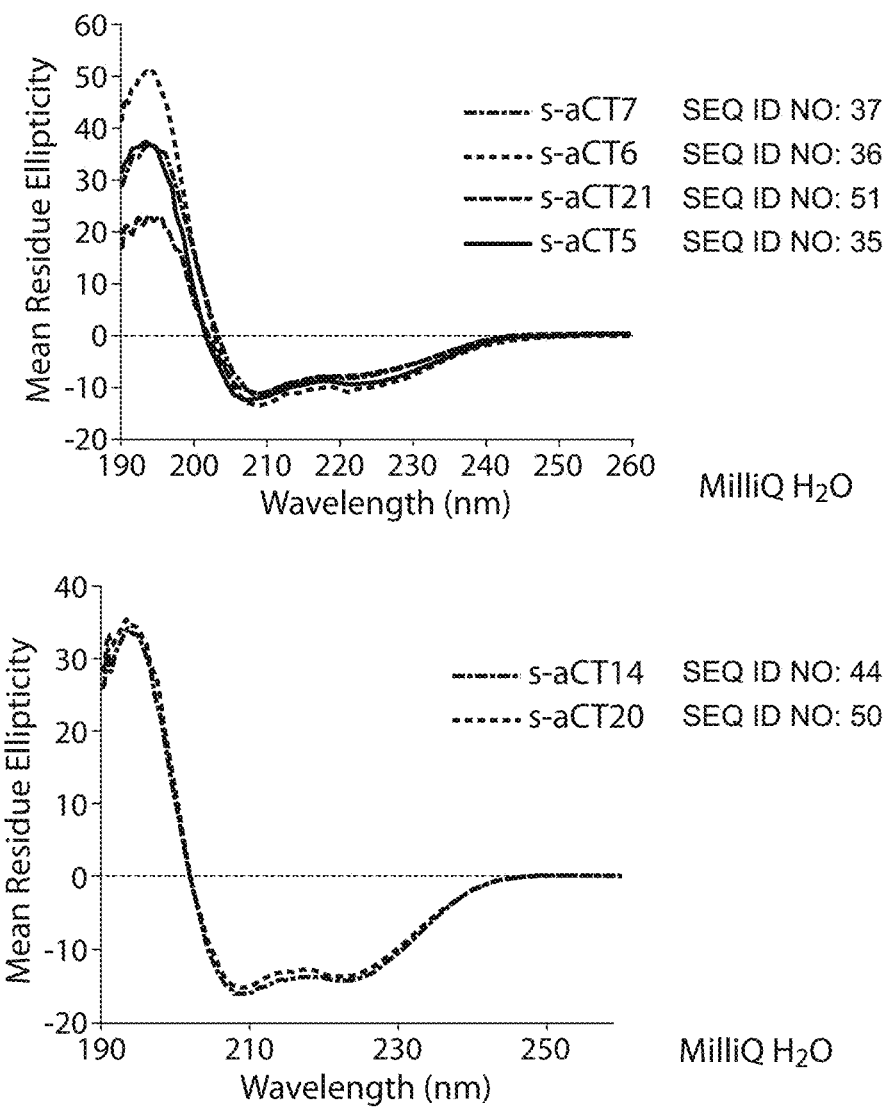
FIGS. 16-21 depict circular dichroism spectroscopy of exemplified insulin α-CT polypeptides from Table 4 in FIG. 23. The polypeptides are dissolved in either 10 mM sodium phosphate (pH 7.0) buffer, PBS, or MilliQ $H_2O$. The raw data have been converted to the concentration-independent units of mean residue ellipticity (first two plots) or molar ellipticity (the remainder of the plots). α-Helices typically show dual minima at approximately 208 nm and 222 nm and a maximum at approximately 192 nm. In PBS, buffer interference disrupts data at less than 200 nm. Spectra were obtained using a JASCO J-710 spectropolarimeter (see Example 2).
Figure 17:
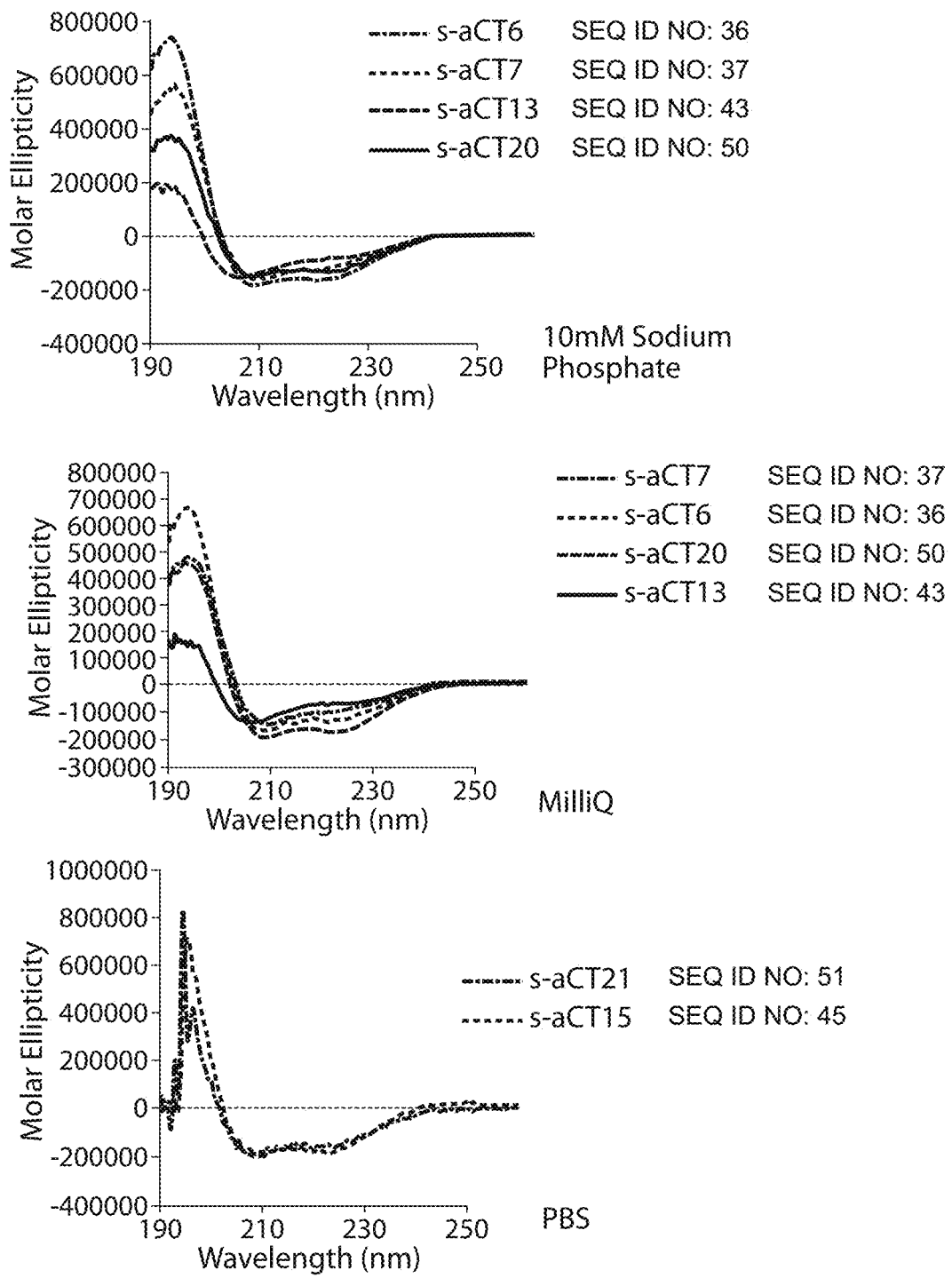
Figure 18:
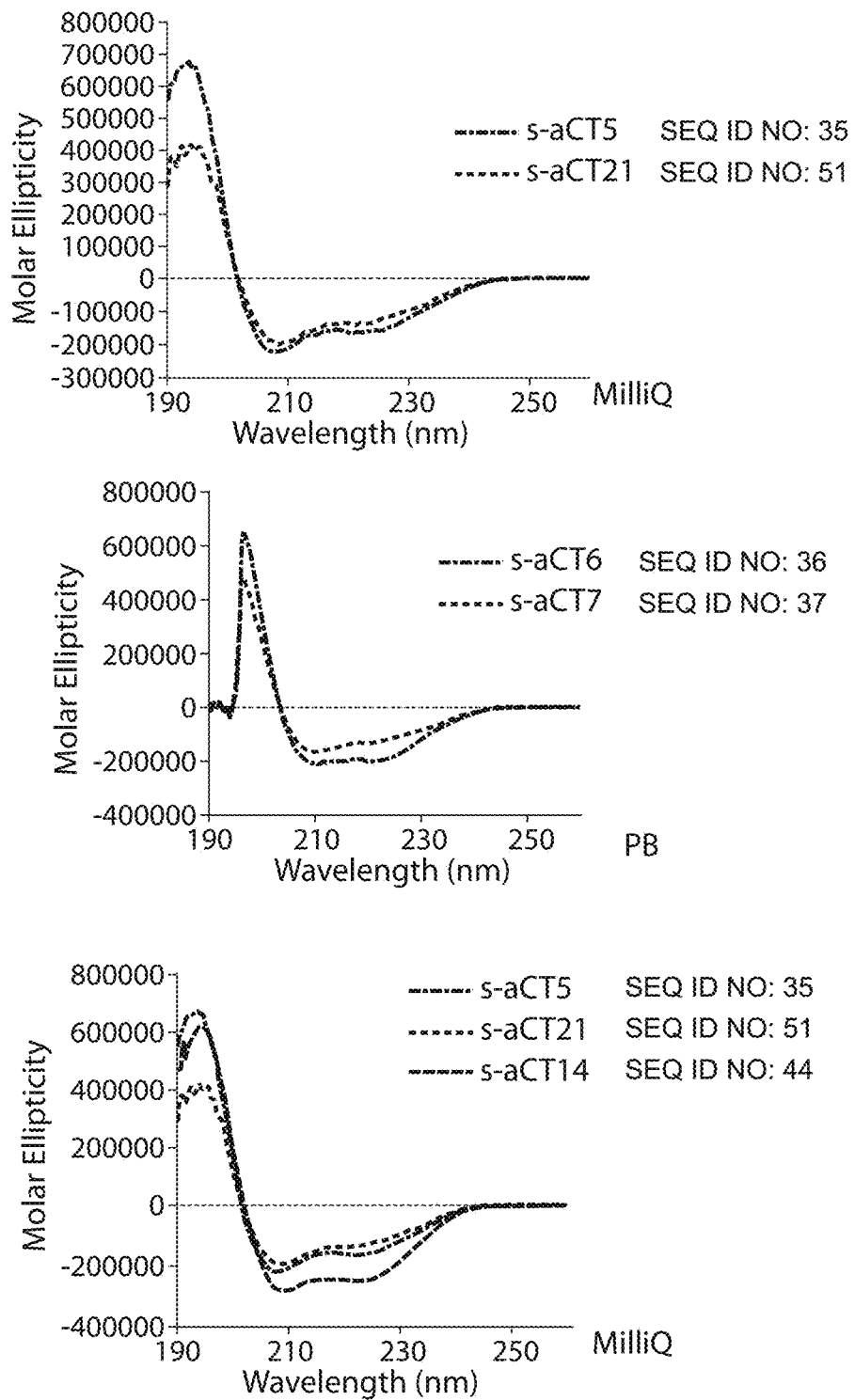
Figure 19:
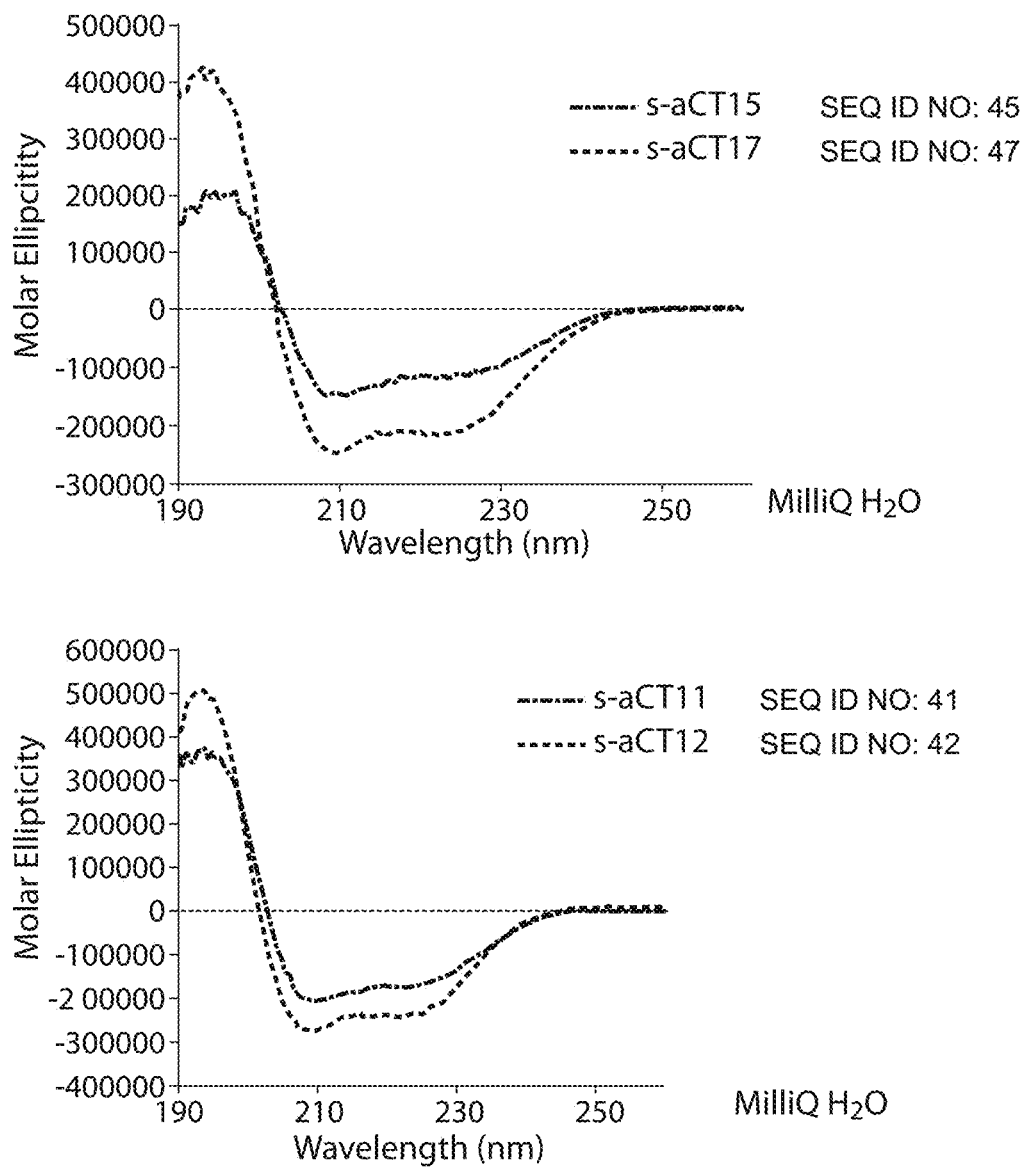
Figure 20:
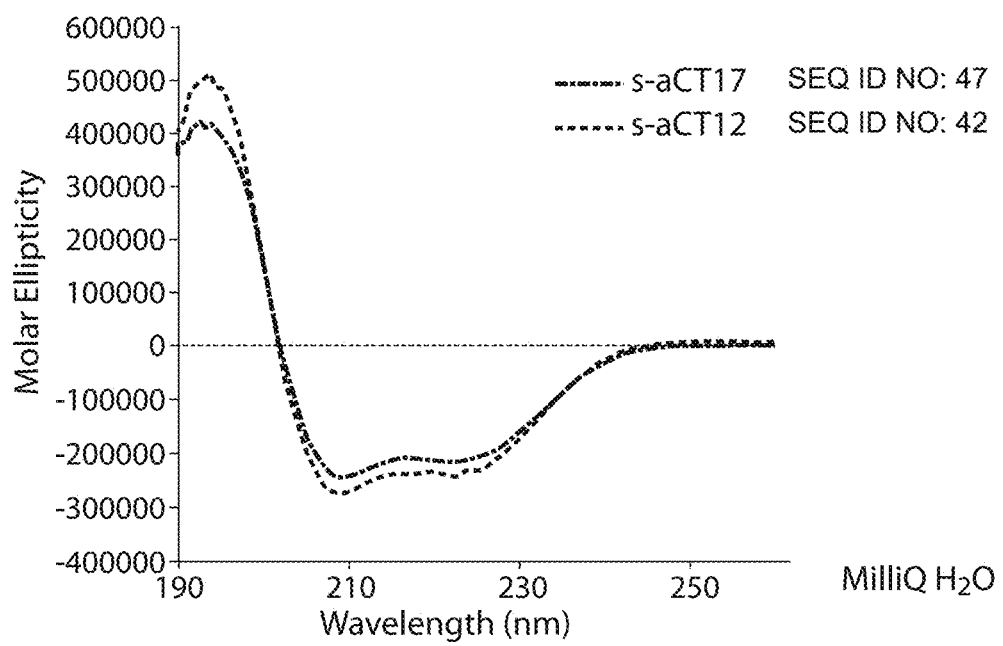
Figure 21:
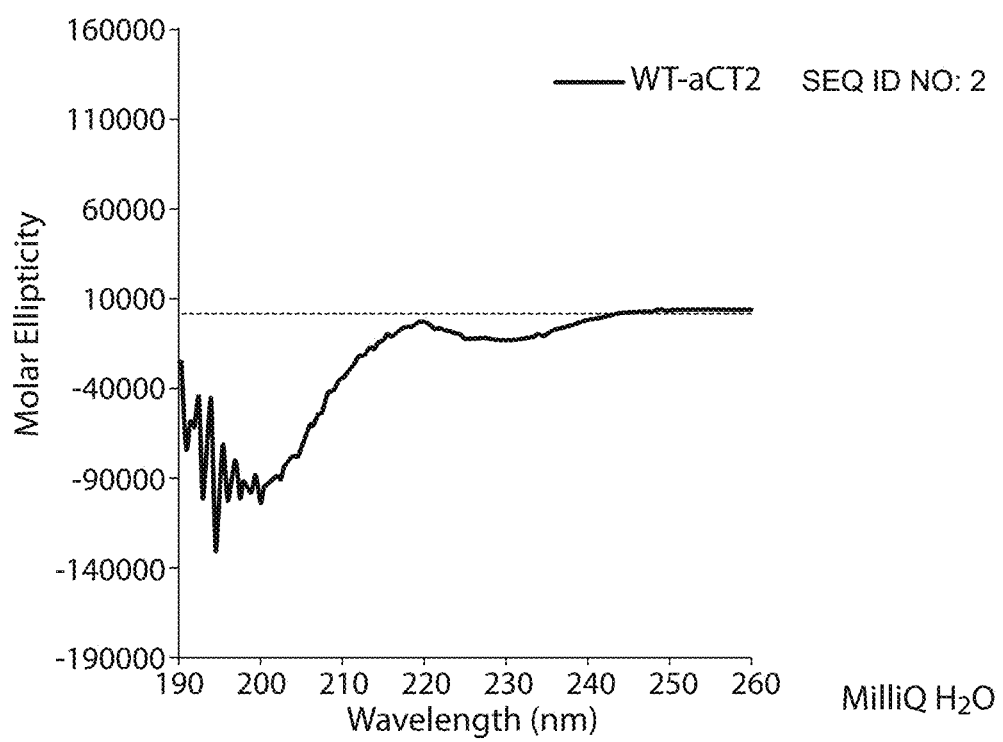
Figure 22A:
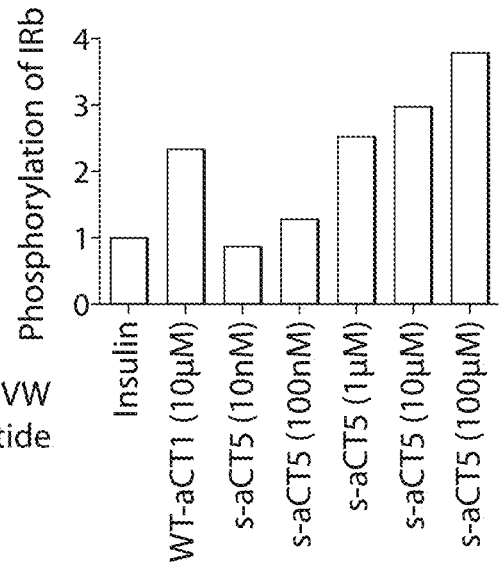
FIG. 22A shows the dose-response assay with s-αCT5.
Figure 22B:
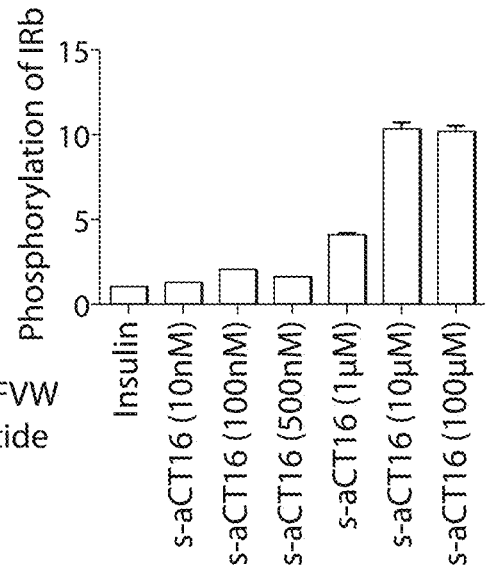
FIG. 22B shows the dose-response assay with s-αCT16.
Figure 24:
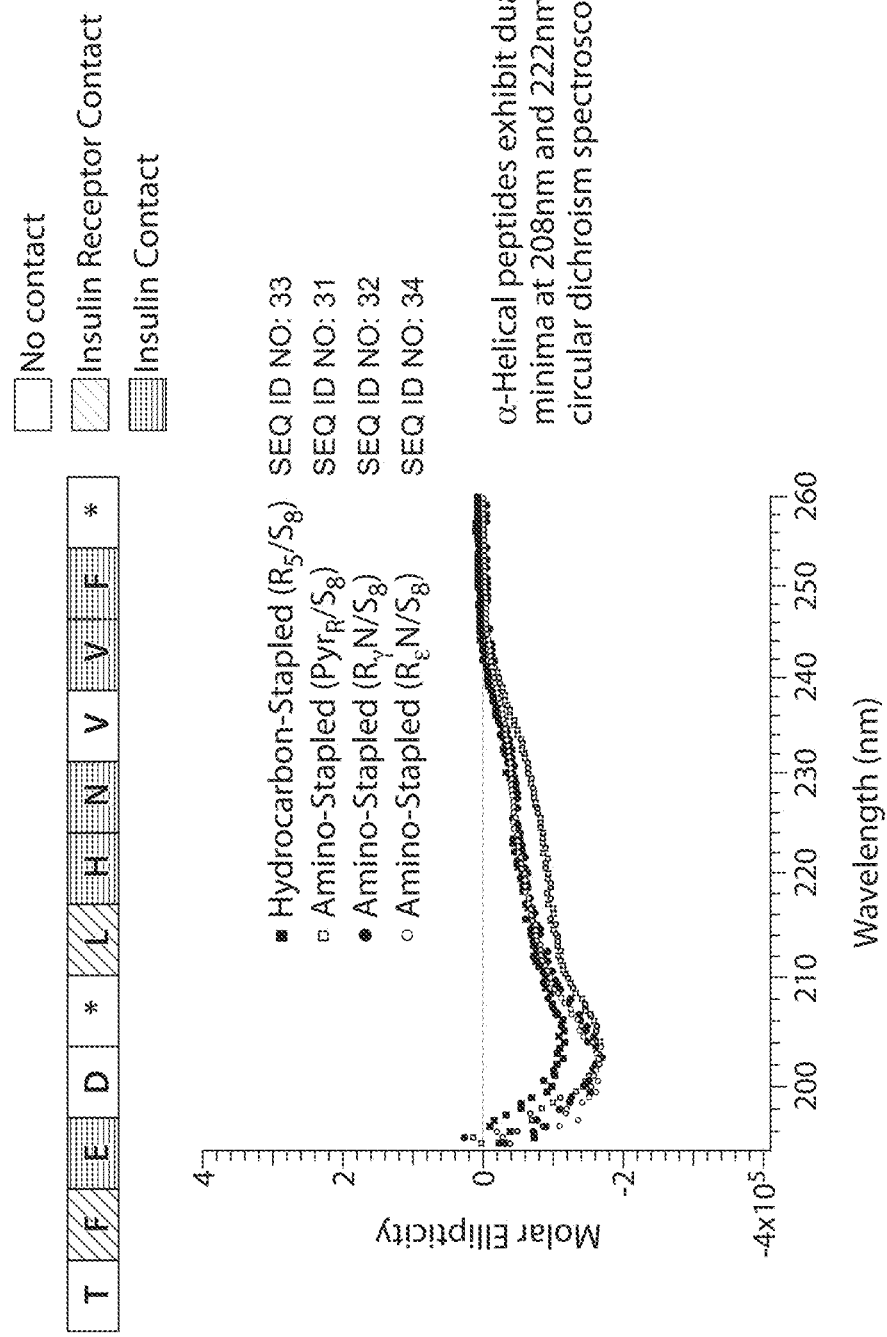
FIG. 24-29 depict exemplified hydrocarbon-stapled, amino stapled, and Alloc-stapled insulin α-CT polypeptides. RγN is $R_GN$ as shown in FIG. 15. RεN is $R_EN$ as shown in FIG. 15. SεN is $S_EN$ as shown in FIG. 15.
Figure 25:
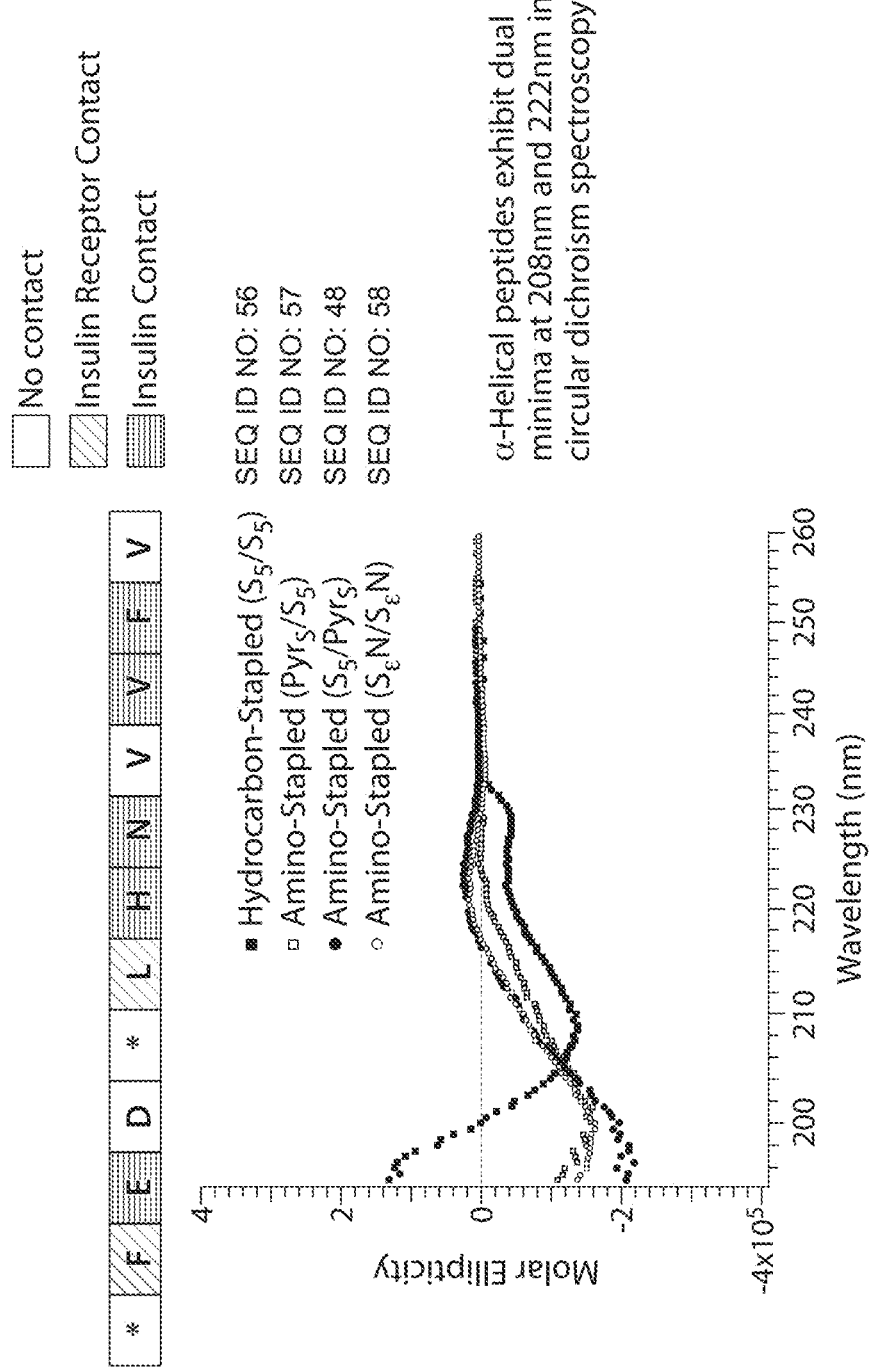
Figure 26:
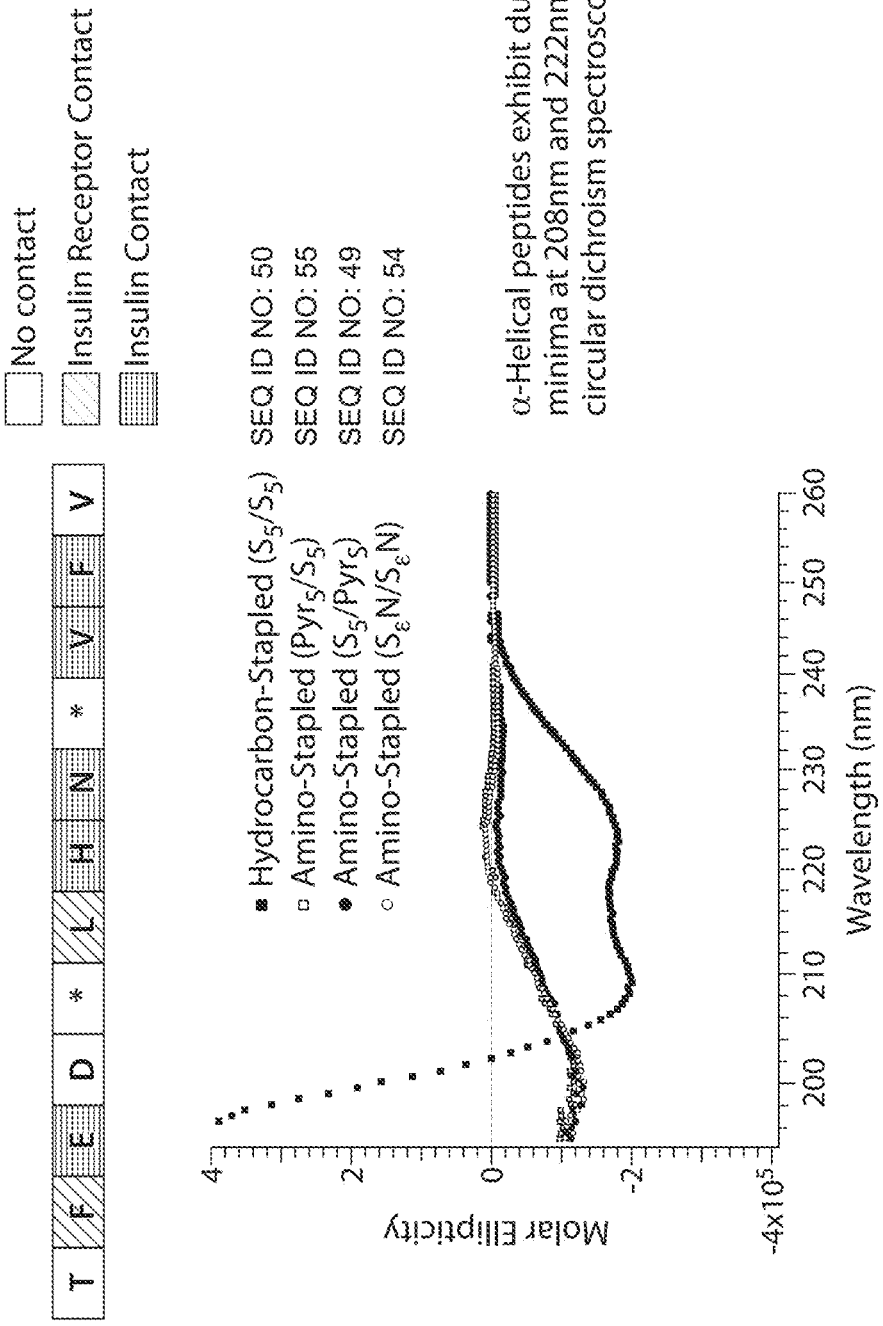
Figure 27:
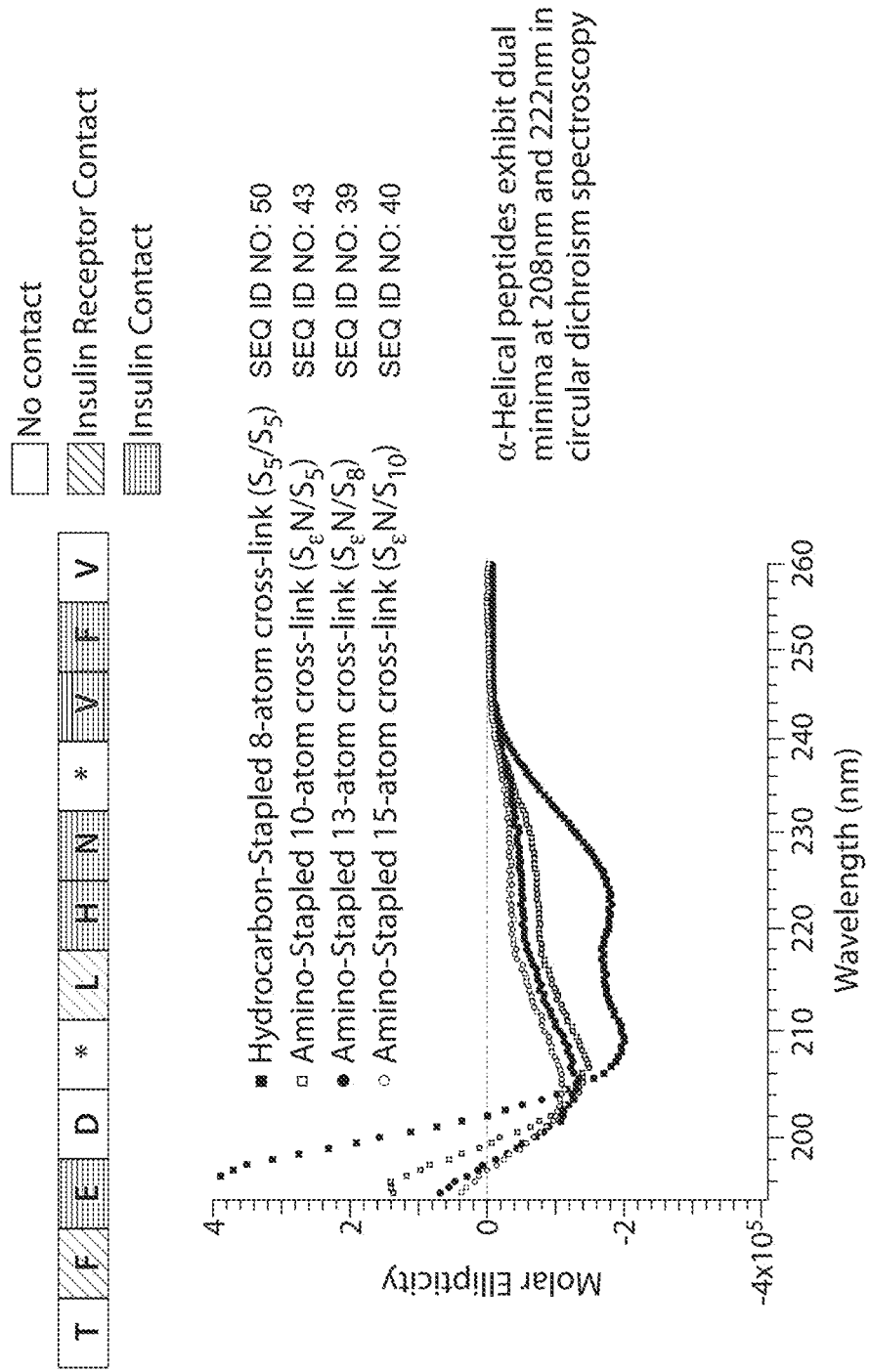
Figure 28:
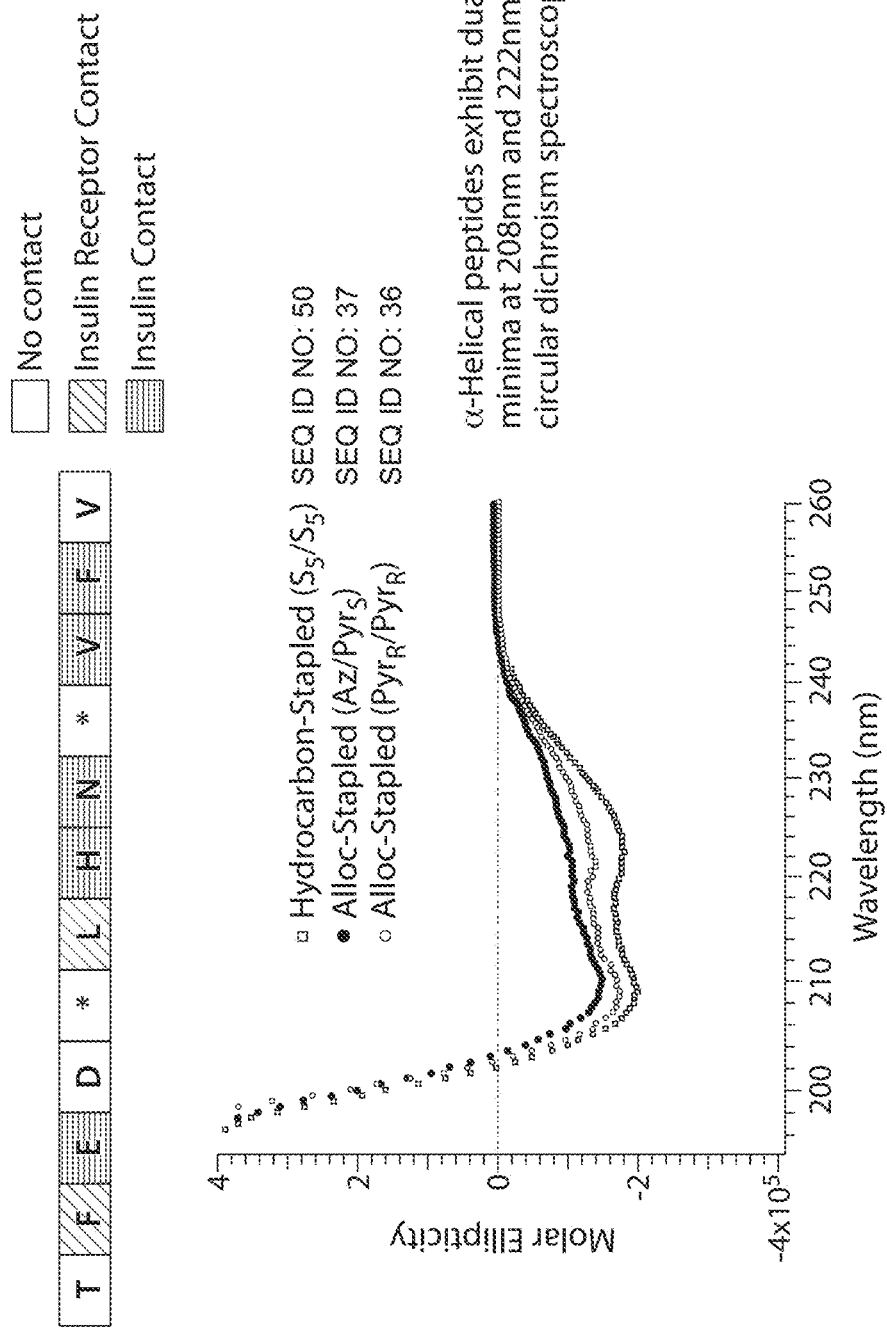
Figure 29:
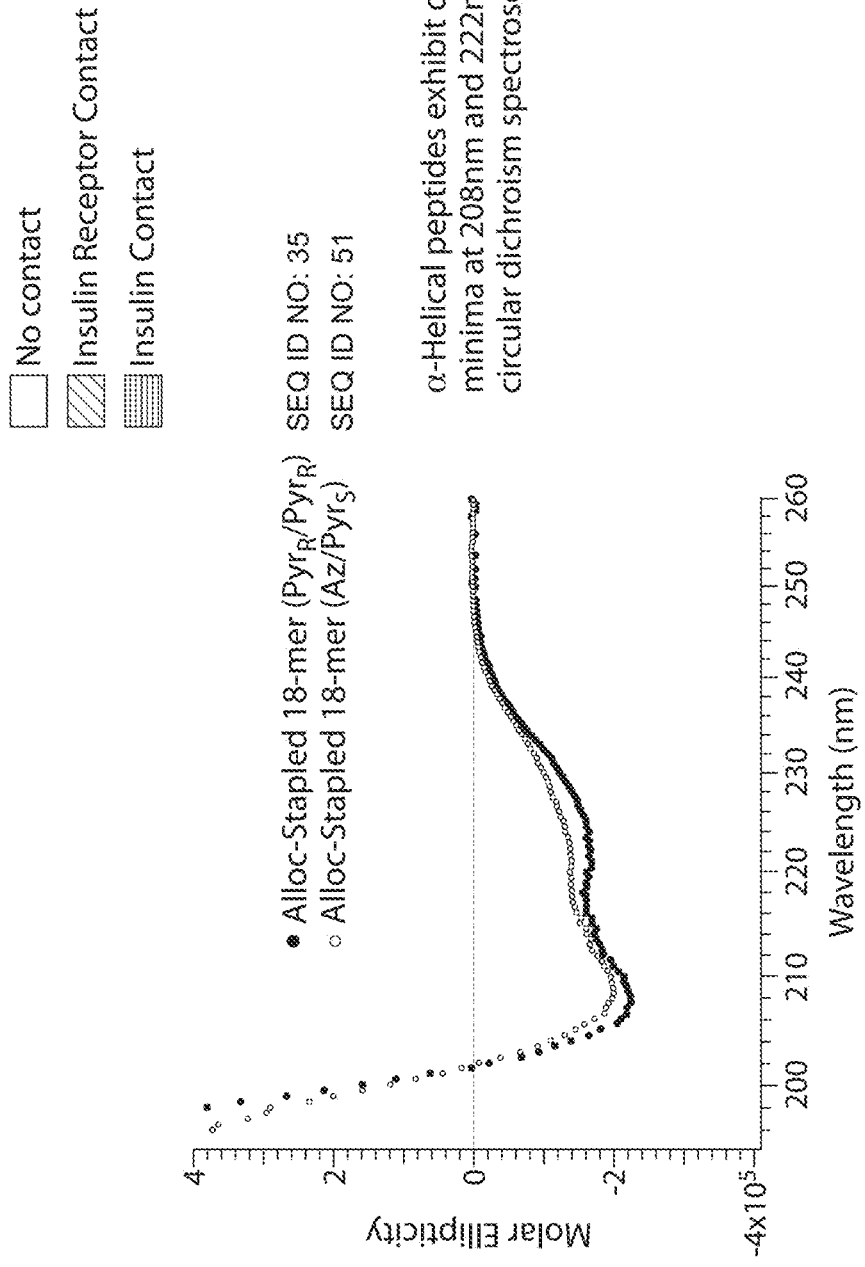
Figure 30:
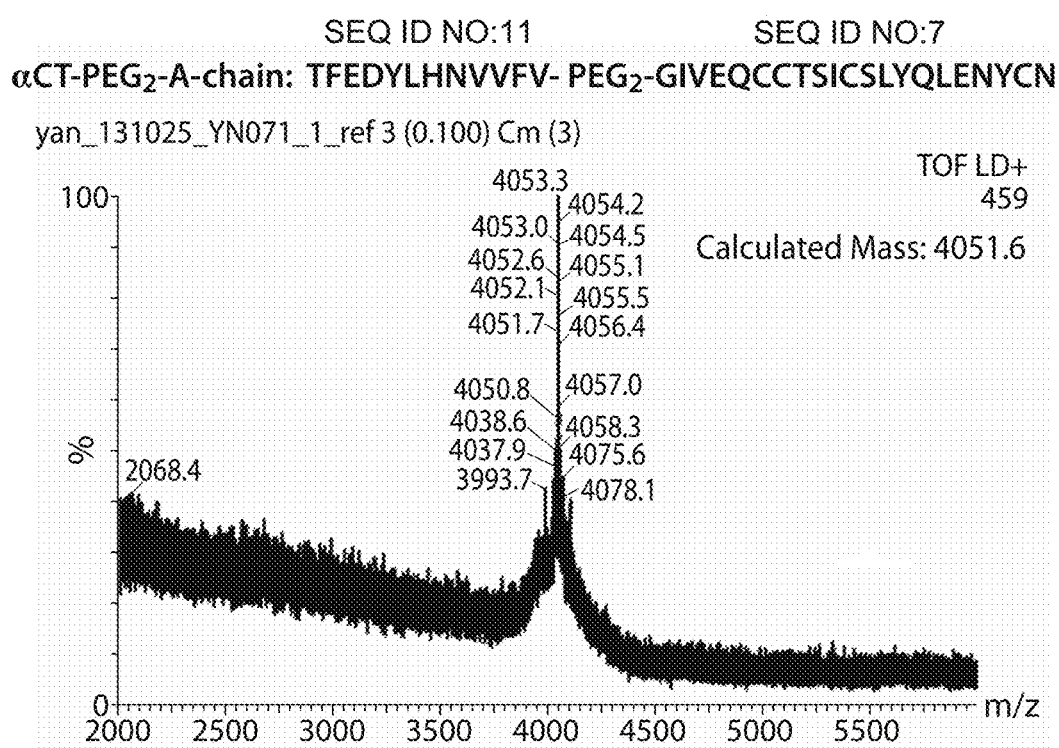
FIG. 30 depicts exemplified Mass-spectrum of an exemplified insulin analog of α-CT-PEG2-A-chain.
Figure 31:
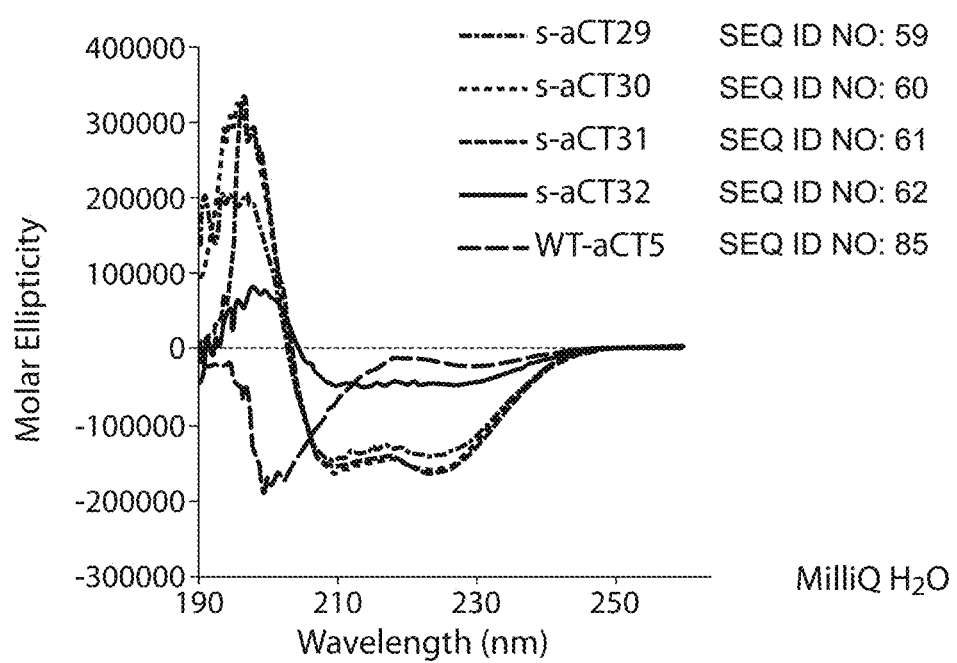
FIGS. 31-32 depict circular dichroism spectroscopy of exemplified insulin α-CT polypeptides from Table 4 as shown in FIG. 23.
Figure 32:
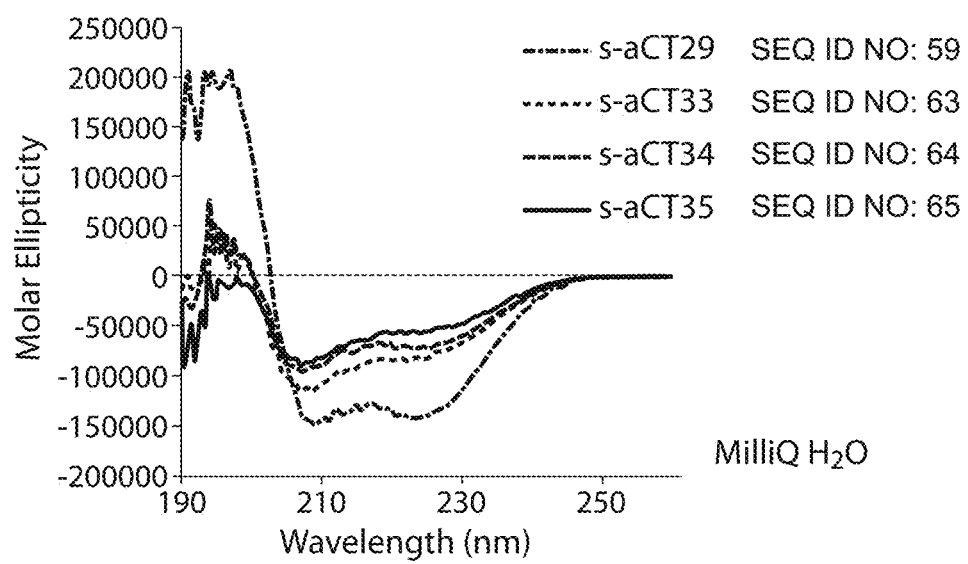
Figure 33:
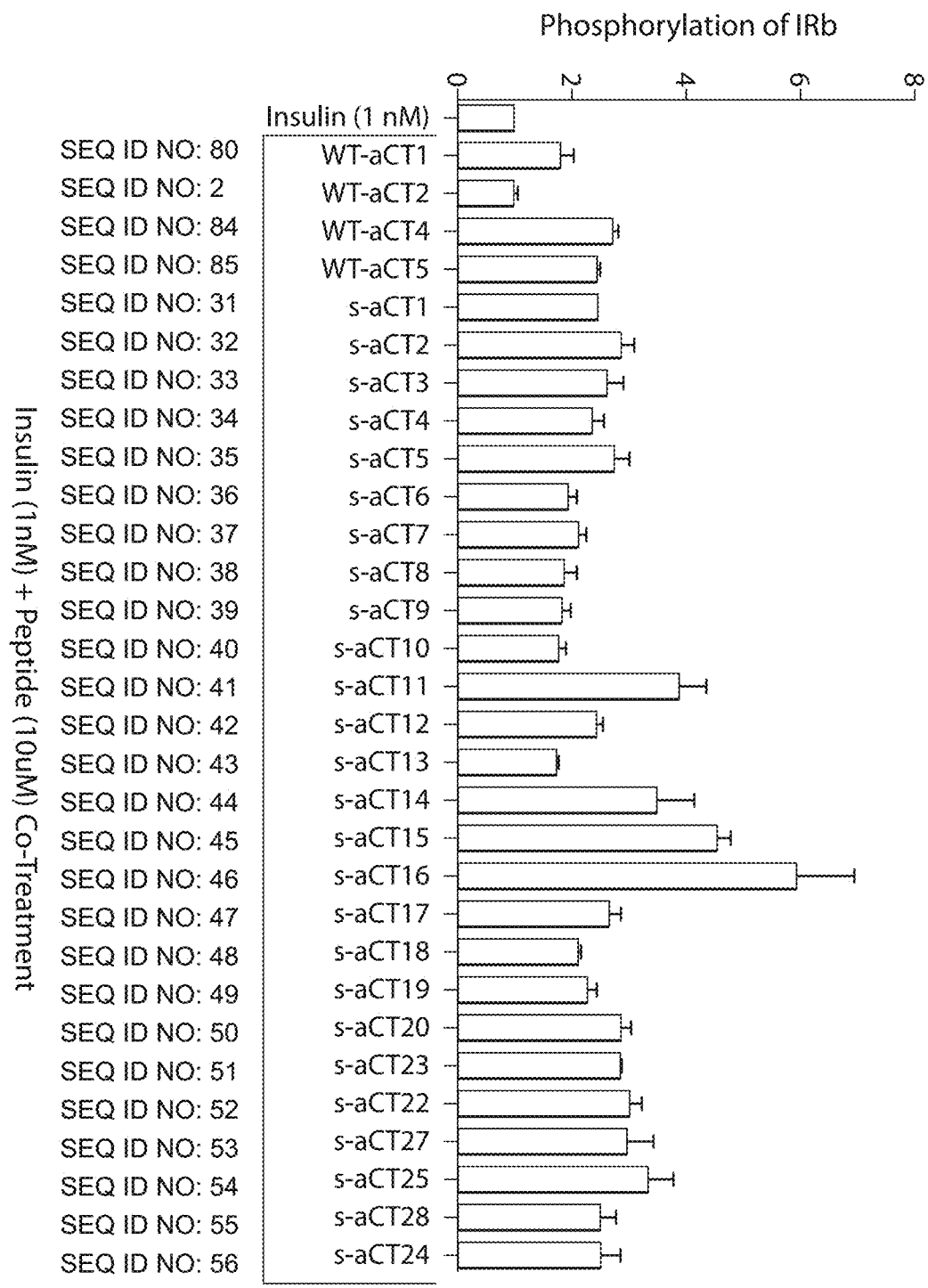
FIG. 33 depicts the effect of exemplified insulin α-CT polypeptides on IRβ phosphorylation. (see Example 3)
Figure 35:
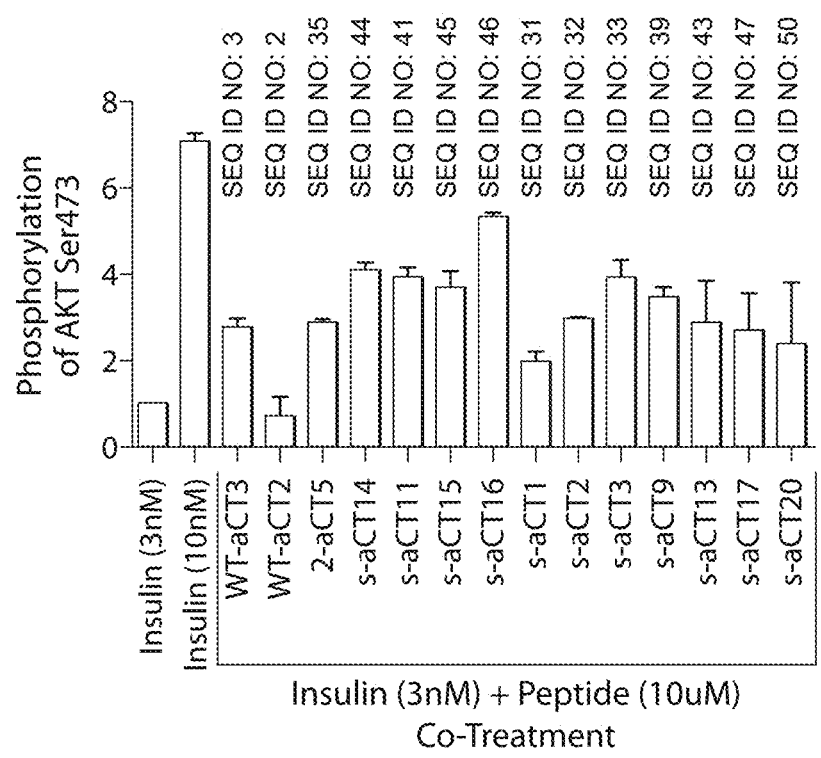
Figure 38:
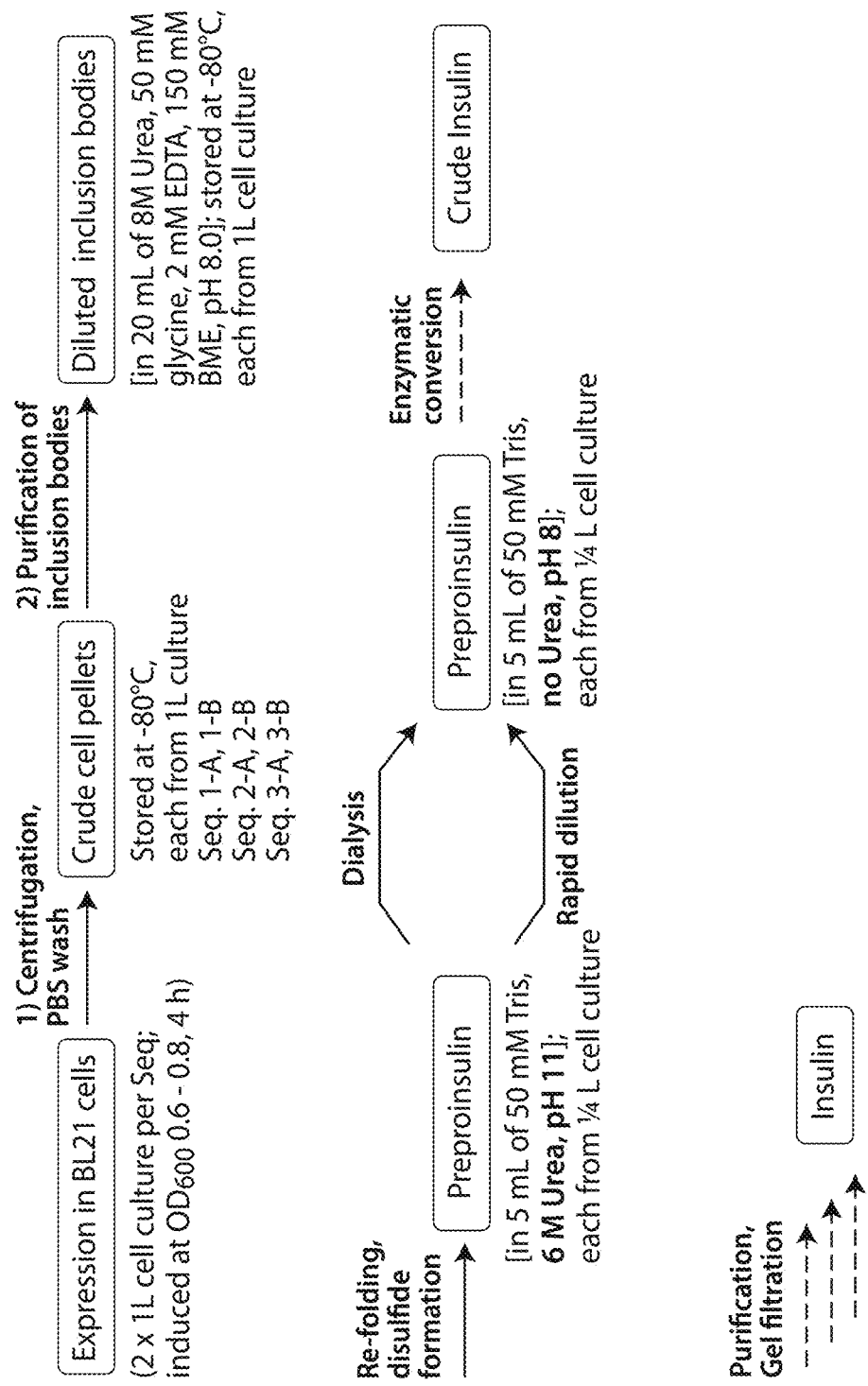
FIG. 38 depicts the biosynthesis of insulin analogues as described herein.
Figure 39:
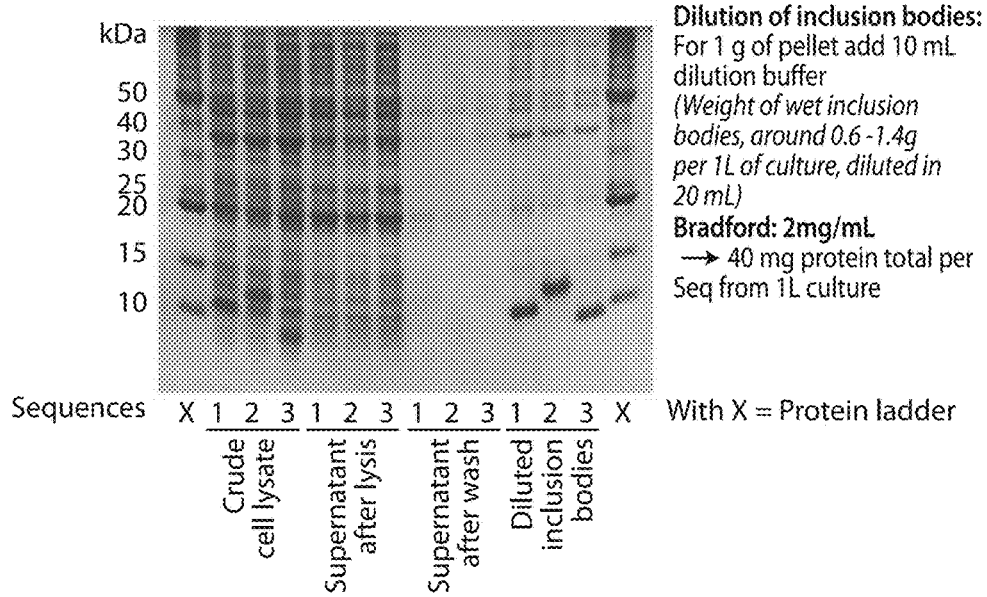
FIG. 39 depicts purification of inclusion bodies in biosynthesis of insulin analogues.
Figure 40:
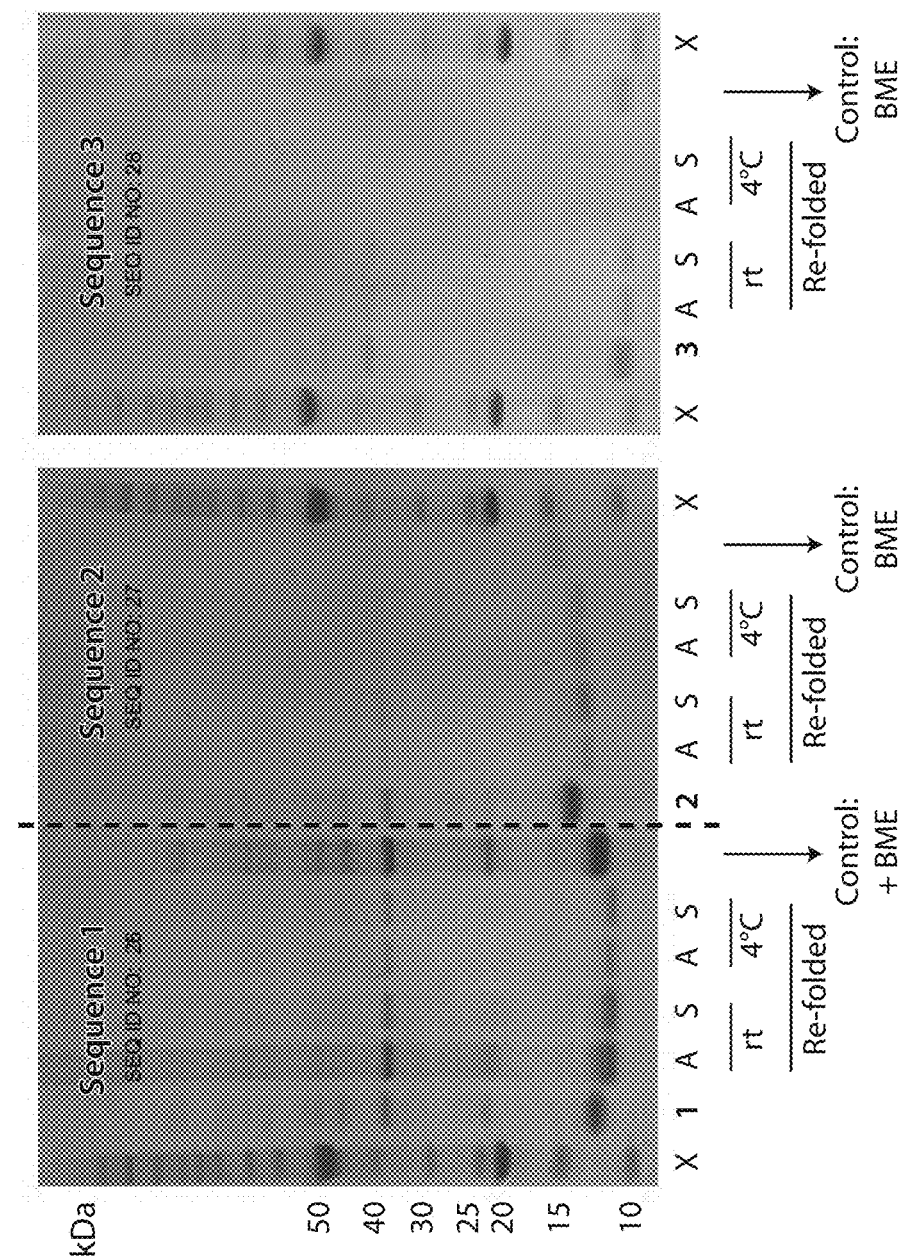
FIG. 40 depicts small scale test of re-folding conditions in the exemplified biosynthesis of insulin analogues. Diluted inclusion bodies were dissolved in 10 mM glycine, 1 mM EDTA, 2 mM cystine, and 1 g/L PEG 1500, at pH 11.2. The dilution ratio is 1:100. The folding reaction ran for 6 h at different conditions: rt vs. 4° C., and with agitating vs. standing. Then $Zn^{2+}$ was added to reach a final concentration of 3 mM. The pH value was adjusted to 6.2 to give precipitation. Subsequent centrifugation and the pellets were dissolved in 50 mM Tris, 6M Urea, with the pH 8 to 11. Re-folding seems to take place at rt or 4° C., agitating or standing. Sequences 1, 2, and 3: diluted inclusion bodies from FIG. 39 as reference. A: agitating; B: standing

An exemplified convergent synthetic approach is shown in FIG. 8: A-chain-B-chain adduct, bearing an additional cysteine on the N-terminus of the A-chain, is synthesized and folded using the sequential synthetic approach. Native Chemical Ligation (NCL) is then used to couple the stapled or stitched polypeptide with the N-terminal amino acid of the A-chain-B-chain adduct to provide an insulin analogue.

Pharmaceutical Compositions

The present disclosure provides pharmaceutical compositions comprising a stabilized (stitched or stapled) polypeptide as described herein and, optionally, a pharmaceutically acceptable excipient. The present disclosure also provides pharmaceutical compositions comprising an insulin analogue as described herein and, optionally, a pharmaceutically acceptable excipient. For the purposes of the present disclosure, the phrase "active ingredient" generally refers to a stabilized polypeptide as described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

The formulations of the pharmaceutical compositions described herein may be prepared by any method known or hereafter developed in the art of pharmacology. In general, such preparatory methods include the step of bringing the active ingredient into association with a carrier and/or one or more other accessory ingredients, and then, if necessary and/or desirable, shaping and/or packaging the product into a desired single- or multi-dose unit.

A pharmaceutical composition may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable excipient, and/or any additional ingredients in a pharmaceutical composition of the disclosure will vary, depending upon the identity, size, and/or condition of the subject treated and further depending upon the route by which the composition is to be administered. By way of example, the composition may comprise between 0.1% and 100% (w/w) active ingredient.

Pharmaceutical compositions may comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$ Edition, A. R. Gennaro, (Lippincott, Williams & Wilkins, Baltimore, Md., 2006) discloses various carriers used in formulating pharmaceutical compositions and known techniques for the preparation thereof. Except insofar as any conventional carrier medium is incompatible with a substance or its derivatives, such as by producing any undesirable biological effect or otherwise interacting in a deleterious manner with any other component(s) of the pharmaceutical composition, its use is contemplated to be within the scope of this disclosure.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol,); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In some embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In some embodiments for parenteral administration, the polypeptides of the disclosure are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a polypeptide of the disclosure may include ointments, pastes, creams, lotions, gels, powders, solutions, sprays, inhalants and/or patches. Generally, the active component is admixed under sterile conditions with a pharmaceutically acceptable carrier and/or any needed preservatives and/or buffers as may be required. Additionally, the present disclosure contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

General considerations in the formulation and/or manufacture of pharmaceutical agents may be found, for example, in *Remington: The Science and Practice of Pharmacy* 21$^{st}$ ed., Lippincott Williams & Wilkins, 2005.

Methods of Use and Treatment

The inventive polypeptides and insulin analogues typically have IR-modulating activity. In some embodiments, the provided polypeptides act as insulin sensitizers, i.e. enhancing the sensitivity of IR to insulin. Generally, exogenous αCT peptides as insulin sensitizers often demonstrate poor binding affinity, exhibit short in vivo half-lives due to proteolytic degradation and rapid clearance by renal filtration, and, in the case of intracellular targets, are incapable of penetrating the cell membrane (Jenssen, H. & Aspmo, S. I. Serum stability of peptides. *Methods Mol Biol* 494, 177-186 (2008)). The polypeptides as described herein are stabilized αCT polypeptides in their native bioactive conformation and facilitate a postulated conformational shift in insulin into an "active" structure that is capable of high-affinity interaction with the IR. In some embodiments, the stabilized polypeptides demonstrate a longer in vivo half-live and/or improved cell penetration capability.

In some embodiments, the inventive stabilized αCT polypeptide improves the affinity of insulin to the IR with an $EC_{50}$ value of about $1.0\times10^{-15}$ to about $1.0\times10^{-5}$ M. In some embodiments, the inventive stabilized αCT polypeptide improves the affinity of insulin to the IR with an $IC_{50}$ value of about $1.0\times10^{-13}$ to about $1.0\times10^{-7}$ M. In some embodiments, the inventive stabilized αCT polypeptide improves the affinity of insulin to the IR with an $IC_{50}$ value of about $1.0\times10^{-12}$ to about $1.0\times10^{-8}$ M. In some embodiments, the inventive stabilized αCT polypeptide improves the affinity of insulin to the IR with an $IC_{50}$ value of about $1.0\times10^{-11}$ to about $1.0\times10^{-9}$ M. In some embodiments, the inventive stabilized αCT polypeptide improves the affinity of insulin to IR with an $IC_{50}$ value of about $1.0\times10^{-11}$ to about $1.0\times10^{-8}$ M. In some embodiments, the inventive stabilized αCT polypeptide improves the affinity of insulin to the IR with an $IC_{50}$ value of about $1.0\times10^{-11}$ to about $1.0\times10^{-10}$ M.

In some embodiments, the inventive insulin analogues exhibit partial or full IR agonist or agonistic activity, i.e., the inventive insulin analogues bind to IR, activate IR and agonize IR-mediated activity. In some embodiments, the inventive insulin analogues demonstrate improved affinity to IR and more efficient folding. In some embodiments, the insulin analogues modulate IR activity by activating the IR signaling pathway.

In some embodiments, the inventive insulin analogue exhibits binding affinity to IR with an $EC_{50}$ value of about $1.0\times10^{-15}$ to about $1.0\times10^{-5}$ M. In some embodiments, the inventive insulin analogue exhibits binding affinity to IR with an $IC_{50}$ value of about $1.0\times10^{-13}$ to about $1.0\times10^{-7}$ M. In some embodiments, the inventive insulin analogue exhibits binding affinity to the IR with an $IC_{50}$ value of about $1.0\times10^{-12}$ to about $1.0\times10^{-8}$ M. In some embodiments, the inventive insulin analogue exhibits binding affinity to the IR with an $IC_{50}$ value of about $1.0\times10^{-11}$ to about $1.0\times10^{-9}$ M. In some embodiments, the inventive insulin analogue exhibits binding affinity to the IR with an $IC_{50}$ value of about $1.0\times10^{-11}$ to about $1.0\times10^{-8}$ M. In some embodiments, the inventive insulin analogue exhibits binding affinity to the IR with an $IC_{50}$ value of about $1.0\times10^{-11}$ to about $1.0\times10^{-10}$ M.

As generally described herein, in one aspect, provided is a method of treating a diabetic condition or complication thereof comprising administering to a subject in need thereof an effective amount of a stabilized (stapled or stitched) polypeptide and/or an insulin analogue as described herein.

As used herein, a "diabetic condition" refers to diabetes and pre-diabetes. Diabetes refers to a group of metabolic diseases in which a person has high blood sugar, either because the body does not produce enough insulin, or because cells do not respond to the insulin that is produced. This high blood sugar produces the classical symptoms of polyuria (frequent urination), polydipsia (increased thirst) and polyphagia (increased hunger). There are several types of diabetes. Type I diabetes results from the body's failure to produce insulin, and presently requires the person to inject insulin or wear an insulin pump. Type 2 diabetes results from insulin resistance a condition in which cells fail to use insulin properly, sometimes combined with an absolute insulin deficiency. Gestational diabetes occurs when pregnant women without a previous diagnosis of diabetes develop a high blood glucose level. Other forms of diabetes include congenital diabetes, which is due to genetic defects of insulin secretion, cystic fibrosis-related diabetes, steroid diabetes induced by high doses of glucocorticoids, and several forms of monogenic diabetes, e.g., mature onset diabetes of the young (e.g., MODY 1, 2, 3, 4, 5, 6, 7, 8, 9, or 10). Pre-diabetes indicates a condition that occurs when a person's blood glucose levels are higher than normal but not high enough for a diagnosis of diabetes.

All forms of diabetes increase the risk of long-term complications. These typically develop after many years, but may be the first symptom in those who have otherwise not received a diagnosis before that time. The major long-term complications relate to damage to blood vessels. Diabetes doubles the risk of cardiovascular disease and macrovascular diseases such as ischemic heart disease (angina, myocardial infarction), stroke, and peripheral vascular disease. Diabetes also causes microvascular complications, e.g., damage to the small blood vessels. Diabetic retinopathy, which affects blood vessel formation in the retina of the eye, can lead to visual symptoms, reduced vision, and potentially blindness. Diabetic nephropathy, the impact of diabetes on the kidneys, can lead to scarring changes in the kidney tissue, loss of small or progressively larger amounts of protein in the urine, and eventually chronic kidney disease requiring dialysis. Diabetic neuropathy is the impact of diabetes on the nervous system, most commonly causing numbness, tingling and pain in the feet and also increasing the risk of skin damage due to altered sensation. Together with vascular disease in the legs, neuropathy contributes to the risk of diabetes-related foot problems, e.g., diabetic foot ulcers, that can be difficult to treat and occasionally require amputation.

As generally described herein, in one aspect, provided is a method of modulating the activity of an insulin receptor in a subject comprising administering to the subject a physiologically effective amount of a polypeptide or a pharmaceutically acceptable salt thereof. In another aspect, provided is a method of modulating the activity of an insulin receptor in a subject comprising administering to the subject a physiologically effective amount of an insulin analogue as described herein, or a pharmaceutically acceptable salt thereof. In some embodiments, the responsive IR is bound in an amount and under conditions sufficient to induce, promote, enhance, and/or otherwise modulate an IR-mediated activity or response.

As generally described herein, in one aspect, provided is a method of lowering blood glucose levels in a subject comprising administering to the subject in need thereof an effective amount of a polypeptide as described herein or a pharmaceutically acceptable salt thereof. In another aspect, provided is a method of lowering blood glucose levels in a subject comprising administering to the subject in need thereof an effective amount of an insulin analogue as described herein or a pharmaceutically acceptable salt thereof. In another aspect, the invention provides the use of the polypeptides or insulin analogues in the manufacture of a medicament used in the reducing of blood glucose levels. In some embodiments, the provided polypeptides and/or insulin analogues may have the ability to lower blood glucose levels, for example, reflected by the results of a fat cell lipogenesis assay, by at least about 10%, at least about 20%, at least about 30%, at least about 40%, at least about 50%, at least about 60%, or more (e.g., about 70-100%) of the blood glucose lowering abilities of human insulin in human insulin receptor-bearing cells.

As generally described herein, in one aspect, provided is a method of activating an insulin receptor comprising contacting the insulin receptor with an effective amount of a polypeptide as described herein or a pharmaceutically acceptable salt thereof. In another aspect, provided is a method of activating an insulin receptor comprising contacting the insulin receptor with an effective amount of an insulin analogue as described herein or a pharmaceutically acceptable salt thereof. In some embodiments, the insulin receptor is contacted is in vivo. In some embodiments, the insulin receptor is contacted is in vitro.

The stabilized polypeptide or insulin analogue may be administered using any amount and any route of administration effective for the treatment of the diabetic condition or complication. The exact amount required will vary from subject to subject, depending on the species, age, and general condition of the subject, the severity of the infection, the particular composition, its mode of administration, its mode of activity, and the like.

The stabilized polypeptide or insulin analogue is typically formulated in dosage unit form for ease of administration and uniformity of dosage. It will be understood, however, that the total daily usage of the pharmaceutical compositions will be decided by the attending physician within the scope of sound medical judgment. The specific effective dose level for any particular subject will depend upon a variety of factors including the disorder being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The stabilized polypeptide or insulin analogue may be administered by any route. In some embodiments, the stabilized polypeptide may be administered by a variety of routes, including oral, intravenous, intramuscular, intraarterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. In general the most appropriate route of administration will depend upon a variety of factors including the nature of the stabilized polypeptide (e.g., its stability in the environment of the gastrointestinal tract), and/or the condition of the subject (e.g., whether the subject is able to tolerate oral administration). The disclosure embraces the delivery of the pharmaceutical compositions as described herein by any appropriate route taking into consideration likely advances in the sciences of drug delivery.

In some embodiments, the stabilized polypeptide or insulin analogue may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In some embodiments, the desired dosage may be delivered using multiple administrations (e.g., two, three, four, five, six, seven, eight, nine, ten, eleven, twelve, thirteen, fourteen, or more administrations).

In some embodiments, the method comprises administering the stabilized polypeptide as the sole therapeutic agent, but in some embodiments, the method comprises administering the stabilized polypeptide in combination with another therapeutic agent, such as insulin and/or another anti-diabetic agent. The particular combination will take into account compatibility of the therapeutics and/or procedures and the desired therapeutic effect to be achieved. By "in combination with," it is not intended to imply that the agents must be administered at the same time and/or formulated for delivery together, although these methods of delivery are within the scope of the disclosure. The agents can be administered concurrently with, prior to, or subsequent to, one or more other desired therapeutics or medical procedures. In general, each agent will be administered at a dose and/or on a time schedule determined for that agent. Additionally, the disclosure encompasses the delivery of the stabilized polypeptide in combination with agents that may improve their bioavailability, reduce and/or modify their metabolism, inhibit their excretion, and/or modify their distribution within the body. It will further be appreciated that the agents utilized in this combination may be administered together in a single pharmaceutical composition or administered separately in different pharmaceutical compositions. In general, it is expected that agents utilized in combination be utilized at levels that do not exceed the levels at which they are utilized individually. In some embodiments, the levels utilized in combination will be lower than those utilized individually.

Insulin is usually given subcutaneously, either by injection or by an insulin pump. In acute-care settings, insulin may also be given intravenously. In general, there are three types of insulin, characterized by the rate which they are metabolized by the body. They are rapid acting insulins, intermediate acting insulins and long acting insulins. Examples of rapid acting insulins include regular insulin (Humulin R, Novolin R), insulin lispro (Humalog), insulin aspart (Novolog), insulin glulisine (Apidra), and prompt insulin zinc (Semilente, Slightly slower acting). Examples of intermediate acting insulins include isophane insulin, neutral protamine Hagedom (NPH) (Humulin N, Novolin N), and insulin zinc (Lente). Examples of long acting insulins include extended insulin zinc insulin (Ultralente), insulin glargine (Lantus), and insulin detemir (Levemir).

Other anti-diabetic agents, typically given orally, include, but are not limited to, sulfonylureas (e.g., tolbutamide, acetohexamide, tolazamide, chlorpropamide, glyburide, glimepiride, glipizide, glucopyramide, gliquidone), biguanides (e.g., metformin, phenformin, buformin), meglitinides (e.g., repaglinide, nateglinide), alpha-glucosidase inhibitors (e.g., acarbose, miglitol, voglibose), and thiazolidinediones (e.g., rosiglitazone, pioglitazone, troglitazone).

Further contemplated are uses of the stabilized polypeptides as research tools, i.e., to probe the activation mechanism of the IR.

Kits

The disclosure provides a variety of kits comprising one or more of the polypeptides and/or insulin analogues disclosed herein. For example, the disclosure provides a kit comprising a stitched or stapled polypeptide and/or insulin analogue as described herein and instructions for use. A kit may comprise multiple different polypeptides. A kit may comprise any of a number of additional components or reagents in any combination. All of the various combinations are not set forth explicitly but each combination is included in the scope of the disclosure According to some embodiments of the disclosure, a kit may include, for example, (i) one or more polypeptides and one or more particular biologically active agents to be delivered; and/or (ii) one or more insulin analogues and one or more particular biologically active agents to be delivered; (iii) instructions for administering the polypeptide and/or insulin analogue to a subject in need thereof.

Kits typically include instructions which may, for example, comprise protocols and/or describe conditions for production of the polypeptides and/or insulin analogues, administration of the polypeptides and/or insulin analogues to a subject in need thereof, design of the polypeptides and/or insulin analogues, etc. Kits will generally include one or more vessels or containers so that some or all of the individual components and reagents may be separately housed. Kits may also include a means for enclosing individual containers in relatively close confinement for commercial sale, e.g., a plastic box, in which instructions, packaging materials such as styrofoam, etc., may be enclosed. An identifier, e.g., a bar code, radio frequency identification (ID) tag, etc., may be present in or on the kit or in or one or more of the vessels or containers included in the kit. An identifier can be used, e.g., to uniquely identify the kit for purposes of quality control, inventory control, tracking, movement between workstations, etc.

EXAMPLES

In order that the invention described herein may be more fully understood, the following examples are set forth. It should be understood that these examples are for illustrative purposes only and are not to be construed as limiting this invention in any manner.

Example 1. Synthesis of αCT Peptides and/or Insulin Analogues

Solid-Phase Peptide Synthesis:

All peptides were prepared using Fmoc chemistry on one of the following resins: Rink Amide MBHA, Rink Amide MBHA Low Loading, PAL-NovaSyn TG, NovaPEG Rink Amide resin, or NovaPEG Rink Amide Low Loading Resin. The dry resin was typically swelled in dichloromethane and then N-methyl-2-pyrrolidone (NMP) before use. Fmoc protecting groups were removed using 25% (v/v) piperidine in NMP (4×5 min). Natural amino acids were typically coupled for 60 minutes using 4 equivalents of Fmoc-protected amino acid, 4 equivalents of (1-Cyano-2-ethoxy-2-oxoethylidenaminooxy)dimethylamino-morpholino-carbenium hexafluorophosphate (COMU) as the coupling reagent, and 8 equivalents of N,N-diisopropylethylamine (DIPEA) as the base. Non-natural amino acids (e.g. $S_5$, $Pyr_R$ et al.) were typically coupled for 120 minutes using 3 equivalents of Fmoc-protected amino acid, 3 equivalents of (1-Cyano-2-ethoxy-2-oxoethylidenaminooxy)dimethylamino-morpholino-carbenium hexafluorophosphate (COMU) as the coupling reagent, and 6 equivalents of N,N-diisopropylethylamine (DIPEA) as the base. NMP was used to wash the resin (5×1 min) in between each coupling and deprotection step.

N-Terminal Acetylation:

Peptides used for Circular Dichroism Spectroscopy (CD) were prepared with either free N-termini or acetylated N-termini. To acetylate the N-terminus on the solid phase, the N-terminal Fmoc is deprotected and the resin subsequently washed with NMP. Acetylation is typically carried out by treating the resin-bound peptide for 1-2 hours with a solution of 20 equivalents of acetic anhydride and 40 equivalents of DIPEA in NMP. After completion of the reaction, the resin is typically washed with NMP (5×1 min), DCM (3×1 min), and dried with methanol.

Ring-Closing Metathesis:

In all cases, ring-closing metathesis was performed on the solid phase on peptides that contained either an N-terminal acetyl cap or an N-terminal Fmoc using the following general procedure. The resin was swelled in dry 1,2-dichloroethane (DCE) for at least 20 minutes. The resin-bound peptide typically was then treated for 2 hours with 25 mole % (relative to the initial loading of the resin) of Grubbs $1^{st}$ Generation metathesis catalyst (Benzylidene-bis(tricyclohexylphosphine)dichlororuthenium, Bis(tricyclohexylphosphine) benzylidine ruthenium(IV) dichloride) dissolved to a concentration of approximately 8-10 mg/mL in DCE. In most cases, 2 or 3 treatments with catalyst were necessary to achieve complete conversion to the hydrocarbon-stapled or alloc-stapled product. In between each treatment, excess catalyst was removed by washing with DCE (3×1 min). After the final treatment with catalyst, the resin was typically washed multiple times with DCE, multiple times with DCM, and dried with methanol.

Palladium-Catalyzed $CO_2$ Extrusion:

Resin containing alloc-stapled peptides prepared by ring closing metathesis using the above procedures was swelled in dry dichloromethane (DCM) for at least 20 minutes. The resin was then treated for 15-30 minutes with 20-40 mole % (relative to the moles of carbamates present in the staple, calculated relative to the initial loading of the resin) of $Pd(PPh_3)_4$ dissolved in dry DCM to a final concentration of approximately 5-10 mM. Typically, 2 treatments were performed to ensure complete reaction of the alloc-stapled starting material. In between each treatment, the resin was washed with dry DCM (3×1 min).

Peptide Cleavage/Deprotection and Purification:

The side-chain protecting groups were removed and the peptides cleaved from the resin simultaneously using the following procedure. Dry resin was treated with a solution of trifluoroacetic acid:triisopropylsilane:water (95:2.5:2.5) for 3 hours. After completion of the incubation, the volume of the solution was reduced by evaporation under a stream of $N_{2(g)}$ and the resulting residue was treated with cold diethyl ether. The precipitated peptide was pelleted by centrifugation, the supernatant decanted, and the pellet air-dried. The crude peptides were typically dissolved in a 1:1 solution of acetonitrile:water and then purified by reverse phase HPLC using acetonitrile containing 0.1% (v/v) trifluoroacetic acid and water containing 0.1% (v/v) trifluoroacetic acid as the components of the mobile phase. The purity of the HPLC fractions was assessed by LC/MS, and clean fractions were pooled and concentrated by speedvac. The peptides were then lyophilized to dryness.

Example 2. Biophysical Characterization of Exemplified Insulin αCT Peptides

All of the following spectra were obtained using native αCT peptide and all stapled or stitched αCT peptides dissolved (FIGS. 16-21) in either 10 mM sodium phosphate pH7.0 buffer, PBS, or MilliQ $H_2O$. The raw data have been converted to the concentration-independent units of mean residue ellipticity (first two plots) or molar ellipticity (the remainder of the plots). α-Helices typically show dual minima at approximately 208 nm and 222 nm and a maximum at approximately 192 nm. In PBS, buffer interference disrupts data at less than 200 nm. Spectra were obtained using a JASCO J-710 spectropolarimeter.

Example 3. Insulin Receptor (IR) Phosphorylation Assays

General Procedure for Treatment of CHO-IR Cells with Insulin Sensitizer Peptides CHO-IR cells were seeded in 24-well plates and grown in Ham's F-12 medium with 10% FBS to >80% confluency. The cells were then starved in Ham's F-12 medium without FBS for two hours prior to peptide treatment. For control samples, cells were incubated in fresh Ham's F-12 without FBS (negative control) or the same medium with 1 nM insulin (positive control). For the initial peptide screen, experimental wells were incubated in the 1 nM insulin-containing medium supplemented with peptides at a concentration of 10 μM. For the dose-response assays, co-treatment with 1 nM insulin and varying concentration of peptide (10 nM, 100 nM, 1 μM, 10 μM, 100 μM) was performed. All treatments were performed for 30 minutes at 37° C.

For assays testing the activity of the insulin sensitizer peptides in the absence of insulin, treatments with 10 M peptide in the absence of insulin were used.

General Procedure for IR Auto-Phosphorylation ELISA Assay

For the phospho-IR ELISA assay, the clarified lysates were first quantified using the standard BCA method and then adjusted to a uniform concentration. All samples were then added to IRβ mouse mAb-coated microwells at a concentration of 0.2 mg/ml of total protein. Microwells were sealed firmly with tape and incubated at 4° C. overnight.

The following day, the wells were drained and washed four times with 1× Wash Buffer. 100 μl of detection antibody (Phospho-IRβ Tyr1150/1151 Rabbit mAb) was added to each well and the samples were incubated for 1 h at 37° C. After washing with 1× Wash Buffer four times, 100 μl of HRP-conjugated Anti-Rabbit IgG was added to each well and the samples were incubated for 30 minutes at 37° C. The wash procedure was repeated, and 100 μl of TMB substrate was added. After incubating for 10 minutes at 37° C., 100 μl of stop solution was added. The absorbance at 450 nm was read by Hewlett-Packard SpectraMax M5 Plate Reader within 30 minutes after adding the stop solution.

Akt Phosphorylation Assays

General Procedure for Treatment of CHO-IR Cells with Insulin Sensitizer Peptides:

CHO-IR cells were seeded in 24-well plates and grown in Ham's F-12 medium with 10% FBS to >80% confluency. The cells were then starved in Ham's F-12 medium without FBS for two hours prior to peptide treatment. For control samples, cells were incubated in fresh Ham's F-12 without FBS (negative control) or the same medium with 3 nM insulin (positive control). For the initial peptide screen, experimental wells were incubated in the 3 nM insulin-containing medium supplemented with peptides at a concentration of 10 μM. For the dose-response assays, co-treatment with 3 nM insulin and varying concentration of peptide (10 nM, 100 nM, 1 μM, 10 μM, 100 μM) was performed. All treatments were performed for 30 minutes at 37° C.

General Procedure for Akt Phosphorylation ELISA Assay:

For the phospho-Akt ELISA assay, the clarified lysates were first quantified using the standard BCA method and then adjusted to a uniform concentration. Cell Signaling Technologies PathScan® Phospho-Akt1 (Ser473) Chemiluminescent Sandwich ELISA Kit #7134 was then used for the ELISA assay according to the manufacturer's instructions.

Example 4. Biological Evaluation of Insulin Analogues

All insulin analogues are evaluated for the ability to induce activation of the insulin signaling pathway using the in vitro assays as described above. The only major difference in performing these assays with insulin analogues is that the treatments are performed as co-treatments with insulin. Specifically, unstimulated cells are treated with the insulin analogues, and control samples are similarly treated with insulin. In the event that an insulin analogue acts as an agonist of the insulin receptor, treatment produces an $EC_{50}$ for insulin receptor activation that is lower than that observed upon treatment with insulin.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, some embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A polypeptide comprising an alpha-helical segment, wherein the polypeptide binds to the insulin receptor, and wherein the polypeptide is of Formula (I-2):

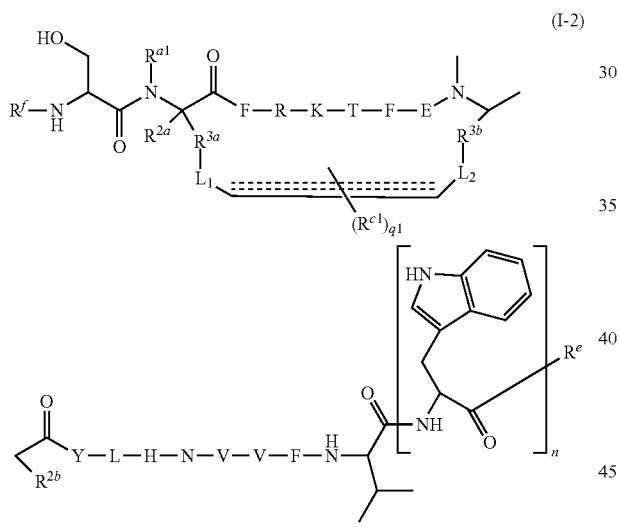

(I-2)

or a pharmaceutically acceptable salt thereof;
wherein:
n=0 or 1;
each instance of ≡≡≡ independently represents a single bond, a double bond, or a triple bond;
each of $R^{a1}$ and $R^{a2}$, are, independently, hydrogen; acyl; optionally substituted $C_{1-6}$ alkyl; or an amino protecting group;
each of $R^{2a}$ and $R^{2b}$ is, independently, optionally substituted alkyl; optionally substituted alkenyl; optionally substituted alkynyl; optionally substituted heteroalkyl; optionally substituted carbocyclyl; optionally substituted heterocyclyl;
each of $R^{3a}$ and $R^{3b}$ is, independently, optionally substituted alkylene; unsubstituted heteroalkylene; optionally substituted carbocyclylene; or optionally substituted heterocyclylene; or optionally $R^{2a}$ and $R^{3a}$ are joined to form a ring; or optionally $R^{2b}$ and $R^{3b}$ are joined to form a ring;

$L_1$ is independently, a bond; optionally substituted $C_{1-10}$ alkylene; or $C(=O)OR^{L1}$—;
$L_2$ is independently, a bond; optionally substituted $C_{1-10}$ alkylene; or —$C(=O)OR^{L2}$—;
each of $R^{L1}$ and $R^{L2}$ is independently optionally substituted $C_{1-10}$ alkylene;
each instance of $R^{c1}$ is independently hydrogen; optionally substituted aliphatic; optionally substituted heteroaliphatic; optionally substituted aryl; optionally substituted heteroaryl; acyl; optionally substituted hydroxyl; optionally substituted thiol; optionally substituted amino; azido; cyano; isocyano; halogen; or nitro;
q1 is 0, 1, or 2;
$R^f$ is (i) hydrogen; (ii) unsubstituted aliphatic; (iii) acetyl; (iv) acyl; or (v) aliphatic substituted with halogen, =O, =S, =NN($R^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, =NOR$^{cc}$, —CN, —NO$_2$, —N$_3$, —SO$_2$H, —SO$_3$H, —OH, —OR$^{aa}$, —ON(R$^{bb}$)$_2$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —C(=O)NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, or 5-14 membered heteroaryl; wherein each instance of $R^{aa}$ is, independently, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$alkenyl, heteroC$_{2-10}$alkynyl, $C_{3-10}$ carbocyclyl, 3-14 membered heterocyclyl, $C_{6-14}$ aryl, or 5-14 membered heteroaryl, or two $R^{aa}$ groups are joined to form a 3-14 membered heterocyclyl or 5-14 membered heteroaryl ring; wherein each instance of $R^{bb}$ is, independently, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, or 5-14 membered heteroaryl, or two R$^{bb}$ groups are joined to form a 3-14 membered heterocyclyl or 5-14 membered heteroaryl ring; and wherein each instance of R$^{cc}$ is, independently, hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, or 5-14 membered heteroaryl, or two R$^{cc}$ groups are joined to form a 3-14 membered heterocyclyl or 5-14 membered heteroaryl ring;

R$^e$ is —OR$^E$; —N(R$^E$)$_2$; or —SR$^E$, wherein each instance of R$^E$ is, independently, (i) hydrogen; (ii) unsubstituted-aliphatic; (iii) unsubstituted-heteroaliphatic; (iv) optionally substituted aryl; (v) optionally substituted heteroaryl; or (vi) aliphatic substituted with —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CHO, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —OC(=NR$^{bb}$)N(R$^{bb}$)$_2$, —NR$^{bb}$C(=NR$^{bb}$)N(R$^{bb}$)$_2$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, or 5-14 membered heteroaryl; wherein each instance of R$^{aa}$ is, independently, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, or 5-14 membered heteroaryl, or two R$^{aa}$ groups are joined to form a 3-14 membered heterocyclyl or 5-14 membered heteroaryl ring; wherein each instance of R$^{bb}$ is, independently, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, or 5-14 membered heteroaryl, or two R$^{bb}$ groups are joined to form a 3-14 membered heterocyclyl or 5-14 membered heteroaryl ring; and wherein each instance of R$^{cc}$ is, independently, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, or 5-14 membered heteroaryl, or two R$^{cc}$ groups are joined to form a 3-14 membered heterocyclyl or 5-14 membered heteroaryl ring; or (vii) two R$^E$ groups taken together form an optionally substituted heterocyclic or optionally substituted heteroaryl ring.

2. The polypeptide of claim 1, wherein each instance of the cross-linked amino acids is independently of Formula (i-d), (ii-d), (i-e), or (ii-e):

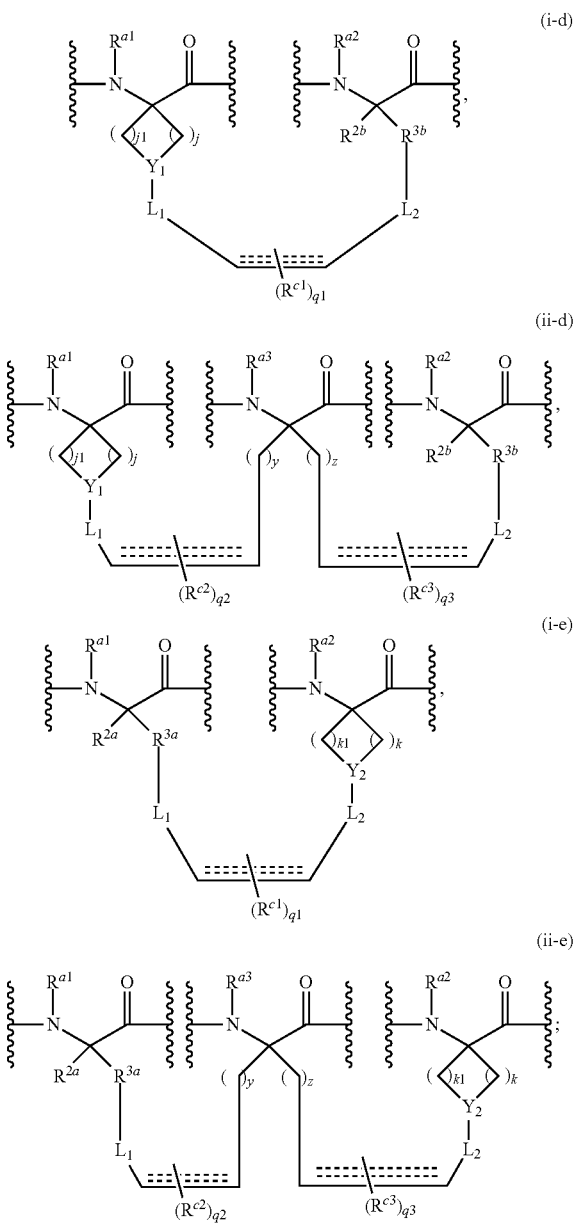

wherein
each of Y$_1$ and Y$_2$ is, independently, CR$^5$ or N;
R$^5$ is hydrogen, halogen, —NO$_2$, —OH, —CN, or C$_{1-6}$ alkyl; and each of j and j1 is, independently, 0, 1, 2, 3, 4, 5, or 6; and
each of k and k1 is, independently, 0 or an integer from 1 to 10, inclusive.

3. The polypeptide of claim 1, wherein $R^{3a}$ is of Formula (G-1):

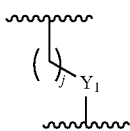

(G-1)

wherein
$Y_1$ is a bond, —$CR^5R^6$— or —$NR^1$—;
each of $R^5$ and $R^6$ is, independently, hydrogen, halogen, —$NO_2$, —OH, —CN, or $C_{1-6}$ alkyl;
$R^1$ is hydrogen; acyl; optionally substituted $C_{1-6}$ alkyl; or an amino protecting group; and
j is 0 or an integer between 1 and 10, inclusive.

4. The polypeptide of claim 1, wherein $L_1$ is of Formula (G-4) or Formula (G-5):

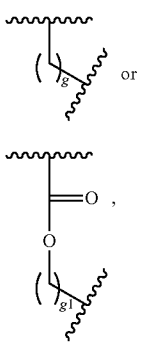

(G-4)

(G-5)

wherein each of g and g1 is, independently, 0 or an integer between 1 and 10, inclusive.

5. The polypeptide of claim 1, wherein $R^{3b}$ is of Formula (G-6):

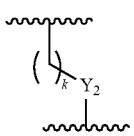

(G-6)

wherein
$Y_2$ is a bond, —$CR^5R^6$—, or —$NR^1$—;
each of $R^5$ and $R^6$ is independently hydrogen, halogen, —$NO_2$, —OH, —CN, or $C_{1-6}$ alkyl;
$R^1$ is hydrogen; acyl; optionally substituted $C_{1-6}$ alkyl; or an amino protecting group; and
k is 0 or an integer between 1 and 10, inclusive.

6. The polypeptide of claim 1, wherein $L_2$ is of Formula (G-9) or Formula (G-10):

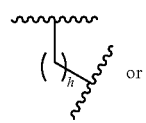

(G-9)

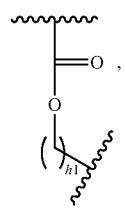

(G-10)

wherein each of h and h1 is, independently, 0 or an integer between 1 and 10, inclusive.

7. The polypeptide of claim 1, wherein ═════ is a single bond or a double bond.

8. An insulin analogue comprising:
(i) a polypeptide of claim 1;
(ii) an insulin A-chain polypeptide; and
(iii) an insulin B-chain polypeptide;
wherein
the polypeptide is linked to the insulin A chain polypeptide via a linker; and
the linker is optionally substituted alkylene-C(═O)—, optionally substituted heteroalkylene-C(═O)—, optionally substituted alkenylene-C(═O)—, optionally substituted heteroalkenylene-C(═O)—, optionally substituted alkynylene-C(═O)—, optionally substituted heteroalkynylene-C(═O)—, optionally substituted cycloalkylene-C(═O)—, optionally substituted heterocycloalkylene-C(═O)—, optionally substituted arylene-C(═O)—, optionally substituted heteroarylene-C(═O)—, optionally substituted aralkylene-C(═O)—, or optionally substituted heteroaralkylene-C(═O)—.

9. A pharmaceutical composition comprising a polypeptide of claim 1 or a pharmaceutically acceptable salt thereof and a pharmaceutically acceptable excipient.

10. A method of treating a diabetic condition or a complication thereof comprising administering to a subject in need thereof an effective amount of a polypeptide of claim 1 or a pharmaceutically acceptable salt thereof.

11. A method of treating a diabetic condition or a complication thereof comprising administering to a subject in need thereof an effective amount of an insulin analogue of claim 8 or a pharmaceutically acceptable salt thereof.

12. A method of lowering blood glucose levels in a subject comprising administering to the subject in need thereof an effective amount of a polypeptide of claim 1 or a pharmaceutically acceptable salt thereof.

13. A method of lowering blood glucose levels in a subject comprising administering to the subject in need thereof an effective amount of an insulin analogue of claim 8 or a pharmaceutically acceptable salt thereof.

14. A method of activating an insulin receptor comprising contacting the insulin receptor with an effective amount of a polypeptide of claim 1 or a pharmaceutically acceptable salt thereof.

15. The polypeptide of claim 1, wherein Rt is hydrogen; unsubstituted aliphatic; acetyl; acyl; or aliphatic substituted with ═O; and $R^e$ is —$OR^E$; —$N(R^E)_2$; or —$SR^E$, wherein each instance of $R^E$ is, independently, hydrogen or unsubstituted aliphatic.

16. The polypeptide of claim 1, wherein n is 1.

* * * * *